(12) United States Patent
Hamada et al.

(10) Patent No.: US 11,802,135 B2
(45) Date of Patent: Oct. 31, 2023

(54) LYSOPHOSPHATIDIC ACID DERIVATIVE

(71) Applicants: MITSUBISHI TANABE PHARMA CORPORATION, Osaka (JP); OSAKA UNIVERSITY, Suita (JP)

(72) Inventors: Maiko Hamada, Osaka (JP); Yuki Arai, Osaka (JP); Shuhei Yamakoshi, Osaka (JP); Hiroko Wada, Osaka (JP); Kazufumi Otsuki, Osaka (JP); Hiroaki Shitama, Osaka (JP); Nobuyuki Takakura, Suita (JP)

(73) Assignees: MITSUBISHI TANABE PHARMA CORPORATION, Osaka (JP); OSAKA UNIVERSITY, Suita (JP)

( * ) Notice: Subject to any disclaimer, the term of this patent is extended or adjusted under 35 U.S.C. 154(b) by 45 days.

(21) Appl. No.: 17/518,212

(22) Filed: Nov. 3, 2021

(65) Prior Publication Data

US 2023/0146210 A1 May 11, 2023

(51) Int. Cl.
| | | |
|---|---|---|
| *C07F 9/568* | (2006.01) | |
| *A61K 45/06* | (2006.01) | |
| *C07F 9/58* | (2006.01) | |

(52) U.S. Cl.
CPC ............. *C07F 9/568* (2013.01); *A61K 45/06* (2013.01); *C07F 9/58* (2013.01)

(58) Field of Classification Search
CPC ........................................................ C07F 9/568
USPC ............................................................ 514/79
See application file for complete search history.

(56) References Cited

U.S. PATENT DOCUMENTS

| | | |
|---|---|---|
| 7,169,818 B2 | 1/2007 | Lynch et al. |
| 2004/0122236 A1 | 6/2004 | Lynch et al. |
| 2017/0112861 A1 | 4/2017 | Takakura et al. |
| 2021/0205337 A1 | 7/2021 | Takakura et al. |

FOREIGN PATENT DOCUMENTS

| | | |
|---|---|---|
| JP | 2018-177710 A | 11/2018 |
| JP | 2021-080183 A | 5/2021 |
| WO | WO 2002/029001 A2 | 4/2002 |
| WO | WO 2015/152412 A1 | 10/2015 |

OTHER PUBLICATIONS

Folkman et al., "Isolation of a Tumor Factor Responsible for Angiogenesis," *J. Exp. Med.*, 133(2): 275-288 (1971).
Gerber et al., "Pharmacology and Pharmacodynamics of Bevacizumab as Monotherapy or in Combination with Cytotoxic Therapy in Preclinical Studies," *Cancer Res.*, 65(3): 671-680 (2005).
Jain, "Normalization of Tumor Vasculature: An Emerging Concept in Antiangiogenic Therapy," *Science*, 307(5706): 58-62 (2005).
Yanagida et al., "Current progress in non-Edg family LPA receptor research," *Biochem. Biophys. Acta.*, 1831(1): 33-41 (2013).

*Primary Examiner* — Taofiq A Solola
(74) *Attorney, Agent, or Firm* — Leydig, Voit & Mayer, Ltd.

(57) ABSTRACT

The present invention aims to provide a compound acting as a specific agonist for LPA4 receptors, and a pharmaceutical composition containing the compound. The present invention relates to a novel lysophosphatidic acid derivative having an agonistic action on LPA4 receptors and useful for the prophylaxis and/or treatment of diseases associated with angiogenesis abnormalities involving LPA4 receptors, diseases associated with vascular disorders, or the symptoms associated therewith, and a pharmaceutical composition containing the derivative.

16 Claims, 4 Drawing Sheets

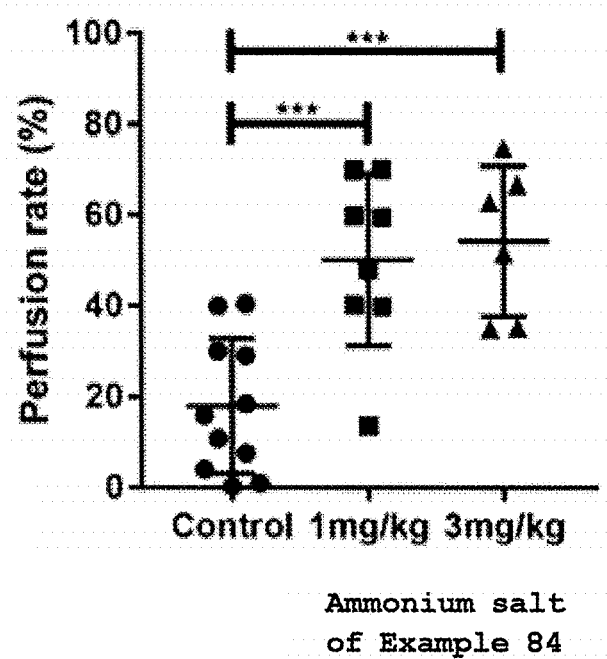

LYSOPHOSPHATIDIC ACID DERIVATIVE

TECHNICAL FIELD OF THE INVENTION

The present invention relates to a novel lysophosphatidic acid derivative having an agonistic action on LPA4 receptors and useful for the prophylaxis and/or treatment of diseases associated with angiogenesis abnormalities involving LPA4 receptors, diseases associated with vascular disorders, or the symptoms associated therewith.

The present invention also relates to a drug delivery promoter containing the aforementioned novel lysophosphatidic acid derivative which activates lysophospholipid receptors, and a pharmaceutical composition containing the aforementioned novel lysophosphatidic acid derivative which activates lysophospholipid receptors.

Furthermore, the present invention also relates to a use of a pharmaceutical composition containing the aforementioned novel lysophosphatidic acid derivative in combination with other drug.

BACKGROUND OF THE INVENTION

Lysophosphatidic acid (hereinafter abbreviated as LPA) is a phospholipid derivative capable of transmitting various signals into the cell, and LPA is known to exhibit various pharmacological actions via some G protein-coupled receptors on the cell surface. The LPA receptor subtype includes subtypes with different roles and there are eight subtypes at present, which are called LPA1, LPA2, LPA3, LPA4, LPA5, LPA6, GPR87, and GPR35 (patent document 1). For example, agonistic actions on LPA1 receptors which produce cancer invasion and metastasis (non-patent literature 1) and agonistic actions on LPA4 receptors which normalize tumor blood vessels (non-patent literature 1) have been reported.

It is known that when LPA is administered to mice that have a tumor formed under the skin, LPA activates LPA receptors to induce construction of the network of tumor blood vessels to normalize the reticular structure, smooth the vascular lumen, and normalize vascular permeability (patent document 1).

However, LPA is not considered to be sufficiently stable as a pharmaceutical product due to the cis-trans photoisomerization reaction that proceeds at the carbon-carbon double bond present in the LPA.

From these, compounds that act on LPA receptors have attracted attention as methods that prevent, treat and/or improve the prognosis of various diseases or pathological conditions caused by the LPA receptors (patent document 1).

As the lysophosphatidic acid derivative having an agonist activity on the LPA receptor, for example, the compounds described in patent documents 1 to 3 are known to date. However, it has not been reported that novel lysophosphatidic acid derivatives such as the compound of the present invention have superior selectivity and superior agonistic action on the LPA4 receptor.

Angiogenesis is involved in many diseases such as tumor, diabetic retinopathy, age-related macular degeneration, chronic inflammatory diseases such as rheumatoid arthritis and the like, acute inflammations such as infections and the like, vascular malformation, pulmonary fibrosis, cerebral infarction, arteriosclerosis and the like. The diseases in which angiogenesis is involved in pathology formation are generically named angiopathy. In the fetal stage, new blood vessels are formed from the state where a blood vessel does not exist at all. This process is called vascular development or vasculogenesis. In contrast, the process of forming a new blood vessel from an existing blood vessel is called angiogenesis. Angiogenesis is involved in the formation of blood vessels in various pathologies.

VEGF (vascular endothelial growth factor) known as a vascular endothelial cell factor plays an important role in any angiogenesis such as physiological angiogenesis from the fetal stage to the growth phase, pathological angiogenesis in pathology formation, and the like. VEGF strongly induces proliferation of vascular endothelial cells. In addition, at the onset of angiogenesis, VEGF phosphorylates VE-cadherin, which is involved in the adhesion between vascular endothelial cells, via Src, and induces intracellular transfer to cause looseness between vascular endothelial cells, thus enhancing vascular permeability.

Generally, the lumen of normal blood vessels is structurally stabilized by adhesion of vascular endothelial cells and parietal cells generically named vascular smooth muscle cells or pericytes. Zonula adherens is formed between vascular endothelial cells and parietal cells, and vascular permeability is controlled through molecular exchange between vascular endothelial cells and parietal cells. The vascular endothelial cells are closely contacted with each other by the aforementioned VE-cadherin and various adhesion molecules such as claudin-5, integrin, connexin and the like mentioned above, and are controlled so that substances and cells will not easily leak out from the inside of the blood vessel to the outside of the blood vessel. Arteries and veins, usually left and right blood vessels, show parallel running performance.

Various abnormalities are observed in blood vessels in tumor. Tumor blood vessels develop disorderly, are promoted in permeability, show meandering and expansion, and show sacciform in part. Blood vessel branching is also disorderly. Vascular endothelial cell itself shows an abnormal form, parietal cell lining is also extremely sparse in the center of the tumor, adhesion to vascular endothelial cell is also weak, and lining of parietal cells is missing in many regions. Therefore, the crosstalk between these cells becomes unstable, and the homeostasis of blood vessels is not maintained. Many of these abnormalities have been reported to be due to excessive VEGF secretion within the tumor.

The main target of the angiogenesis inhibitor is VEGF or a receptor thereof, and VEGF neutralizing antibodies, soluble VEGF receptors, and plural VEGF receptor phosphorylation inhibitors have been clinically applied. Based on the fact that cancer growth accompanies angiogenesis, the development of angiogenesis inhibitors is expected to suppress the angiogenesis in the tumor, cut off the supply of enzymes and nutrients, and suppress the growth of the tumor. This concept of cancer treatment targeting the new blood vessel was proposed by Dr. J. Folkman et al. in the 1970s (non-patent document 2). In preclinical studies using mice, a remarkable antitumor effect was observed with the angiogenesis inhibitor alone, but in humans, the antitumor effect of the angiogenesis inhibitor alone was limited. It has been found that the combined use of an angiogenesis inhibitor and an anticancer drug has an inhibitory effect on tumor enlargement as compared with the anticancer drug alone (non-patent document 3).

Given these findings, Dr. R. Jain proposed the concept that the effect of the combined use of an angiogenesis inhibitor and an anticancer drug is due to the normalization of tumor blood vessels by the angiogenesis inhibitor (non-patent document 4). That is, by shutting off the intracellular signal of the VEGF receptor induced by VEGF, the dissociation between vascular endothelial cells is suppressed, and the vascular permeability promoted by excess VEGF decreases and returns to normal. As a result, from the state of no difference between the tumor tissue pressure and the intravascular pressure, the intravascular pressure becomes higher than the tumor tissue pressure, and the permeability of the anticancer agent from the inside of the blood vessel to the inside of the tumor is recovered, whereby the effect of the anti-cancer drug becomes remarkably high.

With such background, a means for improving vascular permeability in the tumor and inducing the delivery of a drug into the tumor has been considered as one of the effective treatments for cancer. On the other hand, it has been suggested that angiogenesis inhibitors suppress the survival of vascular endothelial cells, induce cell death of vascular endothelial cells and vascular parietal cells interacting therewith, and promote ischemic state in tumors. It has also been suggested that disruption of tumor blood vessels due to inhibition of the VEGF pathway may enhance cancer infiltration and metastatic capacity via hypoxia of cancer tissues. In addition, it has been reported that angiogenesis inhibitors also damage blood vessels in normal tissues and cause serious side effects such as increased blood pressure, pulmonary hemorrhage, nephropathy, and the like. Therefore, the development of a drug that does not regress tumor blood vessels, does not affect normal blood vessels, and normalizes the permeability of tumor blood vessels is expected. Furthermore, the development of a drug that does not affect normal blood vessels and normalizes blood vessels in the pathological site even in diseases associated with vascular abnormalities other than tumors has been desired.

DOCUMENT LIST

Patent Documents

[patent document 1] WO 2015/152412
[patent document 2] WO 2002/029001
[patent document 3] JP-A-2018/177710

Non-Patent Documents

[non-patent document 1] Biochimica et Biophysica Acta, 2013; 1831: p. 33-41
[non-patent document 2] Journal of Experimental Medicine, 1971; 133: p. 275-288
[non-patent document 3] Cancer Res, 2005; 65: p. 671-680
[non-patent document 4] Science, 2005; 307: p. 58-62

SUMMARY OF THE INVENTION

Problems to be Solved by the Invention

The present invention relates to a compound having an agonistic action on LPA4 receptor and a sufficient stability, or a pharmacologically acceptable salt thereof. The compound of the present invention is useful for the prophylaxis, treatment and/or prognosis improvement of diseases associated with angiogenesis abnormalities involving LPA4 receptors, diseases associated with vascular disorders, or pathological conditions thereof.

Means of Solving the Problems

The present inventors have conducted intensive studies in an attempt to solve the above-mentioned problems and found that a compound represented by the following formula (I):

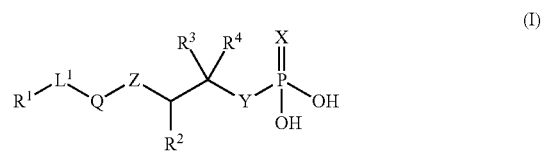

wherein X is oxygen or sulfur,
Y is oxygen, sulfur, NH, $CH_2$, —O—$CH_2$—, or —$CH_2$—O—,
Q is a group represented by the following formula (A-1)

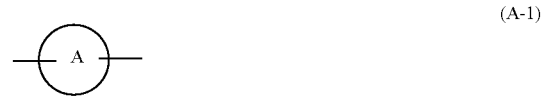

wherein ring A is
an aromatic heterocycle optionally further substituted by a substituent selected independently from the group consisting of halogen;
optionally substituted alkyl;
optionally substituted cycloalkyl; and
optionally substituted alkoxy (wherein the aromatic heterocycle excludes indole and purine),
or
—C(=O)—,
$R^1$ is a group represented by the following formula (A-2)

wherein ring B is cycloalkane or benzene, $R^7$ in the number of n are each independently halogen, cyano, optionally substituted alkyl, optionally substituted cycloalkyl, optionally substituted alkoxy, or an optionally substituted aromatic hydrocarbon group, and n is an integer of 0-5,
$L^1$ is a single bond, NH, oxygen, sulfur, —$R^6$—, —$R^6$O—, —$OR^6$—, —$R^6NH$—, —$NHR^6$—, —$R^6S$—, or —$SR^6$—,
$R^6$ is an optionally substituted alkylene,
(i) when Q is a group represented by the aforementioned formula (A-1),
Z is $CH_2$, oxygen, sulfur, or $NR^5$, and
$R^2$, $R^3$, $R^4$, and $R^5$ are each any of the following (i)-1 to (i)-4;
(i)-1:
$R^2$ is hydrogen or optionally substituted alkyl,
$R^3$ and $R^4$ are each independently hydrogen or optionally substituted alkyl, and
$R^5$ is hydrogen or optionally substituted alkyl, and the substituent of the optionally substituted alkyl is halogen;
hydroxy;
alkoxy;
cycloalkyl optionally substituted by alkyl;
amino optionally substituted by alkyl or acyl;
phenyl optionally substituted 1 or 2 substituents selected independently from the group consisting of
hydroxy, halogen,
alkoxy,
cycloalkyl optionally substituted by alkyl,
amino optionally substituted by alkyl or acyl,
alkyl optionally substituted by hydroxy or alkoxy, and
alkylaminosulfonyl; or
an aromatic heterocyclic group optionally substituted by 1 or 2 substituents selected independently from the group consisting of
hydroxy,
halogen,
alkoxy,
cycloalkyl optionally substituted by alkyl,
amino optionally substituted by alkyl or acyl,
alkyl optionally substituted by hydroxy or alkoxy, and
alkylaminosulfonyl,
or
(i)-2:
$R^2$ is hydrogen or optionally substituted alkyl, and one of $R^3$ and $R^4$ is hydrogen or optionally substituted alkyl, and the other is bonded to $R^5$ to form, together with a carbon atom bonded to $R^3$ and $R^4$ and a nitrogen atom bonded to $R^5$, an optionally substituted cyclic amine,
or
(i)-3:
$R^3$ and $R^4$ are each independently hydrogen or optionally substituted alkyl, and
$R^2$ is bonded to $R^5$ to form, together with a carbon atom bonded to $R^2$ and a nitrogen atom bonded to $R^5$, an optionally substituted cyclic amine,
or
(i)-4:
$R^5$ is hydrogen or optionally substituted alkyl, and the substituent of the optionally substituted alkyl is
halogen;
hydroxy;
alkoxy;
cycloalkyl optionally substituted by alkyl;
amino optionally substituted by alkyl or acyl;
phenyl optionally substituted 1 or 2 substituents selected independently from the group consisting of
hydroxy,
halogen,
alkoxy,
cycloalkyl optionally substituted by alkyl,
amino optionally substituted by alkyl or acyl,
alkyl optionally substituted by hydroxy or alkoxy, and
alkylaminosulfonyl; or
an aromatic heterocyclic group optionally substituted by 1 or 2 substituents selected independently from the group consisting of
hydroxy,
halogen,
alkoxy,
cycloalkyl optionally substituted by alkyl,
amino optionally substituted by alkyl or acyl,
alkyl optionally substituted by hydroxy or alkoxy, and
alkylaminosulfonyl, and
one of $R^3$ and $R^4$ is hydrogen or optionally substituted alkyl, and the other is bonded to $R^2$ to form, together with a carbon atom bonded to $R^3$ and $R^4$ and a carbon atom bonded to $R^2$, an optionally substituted cycloalkane;
or
(ii) when Q is represented by —C(=O)—,
Z is oxygen, sulfur, or $NR^5$, and $R^2$, $R^3$, $R^4$, and $R^5$ are each any of the following (ii)-1 to (ii)-4;
(ii)-1:
$R^2$ is hydrogen or alkyl,
$R^3$ and $R^4$ are each independently hydrogen or optionally substituted alkyl, and
$R^5$ is optionally substituted alkyl, and the substituent of the optionally substituted alkyl is
halogen;
hydroxy;
alkoxy;
cycloalkyl optionally substituted by alkyl;
amino optionally substituted by alkyl or acyl;
phenyl optionally substituted 1 or 2 substituents selected independently from the group consisting of
hydroxy,
halogen,
alkoxy,
cycloalkyl optionally substituted by alkyl,
amino optionally substituted by alkyl or acyl,
alkyl optionally substituted by hydroxy or alkoxy, and
alkylaminosulfonyl; or
an aromatic heterocyclic group optionally substituted by 1 or 2 substituents selected independently from the group consisting of
hydroxy,
halogen,
alkoxy,
cycloalkyl optionally substituted by alkyl,
amino optionally substituted by alkyl or acyl,
alkyl optionally substituted by hydroxy or alkoxy, and
alkylaminosulfonyl,
or
(ii)-2:
$R^2$ is hydrogen, or alkyl, and one of $R^3$ and $R^4$ is hydrogen or optionally substituted alkyl, and the other is bonded to $R^5$ to form, together with a carbon atom bonded to $R^3$ and $R^4$ and a nitrogen atom bonded to $R^5$, an optionally substituted cyclic amine,
or
(ii)-3:
$R^3$ and $R^4$ are each independently hydrogen or optionally substituted alkyl, and
$R^2$ is bonded to $R^5$ to form, together with a carbon atom bonded to $R^2$ and a nitrogen atom bonded to $R^5$, an optionally substituted cyclic amine,
or
(ii)-4:
$R^5$ is optionally substituted alkyl, and the substituent of the optionally substituted alkyl is
halogen;
hydroxy;
alkoxy;
cycloalkyl optionally substituted by alkyl;
amino optionally substituted by alkyl or acyl;
phenyl optionally substituted 1 or 2 substituents selected independently from the group consisting of
hydroxy,
halogen,
alkoxy,
cycloalkyl optionally substituted by alkyl,
amino optionally substituted by alkyl or acyl,
alkyl optionally substituted by hydroxy or alkoxy, and
alkylaminosulfonyl; or
an aromatic heterocyclic group optionally substituted by 1 or 2 substituents selected independently from the group consisting of hydroxy,
halogen,
alkoxy,
cycloalkyl optionally substituted by alkyl,
amino optionally substituted by alkyl or acyl,
alkyl optionally substituted by hydroxy or alkoxy, and
alkylaminosulfonyl, and
one of $R^3$ and $R^4$ is hydrogen or optionally substituted alkyl, and the other is bonded to $R^2$ to form, together with a carbon atom bonded to $R^3$ and $R^4$ and a carbon atom bonded to $R^2$, an optionally substituted cycloalkane (hereinafter sometimes to be abbreviated as "compound (I)"), or a pharmacologically acceptable salt thereof has a selective and superior agonistic action on LPA4 receptor, and completed the present invention.

That is, the present invention provides the following.

[1] A compound represented by the following formula (I)

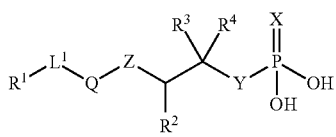

(I)

wherein X is oxygen or sulfur,
Y is oxygen, sulfur, NH, $CH_2$, —O—$CH_2$—, or —$CH_2$—O—,
Q is a group represented by the following formula (A-1)

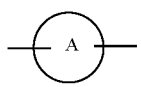

(A-1)

wherein ring A is
an aromatic heterocycle optionally further substituted by a substituent selected from the group consisting of
halogen;
optionally substituted alkyl;
optionally substituted cycloalkyl; and
optionally substituted alkoxy (wherein the aromatic heterocycle excludes indole and purine),
or
—C(=O)—,
$R^1$ is a group represented by the following formula (A-2)

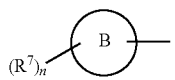

(A-2)

wherein ring B is cycloalkane or benzene,
$R^7$ in the number of n are each independently halogen;
cyano;
optionally substituted alkyl;
optionally substituted cycloalkyl;
optionally substituted alkoxy; or
an optionally substituted aromatic hydrocarbon group, and n is an integer of 0-5,
$L^1$ is a single bond, NH, oxygen, sulfur, —$R^6$—, —$R^6$O—, —O$R^6$—, —$R^6$NH—, —NH$R^6$—, —$R^6$S—, or —S$R^6$—, $R^6$ is an optionally substituted alkylene,
(i) when Q is a group represented by the aforementioned formula (A-1),
Z is $CH_2$, oxygen, sulfur, or $NR^5$, and
$R^2$, $R^3$, $R^4$, and $R^5$ are each any of the following (i)-1 to (i)-4;
(i)-1:
$R^2$ is hydrogen or optionally substituted alkyl,
$R^3$ and $R^4$ are each independently hydrogen or optionally substituted alkyl, and
$R^5$ is hydrogen or optionally substituted alkyl, and the substituent of the optionally substituted alkyl is
halogen;
hydroxy;
alkoxy;
cycloalkyl optionally substituted by alkyl;
amino optionally substituted by alkyl or acyl;
phenyl optionally substituted 1 or 2 substituents selected independently from the group consisting of
hydroxy,
halogen,
alkoxy,
cycloalkyl optionally substituted by alkyl,
amino optionally substituted by alkyl or acyl,
alkyl optionally substituted by hydroxy or alkoxy, and
alkylaminosulfonyl; or
an aromatic heterocyclic group optionally substituted by 1 or 2 substituents selected independently from the group consisting of
hydroxy,
halogen,
alkoxy,
cycloalkyl optionally substituted by alkyl,
amino optionally substituted by alkyl or acyl,
alkyl optionally substituted by hydroxy or alkoxy, and
alkylaminosulfonyl,
or
(i)-2:
$R^2$ is hydrogen or optionally substituted alkyl, and one of $R^3$ and $R^4$ is hydrogen or optionally substituted alkyl, and the other is bonded to $R^5$ to form, together with a carbon atom bonded to $R^3$ and $R^4$ and a nitrogen atom bonded to $R^5$, an optionally substituted cyclic amine,
or
(i)-3:
$R^3$ and $R^4$ are each independently hydrogen or optionally substituted alkyl, and
$R^2$ is bonded to $R^5$ to form, together with a carbon atom bonded to $R^2$ and a nitrogen atom bonded to $R^5$, an optionally substituted cyclic amine,
or
(i)-4:
$R^5$ is hydrogen or optionally substituted alkyl, and the substituent of the optionally substituted alkyl is
halogen;
hydroxy;
alkoxy;
cycloalkyl optionally substituted by alkyl;
amino optionally substituted by alkyl or acyl;
phenyl optionally substituted 1 or 2 substituents selected independently from the group consisting of
hydroxy,
halogen,
alkoxy,
cycloalkyl optionally substituted by alkyl,
amino optionally substituted by alkyl or acyl, alkyl optionally substituted by hydroxy or alkoxy, and
    alkylaminosulfonyl; or
an aromatic heterocyclic group optionally substituted by
    1 or 2 substituents selected independently from the
    group consisting of
    hydroxy,
    halogen,
    alkoxy,
    cycloalkyl optionally substituted by alkyl,
    amino optionally substituted by alkyl or acyl,
    alkyl optionally substituted by hydroxy or alkoxy, and
        alkylaminosulfonyl, and
one of $R^3$ and $R^4$ is hydrogen or optionally substituted
    alkyl, and the other is bonded to $R^2$ to form, together
    with a carbon atom bonded to $R^3$ and $R^4$ and a carbon
    atom bonded to $R^2$, an optionally substituted cycloalkane;
or
(ii) when Q is represented by —C(=O)—,
Z is oxygen, sulfur, or $NR^5$, and
$R^2$, $R^3$, $R^4$, and $R^5$ are each any of the following (ii)-1 to
    (ii)-4;
(ii)-1:
$R^2$ is hydrogen or alkyl,
$R^3$ and $R^4$ are each independently hydrogen or optionally
    substituted alkyl, and
$R^5$ is optionally substituted alkyl, and the substituent of
    the optionally substituted alkyl is
halogen;
hydroxy;
alkoxy;
cycloalkyl optionally substituted by alkyl;
amino optionally substituted by alkyl or acyl;
phenyl optionally substituted 1 or 2 substituents selected
    independently from the group consisting of
    hydroxy,
    halogen,
    alkoxy,
    cycloalkyl optionally substituted by alkyl,
    amino optionally substituted by alkyl or acyl,
    alkyl optionally substituted by hydroxy or alkoxy, and
        alkylaminosulfonyl; or
an aromatic heterocyclic group optionally substituted by
    1 or 2 substituents selected independently from the
    group consisting of
    hydroxy,
    halogen,
    alkoxy,
    cycloalkyl optionally substituted by alkyl,
    amino optionally substituted by alkyl or acyl,
    alkyl optionally substituted by hydroxy or alkoxy, and
        alkylaminosulfonyl,
or
(ii)-2:
$R^2$ is hydrogen, or alkyl, and
one of $R^3$ and $R^4$ is hydrogen or optionally substituted
    alkyl, and the other is bonded to $R^5$ to form, together
    with a carbon atom bonded to $R^3$ and $R^4$ and a nitrogen
    atom bonded to $R^5$, an optionally substituted cyclic
    amine,
or
(ii)-3:
$R^3$ and $R^4$ are each independently hydrogen or optionally
    substituted alkyl, and
$R^2$ is bonded to $R^5$ to form, together with a carbon atom
    bonded to $R^2$ and a nitrogen atom bonded to $R^5$, an
    optionally substituted cyclic amine, or
(ii)-4:
$R^5$ is optionally substituted alkyl, and the substituent of
    the optionally substituted alkyl is
halogen;
hydroxy;
alkoxy;
cycloalkyl optionally substituted by alkyl;
amino optionally substituted by alkyl or acyl;
phenyl optionally substituted 1 or 2 substituents selected
    independently from the group consisting of
    hydroxy,
    halogen,
    alkoxy,
    cycloalkyl optionally substituted by alkyl,
    amino optionally substituted by alkyl or acyl,
    alkyl optionally substituted by hydroxy or alkoxy, and
        alkylaminosulfonyl; or
an aromatic heterocyclic group optionally substituted by
    1 or 2 substituents selected independently from the
    group consisting of
    hydroxy,
    halogen,
    alkoxy,
    cycloalkyl optionally substituted by alkyl,
    amino optionally substituted by alkyl or acyl,
    alkyl optionally substituted by hydroxy or alkoxy, and
        alkylaminosulfonyl, and
one of $R^3$ and $R^4$ is hydrogen or optionally substituted
    alkyl, and the other is bonded to $R^2$ to form, together
    with a carbon atom bonded to $R^3$ and $R^4$ and a carbon
    atom bonded to $R^2$, an optionally substituted cycloalkane,
or a pharmacologically acceptable salt thereof.
[2] The compound of the above-mentioned [1], wherein
Y is oxygen, $CH_2$, —O—$CH_2$—, or —$CH_2$—O—,
$L^1$ is a single bond, —$R^6$—, —$R^6$O—, —$OR^6$—,
    —$R^6$NH—, or —$NHR^6$—,
$R^6$ is alkylene optionally substituted by alkyl,
$R^7$ in the number of n are each independently halogen;
cyano;
alkyl optionally substituted by
    halogen,
    cycloalkyl, or
    phenyl optionally substituted by alkyl;
cycloalkyl optionally substituted by alkyl;
an aromatic hydrocarbon group optionally substituted by
    alkoxy optionally substituted by phenyl or
    alkyl; or
alkoxy optionally substituted by
    phenyl optionally substituted by
        halogen,
        alkyl,
        haloalkoxy or
        phenyl,
    or
    cycloalkyl optionally substituted by alkyl,
n is 1 or 2, and
(i)' when Q is the aforementioned formula (A-1),
ring A is a 5- to 10-membered, monocyclic aromatic
    heterocycle or fused aromatic heterocycle (wherein the
    aromatic heterocycle excludes indole and purine) containing 1 to 3 hetero atoms selected from oxygen,
    nitrogen, and sulfur,
Z is oxygen or $NR^5$, and
$R^2$, $R^3$, $R^4$, and $R^5$ are each any of the following (i)'-1 to
    (i)'-4;

(i)'-1:
$R^2$ is hydrogen, or alkyl optionally substituted by hydroxy or alkoxy,
$R^3$ and $R^4$ are each independently hydrogen, or alkyl optionally substituted by hydroxy or alkoxy, and
$R^5$ is hydrogen or optionally substituted alkyl, and the substituent of the optionally substituted alkyl is
hydroxy;
alkoxy;
amino optionally substituted by alkyl or alkylsulfonyl;
phenyl optionally substituted 1 or 2 substituents selected independently from the group consisting of
hydroxy,
halogen,
alkoxy,
amino optionally substituted by alkyl or alkylsulfonyl,
alkyl optionally substituted by hydroxy or alkoxy, and
alkylaminosulfonyl; or
an aromatic heterocyclic group optionally substituted by 1 or 2 substituents selected independently from the group consisting of
hydroxy,
halogen,
amino optionally substituted by alkyl or alkylsulfonyl,
alkyl optionally substituted by hydroxy or alkoxy, and
alkylaminosulfonyl,
or
(i)'-2:
$R^2$ is hydrogen, or alkyl optionally substituted by hydroxy or alkoxy, and
one of $R^3$ and $R^4$ is hydrogen, or alkyl optionally substituted by hydroxy or alkoxy, and the other is bonded to $R^5$ to form, together with a carbon atom bonded to $R^3$ and $R^4$ and a nitrogen atom bonded to $R^5$, a cyclic amine optionally substituted by
hydroxy,
alkoxy, or
alkyl optionally substituted by hydroxy or alkoxy,
or
(i)'-3:
$R^3$ and $R^4$ are each independently hydrogen, or alkyl optionally substituted by hydroxy or alkoxy, and
$R^2$ is bonded to $R^5$ to form, together with a carbon atom bonded to $R^2$ and a nitrogen atom bonded to $R^5$, a cyclic amine optionally substituted by
hydroxy,
alkoxy, or
alkyl optionally substituted by hydroxy or alkoxy,
or
(i)'-4:
$R^5$ is hydrogen or optionally substituted alkyl, and the substituent of the optionally substituted alkyl is
hydroxy;
alkoxy;
amino optionally substituted by alkyl or alkylsulfonyl;
phenyl optionally substituted 1 or 2 substituents selected independently from the group consisting of
hydroxy,
alkoxy,
amino optionally substituted by alkyl or alkylsulfonyl,
alkyl optionally substituted by hydroxy or alkoxy, and
alkylaminosulfonyl; or
an aromatic heterocyclic group optionally substituted by 1 or 2 substituents selected independently from the group consisting of
hydroxy,
halogen,
alkoxy,
amino optionally substituted by alkyl or alkylsulfonyl,
alkyl optionally substituted by hydroxy or alkoxy, and
alkylaminosulfonyl, and
one of $R^3$ and $R^4$ is hydrogen, or alkyl optionally substituted by hydroxy or alkoxy, and the other is bonded to $R^2$ to form, together with a carbon atom bonded to $R^3$ and $R^4$ and a carbon atom bonded to $R^2$, cycloalkane optionally substituted by
hydroxy,
alkoxy, or
alkyl optionally substituted by hydroxy or alkoxy;
or
(ii)' when Q is —C(=O)—,
Z is $NR^5$, and
$R^2$, $R^3$, $R^4$, and $R^5$ are each any of the following (ii)'-1 to (ii)'-4;
(ii)'-1:
$R^2$ is hydrogen or alkyl,
$R^3$ and $R^4$ are each independently hydrogen, or alkyl optionally substituted by hydroxy or alkoxy, and
$R^5$ is optionally substituted alkyl, and the substituent of the optionally substituted alkyl is
hydroxy;
alkoxy;
amino optionally substituted by alkyl or alkylsulfonyl;
phenyl optionally substituted 1 or 2 substituents selected independently from the group consisting of
hydroxy,
halogen,
alkoxy,
amino optionally substituted by alkyl or alkylsulfonyl,
alkyl optionally substituted by hydroxy or alkoxy, and
alkylaminosulfonyl; or
an aromatic heterocyclic group optionally substituted by 1 or 2 substituents selected independently from the group consisting of
hydroxy,
halogen,
alkoxy,
amino optionally substituted by alkyl or alkylsulfonyl,
alkyl optionally substituted by hydroxy or alkoxy, and
alkylaminosulfonyl,
or
(ii)'-2:
$R^2$ is hydrogen or alkyl, and
one of $R^3$ and $R^4$ is hydrogen, or alkyl optionally substituted by hydroxy or alkoxy, and the other is bonded to $R^5$ to form, together with a carbon atom bonded to $R^3$ and $R^4$ and a nitrogen atom bonded to $R^5$, a cyclic amine optionally substituted by hydroxy,
alkoxy, or
alkyl optionally substituted by hydroxy or alkoxy,
or
(ii)'-3:
$R^3$ and $R^4$ are each independently hydrogen, or alkyl optionally substituted by hydroxy or alkoxy, and
$R^2$ is bonded to $R^5$ to form, together with a carbon atom bonded to $R^2$ and a nitrogen atom bonded to $R^5$, a cyclic amine optionally substituted by
hydroxy,
alkoxy, or
alkyl optionally substituted by hydroxy or alkoxy,
or
(ii)'-4:
$R^5$ is optionally substituted alkyl, and the substituent of the optionally substituted alkyl is hydroxy;
alkoxy;
amino optionally substituted by alkyl or alkylsulfonyl;
phenyl optionally substituted 1 or 2 substituents selected independently from the group consisting of
hydroxy,
halogen,
alkoxy,
amino optionally substituted by alkyl or alkylsulfonyl,
alkyl optionally substituted by hydroxy or alkoxy, and
alkylaminosulfonyl; or
an aromatic heterocyclic group optionally substituted by 1 or 2 substituents selected independently from the group consisting of
hydroxy,
halogen,
alkoxy,
amino optionally substituted by alkyl or alkylsulfonyl,
alkyl optionally substituted by hydroxy or alkoxy, and
alkylaminosulfonyl, and
one of $R^3$ and $R^4$ is hydrogen, or alkyl optionally substituted by hydroxy or alkoxy, and the other is bonded to $R^2$ to form, together with a carbon atom bonded to $R^3$ and $R^4$ and a carbon atom bonded to $R^2$, cycloalkane optionally substituted by
hydroxy,
alkoxy, or
alkyl optionally substituted by hydroxy or alkoxy, or a pharmacologically acceptable salt thereof.

[3] The compound of the above-mentioned [1] or [2], wherein Q is the aforementioned formula (A-1),
ring A is pyrrole, furan, thiophene, imidazole, pyrazole, oxazole, thiazole, triazole, tetrazole, pyridine, pyrazine, pyrimidine, pyridazine, thiazine, triazine, isoindole, indazole, benzoimidazole, benzothiazole, benzofuran, quinoline, isoquinoline, or imidazopyridine,
Y is oxygen or $CH_2$,
Z is oxygen or $NR^5$,
$L^1$ is a single bond,
$R^1$ is the aforementioned formula (A-2),
ring B is benzene,
$R^2$, $R^3$, $R^4$, and $R^5$ are each any of the following (i)'-1, (i)'-2, and (i)'-4;
(i)'-1:
$R^2$ is hydrogen, or alkyl optionally substituted by hydroxy or alkoxy,
$R^3$ and $R^4$ are each independently hydrogen, or alkyl optionally substituted by hydroxy or alkoxy, and
$R^5$ is hydrogen, or optionally substituted alkyl, and the substituent of the optionally substituted alkyl is
hydroxy;
alkoxy;
amino optionally substituted by alkyl or alkylsulfonyl;
phenyl optionally substituted 1 or 2 substituents selected independently from the group consisting of
hydroxy,
halogen,
alkoxy,
amino optionally substituted by alkyl or alkylsulfonyl,
alkyl optionally substituted by hydroxy or alkoxy, and
alkylaminosulfonyl; or
an aromatic heterocyclic group optionally substituted by 1 or 2 substituents selected independently from the group consisting of
hydroxy,
halogen,
alkoxy,
amino optionally substituted by alkyl or alkylsulfonyl,
alkyl optionally substituted by hydroxy or alkoxy, and
alkylaminosulfonyl,
or
(i)'-2:
$R^2$ is hydrogen, or alkyl optionally substituted by hydroxy or alkoxy, and
one of $R^3$ and $R^4$ is hydrogen, or alkyl optionally substituted by hydroxy or alkoxy, and the other is bonded to $R^5$ to form, together with a carbon atom bonded to $R^3$ and $R^4$ and a nitrogen atom bonded to $R^5$, a cyclic amine optionally substituted by
hydroxy,
alkoxy, or
alkyl optionally substituted by hydroxy or alkoxy,
or
(i)'-4:
$R^5$ is hydrogen, or optionally substituted alkyl, and the substituent of the optionally substituted alkyl is
hydroxy;
alkoxy;
amino optionally substituted by alkyl or alkylsulfonyl;
phenyl optionally substituted 1 or 2 substituents selected independently from the group consisting of
hydroxy,
halogen,
alkoxy,
amino optionally substituted by alkyl or alkylsulfonyl,
alkyl optionally substituted by hydroxy or alkoxy, and
alkylaminosulfonyl; or
an aromatic heterocyclic group optionally substituted by 1 or 2 substituents selected independently from the group consisting of
hydroxy,
halogen,
alkoxy,
amino optionally substituted by alkyl or alkylsulfonyl,
alkyl optionally substituted by hydroxy or alkoxy, and
alkylaminosulfonyl, and
one of $R^3$ and $R^4$ is hydrogen, or alkyl optionally substituted by hydroxy or alkoxy, and the other is bonded to $R^2$ to form, together with a carbon atom bonded to $R^3$ and $R^4$ and a carbon atom bonded to $R^2$, cycloalkane optionally substituted by
hydroxy,
alkoxy, or
alkyl optionally substituted by hydroxy or alkoxy;
$R^7$ in the number of n are each independently halogen;
alkyl optionally substituted by
halogen,
cycloalkyl, or
phenyl optionally substituted by alkyl;
cycloalkyl;
phenyl optionally substituted by alkyl; or
alkoxy optionally substituted by
phenyl optionally substituted by
halogen,
alkyl,
haloalkoxy or
phenyl, or
cycloalkyl, and
n is 1 or 2,
or a pharmacologically acceptable salt thereof.
[4] The compound of any of the above-mentioned [1] to [3], wherein
Q is the aforementioned formula (A-1),
ring A is pyridine or pyrimidine, Y is oxygen,
Z is oxygen or $NR^5$,
$L^1$ is a single bond,
$R^1$ is the aforementioned formula (A-2),
ring B is benzene,
$R^2$ is hydrogen, or alkyl optionally substituted by hydroxy or alkoxy,
$R^3$ and $R^4$ are each independently hydrogen, or alkyl optionally substituted by hydroxy or alkoxy,
$R^5$ is hydrogen or alkyl,
$R^7$ is alkoxy optionally substituted by
  phenyl optionally substituted by
    halogen,
    alkyl,
    haloalkoxy or
    phenyl,
  or
  cycloalkyl, and
n is 1,
or a pharmacologically acceptable salt thereof.

[5] The compound of any of the above-mentioned [1] to [3],
wherein
Q is the aforementioned formula (A-1),
ring A is pyridine or pyrimidine,
Y is oxygen,
Z is $NR^5$,
$L^1$ is a single bond,
$R^1$ is the aforementioned formula (A-2),
ring B is benzene,
$R^5$ is hydrogen or alkyl, and
one of $R^3$ and $R^4$ is hydrogen, and the other is bonded to $R^2$ to form cycloalkane together with a carbon atom bonded to $R^3$ and $R^4$ and a carbon atom bonded to $R^2$;
$R^7$ is alkoxy optionally substituted by
  phenyl optionally substituted by
    halogen,
    alkyl,
    haloalkoxy or
    phenyl,
  or
  cycloalkyl, and
n is 1,
or a pharmacologically acceptable salt thereof.

[6] The compound of any of the above-mentioned [1] to [5], wherein
Q is the aforementioned formula (A-1), and
ring A is pyridine,
or a pharmacologically acceptable salt thereof.

[7] The compound of the above-mentioned [1] or [2], wherein
Q is —C(=O)—,
Y is oxygen, $CH_2$, or —O—$CH_2$—*(wherein*denotes a binding position with a phosphorus atom),
Z is $NR^5$,
$L^1$ is a single bond, —$R^6$—, —$R^6$O—, —O$R^6$—, or —$R^6$NH— (wherein  denotes a binding position with Q),
$R^6$ is alkylene optionally substituted by alkyl,
$R^1$ is the aforementioned formula (A-2),
ring B is cycloalkane or benzene,
$R^7$ in the number of n are each independently halogen;
cyano;
alkyl optionally substituted by
  halogen,
  cycloalkyl, or
  phenyl optionally substituted by alkyl;
cycloalkyl optionally substituted by alkyl;
an aromatic hydrocarbon group optionally substituted by
  alkoxy optionally substituted by phenyl, or
  alkyl; or
alkoxy optionally substituted by
  phenyl optionally substituted by
    halogen,
    alkyl,
    haloalkoxy or
    phenyl,
  or
  cycloalkyl optionally substituted by alkyl,
n is 1 or 2, and
$R^2$, $R^3$, $R^4$, and $R^5$ are each the following (ii)'-1 or (ii)'-2;
(ii)'-1:
$R^2$ is hydrogen or alkyl,
$R^3$ and $R^4$ are each independently hydrogen, or alkyl optionally substituted by hydroxy or alkoxy, and
$R^5$ is optionally substituted alkyl, and the substituent of the optionally substituted alkyl is
hydroxy;
alkoxy;
amino optionally substituted by alkyl or alkylsulfonyl;
phenyl optionally substituted 1 or 2 substituents selected independently from the group consisting of
  hydroxy,
  halogen,
  alkoxy,
  amino optionally substituted by alkyl or alkylsulfonyl,
  alkyl optionally substituted by hydroxy or alkoxy,
  and alkylaminosulfonyl; or
an aromatic heterocyclic group optionally substituted by 1 or 2 substituents selected independently from the group consisting of
  hydroxy,
  halogen,
  alkoxy,
  amino optionally substituted by alkyl or alkylsulfonyl,
  alkyl optionally substituted by hydroxy or alkoxy, and
  alkylaminosulfonyl,
or
(ii)'-2:
$R^2$ is hydrogen or alkyl, and
one of $R^3$ and $R^4$ is hydrogen, or alkyl optionally substituted by hydroxy or alkoxy, and the other is bonded to $R^5$ to form, together with a carbon atom bonded to $R^3$ and $R^4$ and a nitrogen atom bonded to $R^5$, a cyclic amine optionally substituted by hydroxy,
alkoxy, or
alkyl optionally substituted by hydroxy or alkoxy, or a pharmacologically acceptable salt thereof.

[8] The compound of the above-mentioned [1], [2] or [7], wherein
Q is —C(=O)—,
X is oxygen,
Y is oxygen,
Z is $NR^5$,
$L^1$ is a single bond, —$R^6$—, or —$R^6$O—* (wherein*denotes a binding position with Q),
$R^6$ is alkylene,
$R^7$ in the number of n are each independently
halogen;
alkyl optionally substituted by
  halogen,
  cycloalkyl, or
  phenyl optionally substituted by alkyl;

cycloalkyl;
phenyl optionally substituted by alkyl; or
alkoxy optionally substituted by
　　phenyl optionally substituted by
　　　　halogen,
　　　　alkyl,
　　　　haloalkoxy or
　　　　phenyl, or
　　cycloalkyl,
n is 1 or 2, and
$R^2$, $R^3$, $R^4$, and $R^5$ are each the following (ii)"-1 or (ii)"-2;
(ii)"-1:
$R^2$ is hydrogen,
$R^3$ and $R^4$ are each independently hydrogen or alkyl, and
$R^5$ is
alkyl optionally substituted by
hydroxy;
alkoxy;
amino optionally substituted by alkyl or alkylsulfonyl;
phenyl optionally substituted 1 or 2 substituents selected
　　independently from the group consisting of
　　hydroxy,
　　halogen,
　　alkoxy,
　　amino optionally substituted by alkyl or alkylsulfonyl,
　　alkyl optionally substituted by hydroxy or alkoxy, and
　　alkylaminosulfonyl; or
a 5-membered or 6-membered monocyclic aromatic heterocyclic group optionally substituted 1 or 2 substituents selected independently from the group consisting of
　　hydroxy,
　　halogen,
　　alkoxy,
　　amino optionally substituted by alkyl or alkylsulfonyl,
　　alkyl optionally substituted by hydroxy or alkoxy, and
　　alkylaminosulfonyl,
or
(ii)"-2:
$R^2$ is hydrogen or alkyl, and
one of $R^3$ and $R^4$ is hydrogen,
and the other is bonded to $R^5$ to form, together with a carbon atom bonded to $R^3$ and $R^4$ and a nitrogen atom bonded to $R^5$, azetidine, pyrrolidine or piperidine each optionally substituted by
hydroxy,
alkoxy, or
alkyl optionally substituted by hydroxy or alkoxy, or a pharmacologically acceptable salt thereof.
[9] The compound of any of the above-mentioned [1], [2], [7] and [8], wherein
Q is —C(=O)—,
X is oxygen,
Y is oxygen,
Z is $NR^5$,
$L^1$ is a single bond, —$R^6$—, or —$R^6$O—***(wherein denotes a binding position with Q),
$R^6$ is alkylene,
$R^2$ is hydrogen,
$R^3$ and $R^4$ are each independently hydrogen or alkyl, and
$R^5$ is alkyl optionally substituted by
phenyl optionally substituted 1 or 2 substituents selected independently from the group consisting of
　　hydroxy,
　　halogen,
　　alkoxy,
　　amino optionally substituted by alkyl or alkylsulfonyl,
　　alkyl optionally substituted by hydroxy or alkoxy, and
　　alkylaminosulfonyl; or
pyridyl, thiazolyl, isothiazolyl or pyridazinyl, each optionally substituted by 1 or 2 substituents selected independently from the group consisting of
　　hydroxy,
　　halogen,
　　alkoxy,
　　amino optionally substituted by alkyl or alkylsulfonyl,
　　alkyl optionally substituted by hydroxy or alkoxy, and
　　alkylaminosulfonyl,
or a pharmacologically acceptable salt thereof.
[10] The compound of any of the above-mentioned [1], [2], [7] and [8], wherein
Q is —C(=O)—,
X is oxygen,
Y is oxygen,
Z is $NR^5$,
$L^1$ is a single bond, —$R^6$—, or —$R^6$O—* (wherein*denotes a binding position with Q),
$R^6$ is alkylene,
$R^2$ is hydrogen, and
one of $R^3$ and $R^4$ is hydrogen, and the other is bonded to $R^5$ to form, together with a carbon atom bonded to $R^3$ and $R^4$, and a nitrogen atom bonded to $R^5$, azetidine optionally substituted by
hydroxy,
alkoxy, or
alkyl optionally substituted by hydroxy or alkoxy, or a pharmacologically acceptable salt thereof.
[11] The compound of any of the above-mentioned [1], [2], and [7] to [10], wherein
Q is —C(=O)—, and
ring B is benzene, or a pharmacologically acceptable salt thereof.
[12] The compound of any of the above-mentioned [1] to [11], wherein
the compound of the formula (I) is any of the following a to m, or a pharmacologically acceptable salt thereof:
　　a. 1-[9-(4-ethylphenyl)nonanoyl]azetidin-3-yl dihydrogen phosphate,
　　b. 1-{4-[4-(octyloxy)phenyl]butanoyl}azetidin-3-yl dihydrogen phosphate,
　　c. 1-[8-(3-octylphenyl)octanoyl]azetidin-3-yl dihydrogen phosphate,
　　d. 1-[9-(4-butylphenyl)nonanoyl]azetidin-3-yl dihydrogen phosphate,
　　e. 1-[9-(biphenyl-4-yl)nonanoyl]azetidin-3-yl dihydrogen phosphate,
　　f. 1-[9-(4-tert-butylphenyl)nonanoyl]azetidin-3-yl dihydrogen phosphate,
　　g. 1-[9-(4-cyclopropylphenyl)nonanoyl]azetidin-3-yl dihydrogen phosphate,
　　h. 1-[9-(4-cyclohexylphenyl)nonanoyl]azetidin-3-yl dihydrogen phosphate,
　　i. 2-{[9-(4-propylphenyl)nonanoyl](1,3-thiazol-5-ylmethyl)amino}ethyl dihydrogen phosphate,
　　j. 1-[9-(4-hexylphenyl)nonanoyl]azetidin-3-yl dihydrogen phosphate,
　　k. (2R)-1-({4-[3-(undecyloxy)phenyl]pyridin-2-yl}amino)propan-2-yl dihydrogen phosphate,
　　l. O-[(2R)-1-({4-[3-(undecyloxy)phenyl]pyridin-2-yl}amino)propan-2-yl] dihydrogen phosphorothioate, and
　　m. (1S,2R)-2-({4-[3-(undecyloxy)phenyl]pyridin-2-yl}amino)cyclopentyl dihydrogen phosphate.

[13] A pharmaceutical composition comprising the compound of any of the above-mentioned [1] to [12] or a pharmacologically acceptable salt thereof, and a pharmacologically acceptable carrier.

[14] A pharmaceutical composition of the above-mentioned [13] for use in the treatment and/or prophylaxis of a disease associated with angiogenesis abnormality, or a disease associated with a vascular disorder.

[15] The pharmaceutical composition of the above-mentioned [14], wherein the disease associated with angiogenesis abnormality, or the disease associated with a vascular disorder is solid cancer, pressure ulcer, diabetic necrosis, diabetic nephropathy, diabetic retinopathy, acute nephropathy, cerebral infarction, age-related macular degeneration, rheumatoid arthritis, scleroderma, psoriasis, systemic lupus erythematosus, lung fibrosis, arteriosclerosis obliterans, arteriosclerosis, angina pectoris, myocardial infarction, Buerger disease, brain edema due to infectious disease, hemorrhage due to hemorrhagic virus (Ebola, dengue), or acute respiratory distress syndrome.

[16] The pharmaceutical composition of the above-mentioned [13] for use in combination with other drug.

[17] The pharmaceutical composition of the above-mentioned [16], wherein the other drug is a drug for treating a disease associated with angiogenesis abnormality, or a disease associated with a vascular disorder.

[18] The pharmaceutical composition of the above-mentioned [16], wherein the other drug is an anticancer drug.

[19] The pharmaceutical composition of the above-mentioned [18], wherein the anticancer drug is at least one kind of drug selected from the group consisting of a chemotherapeutic agent, an immunotherapeutic agent, and a hormonal therapeutic agent.

[20] The pharmaceutical composition of any of the above-mentioned [16] to [19], wherein the compound of any of the above-mentioned [1] to [12] or a pharmacologically acceptable salt thereof, and the other drug are separately administered.

[21] The pharmaceutical composition of any of the above-mentioned [16] to [19], wherein the compound of any of the above-mentioned [1] to [12] or a pharmacologically acceptable salt thereof, and the other drug are simultaneously or sequentially administered.

[22] The pharmaceutical composition of any of the above-mentioned [16]-[21], wherein the disease associated with angiogenesis abnormality, or the disease associated with a vascular disorder is solid cancer, pressure ulcer, diabetic necrosis, diabetic nephropathy, diabetic retinopathy, acute nephropathy, cerebral infarction, age-related macular degeneration, rheumatoid arthritis, scleroderma, psoriasis, systemic lupus erythematosus, lung fibrosis, arteriosclerosis obliterans, arteriosclerosis, angina pectoris, myocardial infarction, Buerger disease, brain edema due to infectious disease, hemorrhage due to hemorrhagic virus (Ebola, dengue), or acute respiratory distress syndrome.

[23] The pharmaceutical composition of the above-mentioned [18] for use in enhancing a therapeutic effect of other drug by a combination use with the other drug.

[24] The pharmaceutical composition of the above-mentioned [23], wherein the other drug is a drug for treating a disease associated with angiogenesis abnormality or a disease associated with a vascular disorder, or a drug to be administered into blood vessels.

[25] The pharmaceutical composition of the above-mentioned [23], wherein the other drug is an anticancer drug.

[26] A LPA4 receptor agonist comprising the compound of any of the above-mentioned [1] to [12] or a pharmacologically acceptable salt thereof.

[27] A drug delivery promoter comprising the compound of any of the above-mentioned [1] to [12] or a pharmacologically acceptable salt thereof, to promote delivery to a disease site of a disease associated with angiogenesis abnormality, or a disease associated with a vascular disorder.

[28] A medicament comprising the compound of any of the above-mentioned [1] to [12] or a pharmacologically acceptable salt thereof, and at least one kind of other drug in combination for the prophylaxis or treatment of a disease associated with angiogenesis abnormality, or a disease associated with a vascular disorder.

[29] The medicament of the above-mentioned [28], wherein the compound of any of the above-mentioned [1] to [12] or a pharmacologically acceptable salt thereof, and at least one kind of other drug are separately administered.

[30] The medicament of the above-mentioned [28], wherein the compound of any of the above-mentioned [1] to [12] or a pharmacologically acceptable salt thereof, and at least one kind of other drug are simultaneously or sequentially administered.

[31] The medicament of the above-mentioned [28], wherein the medicament is a combination agent.

[32] The medicament of any of the above-mentioned [28] to [31], wherein the other drug is a drug for treating a disease associated with angiogenesis abnormality or a disease associated with a vascular disorder, or a drug to be administered into blood vessels.

[33] The medicament of any of the above-mentioned [28] to [31], wherein the other drug is an anticancer drug.

[34] The medicament of any of the above-mentioned [28] to [33], wherein the disease associated with angiogenesis abnormality, or the disease associated with a vascular disorder is solid cancer, pressure ulcer, diabetic necrosis, diabetic nephropathy, diabetic retinopathy, acute nephropathy, cerebral infarction, age-related macular degeneration, rheumatoid arthritis, scleroderma, psoriasis, systemic lupus erythematosus, lung fibrosis, arteriosclerosis obliterans, arteriosclerosis, angina pectoris, myocardial infarction, Buerger disease, brain edema due to infectious disease, hemorrhage due to hemorrhagic virus (Ebola, dengue), or acute respiratory distress syndrome.

[35] A method for preventing or treating a disease associated with angiogenesis abnormality, or a disease associated with a vascular disorder in a mammal, comprising administering an effective amount of the compound of any of the above-mentioned [1] to [12] or a pharmacologically acceptable salt thereof to the mammal.

[36] The method of the above-mentioned [35], wherein the disease associated with angiogenesis abnormality, or the disease associated with a vascular disorder is solid cancer, pressure ulcer, diabetic necrosis, diabetic nephropathy, diabetic retinopathy, acute nephropathy, cerebral infarction, age-related macular degeneration, rheumatoid arthritis, scleroderma, psoriasis, systemic lupus erythematosus, lung fibrosis, arteriosclerosis obliterans, arteriosclerosis, angina pectoris, myocardial infarction, Buerger disease, brain edema due to infectious disease, hemorrhage due to hemorrhagic virus (Ebola, dengue), or acute respiratory distress syndrome.

[37] Use of the compound of any of the above-mentioned [1] to [12] or a pharmacologically acceptable salt thereof in the production of a therapeutic agent or a prophylactic agent for a disease associated with angiogenesis abnormality, or a disease associated with a vascular disorder.

[38] The use of the above-mentioned [37], wherein the disease associated with angiogenesis abnormality, or the disease associated with a vascular disorder is solid cancer, pressure ulcer, diabetic necrosis, diabetic nephropathy, diabetic retinopathy, acute nephropathy, cerebral infarction, age-related macular degeneration, rheumatoid arthritis, scleroderma, psoriasis, systemic lupus erythematosus, lung fibrosis, arteriosclerosis obliterans, arteriosclerosis, angina pectoris, myocardial infarction, Buerger disease, brain edema due to infectious disease, hemorrhage due to hemorrhagic virus (Ebola, dengue), or acute respiratory distress syndrome.

[39] The compound of any of the above-mentioned [1] to [12] or a pharmacologically acceptable salt thereof for use in the prophylaxis or treatment of a disease associated with angiogenesis abnormality, or a disease associated with a vascular disorder.

[40] The compound of the above-mentioned [39] or a pharmacologically acceptable salt thereof, wherein the disease associated with angiogenesis abnormality, or the disease associated with a vascular disorder is solid cancer, pressure ulcer, diabetic necrosis, diabetic nephropathy, diabetic retinopathy, acute nephropathy, cerebral infarction, age-related macular degeneration, rheumatoid arthritis, scleroderma, psoriasis, systemic lupus erythematosus, lung fibrosis, arteriosclerosis obliterans, arteriosclerosis, angina pectoris, myocardial infarction, Buerger disease, brain edema due to infectious disease, hemorrhage due to hemorrhagic virus (Ebola, dengue), or acute respiratory distress syndrome.

[41] The pharmaceutical composition of the above-mentioned [13] for use in the treatment and/or prophylaxis of a disease or symptom involving LPA4 receptor.

[42] The pharmaceutical composition of the above-mentioned [41], wherein the disease or symptom involving LPA4 receptor is solid cancer, pressure ulcer, diabetic necrosis, diabetic nephropathy, diabetic retinopathy, acute nephropathy, cerebral infarction, age-related macular degeneration, rheumatoid arthritis, scleroderma, psoriasis, systemic lupus erythematosus, lung fibrosis, arteriosclerosis obliterans, arteriosclerosis, angina pectoris, myocardial infarction, Buerger disease, brain edema due to infectious disease, hemorrhage due to hemorrhagic virus (Ebola, dengue), or acute respiratory distress syndrome.

[43] A method for producing the compound of any of the above-mentioned [1] to [12] or a pharmacologically acceptable salt thereof.

[44] A prodrug of the compound of any of the above-mentioned [1] to [12] or a pharmacologically acceptable salt thereof.

Effect of the Invention

The compound (I) of the present invention or a pharmacologically acceptable salt thereof has a selective and superior agonistic activity for LPA4 receptor. Therefore, a pharmaceutical composition containing the compound (I) of the present invention or a pharmacologically acceptable salt thereof is useful for the treatment and/or prophylaxis of a disease associated with angiogenesis abnormality, or a disease associated with a vascular disorder. Examples of the diseases include solid cancer, pressure ulcer, diabetic necrosis, diabetic nephropathy, diabetic retinopathy, acute nephropathy, cerebral infarction, age-related macular degeneration, rheumatoid arthritis, scleroderma, psoriasis, systemic lupus erythematosus, lung fibrosis, arteriosclerosis obliterans, arteriosclerosis, angina pectoris, myocardial infarction, Buerger disease, brain edema due to infectious disease, hemorrhage due to hemorrhagic virus (Ebola, dengue), acute respiratory distress syndrome and the like.

It is known that disease sites accompanying angiogenesis abnormality show excessively promoted vascular permeability as well as poor blood flow. In such diseases, when drugs containing active ingredients other than the compounds of the present invention (which may be referred to herein as "other drugs") are administered, there has been a known problem that said other drugs have difficulty reaching the disease sites via the blood flow due to the above reason. For example, it is known that in solid cancer, the tumor interstitial fluid pressure is increased, the difference in osmotic pressure between in the tumor stroma and in the blood vessel is eliminated, and movement of substances from the lumen of blood vessel into a tumor tissue is difficult. Therefore, when a drug with an anticancer action (sometimes referred to herein as "anticancer drug") is administered, it is difficult for said drug to reach the tumor tissue. The compound (I) of the present invention or a pharmacologically acceptable salt thereof that activates lysophospholipid receptors is a drug delivery promoter for promoting delivery to the disease sites of diseases associated with angiogenesis abnormality, or diseases associated with vascular disorders, and can normalize abnormal blood vessels at disease sites associated with angiogenesis abnormality and normalize vascular permeability. The compound (I) of the present invention, or a pharmacologically acceptable salt thereof, when administered together with other drugs (in combination with other drugs) to patients with the disease associated with angiogenesis abnormality, or the disease associated with a vascular disorder, can normalize abnormal blood vessels and a vascular permeability. Thus, the efficiency of delivery of the other drugs used in combination to the disease site can be remarkably improved. Hence, the drug delivery promoter of the present invention is useful for the treatment or prophylaxis of diseases associated with angiogenesis abnormality, or diseases associated with vascular disorders when used in combination with one or more kinds of drugs (therapeutic agents) for diseases associated with angiogenesis abnormality.

BRIEF DESCRIPTION OF THE DRAWINGS

FIG. 5 shows the perfusion rate of human tumor blood vessels in the compound (I) of the present invention (ammonium salt of Example Compound 84)-treated group (1 mg/kg or 3 mg/kg dose) and the control group (solvent-treated group) on day 19 after transplantation of human tumor colon tissue into mouse.

DESCRIPTION OF EMBODIMENTS

Figure 1:
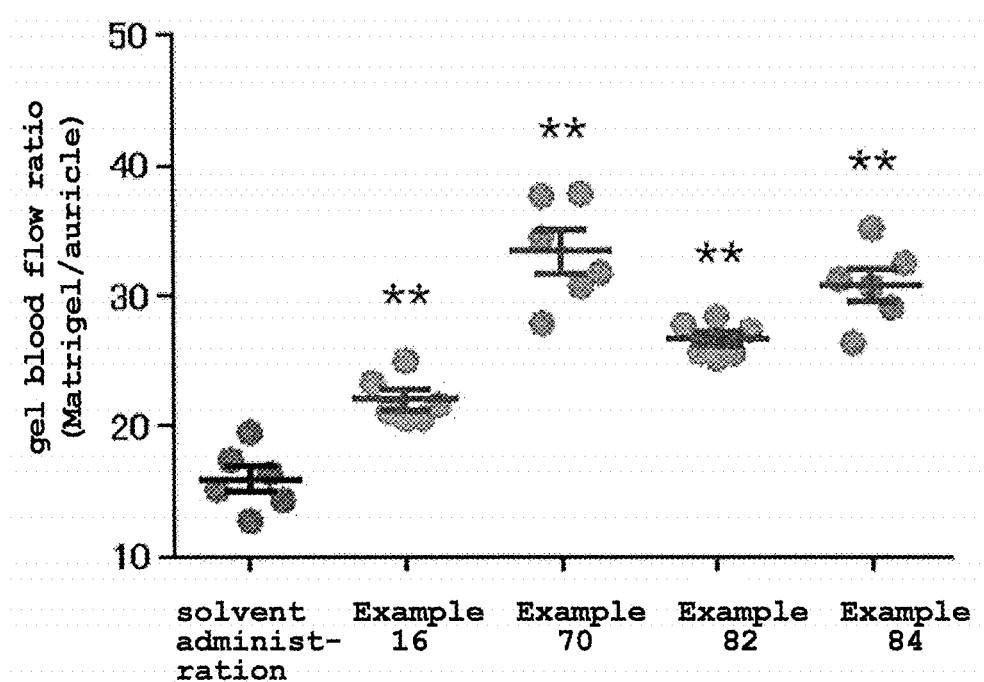
FIG. 1 shows the in-gel blood flow ratio of a group administered with the compound (I) of the present invention and a solvent administration group after administration of the compound (I) of the present invention (Example compounds 16, 70, 82, and 84) or solvent (control) into the tail vein of mice after 7 days from the transplantation of Matrigel.

The definitions of the terms and respective symbols used in the present specification are explained below.

In the present specification, alkyl refers to a straight chain or branched chain saturated hydrocarbon group having 1-15 carbon atoms ($C_{1-15}$). Among them, a group having 1-11 carbon atoms ($C_{1-11}$) is preferable, a group having 1-6 carbon atoms ($C_{1-6}$) is more preferable, and a group having 1-4 carbon atoms ($C_{1-4}$) is further preferable. Specifically, methyl, ethyl, n-propyl, i-propyl, n-butyl, tert-butyl, i-amyl, n-pentyl, n-hexyl and the like can be mentioned, and methyl, ethyl, n-propyl, i-propyl, n-butyl, or tert-butyl is preferred.

In the present specification, alkylene refers to a divalent group obtained by removing one hydrogen atom from the aforementioned alkyl. Specifically, methylene, ethylene, propylene, trimethylene, butylene, pentylene, hexylene, heptylene, octylene, nonylene, decylene and the like can be mentioned. Of these, methylene, ethylene, propylene, butylene, or pentylene is preferable, and methylene, ethylene, or trimethylene is more preferable.

In the present specification, cycloalkyl refers to a monocyclic saturated hydrocarbon group having 3-8 carbon atoms ($C_{3-8}$). Of these, a group having 3-6 carbon atoms ($C_{3-6}$) is preferable. Specifically, cyclopropyl, cyclobutyl, cyclopentyl, cyclohexyl, cycloheptyl, cyclooctyl and the like can be mentioned. Of these, cyclopropyl, cyclobutyl, cyclopentyl, or cyclohexyl is preferable.

In the present specification, cycloalkane refers to a monocyclic saturated hydrocarbocycle having 3-8 carbon atoms ($C_{3-8}$). Of these, a saturated hydrocarbocycle having 3-6 carbon atoms ($C_{3-6}$) is preferable. Specifically, cyclopropane, cyclobutane, cyclopentane, cyclohexane, cycloheptane, cyclooctane and the like can be mentioned, and cyclopropane, cyclobutane, cyclopentane, or cyclohexane is particularly preferable.

In the present specification, alkoxy refers to a monovalent group in which the aforementioned alkyl is bonded to oxygen (—O—), and straight chain or branched chain alkoxy having 1-15 carbon atoms ($C_{1-15}$) can be mentioned. Of these, alkoxy having 1-11 carbon atoms ($C_{1-11}$) is preferable, and alkoxy having 1-4 carbon atoms ($C_{1-4}$) is more preferable. Specifically, methoxy, ethoxy, n-propoxy, i-propoxy, n-butoxy, tert-butoxy, pentyloxy, hexyloxy, heptyloxy, octyloxy, nonyloxy, decyloxy, undecyloxy and the like can be mentioned.

In the present specification, alkylaminosulfonyl refers to a monovalent group in which an amino bonded to one or two of the aforementioned alkyl is bonded to sulfonyl (—SO$_2$—). Specifically, methylaminosulfonyl, dimethylaminosulfonyl, ethylaminosulfonyl, diethylaminosulfonyl and the like can be mentioned, and methylaminosulfonyl is preferred.

In the present specification, heterocycle (group) means a 3- to 14-membered (monocyclic, bicyclic or tricyclic) heterocycle (group) containing at least one hetero atom selected from the group consisting of an oxygen atom, a nitrogen atom and a sulfur atom, and an aromatic heterocycle (group) and a non-aromatic heterocyclic (group) can be mentioned.

In the present specification, the aromatic heterocycle (group) means a 5- to 14-membered monocyclic aromatic heterocycle (group) and a fused aromatic heterocycle (group) containing at least one hetero atom selected from the group consisting of oxygen atom, nitrogen atom and sulfur atom. The fused aromatic heterocycle (group) in the present specification is bicyclic or tricyclic and optionally has a hetero atom on a plurality of rings. As the monocyclic aromatic heterocycle (group), 5- or 6-membered ring (group) can be mentioned, and as the fused aromatic heterocycle (group), a ring (group) in which each ring constituting the ring (group) is a 5- or 6-membered ring can be mentioned. Examples of the monovalent group of the aromatic heterocycle (group) include 5- or 6-membered monocyclic aromatic heterocyclic groups such as furyl, thienyl, pyrrolyl, imidazolyl, pyrazolyl, oxazolyl, isoxazolyl, thiazolyl, triazolyl, tetrazolyl, thiadiazolyl, oxadiazolyl, pyridyl, pyrazinyl, pyridazinyl, pyrimidinyl and the like; 8- to 14-membered fused aromatic heterocyclic groups such as isoindolyl, indazolyl, benzofuranyl, benzothiophenyl, benzoimidazolyl (e.g., 5-benzoimidazolyl), benzoxazolyl, benzothiazolyl, quinolyl, isoquinolyl, benzoxazinyl, benzothiazinyl, furo[2,3-b]pyridyl, thieno[2,3-b]pyridyl, naphthyridinyl, imidazopyridyl, oxazolopyridyl, thiazolopyridyl, quinoxalinyl, quinazolinyl, pyridopyrazinyl, carbazolyl, dibenzothiophenyl and the like; and the like.

In the present specification, the non-aromatic heterocycle (group) means a 3- to 14-membered monocyclic non-aromatic heterocycle (group) and a fused non-aromatic heterocycle (group) containing at least one hetero atom selected from the group consisting of oxygen atom, nitrogen atom and sulfur atom. The fused non-aromatic heterocycle (group) in the present specification is bicyclic or tricyclic (preferably bicyclic) and optionally has hetero atoms on both rings. As the monocyclic non-aromatic heterocycle (group), 3- to 9-membered ring group (preferably 3- to 7-membered ring group) can be mentioned, and as the fused non-aromatic heterocycle (group), a ring (group) in which each ring constituting the ring (group) is a 5- or 6-membered ring can be mentioned. Examples of the monovalent group of the non-aromatic heterocycle (group) include 3- to 9-membered monocyclic non-aromatic heterocyclic groups such as oxetanyl (e.g., 3-oxetanyl), tetrahydrofuryl (e.g., tetrahydrofuran-3-yl), dioxolyl (e.g., 1,3-dioxol-4-yl), dioxolanyl (e.g., 1,3-dioxolan-4-yl), oxazolidinyl, imidazolinyl (e.g., 1-imidazolinyl, 2-imidazolinyl, 4-imidazolinyl), aziridinyl (e.g., 1-aziridinyl, 2-aziridinyl), azetidinyl (e.g., 1-azetidinyl, 2-azetidinyl, 3-azetidinyl), pyrrolidinyl (e.g., 1-pyrrolidinyl, 2-pyrrolidinyl, 3-pyrrolidinyl), piperidyl (e.g., 1-piperidyl, 2-piperidyl, 3-piperidyl, 4-piperidyl), dioxanyl (e.g., 1,4-dioxan-2-yl), azepanyl (e.g., 1-azepanyl, 2-azepanyl, 3-azepanyl, 4-azepanyl), azocanyl (e.g., 1-azocanyl, 2-azocanyl, 3-azocanyl, 4-azocanyl), azonanyl (e.g., 1-azonanyl, 2-azonanyl, 3-azonanyl, 4-azonanyl, 5-azonanyl), piperazinyl (e.g., piperazin-1-yl, piperazin-2-yl), diazepinyl (e.g., 1,4-diazepin-1-yl, 1,4-diazepin-2-yl, 1,4-diazepin-5-yl, 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, 1,5-diazocan-3-yl), tetrahydropyranyl (e.g., tetrahydropyran-4-yl, tetrahydropyran-2-yl), morpholinyl (e.g., 4-morpholinyl), thiomorpholinyl (e.g., 4-thiomorpholinyl), dihydrofuryl, dihydropyranyl and the like; 8- to 14-membered fused non-aromatic heterocyclic groups such as benzopyranyl, dihydroquinolyl, dihydroisoquinolyl (e.g., 3,4-dihydroisoquinolin-2-yl), dihydroindolyl (e.g., 2,3-dihydroindol-5-yl, 2,3-dihydroindol-1-yl), dihydroisoindolyl (e.g., 2,3-dihydroisoindol-2-yl) and the like; and the like.

In the present specification, the cyclic amine means a secondary saturated or partially unsaturated nitrogen-containing non-aromatic heterocycle. As the cyclic amine, a 3- to 7-membered (preferably 4- to 6-membered) monocyclic nitrogen-containing non-aromatic heterocycle and nitrogen-containing fused non-aromatic heterocycle having, as a ring-constituting atom other than nitrogen atom of the amino group, a hetero atom selected from oxygen atom, sulfur atom and nitrogen atom besides carbon atom can be mentioned. Specific examples of the cyclic amine include 3- to 7-membered monocyclic nitrogen-containing non-aromatic heterocycles such as aziridine, azetidine, pyrrolidine, pyrroline, piperidine, azepane, morpholine, thiomorpholine, piperazine, oxazolidine, thiazolidine, imidazolidine, oxazoline, thiazoline, imidazoline, pyrazolidine, pyrazoline, dihydropyridine, tetrahydropyridine, tetrahydropyrimidine, dihydrotriazoline, tetrahydrotriazoline and the like, and secondary cyclic amine such as a nitrogen-containing fused non-aromatic heterocycle in which the monocyclic nitrogen-containing non-aromatic heterocycle is fused to one or two carbocycles (e.g., benzene ring, etc.) or a heterocycle. Of these, azetidine, pyrrolidine, or piperidine is preferable.

In the present specification, halogen or halo refers to a fluorine atom, a chlorine atom, a bromine atom or an iodine atom. Preferably, it is a fluorine atom, a chlorine atom, or a bromine atom.

In the present specification, haloalkyl means alkyl having one or more halogens (in this case, alkyl and halogen are as defined above).

In the present specification, haloalkoxy means alkoxy having one or more halogens (in this case, alkoxy and halogen are as defined above).

In the present specification, the aromatic hydrocarbon (group) refers to an aromatic hydrocarbon (group) having 6-14 carbon atoms. It is preferably a monocyclic aromatic hydrocarbon (group) or a fused aromatic hydrocarbon (group). Specifically, as the monocyclic aromatic hydrocarbon (group), benzene (phenyl group) can be mentioned. As the fused aromatic hydrocarbon (group), naphthalene (1-naphthyl group, 2-naphthyl group), anthracene (anthryl group), phenanthrene (phenanthryl group) and the like can be mentioned. Of these, benzene is preferable.

In the present specification, as the optionally substituted alkyl, unless particularly indicated, alkyl optionally substituted by 1 to 3 groups independently selected from
  halogen;
  cyano;
  hydroxy;
  optionally substituted alkoxy;
  optionally substituted amino;
  optionally substituted cycloalkyl;
  optionally substituted aromatic hydrocarbon group ($C_{6-14}$ aromatic hydrocarbon group); and
  optionally substituted aromatic heterocyclic group can be mentioned.

Of these, alkyl optionally substituted by 1 or 2 groups independently selected from
  halogen;
  hydroxy;
  alkoxy;
  cycloalkyl optionally substituted by alkyl;
  amino optionally substituted by alkyl or acyl;
  phenyl optionally substituted 1 or 2 substituents selected independently from the group consisting of
    hydroxy,
    halogen,
    alkoxy,
    cycloalkyl optionally substituted by alkyl,
    amino optionally substituted by alkyl or acyl,
    alkyl optionally substituted by hydroxy or alkoxy, and
    alkylaminosulfonyl; or
  an aromatic heterocyclic group optionally substituted by 1 or 2 substituents selected independently from
    hydroxy,
    halogen,
    alkoxy,
    cycloalkyl optionally substituted by alkyl,
    amino optionally substituted by alkyl or acyl,
    alkyl optionally substituted by hydroxy or alkoxy, and
    alkylaminosulfonyl
is preferred, alkyl optionally substituted by 1 or 2 groups independently selected from
  hydroxy;
  alkoxy;
  amino optionally substituted by alkyl or alkylsulfonyl;
  phenyl optionally substituted 1 or 2 substituents selected independently from the group consisting of
    hydroxy,
    halogen,
    alkoxy,
    amino optionally substituted by alkyl or alkylsulfonyl,
    alkyl optionally substituted by hydroxy or alkoxy, and
    alkylaminosulfonyl; or
  an aromatic heterocyclic group optionally substituted by 1 or 2 substituents selected independently from the group consisting of
    hydroxy,
    halogen,
    alkoxy,
    amino optionally substituted by alkyl or alkylsulfonyl,
    alkyl optionally substituted by hydroxy or alkoxy, and
    alkylaminosulfonyl
is more preferred, alkyl optionally substituted by 1 or 2 groups independently selected from
  hydroxy;
  alkoxy;
  amino optionally substituted by alkyl or alkylsulfonyl;
  phenyl optionally substituted by 1 or 2 substituents selected independently from the group consisting of
    hydroxy,
    halogen,
    alkoxy,
    amino optionally substituted by alkyl or alkylsulfonyl,
    alkyl optionally substituted by hydroxy or alkoxy, and
    alkylaminosulfonyl; and
  a 5-membered or 6-membered monocyclic aromatic heterocyclic group optionally substituted by 1 or 2 substituents selected independently from the group consisting of
    hydroxy, halogen,
alkoxy,
amino optionally substituted by alkyl or alkylsulfonyl,
alkyl optionally substituted by hydroxy or alkoxy, and
alkylaminosulfonyl
is further preferred, and alkyl optionally substituted by 1 or 2 groups independently selected from
hydroxy or
alkoxy (e.g., $C_{1-6}$ alkoxy) is particularly preferred.

In the present specification, as the optionally substituted alkoxy, unless particularly indicated, alkyl optionally substituted by 1 to 3 groups independently selected from
halogen;
cyano;
hydroxy;
optionally substituted alkoxy;
optionally substituted alkyl;
optionally substituted amino;
optionally substituted cycloalkyl;
optionally substituted aromatic hydrocarbon; and
optionally substituted aromatic heterocycle can be mentioned. Of these, alkoxy optionally substituted by 1 or 2 groups selected independently from
hydroxy;
alkoxy;
cycloalkyl optionally substituted by alkyl;
amino optionally substituted by alkyl or acyl;
phenyl optionally substituted 1 or 2 substituents selected independently from the group consisting of
hydroxy,
halogen,
haloalkoxy,
alkoxy,
amino optionally substituted by alkyl or acyl,
alkyl optionally substituted by hydroxy or alkoxy,
phenyl, and
alkylaminosulfonyl; and
an aromatic heterocyclic group optionally substituted by 1 or 2 substituents selected independently from the group consisting of
hydroxy,
halogen,
alkoxy,
amino optionally substituted by alkyl or acyl,
alkyl optionally substituted by hydroxy or alkoxy, and
alkylaminosulfonyl
is preferred, and
alkoxy optionally substituted by
phenyl optionally substituted by
halogen
alkyl,
haloalkoxy, or
phenyl, or
cycloalkyl optionally substituted by alkyl is more preferred.

In the present specification, as the optionally substituted alkylene, unless particularly indicated, alkylene optionally substituted by 1 to 3 groups selected independently from halogen, cyano, hydroxy, alkyl, and alkoxy can be mentioned. Of these, alkylene optionally substituted by 1 or 2 groups selected from alkyl and alkoxy is preferred.

In the present specification, as the optionally substituted cycloalkyl, unless particularly indicated, cycloalkyl optionally substituted by 1 to 3 groups selected independently from halogen, cyano, hydroxy, alkyl and alkoxy can be mentioned. Of these, cycloalkyl optionally substituted by 1 or 2 groups selected from alkyl, and alkoxy is preferred, and cycloalkyl optionally substituted by 1 or 2 alkyl is more preferred.

In the present specification, as the optionally substituted cycloalkane, unless particularly indicated, cycloalkane optionally substituted by 1 to 3 groups selected independently from halogen, cyano, hydroxy, alkyl, and alkoxy can be mentioned. Of these, cycloalkane optionally substituted by 1 or 2 groups selected from alkyl and alkoxy is preferable.

In the present specification, as the optionally substituted cyclic amine, unless particularly indicated, cyclic amine optionally substituted by 1 to 3 groups selected independently from halogen; cyano; hydroxy; alkoxy; and alkyl optionally substituted by hydroxy or alkoxy can be mentioned. Of these, cyclic amine optionally substituted by hydroxy, alkoxy, or alkyl optionally substituted by hydroxy or alkoxy is preferred, and cyclic amine optionally substituted by 1 or 2 groups selected from alkyl and alkoxy is more preferred.

In the present specification, as the optionally substituted aromatic hydrocarbon group, unless particularly indicated, aromatic hydrocarbon group optionally substituted by 1 to 3 groups selected independently from halogen; cyano; hydroxy; optionally substituted alkyl; optionally substituted alkoxy; optionally substituted amino; optionally substituted cycloalkyl; and alkylaminosulfonyl can be mentioned. Of these, an aromatic hydrocarbon group optionally substituted by 1 or 2 substituents selected independently from the group consisting of hydroxy; halogen; alkoxy; amino optionally substituted by alkyl or alkylsulfonyl; alkyl optionally substituted by halogen, hydroxy or alkoxy; and alkylaminosulfonyl is preferred, an aromatic hydrocarbon group optionally substituted by 1 or 2 substituents selected independently from the group consisting of hydroxy; halogen; alkoxy; amino optionally substituted by alkyl or alkylsulfonyl; alkyl optionally substituted by hydroxy or alkoxy; and alkylaminosulfonyl is more preferred, and an aromatic hydrocarbon group optionally substituted by 1 or 2 substituents selected independently from the group consisting of alkyl and alkoxy is particularly preferred.

In the present specification, as the optionally substituted aromatic heterocyclic group, unless particularly indicated, an aromatic heterocyclic group optionally substituted by 1 or 2 substituents selected independently from the group consisting of hydroxy; halogen; cyano; alkoxy; amino optionally substituted by alkyl or acyl; alkyl optionally substituted by hydroxy, halogen or alkoxy; and alkylaminosulfonyl can be mentioned. Of these, an aromatic heterocyclic group optionally substituted by 1 or 2 substituents selected independently from the group consisting of hydroxy; halogen; alkoxy; amino optionally substituted by alkyl or alkylsulfonyl; alkyl optionally substituted by hydroxy or alkoxy; and alkylaminosulfonyl is preferred, an aromatic heterocyclic group optionally substituted 1 or 2 groups selected independently from halogen, hydroxy, alkyl, and alkoxy is more preferred, and an aromatic heterocyclic group optionally substituted by 1 or 2 substituents selected independently from the group consisting of alkyl and alkoxy is further preferred.

In the present specification, unless particularly indicated, the optionally substituted amino means unsubstituted, or mono- or di-substituted amino group. Examples of the substituent of the optionally substituted amino include the aforementioned optionally substituted alkyl, optionally substituted cycloalkyl, optionally substituted aromatic hydrocarbon group, optionally substituted aromatic heterocyclic group, acyl group and the like. Of these, an amino substituted by one or two alkyl or acyl (e.g., methylamino, methanesulfonylamino) is preferable.

Preferable examples of the acyl group as a substituent of the aforementioned optionally substituted amino group include, unless particularly indicated, formyl, alkyl-carbonyl (e.g., $C_{1-6}$ alkyl-carbonyl group such as acetyl, n-propionyl, isopropionyl, n-butyryl, isobutyryl, pivaloyl, valeryl, hexanoyl and the like), alkylsulfonyl (e.g., methanesulfonyl), alkoxy-carbonyl (e.g., methoxycarbonyl, ethoxycarbonyl etc.), aroyl (e.g., benzoyl, 1-naphthoyl, 2-naphthoyl etc.), arylsulfonyl (e.g., benzenesulfonyl, p-toluenesulfonyl etc.), carbamoyl (—$CONH_2$), alkyl-carbamoyl (e.g., methylcarbamoyl, dimethylcarbamoyl etc.), thiocarbamoyl(—$CSNH_2$), sulfamoyl group (—$S(O)_2NH_2$), alkylsulfamoyl (e.g., methylsulfamoyl, dimethylsulfamoyl etc.) and the like. Of these, amino substituted by alkylsulfonyl (e.g., methanesulfonylamino) is preferable.

In the present specification, the "disease" includes not only the disease itself but also various symptoms (pathological conditions) caused by the disease.

In the present specification, the "prophylaxis" includes preventing the onset of the disease and delaying the onset of the disease. The "effective amount" refers to a dose of the compound (I) of the present invention or a pharmacologically acceptable salt thereof which is sufficient to achieve the prophylactic purposes.

In the present specification, the "treatment" includes recovery of the disease, improvement of pathological conditions (e.g., one or more symptoms) of the disease, and suppression of the progression (severity) of the disease. The "prognosis improvement" is also encompassed in the treatment. The "effective amount" refers to a dose of the compound (I) of the present invention or a pharmacologically acceptable salt thereof which is sufficient to achieve the therapeutic purposes.

In the present specification, "subject" means an object to which a medicament (or pharmaceutical composition) containing a n effective amount of an active ingredient necessary to treat a disease or a condition of a disease is administered. Such "subject" may be a human or a non-human animal, especially a mammal (e.g., mouse, rat, guinea pig, hamster, rabbit, cat, dog, swine, sheep, monkey, etc.). According to some embodiments, the subject is a human, but the compound (I) of the present invention or a pharmacologically acceptable salt thereof is also useful in veterinary applications. The terms "subject" and "patient" may be used interchangeably.

(Compound (I) of the Present Invention)

Each group of the compound (I) of the present invention is explained in the following.

X is oxygen or sulfur.

X is preferably oxygen.

Y is oxygen, sulfur, NH, $CH_2$, —O—$CH_2$—, or —$CH_2$—O—.

Y is preferably oxygen, $CH_2$, —O—$CH_2$—, or —$CH_2$—O—, more preferably oxygen, $CH_2$, or —O—$CH_2$—* (wherein*denotes a binding position with a phosphorus atom), further preferably, oxygen or $CH_2$, particularly preferably oxygen.

Q is a group represented by the following formula (A-1)

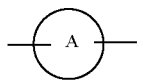
(A-1)

wherein ring A is aromatic heterocycle optionally further substituted by a substituent selected independently from the group consisting of
halogen;
optionally substituted alkyl;
optionally substituted cycloalkyl; and
optionally substituted alkoxy (wherein the aromatic heterocycle excludes indole and purine),
or
—C(=O)—.

When Q is a group represented by the aforementioned formula (A-1),
ring A is preferably a 5- to 10-membered, monocyclic aromatic heterocycle or fused aromatic heterocycle (wherein the aromatic heterocycle excludes indole and purine) containing 1 to 3 hetero atoms selected from oxygen, nitrogen and sulfur, more preferably pyrrole, furan, thiophene, imidazole, pyrazole, oxazole, thiazole, triazole, tetrazole, pyridine, pyrazine, pyrimidine, pyridazine, thiazine, triazine, isoindole, indazole, benzoimidazole, benzothiazole, benzofuran, quinoline, isoquinoline, or imidazopyridine, further preferably pyridine or pyrimidine, particularly preferably pyridine.

Another preferred embodiment of Q is —C(=O)—.

$R^1$ is a group represented by the aforementioned formula (A-2)

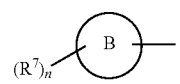
(A-2)

wherein ring B is cycloalkane or benzene,
$R^7$ in the number of n are each independently
halogen,
cyano,
optionally substituted alkyl,
optionally substituted cycloalkyl,
optionally substituted alkoxy, or
optionally substituted aromatic hydrocarbon group,
n is an integer of 0-5.

Ring B is preferably $C_{3-8}$ cycloalkane or benzene, more preferably $C_{3-6}$ cycloalkane (e.g., cyclopropane) or benzene, further preferably benzene.

$R^7$ in the number of n are each preferably independently
halogen (e.g., fluorine atom, chlorine atom);
cyano;
alkyl (e.g., $C_{1-11}$ alkyl) optionally substituted by
halogen (e.g., fluorine atom, chlorine atom),
cycloalkyl (e.g., $C_{3-8}$ cycloalkyl), or
phenyl optionally substituted by alkyl (e.g., $C_{1-11}$ alkyl);
cycloalkyl (e.g., $C_{3-8}$ cycloalkyl) optionally substituted by alkyl (e.g., $C_{1-4}$ alkyl);
aromatic hydrocarbon group (e.g., phenyl) optionally substituted by
alkoxy (e.g., $C_{1-4}$ alkoxy) optionally substituted by phenyl or
alkyl (e.g., $C_{1-11}$ alkyl); or
alkoxy (e.g., $C_{1-11}$ alkoxy) optionally substituted by
phenyl optionally substituted by
halogen (e.g., fluorine atom, chlorine atom),
alkyl (e.g., $C_{1-4}$ alkyl),
haloalkoxy (e.g., halo $C_{1-4}$ alkoxy (preferably, trifluoromethoxy)) or phenyl, or
cycloalkyl (e.g., $C_{3-8}$ cycloalkyl) optionally substituted by alkyl (e.g., $C_{1-4}$ alkyl), more preferably
halogen (e.g., fluorine atom, chlorine atom);
alkyl (e.g., $C_{1-11}$ alkyl) optionally substituted by halogen (e.g., fluorine atom, chlorine atom), cycloalkyl (e.g., $C_{3-6}$ cycloalkyl), or
phenyl optionally substituted by alkyl (e.g., $C_{1-4}$ alkyl (preferably, methyl));
cycloalkyl (e.g., $C_{3-6}$ cycloalkyl);
phenyl optionally substituted by alkyl (e.g., $C_{1-11}$ alkyl); or
alkoxy (e.g., $C_{1-11}$ alkoxy) optionally substituted by
phenyl optionally substituted by
halogen (e.g., fluorine atom, chlorine atom),
alkyl (e.g., $C_{1-4}$ alkyl),
haloalkoxy (e.g., halo $C_{1-4}$ alkoxy (preferably, trifluoromethoxy)) or
phenyl, or
cycloalkyl (e.g., $C_{3-6}$ cycloalkyl) (Of these, alkoxy (e.g., $C_{1-11}$ alkoxy) optionally substituted by
phenyl optionally substituted by
halogen (e.g., fluorine atom, chlorine atom),
alkyl (e.g., $C_{1-4}$ alkyl),
haloalkoxy (e.g., halo $C_{1-4}$ alkoxy (preferably, trifluoromethoxy)) or
phenyl, or
cycloalkyl (e.g., $C_{3-6}$ cycloalkyl) is preferable.),
further preferably
halogen (e.g., fluorine atom, chlorine atom);
alkyl (e.g., $C_{1-11}$ alkyl) optionally substituted by halogen (e.g., fluorine atom, chlorine atom), cycloalkyl (e.g., $C_{3-7}$ cycloalkyl), or phenyl optionally substituted by alkyl (e.g., $C_{1-4}$ alkyl (preferably, methyl));
cycloalkyl (e.g., $C_{3-6}$ cycloalkyl);
phenyl optionally substituted by alkyl (e.g., $C_{1-11}$ alkyl); or
alkoxy (e.g., $C_{1-11}$ alkoxy) optionally substituted by
phenyl optionally substituted by
halogen (e.g., fluorine atom, chlorine atom),
haloalkoxy (e.g., halo $C_{1-4}$ alkoxy (preferably, trifluoromethoxy)) or
phenyl, or
cycloalkyl (e.g., $C_{3-6}$ cycloalkyl) (Of these, alkoxy (e.g., $C_{1-11}$ alkoxy) optionally substituted by
phenyl optionally substituted by
halogen (e.g., fluorine atom, chlorine atom),
haloalkoxy (e.g., halo $C_{1-4}$ alkoxy (preferably, trifluoromethoxy)) or
phenyl
is particularly preferable.),
And, as another preferable embodiment, $R^7$ in the number of n are each independently alkyl (e.g., $C_{1-11}$ alkyl);
cycloalkyl (e.g., $C_{3-6}$ cycloalkyl);
phenyl; or
alkoxy (e.g., $C_{1-11}$ alkoxy).
n is preferably 1 or 2,
more preferably 1.
$L^1$ is a single bond, NH, oxygen, sulfur, —$R^6$—, —$R^6O$—, —$OR^6$—, —$R^6NH$—, —$NHR^6$—, —$R^6S$—, or —$SR^6$— (wherein $R^6$ is an optionally substituted alkylene). $L^1$ is preferably a single bond, —$R^6$—, —$R^6O$—, —$OR^6$—, or —$R^6NH$—**(wherein* is a binding position with Q), more preferably a single bond, —$R^6$—, or —$R^6O$—* (wherein*is a binding position with Q).

$R^6$ is preferably alkylene (e.g., $C_{1-11}$ alkylene) optionally substituted by alkyl (e.g., $C_{1-4}$ alkyl), more preferably alkylene (e.g., $C_{1-11}$ alkylene).
i) When Q is a group represented by the aforementioned formula (A-1),
Z is $CH_2$, oxygen, sulfur, or $NR^5$, and $R^2$, $R^3$, $R^4$, and $R^5$ are each any of the following (i)-1 to (i)-4.
i)-1:
$R^2$ is hydrogen or optionally substituted alkyl,
$R^3$ and $R^4$ are each independently hydrogen or optionally substituted alkyl, and
$R^5$ is hydrogen or optionally substituted alkyl, and the substituent of the optionally substituted alkyl is
halogen;
hydroxy;
alkoxy;
cycloalkyl optionally substituted by alkyl;
amino optionally substituted by alkyl or acyl;
phenyl optionally substituted 1 or 2 substituents selected independently from the group consisting of
hydroxy,
halogen,
alkoxy,
cycloalkyl optionally substituted by alkyl,
amino optionally substituted by alkyl or acyl,
alkyl optionally substituted by hydroxy or alkoxy, and alkylaminosulfonyl; or
an aromatic heterocyclic group optionally substituted by 1 or 2 substituents selected independently from the group consisting of
hydroxy,
halogen,
alkoxy,
cycloalkyl optionally substituted by alkyl,
amino optionally substituted by alkyl or acyl,
alkyl optionally substituted by hydroxy or alkoxy, and alkylaminosulfonyl,
or
(i)-2:
$R^2$ is hydrogen, or optionally substituted alkyl, and one of $R^3$ and $R^4$ is hydrogen, or optionally substituted alkyl, and the other is bonded to $R^5$ to form, together with a carbon atom bonded to $R^3$ and $R^4$ and a nitrogen atom bonded to $R^5$, an optionally substituted cyclic amine,
or
(i)-3:
$R^3$ and $R^4$ are each independently hydrogen, or optionally substituted alkyl, and
$R^2$ is bonded to $R^5$ to form, together with a carbon atom bonded to $R^2$ and a nitrogen atom bonded to $R^5$, an optionally substituted cyclic amine,
or
(i)-4:
$R^5$ is hydrogen or optionally substituted alkyl, and the substituent of the optionally substituted alkyl is
halogen;
hydroxy;
alkoxy;
cycloalkyl optionally substituted by alkyl;
amino optionally substituted by alkyl or acyl;
phenyl optionally substituted 1 or 2 substituents selected independently from the group consisting of
hydroxy,
halogen,
alkoxy,
cycloalkyl optionally substituted by alkyl,
amino optionally substituted by alkyl or acyl, alkyl optionally substituted by hydroxy or alkoxy, and alkylaminosulfonyl; or
an aromatic heterocyclic group optionally substituted by 1 or 2 substituents selected independently from the group consisting of
hydroxy,
halogen,
alkoxy,
cycloalkyl optionally substituted by alkyl,
amino optionally substituted by alkyl or acyl,
alkyl optionally substituted by hydroxy or alkoxy, and alkylaminosulfonyl, and
one of $R^3$ and $R^4$ is hydrogen or optionally substituted alkyl, and the other is bonded to $R^2$ to form, together with a carbon atom bonded to $R^3$ and $R^4$ and a carbon atom bonded to $R^2$, an optionally substituted cycloalkane.

Z is preferably oxygen or $NR^5$, and $R^2$, $R^3$, $R^4$, and $R^5$ are each any of the following (i)'-1 to (i)'-4.

(i)'-1:
$R^2$ is hydrogen, or alkyl (e.g., $C_{1-6}$ alkyl) optionally substituted by hydroxy or alkoxy (e.g., $C_{1-6}$ alkoxy),
$R^3$ and $R^4$ are each independently hydrogen, or alkyl (e.g., $C_{1-6}$ alkyl) optionally substituted by hydroxy or alkoxy (e.g., $C_{1-6}$ alkoxy), and
$R^5$ is hydrogen or optionally substituted alkyl (e.g., $C_{1-6}$ alkyl), and the substituent of the optionally substituted alkyl is
hydroxy;
alkoxy (e.g., $C_{1-6}$ alkoxy);
amino optionally substituted by alkyl (e.g., $C_{1-6}$ alkyl) or alkylsulfonyl (e.g., $C_{1-6}$ alkylsulfonyl);
phenyl optionally substituted 1 or 2 substituents selected independently from the group consisting of
hydroxy,
halogen,
alkoxy (e.g., $C_{1-6}$ alkoxy),
amino optionally substituted by alkyl (e.g., $C_{1-6}$ alkyl) or alkylsulfonyl (e.g., $C_{1-6}$ alkylsulfonyl),
alkyl (e.g., $C_{1-6}$ alkyl) optionally substituted by hydroxy or alkoxy (e.g., $C_{1-6}$ alkoxy), and
alkylaminosulfonyl (e.g., $C_{1-6}$ alkylaminosulfonyl); or
an aromatic heterocyclic group (e.g., 5- or 6-membered monocyclic aromatic heterocyclic group) optionally substituted by 1 or 2 substituents selected independently from the group consisting of
hydroxy,
halogen,
alkoxy (e.g., $C_{1-6}$ alkoxy),
amino optionally substituted by alkyl (e.g., $C_{1-6}$ alkyl) or alkylsulfonyl (e.g., $C_{1-6}$ alkylsulfonyl),
alkyl (e.g., $C_{1-6}$ alkyl) optionally substituted by hydroxy or alkoxy (e.g., $C_{1-6}$ alkoxy), and
alkylaminosulfonyl (e.g., $C_{1-6}$ alkylaminosulfonyl),
or
(i)'-2:
$R^2$ is hydrogen, or alkyl (e.g., $C_{1-6}$ alkyl) optionally substituted by hydroxy or alkoxy (e.g., $C_{1-6}$ alkoxy), and one of $R^3$ and $R^4$ is hydrogen, or alkyl (e.g., $C_{1-6}$ alkyl) optionally substituted by hydroxy or alkoxy (e.g., $C_{1-6}$ alkoxy), and the other is bonded to $R^5$ to form, together with a carbon atom bonded to $R^3$ and $R^4$ and a nitrogen atom bonded to $R^5$, a cyclic amine (e.g., saturated 3- to 7-membered monocyclic nitrogen-containing non-aromatic heterocycle) optionally substituted by
hydroxy,
alkoxy (e.g., $C_{1-6}$ alkoxy), or
alkyl (e.g., $C_{1-6}$ alkyl) optionally substituted by hydroxy or alkoxy (e.g., $C_{1-6}$ alkoxy),
or
(i)'-3:
$R^3$ and $R^4$ are each independently hydrogen, or alkyl (e.g., $C_{1-6}$ alkyl) optionally substituted by hydroxy or alkoxy (e.g., $C_{1-6}$ alkoxy), and
$R^2$ is bonded to $R^5$ to form, together with a carbon atom bonded to $R^2$ and a nitrogen atom bonded to $R^5$, a cyclic amine (e.g., saturated 3- to 7-membered monocyclic nitrogen-containing non-aromatic heterocycle) optionally substituted by
hydroxy,
alkoxy (e.g., $C_{1-6}$ alkoxy), or
alkyl (e.g., $C_{1-6}$ alkyl) optionally substituted by hydroxy or alkoxy (e.g., $C_{1-6}$ alkoxy),
or
(i)'-4:
$R^5$ is hydrogen or optionally substituted alkyl (e.g., $C_{1-6}$ alkyl), and the substituent of the optionally substituted alkyl is
hydroxy;
alkoxy (e.g., $C_{1-8}$ alkoxy);
amino optionally substituted by alkyl (e.g., $C_{1-6}$ alkyl) or alkylsulfonyl (e.g., $C_{1-6}$ alkylsulfonyl);
phenyl optionally substituted 1 or 2 substituents selected independently from the group consisting of
hydroxy,
halogen,
alkoxy (e.g., $C_{1-6}$ alkoxy),
amino optionally substituted by alkyl (e.g., $C_{1-6}$ alkyl) or alkylsulfonyl (e.g., $C_{1-6}$ alkylsulfonyl),
alkyl (e.g., $C_{1-6}$ alkyl) optionally substituted by hydroxy or alkoxy (e.g., $C_{1-6}$ alkoxy), and
alkylaminosulfonyl (e.g., $C_{1-6}$ alkylaminosulfonyl); or
an aromatic heterocyclic group (e.g., 5- or 6-membered monocyclic aromatic heterocyclic group) optionally substituted by 1 or 2 substituents selected independently from the group consisting of
hydroxy,
halogen,
alkoxy (e.g., $C_{1-6}$ alkoxy),
amino optionally substituted by alkyl (e.g., $C_{1-6}$ alkyl) or alkylsulfonyl (e.g., $C_{1-6}$ alkylsulfonyl),
alkyl (e.g., $C_{1-6}$ alkyl) optionally substituted by hydroxy or alkoxy (e.g., $C_{1-6}$ alkoxy), and
alkylaminosulfonyl, and
one of $R^3$ and $R^4$ is hydrogen, or alkyl (e.g., $C_{1-6}$ alkyl) optionally substituted by hydroxy or alkoxy (e.g., $C_{1-6}$ alkoxy), and the other is bonded to $R^2$ to form, together with a carbon atom bonded to $R^3$ and $R^4$ and a carbon atom bonded to $R^2$, cycloalkane (e.g., $C_{3-8}$ cycloalkane (preferably, cyclopentane, cyclohexane)) optionally substituted by
hydroxy,
alkoxy (e.g., $C_{1-6}$ alkoxy), or
alkyl (e.g., $C_{1-6}$ alkyl) optionally substituted by hydroxy or alkoxy (e.g., $C_{1-6}$ alkoxy).

Z is more preferably $NR^5$, and
$R^2$, $R^3$, $R^4$, and $R^5$ are each more preferably the aforementioned (i)'-1, (i)'-2, or (i)'-4.

Z is further preferably $NR^5$, and $R^2$, $R^3$, $R^4$, and $R^5$ are each further preferably the following (i)"-1 or (i)"-4.

(i)"-1:

$R^2$ is hydrogen, or alkyl (e.g., $C_{1-4}$ alkyl) optionally substituted by hydroxy or alkoxy (e.g., $C_{1-4}$ alkoxy), $R^3$ and $R^4$ are each independently hydrogen, or alkyl (e.g., $C_{1-4}$ alkyl) optionally substituted by hydroxy or alkoxy (e.g., $C_{1-4}$ alkoxy), and $R^5$ is hydrogen or alkyl (e.g., $C_{1-4}$ alkyl (preferably, methyl or ethyl)), or (i)"-4:

$R^5$ is hydrogen or alkyl (e.g., $C_{1-4}$ alkyl (preferably, methyl or ethyl)), and one of $R^3$ and $R^4$ is hydrogen, and the other is bonded to $R^2$ to form cycloalkane (e.g., $C_{3-6}$ cycloalkane (preferably, cyclopentane, cyclohexane)) together with a carbon atom bonded to $R^3$ and $R^4$ and a carbon atom bonded to $R^2$.

(ii) When Q is —C(=O)—,

Z is oxygen, sulfur, or $NR^5$, and $R^2$, $R^3$, $R^4$, and $R^5$ are each any of the following (ii)-1 to (ii)-4.

(ii)-1:

$R^2$ is hydrogen or alkyl, $R^3$ and $R^4$ are each independently hydrogen or optionally substituted alkyl, and $R^5$ is optionally substituted alkyl, and the substituent of the optionally substituted alkyl is halogen;

hydroxy;

alkoxy;

cycloalkyl optionally substituted by alkyl;

amino optionally substituted by alkyl or acyl;

phenyl optionally substituted by 1 or 2 substituents selected independently from the group consisting of
hydroxy,
halogen,
alkoxy,
cycloalkyl optionally substituted by alkyl,
amino optionally substituted by alkyl or acyl,
alkyl optionally substituted by hydroxy or alkoxy, and
alkylaminosulfonyl; or an aromatic heterocyclic group optionally substituted by 1 or 2 substituents selected independently from the group consisting of
hydroxy,
halogen,
alkoxy,
cycloalkyl optionally substituted by alkyl,
amino optionally substituted by alkyl or acyl,
alkyl optionally substituted by hydroxy or alkoxy, and
alkylaminosulfonyl, or (ii)-2:

$R^2$ is hydrogen or alkyl, and one of $R^3$ and $R^4$ is hydrogen or optionally substituted alkyl, and the other is bonded to $R^5$ to form, together with a carbon atom bonded to $R^3$ and $R^4$ and a nitrogen atom bonded to $R^5$, an optionally substituted cyclic amine, or (ii)-3:

$R^3$ and $R^4$ are each independently hydrogen or optionally substituted alkyl, and $R^2$ is bonded to $R^5$ to form, together with a carbon atom bonded to $R^2$ and a nitrogen atom bonded to $R^5$, an optionally substituted cyclic amine, or (ii)-4:

$R^5$ is optionally substituted alkyl, and the substituent of the optionally substituted alkyl is halogen;

hydroxy;

alkoxy;

cycloalkyl optionally substituted by alkyl;

amino optionally substituted by alkyl or acyl;

phenyl optionally substituted by 1 or 2 substituents selected independently from the group consisting of
hydroxy,
halogen,
alkoxy,
cycloalkyl optionally substituted by alkyl,
amino optionally substituted by alkyl or acyl,
alkyl optionally substituted by hydroxy or alkoxy, and
alkylaminosulfonyl; or an aromatic heterocyclic group optionally substituted by 1 or 2 substituents selected independently from the group consisting of
hydroxy,
halogen,
alkoxy,
cycloalkyl optionally substituted by alkyl,
amino optionally substituted by alkyl or acyl,
alkyl optionally substituted by hydroxy or alkoxy, and
alkylaminosulfonyl, and one of $R^3$ and $R^4$ is hydrogen or optionally substituted alkyl, and the other is bonded to $R^2$ to form, together with a carbon atom bonded to $R^3$ and $R^4$ and a carbon atom bonded to $R^2$, an optionally substituted cycloalkane.

Z is preferably $NR^5$, and $R^2$, $R^3$, $R^4$, and $R^5$ are each preferably any of the following (ii)'-1 to (ii)'-4.

(ii)'-1:

$R^2$ is hydrogen, or alkyl (e.g., $C_{1-6}$ alkyl), $R^3$ and $R^4$ are each independently hydrogen, or alkyl (e.g., $C_{1-6}$ alkyl) optionally substituted by hydroxy or alkoxy (e.g., $C_{1-6}$ alkoxy), and $R^5$ is optionally substituted alkyl (e.g., $C_{1-6}$ alkyl), and the substituent of the optionally substituted alkyl is hydroxy;

alkoxy (e.g., $C_{1-6}$ alkoxy);

amino optionally substituted by alkyl (e.g., $C_{1-6}$ alkyl) or alkylsulfonyl (e.g., $C_{1-6}$ alkylsulfonyl);

phenyl optionally substituted 1 or 2 substituents selected independently from the group consisting of
hydroxy,
halogen,
alkoxy (e.g., $C_{1-6}$ alkoxy),
amino optionally substituted by alkyl (e.g., $C_{1-6}$ alkyl) or alkylsulfonyl (e.g., $C_{1-6}$ alkylsulfonyl),
alkyl (e.g., $C_{1-6}$ alkyl) optionally substituted by hydroxy or alkoxy (e.g., $C_{1-6}$ alkoxy), and
alkylaminosulfonyl (e.g., $C_{1-6}$ alkylaminosulfonyl); or an aromatic heterocyclic group (e.g., 5- or 6-membered monocyclic aromatic heterocyclic group) optionally substituted by 1 or 2 substituents selected independently from the group consisting of
hydroxy,
halogen,
alkoxy (e.g., $C_{1-6}$ alkoxy), amino optionally substituted by alkyl (e.g., $C_{1-6}$ alkyl) or alkylsulfonyl (e.g., $C_{1-6}$ alkylsulfonyl), alkyl (e.g., $C_{1-6}$ alkyl) optionally substituted by hydroxy or alkoxy (e.g., $C_{1-6}$ alkoxy), and alkylaminosulfonyl (e.g., $C_{1-6}$ alkylaminosulfonyl), or (ii)'-2:

$R^2$ is hydrogen, or alkyl (e.g., $C_{1-6}$ alkyl), and one of $R^3$ and $R^4$ is hydrogen, or alkyl (e.g., $C_{1-6}$ alkyl) optionally substituted by hydroxy or alkoxy (e.g., $C_{1-6}$ alkoxy), and the other is bonded to $R^5$ to form, together with a carbon atom bonded to $R^3$ and $R^4$ and a nitrogen atom bonded to $R^5$, a cyclic amine (e.g., saturated 3- to 7-membered monocyclic nitrogen-containing non-aromatic heterocycle) optionally substituted by hydroxy, alkoxy (e.g., $C_{1-6}$ alkoxy), or alkyl (e.g., $C_{1-6}$ alkyl) optionally substituted by hydroxy or alkoxy (e.g., $C_{1-6}$ alkoxy), or (ii)'-3:

$R^3$ and $R^4$ are each independently hydrogen, or alkyl (e.g., $C_{1-6}$ alkyl) optionally substituted by hydroxy or alkoxy (e.g., $C_{1-6}$ alkoxy), and $R^2$ is bonded to $R^5$ to form, together with a carbon atom bonded to $R^2$ and a nitrogen atom bonded to $R^5$, a cyclic amine (e.g., saturated 3- to 7-membered monocyclic nitrogen-containing non-aromatic heterocycle) optionally substituted by hydroxy, alkoxy (e.g., $C_{1-6}$ alkoxy), or alkyl (e.g., $C_{1-6}$ alkyl) optionally substituted by hydroxy or alkoxy (e.g., $C_{1-6}$ alkoxy), or (ii)'-4:

$R^5$ is optionally substituted alkyl (e.g., $C_{1-6}$ alkyl), and the substituent of the optionally substituted alkyl is hydroxy;

alkoxy (e.g., $C_{1-6}$ alkoxy);

amino optionally substituted by alkyl (e.g., $C_{1-6}$ alkyl) or alkylsulfonyl (e.g., $C_{1-6}$ alkylsulfonyl);

phenyl optionally substituted 1 or 2 substituents selected independently from the group consisting of hydroxy, halogen, alkoxy (e.g., $C_{1-6}$ alkoxy), amino optionally substituted by alkyl (e.g., $C_{1-6}$ alkyl) or alkylsulfonyl (e.g., $C_{1-6}$ alkylsulfonyl), alkyl (e.g., $C_{1-6}$ alkyl) optionally substituted by hydroxy or alkoxy (e.g., $C_{1-6}$ alkoxy), and alkylaminosulfonyl (e.g., $C_{1-6}$ alkylaminosulfonyl); or an aromatic heterocyclic group (e.g., 5- or 6-membered monocyclic aromatic heterocyclic group) optionally substituted by 1 or 2 substituents selected independently from the group consisting of hydroxy, halogen, alkoxy (e.g., $C_{1-6}$ alkoxy), amino optionally substituted by alkyl (e.g., $C_{1-6}$ alkyl) or alkylsulfonyl (e.g., $C_{1-6}$ alkylsulfonyl), alkyl (e.g., $C_{1-6}$ alkyl) optionally substituted by hydroxy or alkoxy (e.g., $C_{1-6}$ alkoxy), and alkylaminosulfonyl (e.g., $C_{1-6}$ alkylaminosulfonyl), and one of $R^3$ and $R^4$ is hydrogen, or alkyl (e.g., $C_{1-6}$ alkyl) optionally substituted by hydroxy or alkoxy (e.g., $C_{1-6}$ alkoxy), and the other is bonded to $R^2$ to form, together with a carbon atom bonded to $R^3$ and $R^4$ and a carbon atom bonded to $R^2$, cycloalkane (e.g., $C_{3-8}$ cycloalkane (preferably, cyclopentane, cyclohexane)) optionally substituted by hydroxy, alkoxy (e.g., $C_{1-6}$ alkoxy), or alkyl (e.g., $C_{1-6}$ alkyl) optionally substituted by hydroxy or alkoxy (e.g., $C_{1-6}$ alkoxy).

Z is more preferably $NR^5$, and $R^2$, $R^3$, $R^4$, and $R^5$ are each preferably the above-mentioned (ii)'-1 or (ii)'-2, more preferably the following (ii)"-1 or (ii)"-2.

(ii)"-1:

$R^2$ is hydrogen, $R^3$ and $R^4$ are each independently hydrogen or alkyl (e.g., $C_{1-4}$ alkyl), and $R^5$ is alkyl (e.g., $C_{1-4}$ alkyl) optionally substituted by hydroxy;

alkoxy (e.g., $C_{1-4}$ alkoxy);

amino optionally substituted by alkyl (e.g., $C_{1-4}$ alkyl) or alkylsulfonyl (e.g., $C_{1-4}$ alkylsulfonyl);

phenyl optionally substituted by 1 or 2 substituents selected independently from the group consisting of hydroxy, halogen, alkoxy (e.g., $C_{1-4}$ alkoxy), amino optionally substituted by alkyl (e.g., $C_{1-4}$ alkyl) or alkylsulfonyl (e.g., $C_{1-4}$ alkylsulfonyl), alkyl (e.g., $C_{1-4}$ alkyl) optionally substituted by hydroxy or alkoxy (e.g., $C_{1-4}$ alkoxy), and alkylaminosulfonyl (e.g., $C_{1-4}$ alkylaminosulfonyl); or a 5- or 6-membered monocyclic aromatic heterocyclic group (preferably, pyridyl, thiazolyl, isothiazolyl, or pyridazinyl) optionally substituted by 1 or 2 substituents selected independently from the group consisting of hydroxy, halogen, alkoxy (e.g., $C_{1-4}$ alkoxy), amino optionally substituted by alkyl (e.g., $C_{1-4}$ alkyl) or alkylsulfonyl (e.g., $C_{1-4}$ alkylsulfonyl), alkyl (e.g., $C_{1-4}$ alkyl) optionally substituted by hydroxy or alkoxy (e.g., $C_{1-4}$ alkoxy), and alkylaminosulfonyl (e.g., $C_{1-4}$ alkylaminosulfonyl), or (ii)"-2:

$R^2$ is hydrogen or alkyl (e.g., $C_{1-4}$ alkyl), and one of $R^3$ and $R^4$ is hydrogen, and the other is bonded to $R^5$ to form, together with, a carbon atom bonded to $R^3$ and $R^4$, and a nitrogen atom bonded to $R^5$, azetidine, pyrrolidine or piperidine, each optionally substituted by hydroxy, alkoxy (e.g., $C_{1-4}$ alkoxy), or alkyl (e.g., $C_{1-4}$ alkyl) optionally substituted by hydroxy or alkoxy (e.g., $C_{1-4}$ alkoxy).

Z is further preferably $NR^5$, and $R^2$, $R^3$, $R^4$, and $R^5$ are each further preferably the following (ii)'''-1 or (ii)'''-2.

(ii)'''-1:

$R^2$ is hydrogen, $R^3$ and $R^4$ are each independently hydrogen or alkyl (e.g., $C_{1-4}$ alkyl) (preferably both hydrogens), and $R^5$ is alkyl (e.g., methyl or ethyl) optionally substituted by phenyl optionally substituted 1 or 2 substituents selected independently from the group consisting of hydroxy, halogen, alkoxy (e.g., $C_{1-4}$ alkoxy), amino optionally substituted by alkyl (e.g., $C_{1-4}$ alkyl) or alkylsulfonyl (e.g., $C_{1-4}$ alkylsulfonyl), alkyl (e.g., $C_{1-4}$ alkyl) optionally substituted by hydroxy or alkoxy (e.g., $C_{1-4}$ alkoxy), and alkylaminosulfonyl (e.g., $C_{1-4}$ alkylaminosulfonyl); or a 5- or 6-membered monocyclic aromatic heterocyclic group (preferably, pyridyl, thiazolyl, isothiazolyl, or pyridazinyl) optionally substituted by 1 or 2 substituents selected independently from the group consisting of hydroxy, halogen, alkoxy (e.g., $C_{1-4}$ alkoxy), amino optionally substituted by alkyl (e.g., $C_{1-4}$ alkyl) or alkylsulfonyl (e.g., $C_{1-4}$ alkylsulfonyl), alkyl (e.g., $C_{1-4}$ alkyl) optionally substituted by hydroxy or alkoxy (e.g., $C_{1-4}$ alkoxy), and alkylaminosulfonyl (e.g., $C_{1-4}$ alkylaminosulfonyl), or (ii)'''-2:

$R^2$ is hydrogen, and one of $R^3$ and $R^4$ is hydrogen, and the other is bonded to $R^5$ to form, together with, a carbon atom bonded to $R^3$ and $R^4$, and a nitrogen atom bonded to $R^5$, azetidine optionally substituted by hydroxy, alkoxy (e.g., $C_{1-4}$ alkoxy), or alkyl (e.g., $C_{1-4}$ alkyl) optionally substituted by hydroxy or alkoxy (e.g., $C_{1-4}$ alkoxy).

As compound (I) of the present invention, the following compounds are preferred.

[Compound (IA)]

Compound (I) wherein

X is oxygen or sulfur,

Y is oxygen, $CH_2$, $-O-CH_2-$, or $-CH_2-O-$,

Q is a group represented by the aforementioned formula (A-1), ring A is a 5- to 10-membered, monocyclic aromatic heterocycle or fused aromatic heterocycle (wherein the aromatic heterocycle excludes indole and purine) containing 1 to 3 hetero atoms selected from oxygen, nitrogen, and sulfur, $R^1$ is a group represented by the aforementioned formula (A-2), ring B is benzene, $R^7$ in the number of n are each independently halogen (e.g., fluorine atom, chlorine atom); cyano;

alkyl (e.g., $C_{1-11}$ alkyl) optionally substituted by
halogen (e.g., fluorine atom, chlorine atom),
cycloalkyl (e.g., $C_{3-8}$ cycloalkyl), or
phenyl optionally substituted by alkyl (e.g., $C_{1-11}$ alkyl);

cycloalkyl (e.g., $C_{3-8}$ cycloalkyl) optionally substituted by alkyl (e.g., $C_{1-4}$ alkyl);

aromatic hydrocarbon group (e.g., phenyl) optionally substituted by
alkoxy (e.g., $C_{1-4}$ alkoxy) optionally substituted by phenyl or
alkyl (e.g., $C_{1-11}$ alkyl); or alkoxy (e.g., $C_{1-11}$ alkoxy) optionally substituted by
phenyl optionally substituted by
halogen (e.g., fluorine atom, chlorine atom),
alkyl (e.g., $C_{1-4}$ alkyl).
haloalkoxy (e.g., halo $C_{1-4}$ alkoxy (preferably, trifluoromethoxy)) or
phenyl, or cycloalkyl (e.g., $C_{3-6}$ cycloalkyl) optionally substituted by alkyl (e.g., $C_{1-4}$ alkyl), n is 1 or 2, $L^1$ is a single bond, $-R^6-$, $-R^6O-$, $-OR^6-$, $-R^6N-$, or $-NR^6-$, $R^6$ is alkylene (e.g., $C_{1-11}$ alkylene) optionally substituted by alkyl (e.g., $C_{1-4}$ alkyl), Z is oxygen or $NR^5$, and $R^2$, $R^3$, $R^4$, and $R^5$ are each any of the following (i)'-1 to (i)'-4;

(i)'-1:

$R^2$ is hydrogen, or alkyl (e.g., $C_{1-6}$ alkyl) optionally substituted by hydroxy or alkoxy (e.g., $C_{1-6}$ alkoxy), $R^3$ and $R^4$ are each independently hydrogen, or alkyl (e.g., $C_{1-6}$ alkyl) optionally substituted by hydroxy or alkoxy (e.g., $C_{1-6}$ alkoxy), and $R^5$ is hydrogen or optionally substituted alkyl (e.g., $C_{1-6}$ alkyl), and the substituent of the optionally substituted alkyl is hydroxy;

alkoxy (e.g., $C_{1-6}$ alkoxy);

amino optionally substituted by alkyl (e.g., $C_{1-6}$ alkyl) or alkylsulfonyl (e.g., $C_{1-6}$ alkylsulfonyl);

phenyl optionally substituted 1 or 2 substituents selected independently from the group consisting of hydroxy, halogen, alkoxy (e.g., $C_{1-6}$ alkoxy), amino optionally substituted by alkyl (e.g., $C_{1-6}$ alkyl) or alkylsulfonyl (e.g., $C_{1-6}$ alkylsulfonyl), alkyl (e.g., $C_{1-6}$ alkyl) optionally substituted by hydroxy or alkoxy (e.g., $C_{1-6}$ alkoxy), and alkylaminosulfonyl (e.g., $C_{1-6}$ alkylaminosulfonyl); or an aromatic heterocyclic group (e.g., 5- or 6-membered monocyclic aromatic heterocyclic group) optionally substituted by 1 or 2 substituents selected independently from the group consisting of hydroxy, halogen, alkoxy (e.g., $C_{1-6}$ alkoxy), amino optionally substituted by alkyl (e.g., $C_{1-6}$ alkyl) or alkylsulfonyl (e.g., $C_{1-6}$ alkylsulfonyl), alkyl (e.g., $C_{1-6}$ alkyl) optionally substituted by hydroxy or alkoxy (e.g., $C_{1-6}$ alkoxy), and alkylaminosulfonyl (e.g., $C_{1-6}$ alkylaminosulfonyl), or (i)'-2:

$R^2$ is hydrogen, or alkyl (e.g., $C_{1-6}$ alkyl) optionally substituted by hydroxy or alkoxy (e.g., $C_{1-6}$ alkoxy), and one of $R^3$ and $R^4$ is hydrogen, or alkyl (e.g., $C_{1-6}$ alkyl) optionally substituted by hydroxy or alkoxy (e.g., $C_{1-6}$ alkoxy), and the other is bonded to $R^5$ to form, together with a carbon atom bonded to $R^3$ and $R^4$ and a nitrogen atom bonded to $R^5$, a cyclic amine (e.g., saturated 3- to 7-membered monocyclic nitrogen-containing non-aromatic heterocycle) optionally substituted by hydroxy, alkoxy (e.g., $C_{1-6}$ alkoxy), or alkyl (e.g., $C_{1-6}$ alkyl) optionally substituted by hydroxy or alkoxy (e.g., $C_{1-6}$ alkoxy), or (i)'-3:

$R^3$ and $R^4$ are each independently hydrogen, or alkyl (e.g., $C_{1-6}$ alkyl) optionally substituted by hydroxy or alkoxy (e.g., $C_{1-6}$ alkoxy), and R² is bonded to R⁵ to form, together with a carbon atom bonded to R² and a nitrogen atom bonded to R⁵, a cyclic amine (e.g., saturated 3- to 7-membered monocyclic nitrogen-containing non-aromatic heterocycle) optionally substituted by hydroxy, alkoxy (e.g., $C_{1-6}$ alkoxy), or alkyl (e.g., $C_{1-6}$ alkyl) optionally substituted by hydroxy or alkoxy (e.g., $C_{1-6}$ alkoxy), or (i)'-4:

R⁵ is hydrogen or optionally substituted alkyl (e.g., $C_{1-6}$ alkyl), and the substituent of the optionally substituted alkyl is hydroxy;

alkoxy (e.g., $C_{1-6}$ alkoxy):

amino optionally substituted by alkyl (e.g., $C_{1-6}$ alkyl) or alkylsulfonyl;

phenyl optionally substituted 1 or 2 substituents selected independently from the group consisting of hydroxy, halogen, alkoxy (e.g., $C_{1-6}$ alkoxy), amino optionally substituted by alkyl (e.g., $C_{1-6}$ alkyl) or alkylsulfonyl (e.g., $C_{1-6}$ alkylsulfonyl), alkyl (e.g., $C_{1-6}$ alkyl) optionally substituted by hydroxy or alkoxy (e.g., $C_{1-6}$ alkoxy), and alkylaminosulfonyl (e.g., $C_{1-6}$ alkylaminosulfonyl); or is an aromatic heterocyclic group (e.g., 5- or 6-membered monocyclic aromatic heterocyclic group) optionally substituted by 1 or 2 substituents selected independently from the group consisting of hydroxy, halogen, alkoxy (e.g., $C_{1-6}$ alkoxy), amino optionally substituted by alkyl (e.g., $C_{1-6}$ alkyl) or alkylsulfonyl (e.g., $C_{1-6}$ alkylsulfonyl), alkyl (e.g., $C_{1-6}$ alkyl) optionally substituted by hydroxy or alkoxy (e.g., $C_{1-6}$ alkoxy), and alkylaminosulfonyl (e.g., $C_{1-6}$ alkylaminosulfonyl), and one of R³ and R⁴ is hydrogen, or alkyl (e.g., $C_{1-6}$ alkyl) optionally substituted by hydroxy or alkoxy (e.g., $C_{1-6}$ alkoxy), and the other is bonded to R² to form, together with a carbon atom bonded to R³ and R⁴ and a carbon atom bonded to R², cycloalkane (e.g., $C_{3-8}$ cycloalkane (preferably, cyclopentane, cyclohexane)) optionally substituted by hydroxy, alkoxy (e.g., $C_{1-6}$ alkoxy), or alkyl (e.g., $C_{1-6}$ alkyl) optionally substituted by hydroxy or alkoxy (e.g., $C_{1-6}$ alkoxy).

[Compound (IB)]

Compound (I) wherein

X is oxygen or sulfur,

Y is oxygen or $CH_2$,

Q is a group represented by the aforementioned formula (A-1), ring A is pyrrole, furan, thiophene, imidazole, pyrazole, oxazole, thiazole, triazole, tetrazole, pyridine, pyrazine, pyrimidine, pyridazine, thiazine, triazine, isoindole, indazole, benzoimidazole, benzothiazole, benzofuran, quinoline, isoquinoline, or imidazopyridine, R¹ is a group represented by the aforementioned formula (A-2), ring B is benzene, R⁷ in the number of n are each independently halogen (e.g., fluorine atom, chlorine atom);

alkyl (e.g., $C_{1-11}$ alkyl) optionally substituted by halogen (e.g., fluorine atom, chlorine atom), cycloalkyl (e.g., $C_{3-6}$ cycloalkyl), or phenyl optionally substituted by alkyl (e.g., $C_{1-4}$ alkyl (preferably, methyl));

cycloalkyl (e.g., $C_{3-6}$ cycloalkyl);

phenyl optionally substituted by alkyl (e.g., $C_{1-11}$ alkyl);

or alkoxy (e.g., $C_{1-11}$ alkoxy) optionally substituted by phenyl optionally substituted by halogen (e.g., fluorine atom, chlorine atom), haloalkoxy (e.g., halo $C_{1-4}$ alkoxy (preferably, trifluoromethoxy)) or phenyl, or cycloalkyl (e.g., $C_{3-6}$ cycloalkyl), n is 1 or 2, L¹ is a single bond, Z is oxygen or NR⁵, and R², R³, R⁴, and R⁵ are each the aforementioned (i)'-1, (i)'-2, or (i)'-4.

[Compound (IC)]

Compound (I) wherein

X is oxygen or sulfur,

Y is oxygen,

Q is the aforementioned formula (A-1), ring A is pyridine or pyrimidine,

Z is oxygen or NR⁵,

L¹ is a single bond,

R¹ is the aforementioned formula (A-2), ring B is benzene,

R² is hydrogen, or alkyl optionally substituted by hydroxy or alkoxy (e.g., $C_{1-6}$ alkoxy), R³ and R⁴ are each independently hydrogen, or alkyl (e.g., $C_{1-6}$ alkyl) optionally substituted by hydroxy or alkoxy, R⁵ is hydrogen or alkyl (e.g., $C_{1-6}$ alkyl), R⁷ is alkoxy (e.g., $C_{1-11}$ alkoxy) optionally substituted by phenyl optionally substituted by halogen, alkyl (e.g., $C_{1-4}$ alkyl), haloalkoxy (e.g., halo $C_{1-4}$ alkoxy) or phenyl, or cycloalkyl (e.g., $C_{3-6}$ cycloalkyl), and n is 1.

[Compound (ID)]

Compound (I) wherein

X is oxygen or sulfur,

Y is oxygen,

Q is the aforementioned formula (A-1), ring A is pyridine or pyrimidine,

Z is NR⁵,

L¹ is a single bond,

R¹ is the aforementioned formula (A-2), ring B is benzene,

R⁵ is hydrogen or alkyl (e.g., $C_{1-6}$ alkyl), and one of R³ and R⁴ is hydrogen, and the other is bonded to R² to form, together with a carbon atom bonded to R³ and R⁴ and a carbon atom bonded to R², cycloalkane;

R⁷ is alkoxy (e.g., $C_{1-11}$ alkoxy) optionally substituted by phenyl optionally substituted by halogen, alkyl (e.g., $C_{1-4}$ alkyl), haloalkoxy (e.g., halo $C_{1-4}$ alkoxy (preferably, trifluoromethoxy)) or phenyl, or cycloalkyl (e.g., $C_{3-6}$ cycloalkyl), and n is 1.

[Compound (IE)]

Compound (I) wherein

X is oxygen or sulfur,

Y is oxygen,

Q is a group represented by the aforementioned formula (A-1),
ring A is pyridine or pyrimidine,
$R^1$ is a group represented by the aforementioned formula (A-2), ring B is benzene,
$R^7$ is
halogen (e.g., fluorine atom, chlorine atom);
alkyl (e.g., $C_{1-11}$ alkyl) optionally substituted by
   halogen (e.g., fluorine atom, chlorine atom),
   cycloalkyl (e.g., $C_{3-6}$ cycloalkyl), or
   phenyl optionally substituted by alkyl (e.g., $C_{1-4}$ alkyl (preferably, methyl));
cycloalkyl (e.g., $C_{3-6}$ cycloalkyl);
phenyl optionally substituted by alkyl (e.g., $C_{1-11}$ alkyl); or
alkoxy (e.g., $C_{1-11}$ alkoxy) optionally substituted by
   phenyl optionally substituted by
      halogen (e.g., fluorine atom, chlorine atom),
      alkyl (e.g., $C_{1-11}$ alkyl).
      haloalkoxy (e.g., halo $C_{1-4}$ alkoxy (preferably, trifluoromethoxy)) or
      phenyl, or
   cycloalkyl (e.g., $C_{3-6}$ cycloalkyl),
($R^7$ is preferably
halogen (e.g., fluorine atom, chlorine atom);
alkyl (e.g., $C_{1-11}$ alkyl) optionally substituted by
   halogen (e.g., fluorine atom, chlorine atom), or
   cycloalkyl (e.g., $C_{3-6}$ cycloalkyl);
cycloalkyl (e.g., $C_{3-6}$ cycloalkyl);
phenyl optionally substituted by alkyl (e.g., $C_{1-11}$ alkyl); or
alkoxy (e.g., $C_{1-11}$ alkoxy) optionally substituted by
   phenyl optionally substituted by
      halogen (e.g., fluorine atom, chlorine atom),
      alkyl (e.g., $C_{1-11}$ alkyl).
      haloalkoxy (e.g., halo $C_{1-4}$ alkoxy (preferably, trifluoromethoxy)) or
      phenyl, or
   cycloalkyl (e.g., $C_{3-6}$ cycloalkyl),
n is 1,
$L^1$ is a single bond,
Z is oxygen or $NR^5$, and
$R^2$, $R^3$, $R^4$, and $R^5$ are each the aforementioned (i)'-1, (i)'-2, or (i)'-4 (preferably, the aforementioned (i)'-1, or (i)'-4).

[Compound (IF)]
Compound (I) wherein
X is oxygen or sulfur,
Y is oxygen,
Q is a group represented by the aforementioned formula (A-1),
ring A is pyridine or pyrimidine,
$R^1$ is a group represented by the aforementioned formula (A-2),
ring B is benzene,
$R^7$ is
halogen (e.g., fluorine atom, chlorine atom);
alkyl (e.g., $C_{1-11}$ alkyl) optionally substituted by
   halogen (e.g., fluorine atom, chlorine atom),
   cycloalkyl (e.g., $C_{3-6}$ cycloalkyl), or
   phenyl optionally substituted by alkyl (e.g., alkyl (preferably, methyl));
cycloalkyl (e.g., $C_{3-8}$ cycloalkyl);
phenyl optionally substituted by alkyl (e.g., $C_{1-11}$ alkyl); or
alkoxy (e.g., $C_{1-11}$ alkoxy) optionally substituted by
   phenyl optionally substituted by
      halogen (e.g., fluorine atom, chlorine atom),
      haloalkoxy (e.g., halo $C_{1-4}$ alkoxy (preferably, trifluoromethoxy)) or
      phenyl, or
   cycloalkyl (e.g., $C_{3-6}$ cycloalkyl),
($R^7$ is preferably
halogen (e.g., fluorine atom, chlorine atom);
alkyl (e.g., $C_{1-11}$ alkyl) optionally substituted by
   halogen (e.g., fluorine atom, chlorine atom), or
   cycloalkyl (e.g., $C_{3-6}$ cycloalkyl);
cycloalkyl (e.g., $C_{3-6}$ cycloalkyl);
phenyl optionally substituted by alkyl (e.g., $C_{1-11}$ alkyl); or
alkoxy (e.g., $C_{1-11}$ alkoxy) optionally substituted by
   phenyl optionally substituted by
      halogen (e.g., fluorine atom, chlorine atom),
      haloalkoxy (e.g., halo $C_{1-4}$ alkoxy (preferably, trifluoromethoxy)) or
      phenyl, or
   cycloalkyl (e.g., $C_{3-6}$ cycloalkyl), more preferably,
alkoxy (e.g., $C_{1-11}$ alkoxy) optionally substituted by
phenyl optionally substituted by
   halogen (e.g., fluorine atom, chlorine atom),
   haloalkoxy (e.g., halo $C_{1-4}$ alkoxy (preferably, trifluoromethoxy)) or
   phenyl, or
cycloalkyl (e.g., $C_{3-6}$ cycloalkyl)),
n is 1,
$L^1$ is a single bond,
Z is $NR^5$, and
$R^5$ is hydrogen, $R^2$ is hydrogen, and one of $R^3$ and $R^4$ is hydrogen, and the other is hydrogen or alkyl (e.g., $C_{1-4}$ alkyl (preferably, methyl)), or bonded to $R^2$ to form, together with a carbon atom bonded to $R^3$ and $R^4$ and a carbon atom bonded to $R^2$, cycloalkane (e.g., $C_{3-6}$ cycloalkane (preferably, cyclopentane, cyclohexane)).

[Compound (IG)]
Compound (I) wherein
X is oxygen or sulfur,
Y is oxygen,
Q is a group represented by the aforementioned formula (A-1),
ring A is pyridine,
$R^1$ is a group represented by the aforementioned formula (A-2),
ring B is benzene,
$R^7$ is
alkyl (e.g., $C_{1-11}$ alkyl);
cycloalkyl (e.g., $C_{3-6}$ cycloalkyl);
phenyl; or,
alkoxy (e.g., $C_{1-11}$ alkoxy) ($R^7$ is preferably alkoxy (e.g., $C_{1-11}$ alkoxy)),
n is 1,
$L^1$ is a single bond,
Z is $NR^5$, and
$R^5$ is hydrogen, $R^2$ is hydrogen, and one of $R^3$ and $R^4$ is hydrogen, and the other is hydrogen or alkyl (e.g., $C_{1-4}$ alkyl (preferably, methyl)), or bonded to $R^2$ to form, together with a carbon atom bonded to $R^3$ and $R^4$ and a carbon atom bonded to $R^2$, cycloalkane (e.g., $C_{3-6}$ cycloalkane (preferably, cyclopentane, cyclohexane)).

[Compound (IH)]
Compound (I) wherein
X is oxygen or sulfur,
Y is oxygen, $CH_2$, or —O'$CH_2$—*(wherein*denotes a binding position with a phosphorus atom),
Q is —C(=O)—, Z is $NR^5$, $R^1$ is a group represented by the aforementioned formula (A-2), ring B is cycloalkane (e.g., $C_{3-8}$ cycloalkane (preferably, $C_{3-6}$ cycloalkane (e.g., cyclopropane)), or benzene, $R^7$ in the number of n are each independently halogen (e.g., fluorine atom, chlorine atom);

cyano;

alkyl (e.g., $C_{1-11}$ alkyl) optionally substituted by
halogen (e.g., fluorine atom, chlorine atom),
cycloalkyl (e.g., $C_{3-8}$ cycloalkyl), or
phenyl optionally substituted by alkyl (e.g., $C_{1-11}$ alkyl);

cycloalkyl (e.g., $C_{3-8}$ cycloalkyl) optionally substituted by alkyl (e.g., $C_{1-4}$ alkyl);

aromatic hydrocarbon group (e.g., phenyl) optionally substituted by
alkoxy (e.g., $C_{1-4}$ alkoxy) optionally substituted by phenyl or
alkyl (e.g., $C_{1-11}$ alkyl); or alkoxy (e.g., $C_{1-11}$ alkoxy) optionally substituted by
phenyl optionally substituted by
halogen (e.g., fluorine atom, chlorine atom),
alkyl (e.g., $C_{1-4}$ alkyl),
haloalkoxy (e.g., halo $C_{1-4}$ alkoxy (preferably, trifluoromethoxy)) or
phenyl, or
cycloalkyl (e.g., $C_{3-8}$ cycloalkyl) optionally substituted by alkyl (e.g., $C_{1-4}$ alkyl), n is 1 or 2, $L^1$ is a single bond, $—R^6—$, $—R^6N—$ (denotes a binding position with Q), $—R^6O—$, or $—OR^6—$, $R^6$ is alkylene (e.g., $C_{1-11}$ alkylene) optionally substituted by alkyl (e.g., $C_{1-4}$ alkyl), and $R^2$, $R^3$, $R^4$, and $R^5$ are each preferably any of the following (ii)'-1 to (ii)'-4;

(ii)'-1:

$R^2$ is hydrogen, or alkyl (e.g., $C_{1-6}$ alkyl), $R^3$ and $R^4$ are each independently hydrogen, or alkyl (e.g., $C_{1-6}$ alkyl) optionally substituted by hydroxy or alkoxy (e.g., $C_{1-6}$ alkoxy), and $R^5$ is optionally substituted alkyl (e.g., $C_{1-6}$ alkyl), and the substituent of the optionally substituted alkyl is
hydroxy;
alkoxy (e.g., $C_{1-6}$ alkoxy);
amino optionally substituted by alkyl (e.g., $C_{1-6}$ alkyl) or alkylsulfonyl (e.g., $C_{1-6}$ alkylsulfonyl);
phenyl optionally substituted 1 or 2 substituents selected independently from the group consisting of
hydroxy,
halogen,
alkoxy (e.g., $C_{1-6}$ alkoxy),
amino optionally substituted by alkyl (e.g., $C_{1-6}$ alkyl) or alkylsulfonyl (e.g., $C_{1-6}$ alkylsulfonyl),
alkyl (e.g., $C_{1-6}$ alkyl) optionally substituted by hydroxy or alkoxy (e.g., $C_{1-6}$ alkoxy), and
alkylaminosulfonyl (e.g., $C_{1-6}$ alkylaminosulfonyl); or
an aromatic heterocyclic group (e.g., 5- or 6-membered monocyclic aromatic heterocyclic group) optionally substituted by 1 or 2 substituents selected independently from the group consisting of
hydroxy,
halogen,
alkoxy (e.g., $C_{1-6}$ alkoxy),
amino optionally substituted by alkyl (e.g., $C_{1-6}$ alkyl) or alkylsulfonyl (e.g., $C_{1-6}$ alkylsulfonyl),
alkyl (e.g., $C_{1-6}$ alkyl) optionally substituted by hydroxy or alkoxy (e.g., $C_{1-6}$ alkoxy), and
alkylaminosulfonyl (e.g., $C_{1-6}$ alkylaminosulfonyl), or (ii)'-2:

$R^2$ is hydrogen, or alkyl (e.g., $C_{1-6}$ alkyl), and one of $R^3$ and $R^4$ is hydrogen, or alkyl (e.g., $C_{1-6}$ alkyl) optionally substituted by hydroxy or alkoxy (e.g., $C_{1-6}$ alkoxy), and the other is bonded to $R^5$ to form, together with a carbon atom bonded to $R^3$ and $R^4$ and a nitrogen atom bonded to $R^5$, a cyclic amine (e.g., saturated 3- to 7-membered monocyclic nitrogen-containing non-aromatic heterocycle) optionally substituted by
hydroxy,
alkoxy (e.g., $C_{1-6}$ alkoxy), or
alkyl (e.g., $C_{1-6}$ alkyl) optionally substituted by hydroxy or alkoxy (e.g., $C_{1-6}$ alkoxy), or (ii)'-3:

$R^3$ and $R^4$ are each independently hydrogen, or alkyl (e.g., $C_{1-6}$ alkyl) optionally substituted by hydroxy or alkoxy (e.g., $C_{1-6}$ alkoxy), and $R^2$ is bonded to $R^5$ to form, together with a carbon atom bonded to $R^2$ and a nitrogen atom bonded to $R^5$, a cyclic amine (e.g., saturated 3- to 7-membered monocyclic nitrogen-containing non-aromatic heterocycle) optionally substituted by hydroxy,
alkoxy (e.g., $C_{1-6}$ alkoxy), or
alkyl (e.g., $C_{1-6}$ alkyl) optionally substituted by hydroxy or alkoxy (e.g., $C_{1-6}$ alkoxy), or (ii)'-4:

$R^5$ is optionally substituted alkyl (e.g., $C_{1-6}$ alkyl), and the substituent of the optionally substituted alkyl is
hydroxy;
alkoxy (e.g., $C_{1-6}$ alkoxy);
amino optionally substituted by alkyl (e.g., $C_{1-6}$ alkyl) or alkylsulfonyl (e.g., $C_{1-6}$ alkylsulfonyl);
phenyl optionally substituted 1 or 2 substituents selected independently from the group consisting of
hydroxy,
halogen,
alkoxy (e.g., $C_{1-6}$ alkoxy),
amino optionally substituted by alkyl (e.g., $C_{1-6}$ alkyl) or alkylsulfonyl (e.g., $C_{1-6}$ alkylsulfonyl),
alkyl (e.g., $C_{1-6}$ alkyl) optionally substituted by hydroxy or alkoxy (e.g., $C_{1-6}$ alkoxy), and
alkylaminosulfonyl (e.g., $C_{1-6}$ alkylaminosulfonyl); or
an aromatic heterocyclic group (e.g., 5- or 6-membered monocyclic aromatic heterocyclic group) optionally substituted by 1 or 2 substituents selected independently from the group consisting of
hydroxy,
halogen,
alkoxy (e.g., $C_{1-6}$ alkoxy),
amino optionally substituted by alkyl (e.g., $C_{1-6}$ alkyl) or alkylsulfonyl (e.g., $C_{1-6}$ alkylsulfonyl),
alkyl (e.g., $C_{1-6}$ alkyl) optionally substituted by hydroxy or alkoxy (e.g., $C_{1-6}$ alkoxy), and
alkylaminosulfonyl (e.g., $C_{1-6}$ alkylaminosulfonyl), $R^2$ is hydrogen or alkyl (e.g., $C_{1-6}$ alkyl), and one of $R^3$ and $R^4$ is hydrogen, or alkyl (e.g., $C_{1-6}$ alkyl) optionally substituted by hydroxy or alkoxy (e.g., $C_{1-6}$ alkoxy), and the other is bonded to $R^2$ to form, together with a carbon atom bonded to $R^3$ and $R^4$ and a carbon atom bonded to $R^2$, cycloalkane (e.g., $C_{3-8}$ cycloalkane (preferably, cyclopentane, cyclohexane)) optionally substituted by
hydroxy,
alkoxy (e.g., $C_{1-6}$ alkoxy, or
alkyl (e.g., $C_{1-6}$ alkyl) optionally substituted by hydroxy or alkoxy (e.g., $C_{1-6}$ alkoxy) (preferably, $R^2$, $R^3$, $R^4$, and $R^5$ are each preferably the aforementioned (ii)'-1 or (ii)'-2).

[Compound (IJ)]

Compound (I) wherein
X is oxygen,
Y is oxygen,
Q is —C(=O)—,
Z is $NR^5$,
$R^1$ is a group represented by the aforementioned formula (A-2),
ring B is cycloalkane (e.g., $C_{3-8}$ cycloalkane (preferably, $C_{3-6}$ cycloalkane (e.g., cyclopropane)), or benzene,
$R^7$ in the number of n are each independently halogen (e.g., fluorine atom, chlorine atom);
alkyl (e.g., $C_{1-11}$ alkyl) optionally substituted by
halogen (e.g., fluorine atom, chlorine atom),
cycloalkyl (e.g., $C_{3-8}$ cycloalkyl), or
phenyl optionally substituted by alkyl (e.g., $C_{1-11}$ alkyl);
cycloalkyl (e.g., $C_{3-8}$ cycloalkyl) optionally substituted by alkyl (e.g., $C_{1-4}$ alkyl);
aromatic hydrocarbon group (e.g., phenyl) optionally substituted by
alkoxy (e.g., $C_{1-4}$ alkoxy) optionally substituted by phenyl or
alkyl (e.g., $C_{1-11}$ alkyl); or
alkoxy (e.g., $C_{1-11}$ alkoxy) optionally substituted by
phenyl optionally substituted by
halogen (e.g., fluorine atom, chlorine atom),
alkyl (e.g., $C_{1-4}$ alkyl),
haloalkoxy (e.g., halo $C_{1-4}$ alkoxy (preferably, trifluoromethoxy)) or
phenyl, or
cycloalkyl (e.g., $C_{3-8}$ cycloalkyl) optionally substituted by alkyl (e.g., $C_{1-4}$ alkyl), ($R^7$ in the number of n is preferably halogen (e.g., fluorine atom, chlorine atom);
alkyl (e.g., $C_{1-11}$ alkyl) optionally substituted by
halogen (e.g., fluorine atom, chlorine atom),
cycloalkyl (e.g., $C_{3-6}$ cycloalkyl), or
phenyl optionally substituted by alkyl (e.g., $C_{1-4}$ alkyl (preferably, methyl));
cycloalkyl (e.g., $C_{3-6}$ cycloalkyl);
phenyl optionally substituted by alkyl (e.g., $C_{1-11}$ alkyl); or
alkoxy (e.g., $C_{1-11}$ alkoxy) optionally substituted by
phenyl optionally substituted by
halogen (e.g., fluorine atom, chlorine atom),
alkyl (e.g., $C_{1-4}$ alkyl),
haloalkoxy (e.g., halo $C_{1-4}$ alkoxy (preferably, trifluoromethoxy)) or
phenyl, or
cycloalkyl (e.g., $C_{3-6}$ cycloalkyl),
n is 1 or 2,
$L^1$ is a single bond, —$R^6$—, or —$R^6O$—,
$R^6$ is alkylene (e.g., $C_{1-11}$ alkylene), and
$R^2$, $R^3$, $R^4$, and $R^5$ are each preferably the aforementioned (ii)''-1 or (ii)''-2;

(ii)''-1:
$R^2$ is hydrogen,
$R^3$ and $R^4$ are each independently hydrogen or alkyl (e.g., $C_{1-4}$ alkyl), and
$R^5$ is
hydroxy;
alkoxy (e.g., $C_{1-4}$ alkoxy);
amino optionally substituted by alkyl (e.g., $C_{1-4}$ alkyl) or alkylsulfonyl (e.g., $C_{1-4}$ alkylsulfonyl);
phenyl optionally substituted 1 or 2 substituents selected independently from the group consisting of
hydroxy,
halogen,
alkoxy (e.g., $C_{1-4}$ alkoxy),
amino optionally substituted by alkyl (e.g., $C_{1-4}$ alkyl) or alkylsulfonyl (e.g., $C_{1-4}$ alkylsulfonyl),
alkyl (e.g., $C_{1-4}$ alkyl) optionally substituted by hydroxy or alkoxy (e.g., $C_{1-4}$ alkoxy), and
alkylaminosulfonyl (e.g., $C_{1-4}$ alkylaminosulfonyl); or
a 5- or 6-membered monocyclic aromatic heterocyclic group (preferably, pyridyl, thiazolyl, isothiazolyl, or pyridazinyl) optionally substituted by 1 or 2 substituents selected independently from the group consisting of
hydroxy,
halogen,
alkoxy (e.g., $C_{1-4}$ alkoxy).
amino optionally substituted by alkyl (e.g., $C_{1-4}$ alkyl) or alkylsulfonyl (e.g., alkylsulfonyl),
alkyl (e.g., $C_{1-4}$ alkyl) optionally substituted by hydroxy or alkoxy (e.g., $C_{1-4}$ alkoxy), and
alkylaminosulfonyl (e.g., $C_{1-4}$ alkylaminosulfonyl),
or (ii)''-2:
$R^2$ is hydrogen or alkyl (e.g., $C_{1-4}$ alkyl), and
one of $R^3$ and $R^4$ is hydrogen, and the other is bonded to $R^5$ to form, together with, a carbon atom bonded to $R^3$ and $R^4$, and a nitrogen atom bonded to $R^5$, azetidine, pyrrolidine or piperidine each optionally substituted by
hydroxy,
alkoxy (e.g., $C_{1-4}$ alkoxy), or
alkyl (e.g., $C_{1-4}$ alkyl) optionally substituted by hydroxy or alkoxy (e.g., $C_{1-4}$ alkoxy).

[Compound (IK)]

Compound (I) wherein
X is oxygen,
Y is oxygen,
Q is —C(=O)—,
Z is $NR^5$,
$R^1$ is a group represented by the aforementioned formula (A-2),
ring B is cycloalkane (e.g., $C_{3-8}$ cycloalkane (preferably, $C_{3-6}$ cycloalkane (e.g., cyclopropane)) or benzene,
$R^7$ in the number of n are each independently halogen (e.g., fluorine atom, chlorine atom);
alkyl (e.g., alkyl) optionally substituted by
halogen (e.g., fluorine atom, chlorine atom),
cycloalkyl (e.g., $C_{3-8}$ cycloalkyl), or
phenyl optionally substituted by alkyl (e.g., $C_{1-11}$ alkyl); cycloalkyl (e.g., $C_{3-8}$ cycloalkyl) optionally substituted by alkyl (e.g., $C_{1-4}$ alkyl);
aromatic hydrocarbon group (e.g., phenyl) optionally substituted by
alkoxy (e.g., $C_{1-4}$ alkoxy) optionally substituted by phenyl or
alkyl (e.g., $C_{1-11}$ alkyl); or
alkoxy (e.g., $C_{1-11}$ alkoxy) optionally substituted by
phenyl optionally substituted by
halogen (e.g., fluorine atom, chlorine atom), alkyl (e.g., $C_{1-4}$ alkyl),
haloalkoxy (e.g., halo $C_{1-4}$ alkoxy (preferably, trifluoromethoxy)) or
phenyl, or
cycloalkyl (e.g., $C_{3-8}$ cycloalkyl) optionally substituted by alkyl (e.g., $C_{1-4}$ alkyl), ($R^7$ in the number of n is preferably halogen (e.g., fluorine atom, chlorine atom);
alkyl (e.g., $C_{1-11}$ alkyl) optionally substituted by
halogen (e.g., fluorine atom, chlorine atom),
cycloalkyl (e.g., $C_{3-6}$ cycloalkyl), or
phenyl optionally substituted by alkyl (e.g., $C_{1-4}$ alkyl (preferably, methyl));
cycloalkyl (e.g., $C_{3-8}$ cycloalkyl);
phenyl optionally substituted by alkyl (e.g., alkyl); or
alkoxy (e.g., $C_{1-11}$ alkoxy) optionally substituted by
phenyl optionally substituted by
halogen (e.g., fluorine atom, chlorine atom),
haloalkoxy (e.g., halo $C_{1-4}$ alkoxy (preferably, trifluoromethoxy)) or
phenyl, or
cycloalkyl (e.g., $C_{3-6}$ cycloalkyl),
n is 1 or 2,
$L^1$ is a single bond, —$R^6$—, or —$R^6O$—* (wherein*denotes a binding position with Q),
$R^6$ is alkylene (e.g., $C_{1-11}$ alkylene),
$R^2$ is hydrogen or alkyl (e.g., $C_{1-4}$ alkyl), and
one of $R^3$ and $R^4$ is hydrogen, and the other is bonded to $R^5$ to form, together with a carbon atom bonded to $R^3$ and $R^4$, and a nitrogen atom bonded to $R^5$, azetidine, pyrrolidine or piperidine, each optionally substituted by
hydroxy,
alkoxy (e.g., $C_{1-4}$ alkoxy), or
alkyl (e.g., $C_{1-4}$ alkyl) optionally substituted by hydroxy or alkoxy (e.g., $C_{1-4}$ alkoxy).

[Compound (IL)]
Compound (I) wherein
X is oxygen,
Y is oxygen,
Q is —C(=O)—,
Z is $NR^5$,
$R^1$ is a group represented by the aforementioned formula (A-2),
ring B is cycloalkane (e.g., $C_{3-8}$ cycloalkane (preferably, $C_{3-6}$ cycloalkane (e.g., cyclopropane)), or benzene,
$R^7$ in the number of n are each independently halogen (e.g., fluorine atom, chlorine atom);
alkyl (e.g., $C_{1-11}$ alkyl) optionally substituted by
halogen (e.g., fluorine atom, chlorine atom),
cycloalkyl (e.g., $C_{3-8}$ cycloalkyl), or
phenyl optionally substituted by alkyl (e.g., $C_{1-11}$ alkyl);
cycloalkyl (e.g., $C_{3-8}$ cycloalkyl) optionally substituted by alkyl (e.g., $C_{1-4}$ alkyl);
aromatic hydrocarbon group (e.g., phenyl) optionally substituted by
alkoxy (e.g., $C_{1-4}$ alkoxy) optionally substituted by phenyl or
alkyl (e.g., $C_{1-11}$ alkyl); or
alkoxy (e.g., $C_{1-11}$ alkoxy) optionally substituted by
phenyl optionally substituted by
halogen (e.g., fluorine atom, chlorine atom),
alkyl (e.g., $C_{1-4}$ alkyl),
haloalkoxy (e.g., halo $C_{1-4}$ alkoxy (preferably, trifluoromethoxy)) or
phenyl, or
cycloalkyl (e.g., $C_{3-8}$ cycloalkyl) optionally substituted by alkyl (e.g., $C_{1-4}$ alkyl), ($R^7$ in the number of n is preferably halogen (e.g., fluorine atom, chlorine atom); alkyl (e.g., $C_{1-11}$ alkyl) optionally substituted by
halogen (e.g., fluorine atom, chlorine atom),
cycloalkyl (e.g., $C_{3-7}$ cycloalkyl), or
phenyl optionally substituted by alkyl (e.g., $C_{1-4}$ alkyl (preferably, methyl));
cycloalkyl (e.g., $C_{3-6}$ cycloalkyl);
phenyl optionally substituted by alkyl (e.g., $C_{1-11}$ alkyl); or
alkoxy (e.g., $C_{1-11}$ alkoxy) optionally substituted by
phenyl optionally substituted by
halogen (e.g., fluorine atom, chlorine atom),
haloalkoxy (e.g., halo $C_{1-4}$ alkoxy (preferably, trifluoromethoxy)) or
phenyl, or
cycloalkyl (e.g., $C_{3-6}$ cycloalkyl),
n is 1 or 2,
$L^1$ is a single bond, —$R^6$—, or —$R^6O$—,
$R^6$ is alkylene (e.g., $C_{1-11}$ alkylene),
$R^2$ is hydrogen, and
one of $R^3$ and $R^4$ is hydrogen, and the other is bonded to $R^5$ to form, together with a carbon atom bonded to $R^3$ and $R^4$, and a nitrogen atom bonded to $R^5$, azetidine optionally substituted by
hydroxy,
alkoxy (e.g., $C_{1-4}$ alkoxy), or
alkyl (e.g., $C_{1-4}$ alkyl) optionally substituted by hydroxy or
alkoxy (e.g., $C_{1-4}$ alkoxy).

[Compound (IM)]
Compound (I) wherein
X is oxygen,
Y is oxygen,
Q is —C(=O)—,
Z is $NR^5$,
$R^1$ is a group represented by the aforementioned formula (A-2),
ring B is benzene,
$R^7$ is
alkyl (e.g., $C_{1-11}$ alkyl);
cycloalkyl (e.g., $C_{3-6}$ cycloalkyl);
phenyl; or
alkoxy (e.g., $C_{1-11}$ alkoxy).
n is 1,
$L^1$ is —$R^6$—,
$R^6$ is alkylene (e.g., $C_{1-11}$ alkylene).
$R^2$ is hydrogen, and
one of $R^3$ and $R^4$ is hydrogen, and the other is bonded to $R^5$ to form, together with a carbon atom bonded to $R^3$ and $R^4$, and a nitrogen atom bonded to $R^5$, azetidine optionally substituted by
hydroxy,
alkoxy (e.g., $C_{1-4}$ alkoxy), or
alkyl (e.g., $C_{1-4}$ alkyl) optionally substituted by hydroxy or alkoxy (e.g., $C_{1-4}$ alkoxy).

[Compound (IN)]
Compound (I) wherein
Q is —C(=O)—,
X is oxygen,
Y is oxygen,
Z is $NR^5$,
$R^1$ is a group represented by the aforementioned formula (A-2),
ring B is benzene, $R^7$ is halogen (e.g., fluorine atom, chlorine atom);
alkyl (e.g., $C_{1-11}$ alkyl) optionally substituted by
  halogen (e.g., fluorine atom, chlorine atom),
  cycloalkyl (e.g., $C_{3-8}$ cycloalkyl), or
  phenyl (e.g., $C_{1-11}$ alkylphenyl) optionally substituted by alkyl;
cycloalkyl (e.g., $C_{3-8}$ cycloalkyl);
aromatic hydrocarbon group (e.g., phenyl) optionally substituted by
  alkoxy (e.g., $C_{1-4}$ alkoxy) optionally substituted by
    phenyl or
    alkyl (e.g., $C_{1-11}$ alkyl); or
alkoxy (e.g., $C_{1-11}$ alkoxy) optionally substituted by
  phenyl optionally substituted by
    halogen (e.g., fluorine atom, chlorine atom),
    alkyl (e.g., $C_{1-4}$ alkyl).
    haloalkoxy (e.g., halo $C_{1-4}$ alkoxy (preferably, trifluoromethoxy)) or
    phenyl, or
    cycloalkyl (e.g., $C_{3-8}$ cycloalkyl), ($R^7$ in the number of n is preferably
halogen (e.g., fluorine atom, chlorine atom);
alkyl (e.g., $C_{1-11}$ alkyl) optionally substituted by
  halogen (e.g., fluorine atom, chlorine atom),
  cycloalkyl (e.g., $C_{3-6}$ cycloalkyl), or
  phenyl optionally substituted by alkyl (e.g., $C_{1-4}$ alkyl (preferably, methyl));
cycloalkyl (e.g., $C_{3-6}$ cycloalkyl);
phenyl optionally substituted by alkyl (e.g., $C_{1-11}$ alkyl); or
alkoxy (e.g., $C_{1-11}$ alkoxy) optionally substituted by
  phenyl optionally substituted by
    halogen (e.g., fluorine atom, chlorine atom),
    alkyl (e.g., $C_{1-4}$ alkyl),
    haloalkoxy (e.g., halo $C_{1-4}$ alkoxy (preferably, trifluoromethoxy)) or
    phenyl, or
    cycloalkyl (e.g., $C_{3-6}$ cycloalkyl),
n is 1 or 2 (preferably, 1),
$L^1$ is a single bond, —$R^6$—, or —$R^6$O*(wherein * denotes a binding position with Q),
$R^6$ is alkylene,
$R^2$ is hydrogen,
$R^3$ and $R^4$ are each independently hydrogen, or alkyl, and
$R^5$ is alkyl (e.g., $C_{1-4}$ alkyl (preferably, methyl)) optionally substituted by
  phenyl optionally substituted 1 or 2 substituents selected independently from the group consisting of
    hydroxy,
    halogen,
    alkoxy (e.g., $C_{1-4}$ alkoxy),
    amino optionally substituted by alkyl (e.g., $C_{1-4}$ alkyl) or alkylsulfonyl (e.g., $C_{1-4}$ alkylsulfonyl),
    alkyl (e.g., $C_{1-4}$ alkyl) optionally substituted by hydroxy or alkoxy (e.g., $C_{1-4}$ alkoxy), and
    alkylaminosulfonyl (e.g., $C_{1-4}$ alkylaminosulfonyl); or
  a 5- or 6-membered monocyclic aromatic heterocyclic group (preferably, pyridyl, thiazolyl, isothiazolyl, or pyridazinyl) optionally substituted by 1 or 2 substituents selected independently from the group consisting of
    hydroxy,
    halogen,
    alkoxy (e.g., $C_{1-4}$ alkoxy),
    amino optionally substituted by alkyl (e.g., $C_{1-4}$ alkyl) or alkylsulfonyl (e.g., $C_{1-4}$ alkylsulfonyl),
    alkyl (e.g., $C_{1-4}$ alkyl) optionally substituted by hydroxy or alkoxy (e.g., $C_{1-4}$ alkoxy), and
    alkylaminosulfonyl (e.g., $C_{1-4}$ alkylaminosulfonyl).

[Compound (10)]
Compound (I) wherein
X is oxygen,
Y is oxygen,
Q is —C(=O)—,
Z is $NR^5$,
$R^1$ is a group represented by the aforementioned formula (A-2),
ring B is benzene,
$R^7$ is
  alkyl (e.g., $C_{1-11}$ alkyl);
  cycloalkyl (e.g., $C_{3-6}$ cycloalkyl);
  phenyl; or
  alkoxy (e.g., $C_{1-11}$ alkoxy).
n is 1,
$L^1$ is —$R^6$—,
$R^6$ is alkylene (e.g., $C_{1-11}$ alkylene),
$R^2$ is hydrogen,
$R^3$ and $R^4$ are each hydrogen, and
$R^5$ is alkyl (e.g., methyl or ethyl (preferably, methyl)) optionally substituted by
  phenyl optionally substituted 1 or 2 substituents selected independently from the group consisting of
    hydroxy,
    halogen,
    alkoxy (e.g., $C_{1-4}$ alkoxy),
    amino optionally substituted by alkyl (e.g., $C_{1-4}$ alkyl) or alkylsulfonyl (e.g., $C_{1-4}$ alkylsulfonyl),
    alkyl (e.g., $C_{1-4}$ alkyl) optionally substituted by hydroxy or alkoxy (e.g., $C_{1-4}$ alkoxy), and
    alkylaminosulfonyl (e.g., $C_{1-4}$ alkylaminosulfonyl); or
  pyridyl, thiazolyl, isothiazolyl or pyridazinyl, each optionally substituted by 1 or 2 substituents selected independently from the group consisting of
    hydroxy,
    halogen,
    alkoxy (e.g., $C_{1-4}$ alkoxy),
    amino optionally substituted by alkyl (e.g., $C_{1-4}$ alkyl) or alkylsulfonyl (e.g., $C_{1-4}$ alkylsulfonyl),
    alkyl (e.g., $C_{1-4}$ alkyl) optionally substituted by hydroxy or alkoxy (e.g., $C_{1-4}$ alkoxy), and
    alkylaminosulfonyl (e.g., $C_{1-4}$ alkylaminosulfonyl).

Specific preferable examples of the compound (I) of the present invention include the compounds of Examples 1-143 described in the following Examples, especially, a compound selected from the group consisting of a. 1-[9-(4-ethylphenyl)nonanoyl]azetidin-3-yl dihydrogen phosphate,
b. 1-{4-[4-(octyloxy)phenyl]butanoyl}azetidin-3-yl dihydrogen phosphate,
c. 1-[8-(3-octylphenyl)octanoyl]azetidin-3-yl dihydrogen phosphate,
d. 1-[9-(4-butylphenyl)nonanoyl]azetidin-3-yl dihydrogen phosphate,
e. 1-[9-(biphenyl-4-yl)nonanoyl]azetidin-3-yl dihydrogen phosphate,
f. 1-[9-(4-tert-butylphenyl)nonanoyl]azetidin-3-yl dihydrogen phosphate,
g. 1-[9-(4-cyclopropylphenyl)nonanoyl]azetidin-3-yl dihydrogen phosphate,
h. 1-[9-(4-cyclohexylphenyl)nonanoyl]azetidin-3-yl dihydrogen phosphate, i. 2-{[9-(4-propylphenyl)nonanoyl](1,3-thiazol-5-yl methyl) amino}ethyl dihydrogen phosphate,
j. 1-[9-(4-hexylphenyl)nonanoyl]azetidin-3-yl dihydrogen phosphate,
k. (2R)-1-({4-[3-(undecyloxy)phenyl]pyridin-2-yl}amino)propan-2-yl dihydrogen phosphate,
l. O-[(2R)-1-({4-[3-(undecyloxy)phenyl]pyridin-2-yl}amino)propan-2-yl] dihydrogen phosphorothioate, and
m. (1S,2R)-2-({4-[3-(undecyloxy)phenyl]pyridin-2-yl}amino)cyclopentyl dihydrogen phosphate, or a pharmacologically acceptable salt thereof is particularly preferable.

When the compound (I) of the present invention has an asymmetric carbon atom in the molecule, it can exist as a plurality of stereoisomers (that is, diastereomeric isomers, optical isomers) based on the asymmetric carbon atom. The present invention encompasses any one of these stereoisomers and a mixture containing a plurality of the stereoisomers at any ratio. In addition, conformational or tautomeric isomers may be produced and the compound (I) of the present invention encompasses such isomers and mixtures thereof.

The compound (I) of the present invention may be a compound labeled or substituted with an isotope (e.g., $^2$H, $^3$H, $^{13}$C, $^{14}$C, $^{15}$N, $^{18}$F, $^{32}$P, $^{35}$S, $^{125}$I, etc.). A compound labeled or substituted with an isotope can be used as a tracer (PET tracer) used in positron emission tomography (PET), and is useful in the fields of medical diagnosis and the like.

Since the compound (I) of the present invention or a pharmacologically acceptable salt thereof has a superior agonistic activity on LPA4 receptors, it is useful for the prophylaxis and/or treatment of diseases associated with angiogenesis abnormalities, diseases associated with vascular disorders, or improvement of prognosis of these. Examples of these disease include solid cancer, pressure ulcer, diabetic necrosis, diabetic nephropathy, diabetic retinopathy, acute nephropathy, cerebral infarction, age-related macular degeneration, rheumatoid arthritis, scleroderma, psoriasis, systemic lupus erythematosus, lung fibrosis, arteriosclerosis obliterans, arteriosclerosis, angina pectoris, myocardial infarction, Buerger disease, brain edema due to infectious disease, hemorrhage due to hemorrhagic virus (Ebola, dengue), acute respiratory distress syndrome and the like.

In addition, the compound (I) of the present invention or a pharmacologically acceptable salt thereof shows high selectivity for LPA4 receptors. Particularly, the compound (I) of the present invention or a pharmacologically acceptable salt thereof shows high selectivity for LPA4 receptors as compared with LPA1 receptors.

The compound (I) of the present invention is converted to a pharmacologically acceptable salt by a known method.

As the salt, a water-soluble salt is preferable.

Examples of the salt include acid addition salt, alkali metal salt, alkaline earth metal salt, ammonium salt, or amine salt and the like.

Examples of the acid addition salt include inorganic acid salts such as hydrochloride, hydrobromide, hydroiodide, sulfate, phosphate, nitrate and the like, and organic acid salts such as acetate, tartrate, benzoate, citrate, methanesulfonate, isethionate, glucuronate, gluconate and the like.

Examples of the alkali metal salt include potassium salt, sodium salt and the like.

Examples of the alkaline earth metal salt include calcium salt, magnesium salt and the like.

Examples of the ammonium salt include ammonium salt, tetramethylammonium salt and the like.

Examples of the amine salt include triethylamine salt, methylamine salt, dimethylamine salt, cyclopentylamine salt, benzylamine salt, phenethylamine salt, piperidine salt, mono ethanolamine salt, diethanolamine salt, tris(hydroxymethyl)aminomethane salt, lysine salt, arginine salt, N-methyl-glucamine salt and the like.

The compound (I) of the present invention or a pharmacologically acceptable salt thereof may be a crystal, and may be a single crystal form or a mixture of plural crystal forms.

The compound (I) of the present invention or a pharmacologically acceptable salt thereof includes intramolecular salts and adducts thereof, solvates and hydrates thereof and the like.

The compound (I) of the present invention may be a prodrug.

A prodrug of the compound (I) of the present invention refers to a compound that is converted to compound (I) by a reaction with an enzyme, gastric acid, and the like in the living body. As a prodrug of the compound (I) of the present invention, a monoester or diester of a phosphoric acid group, wherein the ester functional group preferably has a structure that is easily hydrolyzed or metabolized after administration to patients. Specific examples of such ester functional group of prodrug include $C_{1-6}$ alkylester optionally substituted by an acyloxy group, phenylester, benzylester and the like (Bioorganic Chemistry, 1984; 12: p. 118-129). As the prodrug other than the above-mentioned monoester or diester of a phosphate group, a compound having a group derived from a phosphate group described in Current opinion in investigational drugs, 2006; 7: p. 109-117, J. Med. Chem. 1994; 37: p. 1857-1864, and J. Med. Chem. 2000; 43: p. 4570-4574, and the like can be mentioned.

Other embodiments of the prodrug of compound (I) include the following. When compound (I) has an amino group, a compound in which the amino group is acylated, alkylated, or phosphorylated (e.g., compound (I) wherein the amino group is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, or tert-butylated, etc.); when compound (I) has a hydroxy group, a compound in which the hydroxy group is acylated, alkylated, phosphorylated, or borated (e.g., compound (I) wherein the hydroxy group is acetylated, palmitoylated, propanoylated, pivaloylated, succinylated, fumarylated, alanylated, dimethylaminomethylcarbonylated, etc.); when compound (I) has a carboxy group, a compound in which the carboxy group is esterified or amidated (e.g., compound (I) wherein the carboxy group is ethylesterified, phenylesterified, carboxymethylesterified, dimethylaminomethylesterified, pivaloyloxymethylesterified, 1-{(ethoxycarbonyl)oxy}ethylesterified, phthalidylesterified, (5-methyl-2-oxo-1,3-dioxolen-4-yl)methylesterified, 1-{[(cyclohexyloxy)carbonyl]oxy}ethylesterified, or methylamidated, etc.) and the like. These compounds can be produced by a method known per se. Furthermore, the prodrug of compound (I) may be a hydrate or a non-hydrate. The prodrug of compound (I) may be one that changes to a compound represented by compound (I) under physiological conditions, such as the one described in "Drug Development" Vol. 7 "Molecular Design", p. 163-198 published by HIROKAWA SHOTEN (1990).

(Production Method of Compound (I) of the Present Invention)

The production method of the compound (I) of the present invention or a pharmacologically acceptable salt thereof is explained below.

While typical production methods are described below as examples of the production method of compound (I), the production method is not limited thereto.

The compound (I) can be produced by the method shown in the following production method, Reference Examples and Examples described later, or a method analogous thereto and the like.

Each starting material compound may form a salt as long as it does not inhibit the reaction, and examples of such salt include those similar to the salts of compound (I).

Unless a specific production method is described, a commercially available compound may be easily obtained and used as the starting material compound, or can be produced according to a method known per se or a method similar thereto. Furthermore, the intermediate produced in the following production method may be isolated and purified by a method such as column chromatography, recrystallization, distillation and the like, or may be used in the next step without isolation.

A schematic diagram of the reaction formula of each step in the production of compound (I) is shown below, in which each symbol of the compound in the schemes has the same meaning as described above.

In the present specification, the contents of all the patent documents, non-patent documents, or reference documents expressly cited herein may be cited as part of the present specification.

The compound (I) of the present invention can be produced by the following methods (1) to (14). While these methods and steps may be combined but the production method thereof is not limited thereto.

(Method (1))

This production method is suitable for producing compound (I) wherein X is an oxygen atom and Y is an oxygen atom or —CH$_2$—O—, i.e., the following compound (I-1).

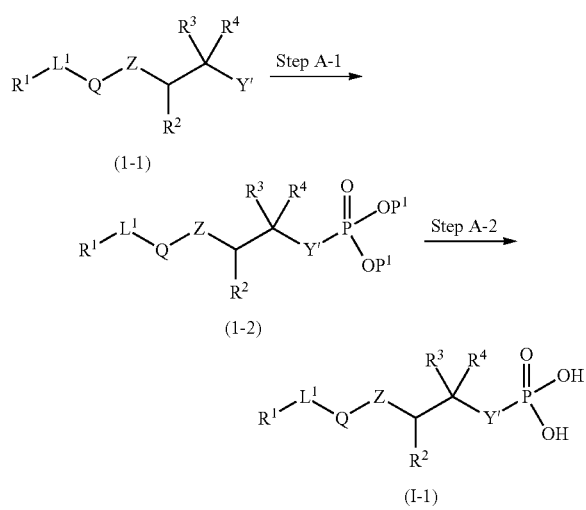

(1-1)

(1-2)

(I-1)

wherein P$^1$ is a protecting group, and the protecting group is not particularly limited as long as it protects a phosphate group. Y' is an oxygen atom or —CH$_2$—O—, and each of other symbols is as defined above.

Step A-1

In this step, compound (1-1) is reacted with a phosphorylating reagent (e.g., phosphite triester, phosphoryl chloride, phosphoramidite and an oxidant, tetrabenzyl pyrophosphate, etc.) to prepare compound (1-2). When phosphite ester is used as a phosphorylating reagent, this step can be performed under nonaqueous conditions, preferably, in a halogen solvent such as dichloromethane and the like and using an organic base such as pyridine, triethylamine and the like and an additive such as carbon tetrabromide and the like. As the reaction conditions, under ice-cooling to 80° C. for about 5-24 hr can be mentioned. After the reaction, purification and the like are performed by conventional methods, whereby the desired product can be obtained. In this reaction, synthesis can also be performed by reacting a conventional phosphorylating reagent (phosphoryl chloride and a base, phosphoramidite and an oxidant, etc.) according to a known method. For example, when phosphoramidite and an oxidant are used, a reaction is performed using phosphoramidite such as di-tert-butyldiisopropyl phosphoramidite and the like in a halogenated solvent such as dichloromethane and the like, an ether solvent such as tetrahydrofuran and the like, a polar solvent such as acetonitrile and the like, or a mixed solvent under ice-cooling to 50° C. for about 10 min-5 hr. A reaction promoter such as 1H-tetrazole and the like can be added to this reaction. For an oxidation reaction of phosphorus subsequent to the phosphorylation, organic peroxide such as m-chloroperbenzoic acid, tert-butyl hydroperoxide and the like and inorganic peroxide such as hydrogen peroxide and the like can be used. The reaction is performed under ice-cooling to 50° C. for about 3 min-1 hr. After the reaction, purification and the like are performed by conventional methods, whereby compound (1-2) can be obtained.

Step A-2

In this step, the compound (I-1) of the present invention is prepared from compound (1-2), and the step can be performed using a general deprotection reaction. Specifically, it can be performed using hydrogenolysis, an acid such as hydrochloric acid, trifluoroacetic acid and the like, or Lewis acid such as trimethylsilyl bromide and the like.

When hydrogenolysis is used for this reaction, for example, this step is performed using a catalyst such as palladium carbon and the like in an alcoholic solvent such as methanol and the like under a hydrogen atmosphere. As the reaction conditions, room temperature –60° C. for about 1-24 hr can be mentioned. The reaction mixture is subjected to filtration, concentration and the like by conventional methods, and purified as necessary by silica gel column chromatography, recrystallization and the like, whereby the compound (I-1) of the present invention can be obtained. When an acid is used for this reaction, the reaction conditions include conditions of stirring with trifluoroacetic acid and dichloromethane at 0° C.-room temperature for about 30 min-6 hr, and conditions of stirring with Lewis acid in an alcoholic solvent such as ethanol and the like or a mixed solvent with water at 0° C.-100° C. for about 30 min-12 hr.

(Method (2))

This production method is suitable for producing compound (I) wherein X is an oxygen atom and Y is CH$_2$, i.e., the following compound (I-2).

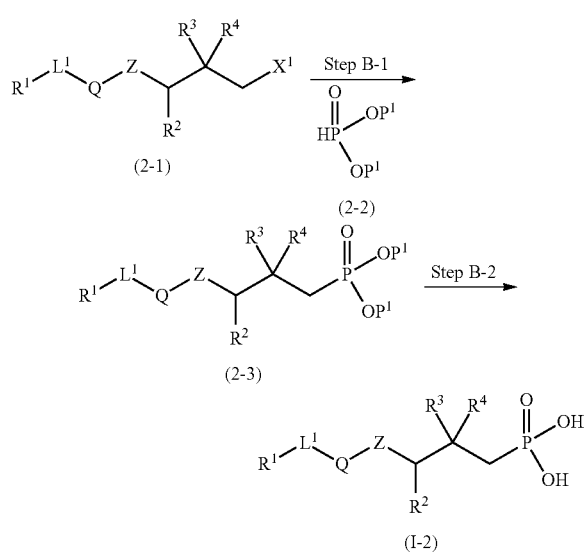

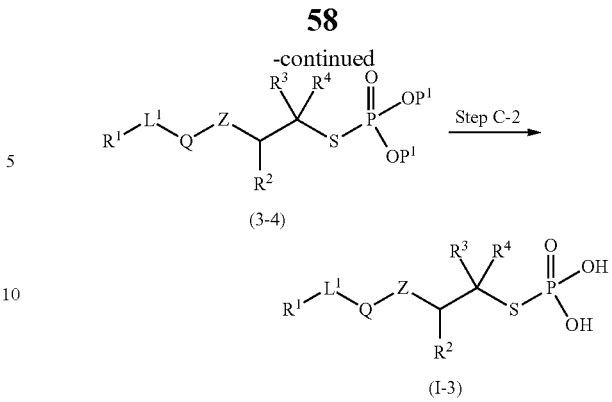

wherein X¹ is a leaving group and is not particularly limited as long as it can be eliminated during reaction with compound (2-2). For example, a halogen atom (specifically, iodine atom, bromine atom, etc.), trifluoromethanesulfonyloxy and the like can be mentioned. Other respective symbols are as defined above.

Step B-1

In this step, compound (2-3) is prepared by reacting compound (2-1) with phosphonic acid (compound (2-2)). For example, it can be performed using a deprotonation reagent such as sodium hydride, n-butyllithium and the like in a solvent such as aprotic solvent, preferably, N,N-dimethylformamide, tetrahydrofuran, toluene and the like. As the reaction conditions, under ice-cooling to 80° C., under heating conditions in some cases, for about 30 min-8 hr can be mentioned. It can also be performed under conditions using an inorganic base such as potassium carbonate, cesium carbonate and the like and an additive such as tetrabutylammonium halide and the like, or conditions using an organic base such as triethylamine, 1,8-diazabicyclo[5.4.0]undec-7-ene and the like. After the reaction, purification and the like are performed by conventional methods, whereby compound (2-3) can be obtained.

Step B-2

In this step, compound (I-2) of the present invention is prepared from compound (2-3). In this step, a method similar to that in the aforementioned step A-2 can be mentioned.

(Method (3))

This production method is suitable for producing compound (I) wherein X is an oxygen atom and Y is a sulfur atom, i.e., the following compound (I-3).

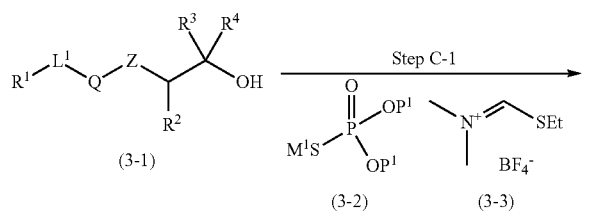

wherein $M^1$ is hydrogen, sodium, or potassium, $P^1$ is a protecting group, and each of other symbols is as defined above.

Step C-1

In this step, phosphorothioate (compound (3-4)) is prepared from compound (3-1). As the reaction conditions, for example, according to the method described in Journal of Organic Chemistry, vol. 82, p. 12735 (2017), conditions using compound (3-2), compound (3-3), and a base such as imidazole and the like in a suitable solvent (toluene, tetrahydrofuran, dioxane, dichloromethane, acetonitrile etc.) at room temperature to 100° C. for about 30 min-12 hr can be mentioned. After the reaction, purification and the like are performed by conventional methods, whereby compound (3-4) can be obtained.

Step C-2

In this step, compound (I-3) of the present invention is prepared from compound (3-4), and the step can be performed using a general deprotection reaction. Specifically, when $P^1$ is alkyl, it can be performed using Lewis acid such as trimethylsilyl bromide and the like, and an acid such as hydrochloric acid, trifluoroacetic acid and the like. As the reaction conditions, in a dichloromethane solvent at room temperature—heating under reflux for about 30 min—a few hours can be mentioned. After quenching with methanol after the reaction, the reaction mixture is subjected to concentration and the like by conventional methods, and purified as necessary by silica gel column chromatography, recrystallization and the like, whereby compound (I-3) of the present invention can be obtained. When $P^1$ is a benzyl group, a method using potassium dihydrogen phosphate and zinc can be mentioned as the reaction conditions.

(Method (4))

This production method is suitable for producing compound (I) wherein X is an oxygen atom and Y is —O—CH₂—, i.e., the following compound (I-4).

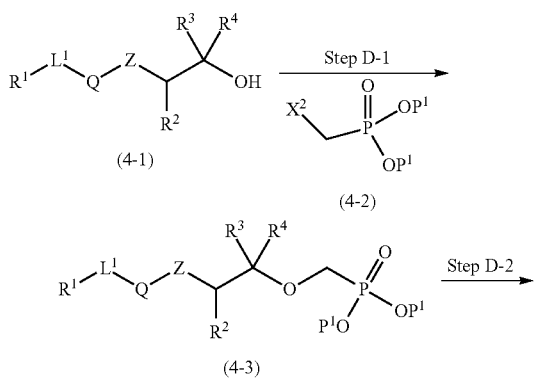

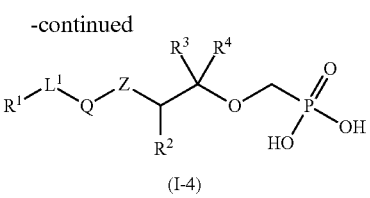

(I-4)

wherein $X^2$ is a leaving group and is not particularly limited as long as it can be eliminated during reaction with compound (4-1). For example, a halogen atom (specifically, iodine atom, bromine atom, chlorine atom, etc.), p-toluenesulfonyloxy, trifluoromethanesulfonyloxy and the like can be mentioned. Other respective symbols are as defined above.

Step D-1

In this step, phosphonate (compound (4-3)) is prepared by reacting compound (4-1) with compound (4-2). For example, it can be performed using a deprotonation reagent such as sodium hydride, n-butyllithium and the like in a solvent such as aprotic solvent, preferably, N,N-dimethylformamide, tetrahydrofuran, toluene and the like. As the reaction conditions, under ice-cooling to 80° C., under heating conditions in some cases, for about 30 min-8 hr can be mentioned. After the reaction, purification and the like are performed by conventional methods, whereby compound (4-3) can be obtained.

Step D-2

In this step, compound (I-4) of the present invention is prepared from compound (4-3). In this step, a method similar to that in the aforementioned step A-2 can be mentioned.

(Method (5))

This production method is suitable for producing compound (I) wherein X is an oxygen atom and Y is NH, i.e., the following compound (I-5).

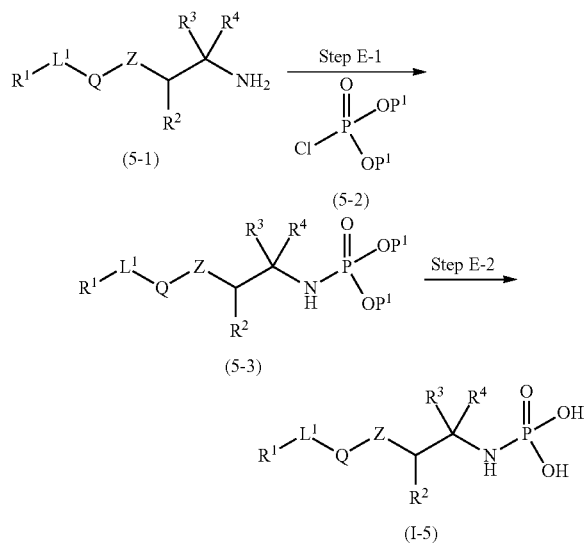

wherein each symbol is as defined above.

Step E-1

In this step, compound (5-3) is prepared by reacting compound (5-1) with chlorophosphoric acid diester (compound (5-2)). For example, it can be performed using an organic base such as triethylamine, diisopropylethylamine, pyridine and the like in a solvent such as an aprotic solvent, preferably, dichloromethane, acetonitrile, tetrahydrofuran and the like. As the reaction conditions, under ice-cooling to 50° C. for about 30 min-8 hr can be mentioned. A reaction promoter such as 1H-tetrazole and the like can be added to this reaction. After the reaction, purification and the like are performed by conventional methods, whereby compound (5-3) can be obtained.

Step E-2

In this step, compound (I-5) of the present invention is prepared from compound (5-3). In this step, a method similar to that in the aforementioned step A-2 can be mentioned.

(Method (6))

This production method is suitable for producing compound (I) wherein X is a sulfur atom, i.e., the following compound (I-6).

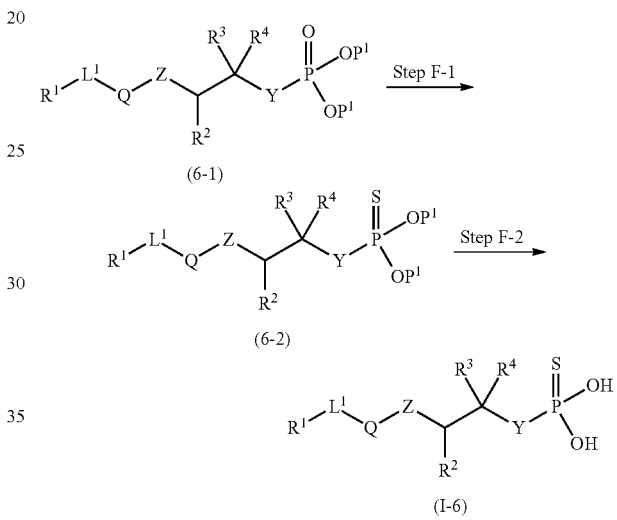

wherein each symbol is as defined above.

Step F-1

In this step, compound (6-1) is converted to compound (6-2) by thiophosphorylation. The thiophosphorylation reaction proceeds using a sulfurizing reagent in an appropriate solvent generally at room temperature to the refluxing temperature of the solvent. While the reaction time varies depending on the starting material and solvent to be used and the reaction temperature, it is generally from about 30 min to about 24 hr. Examples of the sulfurizing reagent include Lawesson reagent, diphosphorus pentasulfide, bis(phenylacetyl)disulfide, and the like. Examples of the solvent include benzene, dichloromethane, 1,2-dichloroethane, acetonitrile, tetrahydrofuran, 1,4-dioxane and the like. After the reaction, purification and the like are performed by conventional methods, whereby compound (6-2) can be obtained.

Step F-2

In this step, compound (I-6) of the present invention is prepared from compound (6-2). In this step, a method similar to that in the aforementioned step A-2 can be mentioned.

(Method (7))

This production method is suitable for producing compound (I) wherein Q is —C(=O)—, Z is oxygen, sulfur, or $NR^5$, and $L^1$ is a single bond, —$R^6$—, —$OR^6$—, —$NHR^6$— or —$SR^6$—, i.e., the following compound (I-7).

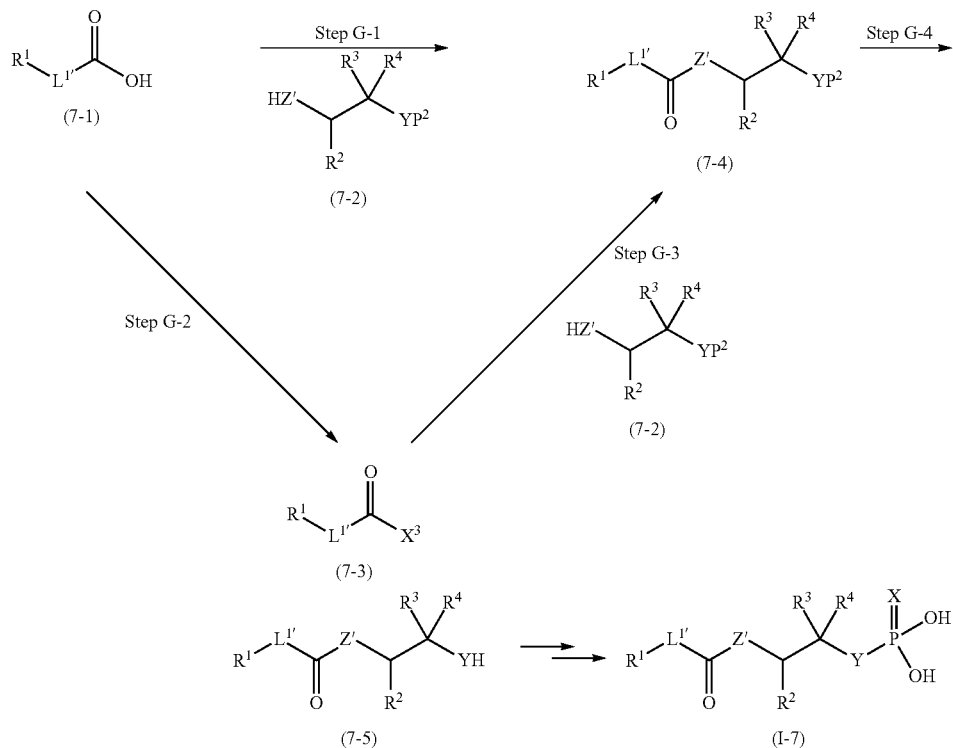

wherein $X^3$ is a chlorine atom or a bromine atom, $P^2$ is hydrogen or a protecting group, and the protecting group is not particularly limited as long as it protects hydroxy, sulfanyl, amino and does not affect other steps. Z' is oxygen, sulfur, or $NR^5$, and $L^{1'}$, is a single bond, $-R^6-$, $-OR^6-$, $-NHR^6-$, or $-SR^6-$. Other respective symbols are as defined above.

Step G-1

In this step, compound (7-4) is obtained by a condensation reaction of compound (7-1) and compound (7-2). The reaction proceeds using a condensing agent in the presence of a suitable base in a suitable solvent at 0° C. to the refluxing temperature of the solvent. While the reaction time varies depending on the starting material and solvent to be used and the reaction temperature, it is generally from about 1 hr to about 24 hr. Examples of the condensing agent include 1-ethyl-3-(3-dimethylaminopropyl)carbodiimide hydrochloride (WSC·HCl), 1-[bis(dimethylamino)methylene]-1H-1,2,3-triazolo[4,5-b]pyridinium 3-oxide hexafluorophosphate (HATU), 4-(4,6-dimethoxy[1.3.5]triazin-2-yl)-4-methylmorpholinium chloride hydrate (DMT-MM), 2-chloro-1-methylpyridinium iodide and the like. Examples of the solvent include methanol, N,N-dimethylformamide, chloroform, dichloromethane, tetrahydrofuran and the like. The reaction is sometimes accelerated by adding 1-hydroxybenzotriazole (HOBt). Examples of the base include triethylamine, N,N-diisopropylethylamine, pyridine and the like.

Step G-2

Compound (7-4) can also be obtained by reacting acid halide (compound (7-3)) with compound (7-2). In this step, compound (7-1) is converted to acid halide (compound (7-3)). The reaction proceeds in an appropriate solvent at generally from 0° C. to the refluxing temperature of the solvent for generally about 1 hr to about 24 hr. Examples of the halogenating agent include thionyl chloride, oxalyl chloride, phenylphosphonyl dichloride and the like. Examples of the base include triethylamine, pyridine and the like. Examples of the solvent include dichloromethane, 1,2-dichloroethane, chloroform, pyridine, toluene and the like.

Step G-3

In this step, compound (7-4) is obtained by reacting compound (7-3) with compound (7-2). The reaction proceeds using a base in a suitable solvent at generally from 0° C. to the refluxing temperature of the solvent. While the reaction time varies depending on the starting material and solvent to be used, the reaction temperature and the like, it is generally from 30 min to 12 hr. Examples of the base include triethylamine, pyridine and the like. Examples of the solvent include dichloromethane, dichloroethane, chloroform, N-methylpyrrolidone, pyridine, toluene and the like.

Step G-4

In this step, compound (7-5) is obtained by deprotection (removal of $P^2$) of compound (7-4). When $P^2$ is a hydrogen atom, this step can be omitted. This step is not particularly limited as long as it is used for the removal of general protecting groups. For example, when $P^2$ is acyl such as acetyl and the like, a method using an inorganic base such as sodium hydroxide and the like in a mixed solvent of an alcoholic solvent and water can be mentioned, and when using an etheric protecting group such as methoxymethyl, tetrahydropyranyl, tert-butyl and the like, and a silyl protecting group such as trimethylsilyl and the like, a method using an acid such as hydrochloric acid, trifluoroacetic acid and the like can be mentioned. When benzyl, substituted benzyl, benzyloxymethyl or the like is used for $P^2$, deprotection can be performed under hydrogenolysis conditions or catalytic hydrogenation conditions. The reaction proceeds in an appropriate solvent generally at room temperature to the refluxing temperature of the solvent, according to the kind of the protecting group. While the reaction time varies depending on the starting material and solvent to be used and the reaction temperature, it is generally from about 1 hr to about 24 hr.

The compound (I-7) of the present invention can be obtained from compound (7-5) by using the conditions of the aforementioned method (1)-(6).

(Method (8))

This production method is suitable for producing compound (I) wherein Q is —C(=O)—, Z is oxygen, sulfur, or NR$^5$, and L$^1$ is NH, oxygen, sulfur, —R$^6$O—, —R$^6$NH—, or —R$^6$S—, i.e., the following compound (I-8).

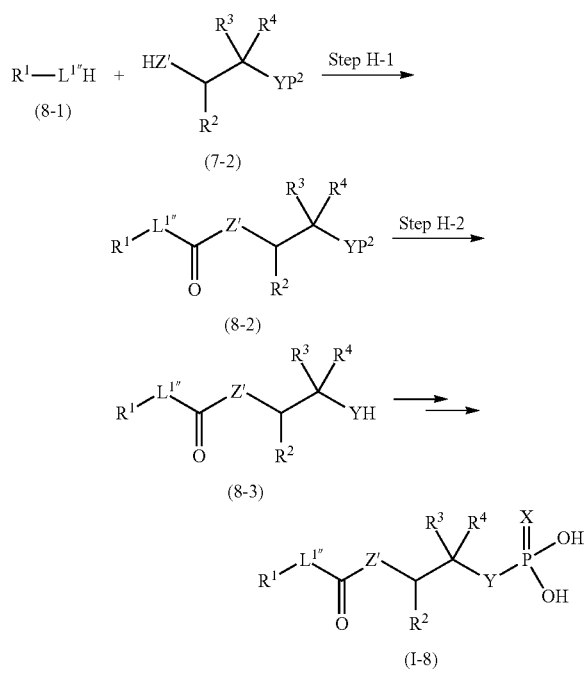

wherein L$^{1''}$ is NH, oxygen, sulfur, —R$^6$)—, —R$^6$NH—, or —R$^6$S—, and other respective symbols are as defined above.

Step H-1

In this step, compound (8-2) is obtained by a condensation reaction of compound (8-1) and compound (7-2). The reaction proceeds using a condensing agent in the presence of a suitable base in a suitable solvent at 0° C. to the refluxing temperature of the solvent. While the reaction time varies depending on the starting material and solvent to be used, and the reaction temperature, it is generally from about 30 min to about 24 hr. Examples of the condensing agent include carbonyldiimidazole (CDI). Examples of the solvent include tetrahydrofuran, N,N-dimethylformamide, dichloromethane, acetonitrile, dioxane and the like. In addition, the reaction may be promoted by using methyliodide according to, for example, the method described in Tetrahedron, vol. 61, p. 7153 (2005). Examples of the base include triethylamine, N,N-diisopropylethylamine, 1,8-diazabicyclo[5.4.0]undec-7-ene (DBU) and the like.

Step H-2

In this step, compound (8-3) is prepared by deprotection (removal of P$^2$) of compound (8-2). In this step, the reaction conditions are the same as those in the aforementioned step G-4.

Compound (1-8) of the present invention can be obtained from compound (8-3) by using the conditions of the aforementioned method (1)-(6).

(Method (9))

This production method is suitable for producing compound (I) wherein Q is —C(=O)—, and Z is NR$^5$ (R$^5$ is optionally substituted alkyl), i.e., the following compound (I-9).

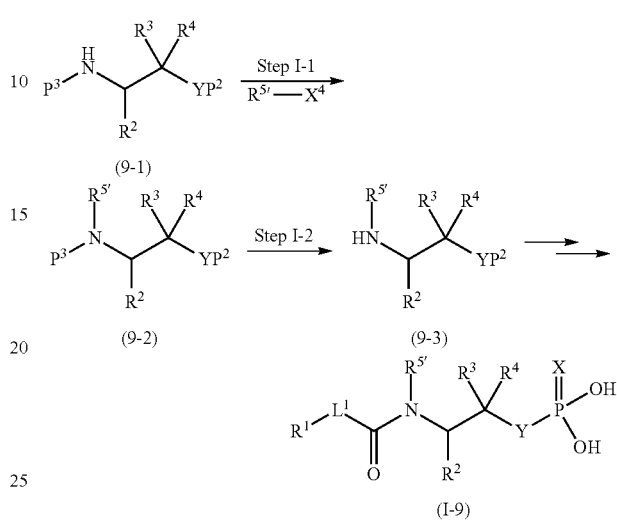

wherein P$^3$ is an amino-protecting group and is not particularly limited as long as it does not affect other steps. R$^{5'}$ is optionally substituted alkyl. X$^4$ is a leaving group and is not particularly limited as long as it can be eliminated during reaction with compound (9-1). For example, a halogen atom (specifically, iodine atom, bromine atom, chlorine atom, etc.), p-toluenesulfonyloxy, trifluoromethanesulfonyloxy and the like can be mentioned. Other respective symbols are as defined above.

Step I-1

In this step, compound (9-2) is obtained by alkylation of compound (9-1). The alkylation reaction proceeds using a base and an alkylating agent (R$^{5'}$—X$^4$) such as alkyl halide and the like in an appropriate solvent at generally 0° C. to the refluxing temperature of the solvent. While the reaction time varies depending on the starting material and solvent to be used and the reaction temperature, it is generally from about 10 min to about 24 hr. Examples of the base include inorganic bases such as sodium hydride, potassium hydroxide, potassium carbonate and the like, alkoxides such as potassium tert-butoxide and the like, and the like. Examples of the solvent include N,N-dimethylformamide, tetrahydrofuran, dimethyl sulfoxide and the like.

Step 1-2

In this step, compound (9-3) is obtained by deprotection (removal of P$^3$) of compound (9-2). Examples of the protecting group P$^3$ include acyl such as acetyl and the like, and carbamate such as tert-butyloxycarbonyl and benzyloxycarbonyl, and the like. The deprotection conditions are not particularly limited as long as they are generally used for the removal of protecting groups. When, for example, P$^3$ is a tert-butyloxycarbonyl group, a reaction using one or more equivalents of an inorganic acid such as hydrochloric acid or the like, trifluoroacetic acid and the like in an alcoholic solvent such as ethanol or the like, an ether solvent such as tetrahydrofuran or the like, a halogenated solvent such as dichloromethane or the like, water or a mixed solvent thereof under ice-cooling to 80° C. for 10 min to about 12 hr can be mentioned. When, for example, P$^3$ is benzyloxycarbonyl, deprotection can be performed by reduction by catalytic hydrogenation. Examples of the catalyst include palladium carbon and the like. The reaction temperature is generally room temperature to the refluxing temperature of the solvent and the hydrogen pressure is 1 to 20 atm. While the reaction time varies depending on the starting material and solvent to be used, the reaction temperature, and the like, it is generally from 1 hr to 48 hr.

Compound (I-9) of the present invention can be obtained from compound (9-3) by using the conditions of the aforementioned method (7)-(8).

(Method (10))

This production method is suitable for producing compound (I) wherein Q is —C(=O)—, Z is $NR^5$ ($R^5$ is alkyl optionally substituted by $R^{5''}$, and $R^{5''}$ and nitrogen atom are bonded via methylene), i.e., the following compound (I-10).

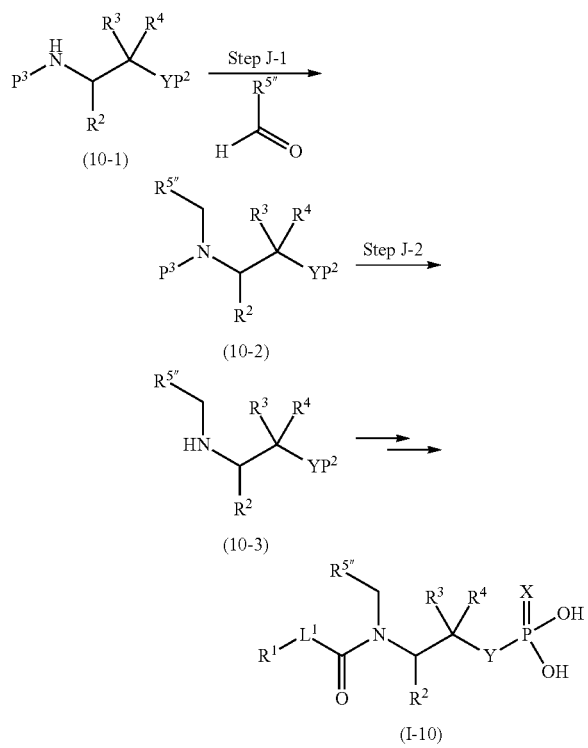

wherein $R^{5''}$ is an optionally substituted substituent when $R^5$ is optionally substituted methyl. Other respective symbols are as defined above.

Step J-1

In this step, compound (10-2) is obtained by a reductive amination reaction of compound (10-1) using the corresponding aldehyde ($R^{5''}$ CHO) in an appropriate solvent. Examples of the solvent used in this reaction include dichloromethane, toluene, tetrahydrofuran and the like. Examples of the reducing agent include sodium triacetoxyborohydride and the like. The reaction temperature is generally from 0° C. to the refluxing temperature of the solvent. While the reaction time varies depending on the starting material and solvent to be used, the reaction temperature, and the like, it is generally from 1 hr to 48 hr.

Step J-2

In this step, compound (10-3) is prepared by deprotection (removal of $P^3$) of compound (10-2). The reaction conditions are the same as those in the aforementioned step I-2.

Compound (I-10) of the present invention can be obtained from compound (10-3) by using the conditions of the aforementioned methods (7)-(8).

(Method (11))

This production method is suitable for producing compound (I) wherein X and Y are oxygen atoms, Q is —C(=O)—, and Z is $NR^5$, i.e., the following compound (I-11).

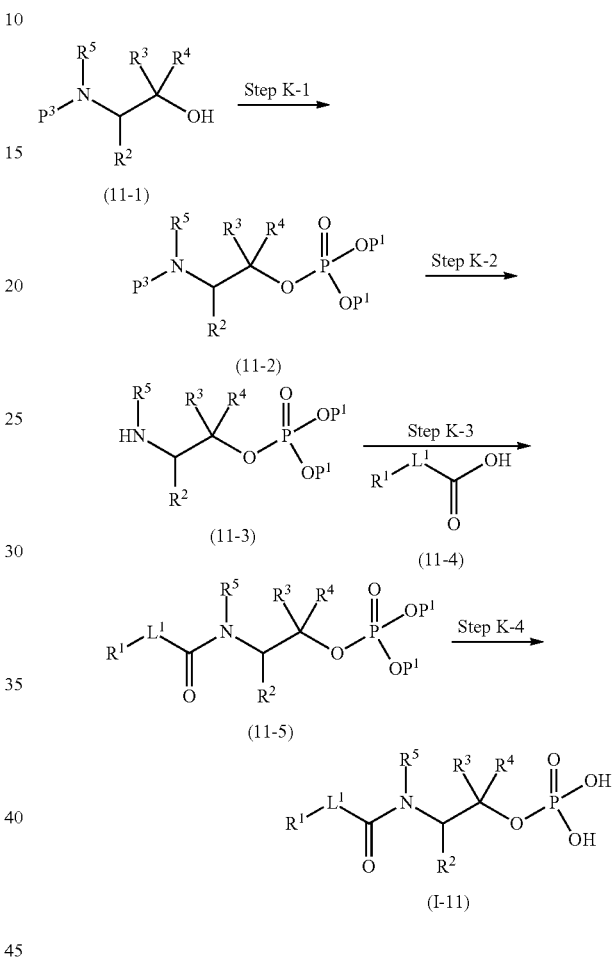

wherein each symbol is as defined above.

Step K-1

In this step, compound (11-1) is phosphorylated. The reaction conditions are the same as those in the aforementioned step A-1.

Step K-2

In this step, compound (11-3) is obtained by the deprotection (removal of $P^3$) of compound (11-2). The reaction conditions are the same as those in the aforementioned step I-2.

Step K-3

In this step, compound (11-5) is obtained by a condensation reaction of compound (11-3) and the corresponding compound (11-4). The reaction conditions are the same as those in the aforementioned step G-1.

Step K-2 and step K-3 can also be performed by a one-pot reaction. For example, when $P^3$ is tert-butyloxycarbonyl, under ice-cooling, trifluoroacetic acid is added in dichloromethane, after stirring, a large excess of N,N-diisopropylethylamine is added, and a condensation reaction with compound (11-4) can be performed.

Step K-4

In this step, compound (I-11) of the present invention is prepared from compound (11-5). In this step, a method similar to that in the aforementioned step A-2 can be mentioned.

(Method (12))

This production method is suitable for producing compound (I) wherein Q is the following formula (A-1)

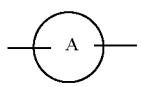
(A-1)

wherein ring A is as defined above, and Z is an oxygen atom, a sulfur atom, or $NR^5$, i.e., the following compound (I-12).

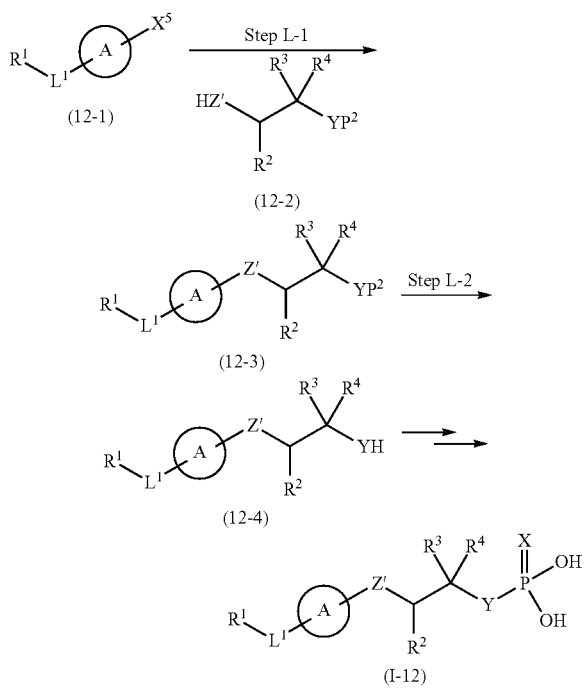

wherein $X^5$ is a leaving group and is not particularly limited as long as it can be eliminated during reaction with compound (12-2). For example, a halogen atom (specifically, bromine atom, chlorine atom, fluorine atom, etc.), trifluoromethanesulfonyloxy and the like can be mentioned. Other respective symbols are as defined above.

Step L-1

In this step, compound (12-3) is obtained by a coupling reaction of compound (12-1) and compound (12-2). The reaction preferably proceeds in the presence of a palladium catalyst, a phosphine ligand and a base in a suitable solvent at 0° C. to under heating, particularly at room temperature to the boiling point of the solvent. While the reaction time varies depending on the starting material and solvent to be used and the reaction temperature, it is generally from 1 hr to 24 hr. Examples of the palladium catalyst include palladium(II) acetate, palladium(II) chloride, tris(dibenzylideneacetone)dipalladium(0) or chloroform adduct thereof and the like. Examples of the phosphine ligand include triphenylphosphine, 2-(dicyclohexylphosphino)-2',4',6'-triisopropyl-1,1'-biphenyl, 2-(dicyclohexylphosphino)-3,6-dimethoxy-2',4',6'-triisopropyl-1,1'-biphenyl, 2-(dicyclohexylphosphino)-2,6-diisopropoxy-1,1'-biphenyl, 2-di-tert-butylphosphino-2'-4'-6'-triisopropylbiphenyl, 2-dicyclohexylphosphino-2'-6'-dimethoxybiphenyl, 2-(dicyclohexylphosphino)-2-(N,N-dimethylamino)biphenyl, tri-ortho-tolylphosphine, 2-(dicyclohexylphosphino)biphenyl, 2-(di-tert-butylphosphino)biphenyl, 2-(di-tert-butylphosphino)-1,1-binaphthyl, tri-tert-butylphosphine, tri-tert-butylphosphonium tetrafluoroborate and the like. A reagent in which a palladium catalyst and a phosphine ligand form a complex may also be used and examples of such reagent include tetrakis(triphenylphosphine)palladium(0), 1,1-bis(diphenylphosphino)ferrocene-palladium(II) dichloride, dichlorobis(triphenylphosphine)palladium(II), dichlorobis(tricyclohexylphosphine)palladium(II), bis(tri-tert-butylphosphine)palladium(0), chloro(2-dicyclohexylphosphino-2',4',6'-triisopropyl-1,1'-biphenyl) (2'-amino-1,1'-biphenyl-2-yl)palladium(II), [(2-dicyclohexylphosphino-3,6-dimethoxy-2',4',6'-triisopropyl-1,1'-biphenyl)-2-(2'-amino-1,1'-biphenyl)palladium(II) methanesulfonate, (2-dicyclohexylphosphino-2,6-diisopropoxy-1,1'-biphenyl)[2-(2'-amino-1,1'-biphenyl)]palladium(II) methanesulfonate, [(2-di-tert-butylphosphino-3,6-dimethoxy-2',4',6'-triisopropyl-1,1'-biphenyl)-2-(2'-amino-1,1'-biphenyl)] palladium(II) methanesulfonate and the like. Examples of the base include sodium tert-butoxide, potassium acetate, tripotassium phosphate, cesium carbonate, potassium carbonate, sodium hydrogen carbonate, triethylamine, diisopropylethylamine, dicyclohexylethylamine, potassium fluoride, cesium fluoride and the like. Examples of the solvent include ether solvents such as tetrahydrofuran, 1,2-dimethoxyethane, 1,4-dioxane and the like, alcohol solvents such as methanol, ethanol, propanol, butanol and the like, N,N-dimethylformamide, or a mixed solvent of the organic solvent and water and the like.

Compound (12-3) can also be obtained by the following reaction depending on the kind of ring A and the substituted position of $X^5$. Such reaction is a reaction using, for example, a polar solvent such as acetonitrile, N,N-dimethylformamide, tetrahydrofuran, N-methylpyrrolidone and the like, or an alcoholic solvent such as ethanol and the like and a base such as cesium carbonate, potassium carbonate, triethylamine, diisopropylethylamine, 1,8-diazabicyclo[5.4.0]undec-7-ene and the like. As the reaction conditions, room temperature—refluxing temperature for about 30 min-24 hr can be mentioned. As the leaving group $X^5$ here, a fluorine atom or a chlorine atom can be mentioned.

Step L-2

In this step, compound (12-4) is obtained by deprotection (removal of $P^2$) of compound (12-3). In this step, the reaction conditions are the same as those in the aforementioned step G-4.

Compound (I-12) of the present invention can be obtained from compound (12-4) by using conditions of the aforementioned methods (1)-(6).

(Method (13)) This production method is suitable for producing compound (I) wherein Q is pyridine, and Z is sulfur or $NR^5$, i.e., the following compound (I-13).

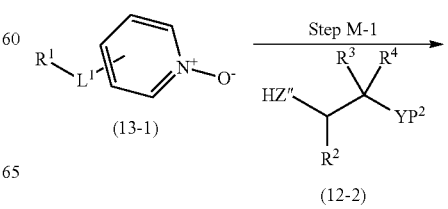

-continued

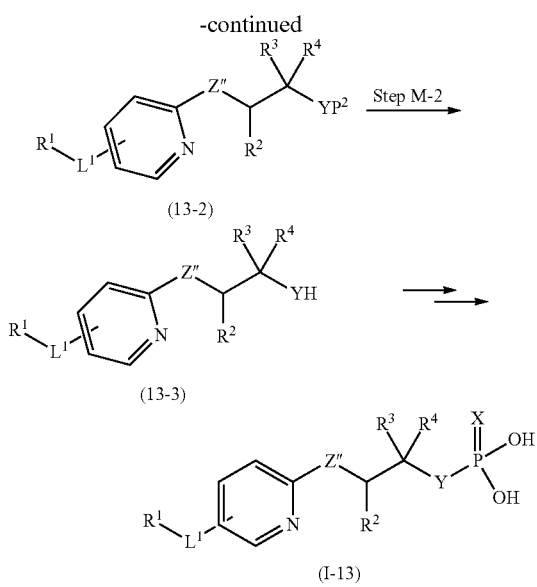

wherein Z" is sulfur or $NR^5$, and other respective symbols are as defined above.

Step M-1

In this step, compound (13-1) is converted to compound (13-2). As the reaction conditions, conditions using a dehydrating agent such as (benzotriazol-1-yloxy) tripyrrolidinophosphonium hexafluorophosphate (PyBOP) and m the like, p-toluenesulfonic anhydride and the like according to the methods described in Journal of Organic Chemistry, vol. 72, page 4554 (2007) and Organic Chemistry, vol. 12, page 5254 (2010) can be mentioned, and a suitable solvent (e.g., tetrahydrofuran, dichloromethane, ethyl acetate, etc.) at 0° C.-50° C. for about 30 min-12 hr can be mentioned. After the reaction, purification and the like are performed by conventional methods, whereby the desired product can be obtained.

Step M-2

In this step, compound (13-3) is obtained by deprotection (removal of $P^2$) of compound (13-2). In this step, the reaction conditions are the same as those in the aforementioned step G-4.

Compound (I-13) of the present invention can be obtained from compound (13-3) by using conditions of the aforementioned methods (1)-(6).

(Method (14))

This production method is suitable for producing compound (I) wherein Q is the following formula (A-1)

wherein ring A is as defined above, $R^2$ is hydrogen, and Z is $CH_2$, i.e., the following compound (I-14).

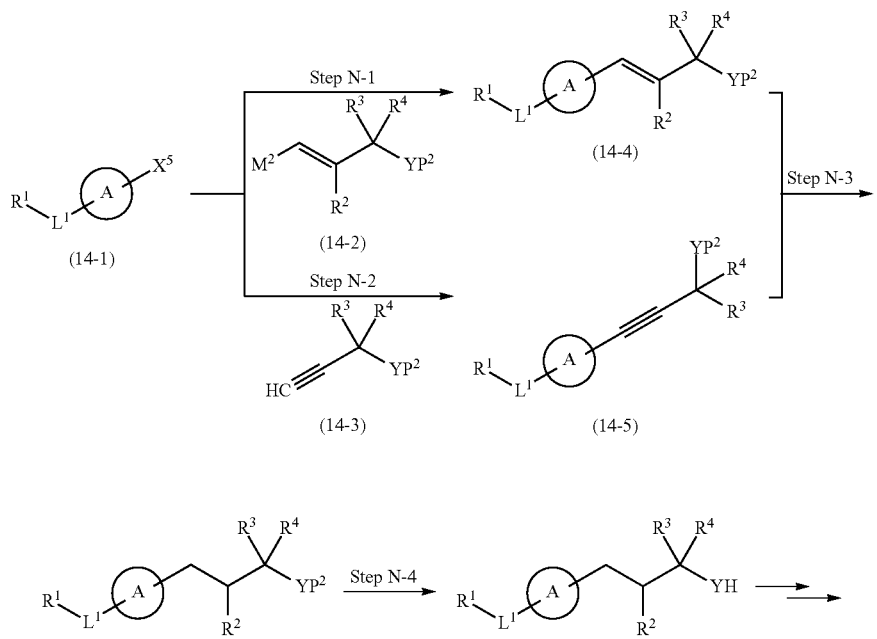

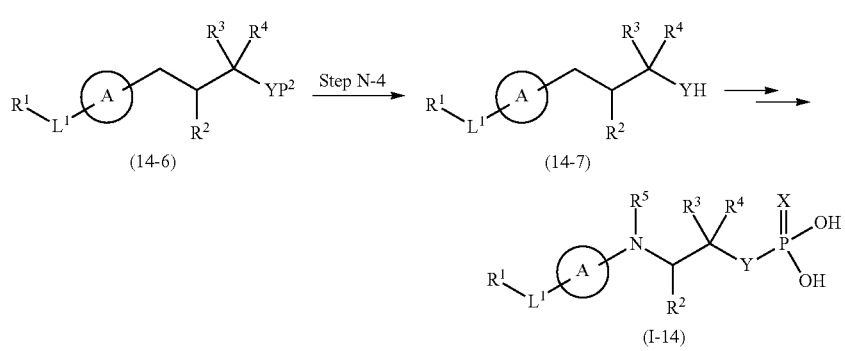

wherein M² is hydrogen, B(OH)₂ or ester thereof, and other respective symbols are as defined above.

Step N-1

In this step, compound (14-4) is obtained by a coupling reaction of compound (14-1) and compound (14-2), and the reaction conditions are the same as those in the aforementioned step L-1.

Step N-2

In this step, compound (14-5) is obtained by a coupling reaction of compound (14-1) and compound (14-3). As the reaction of compound (14-1) and compound (14-3), Sonogashira reaction can be mentioned. Examples of the catalyst to be used include palladium compounds such as tetrakis (triphenylphosphine)palladium (0), tris(dibenzyl ideneacetone)dipalladium (0), dichlorobis(acetonitrile)palladium (II) and the like. To promote the reaction, an additive such as organic base such as triethylamine and the like, an inorganic base such as ammonia and the like, a copper compound such as copper iodide, copper bromide and the like, a phosphine compound such as 2-dicyclohexylphosphino-2',4',6'-triisopropylbiphenyl and the like, and the like can also be added. As the reaction conditions, conditions using an ether solvent such as tetrahydrofuran, dioxane and the like, a polar solvent such as acetonitrile, dimethylformamide and the like, or a hydrocarbon solvent such as benzene and the like under ice-cooling to refluxing temperature of the solvent for about 30 min-24 hr can be mentioned. After the reaction, purification and the like are performed by conventional methods, whereby compound (14-5) can be obtained.

Step N-3

In this step, compound (14-6) is obtained by reducing a double bond or triple bond of olefin (compound (14-4)), or acetylene (compound (14-5)) by using a reducing agent. The reducing agent is not limited as long as it is a reagent used for the reduction of general unsaturated carbon bonds. For example, catalytic hydrogenation using a heterogeneous catalyst such as palladium carbon, Raney-nickel, palladium carbon ethylenediamine complex and the like; a homogeneous catalyst such as rhodium complex (chloro tris(triphenylphosphine)rhodium (I), etc.) and the like, and the like can be mentioned. As the reaction conditions, conditions using an alcoholic solvent such as ethanol and the like, an ether solvent such as dioxane and the like, or a hydrocarbon solvent such as toluene and the like under a 1-20 atm hydrogen pressure under ice-cooling-solvent refluxing temperature for 30 min-1 week can be mentioned. Depending on the reaction rate, the stability of the compound, and the like, an acid such as acetic acid and the like or a base such as triethylamine and the like can also be added to the reaction mixture. After the reaction, purification and the like are performed by conventional methods, whereby compound (14-6) can be obtained.

Step N-4

In this step, compound (14-7) is prepared by deprotection (removal of P²) of compound (14-6). In this step, the reaction conditions are the same as those in the aforementioned step G-4. When P² is a protecting group which is removed under the conditions of the aforementioned step N-3 (e.g., P² is benzyl group, benzyloxycarbonyl group, etc.), this step can be omitted.

Compound (I-14) of the present invention can be obtained from compound (14-7) by using the conditions of the aforementioned methods (1)-(6).

The starting material compounds in each of the above-mentioned methods can be produced by known methods and/or in the same manner as in the methods described in Examples described later.

The introduction of protecting groups into functional groups and the removal of functional group protecting groups can be performed by reference to a known method (PROTECTIVE GROUPS in ORGANIC SYNTHESIS (Theodora W. Greene, Peter G. M. Wuts) etc.).

The compound (I) of the present invention produced as described above is isolated and purified in its free form or as a salt thereof. The salt can be produced by subjecting same to a salt formation treatment generally used. Isolation and purification can be performed by applying general chemical operations such as extraction, concentration, crystallization, filtration, recrystallization, various chromatographies and the like.

When the compound (I) of the present invention or a pharmacologically acceptable salt thereof exists as an optical isomer based on asymmetric carbon, it can be separated into individual optical isomers by general optical resolution means (e.g., fractional crystallization method, resolution method using a chiral column). In addition, an optical isomer can also be synthesized using optically pure starting materials.

Furthermore, optical isomers can also be synthesized by stereoselectively performing each reaction using an asymmetric auxiliary group or an asymmetric catalyst.

(Pharmaceutical Composition of the Present Invention)

The compound (I) of the present invention or a pharmacologically acceptable salt thereof can be administered alone or as a pharmaceutical composition containing the same and a pharmacologically acceptable carrier orally or parenterally. The pharmacologically acceptable carrier may be a carrier conventionally used in the pertinent field and, for example, diluent, binder (syrup, gum arabic, gelatin, sorbit, tragacanth, polyvinylpyrrolidone, etc.), excipient (lactose, sucrose, cornstarch, potassium phosphate, sorbit, glycine, etc.), lubricant (magnesium stearate, talc, polyethylene glycol, silica, etc.), disintegrant (potato starch), wetting agent (sodium lauryl sulfate, etc.) and the like can be mentioned.

The dosage form of these pharmaceutical compositions is not particularly limited. For example, when orally administered, conventional pharmaceutical preparations such as tablet, granule, capsule, powder and the like can be mentioned and when parenterally administered, conventional pharmaceutical preparations such as injection, inhalant, suppository and the like can be mentioned.

The dose of the compound (I) of the present invention or a pharmacologically acceptable salt thereof is determined according to the age, body weight, general health condition, sex, diet, administration time, administration method, clearance rate, and the level of symptom for which patients are undergoing treatments at that time, or further in consideration of other factors. While the daily dose of the compound (I) of the present invention varies depending on the condition and body weight of patient, the kind of the compound, administration route and the like, it is parenterally administered at, for example, about 0.001 to 100 mg/patient/day, preferably about 0.01 to 50 mg/patient/day, by subcutaneous, intravenous, intraarterial, intramuscular, intraarticular, intrathecal, transdermal, transocular, transpulmonary or bronchial, transnasal or rectal administration, or about 0.01 to 1000 mg/patient/day, preferably, about 0.1 to 100 mg/patient/day, by oral administration. The total dose per day may be the amount of a single dose or divided doses.

(Use of Pharmaceutical Composition of the Present Invention)

The pharmaceutical composition of the present invention is used as a therapeutic agent for a disease associated with angiogenesis abnormality, or a disease associated with a vascular disorder. The disease associated with angiogenesis abnormality, or the disease associated with a vascular disorder specifically includes solid cancer, pressure ulcer, diabetic necrosis, diabetic nephropathy, diabetic retinopathy, acute nephropathy, cerebral infarction, age-related macular degeneration, rheumatoid arthritis, scleroderma, psoriasis, systemic lupus erythematosus, lung fibrosis, arteriosclerosis obliterans, arteriosclerosis, angina pectoris, myocardial infarction, Buerger disease, brain edema due to infectious disease, hemorrhage due to hemorrhagic virus (Ebola, dengue), acute respiratory distress syndrome, and the like.

(Use in Combination with Other Drug)

The pharmaceutical composition of the present invention can be used for (administered to) patients with the aforementioned disease associated with angiogenesis abnormality, or the disease associated with a vascular disorder, depending on the disease to be treated and the like, in combination with one or more kinds of other drugs.

The other drug is not limited, and specifically, for example, anticancer drugs, antiinflammatory drugs, neuropsychiatric drugs, sensory system drugs, circulatory system drugs, respiratory system drugs, digestive system drugs, endocrine metabolic system drugs, kidney/urinary system drugs, vitamins/nutrition/infusion/electrolyte preparations, blood fluids/blood preparations, immunosuppressants, analgesics, antiallergic drugs, antibiotics, antibacterial agents, antiviral drugs and the like can be mentioned. Among these, use in combination with an anticancer drug to treat solid tumor and prevent metastasis is more preferable. By administering the pharmaceutical composition of the present invention in combination with other drug, it is possible to promote the delivery of the other drug to the disease site of the disease associated with angiogenesis abnormality, thereby reducing the amount of the other drug to be used. In addition, the reduction in the amount of other drugs to be used is in line with social demands such as the reduction of medical costs.

A cancer therapeutic drug to be used in combination with the pharmaceutical composition of the present invention is not particularly limited. For example, a chemotherapeutic agent, an immunotherapeutic agent or a hormonal therapeutic agent is preferred. These cancer therapeutic drugs may be liposomal formulations. In addition, these cancer therapeutic drugs may be nucleic acid drugs or antibody drugs.

The chemotherapeutic agent is not particularly limited and, for example, alkylating agents such as nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin and the like; antimetabolites such as mercaptopurine, 6-mercaptopurine riboside, thioinosine, methotrexate, pemetrexed, enocitabine, cytarabine, cytarabine ocfosfate, ancitabine hydrochloride, 5-FU drug (e.g., fluorouracil, tegafur, UFT, doxifluridine, carmofour, gallocitabine, emitefur, capecitabine etc.), aminopterine, nelzarabine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine, bendamustine and the like; anticancer antibiotics such as actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride and the like; plant-derived anticancer agents such as etoposide, etoposide phosphate, vinblastine sulfate, vincristine sulfate, vindesine sulfate, teniposide, paclitaxel, docetaxel, vinorelbine, irinotecan, irinotecan hydrochloride and the like; and the like can be mentioned.

The immunotherapeutic agent is not particularly limited and, for example, picibanil, krestin, schizophyllan, lentinan, ubenimex, interferon, interleukin, macrophage colony stimulating factor, granulocyte colony stimulating factor, erythropoietin, lymphotoxin, BCG vaccine, *Corynebacterium parvum*, levamisole, polysaccharide K, procodazole, ipilimumab, nivolumab, ramucirumab, ofatumumab, panitumumab, penbrolizmab, obinutuzumab, trastuzumab emtansine, tocilizumab, bevacizumab, trastuzumab, siltuximab, cetuximab, infliximab, rituximab and the like can be mentioned.

The hormonal therapeutic agent is not particularly limited and, for example, fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogen (e.g., tamoxifen citrate, toremifene citrate, etc.), pill preparation, mepitiostane, testrolactone, aminoglutethimide, LH-RH agonist (e.g., goserelin acetate, buserelin, leuprorelin, etc.), droloxifene, epitiostanol, ethinylestradiol sulfonate, aromatase inhibitor (e.g., fadrozole hydrochloride, anastrozole, retrozole, exemestane, vorozole, formestane, etc.), anti-androgen (e.g., flutamide, bicartamide, nilutamide, etc.), 5α-reductase inhibitor (e.g., finasteride, episteride, etc.), adrenocorticohormone drug (e.g., dexamethasone, predonisolone, betamethasone, triamcinolone, etc.), androgen synthesis inhibitor (e.g., abiraterone, etc.) and the like can be mentioned.

In the present invention, "used in combination" means that the application time of the drug delivery promoter of the present invention overlaps with the application time of the aforementioned other drug, and simultaneous administration is not required. The dose of the other drug may be in accordance with the dose used clinically, and can be appropriately selected according to the subject of administration, the age and body weight of the administration subject, symptoms, administration time, dosage form, administration method, combination, and the like.

That is, the compound (I) of the present invention or a pharmacologically acceptable salt thereof may be combined and administered as a concomitant drug for the purpose of 1. complementing and/or enhancing the prophylactic and/or therapeutic effects of other drugs,
2. improving dynamics/absorption of other drugs, reducing doses, and/or
3. reducing the side effects of other drugs.

A concomitant drug of the compound (I) of the present invention or a pharmacologically acceptable salt thereof and other drug may be administered in the form of a combination agent in which both components are blended in one preparation, or may be administered as separate preparations. When the separate preparations are administered, they may be administered to the subject of administration at the same time or at different times. In the case of administration at different times, the compound (I) of the present invention or a pharmacologically acceptable salt thereof may be administered first, and other drug may be administered later, or the other drug may be administered first and the compound (I) of the present invention or a pharmacologically acceptable salt thereof may be administered later. The administration method for each may be the same or different.

The disease on which a prophylactic and/or therapeutic effect is exerted by the above-mentioned concomitant drug is not particularly limited, and may be any disease that complements and/or enhances the prophylactic and/or therapeutic effect of the compound (I) of the present invention or a pharmacologically acceptable salt thereof, or other drug.

The mass ratio of the compound (I) of the present invention or a pharmacologically acceptable salt thereof to other drug is not particularly limited.

Any two or more kinds of other drugs may be administered in combination.

In addition, the other drug that complements and/or enhances the prophylactic and/or therapeutic effect of the compound (I) of the present invention or a pharmacologically acceptable salt thereof includes not only those that have been found to date based on the above-mentioned mechanism but also those that will be found in the future.
(Kit of the Present Invention)

As another embodiment of the present invention, a kit for the treatment or prophylaxis of a disease associated with angiogenesis abnormality, or a disease associated with a vascular disorder which contains
- (A) at least one selected from the group consisting of a packaging container, a manual and a package insert stating that the compound (I) of the present invention or a pharmacologically acceptable salt thereof is used in combination with the aforementioned other drug,
- (B) a pharmaceutical composition (or preparation) containing the compound (I) of the present invention or a pharmacologically acceptable salt thereof, and
- (C) a pharmaceutical composition (or preparation) containing other drug can be provided.

The kit of the present invention includes a packaging container containing the compound (I) of the present invention or a pharmacologically acceptable salt thereof, or the aforementioned other drug.

The kit of the present invention may further contain a label, instruction manual, or package insert attached on or to the packaging container.

In the present invention, the "manual or package insert" means a document containing information regarding the use of a preparation (e.g., applicable target disease, direction for use, dosage, administration, contraindication and/or warning) which is normally contained in a commercial package of a preparation. The "label" is a sheet-shaped article containing indication of the product name of a preparation containing the compound (I) of the present invention or a pharmacologically acceptable salt thereof, or the aforementioned other drug, direction for use, dosage, dosage form, applicable target disease and the like, and is directly adhered to a packaging container.

The label, manual, or package insert shows applicable target diseases of the drug of the present invention, namely, that it is used for the treatment of a disease associated with angiogenesis abnormality, or a disease associated with a vascular disorder (specifically, for example, solid cancer, pressure ulcer, diabetic necrosis, diabetic nephropathy, diabetic retinopathy, acute renopathy, cerebral infarction, age-related macular degeneration, rheumatoid arthritis, scleroderma, psoriasis, systemic lupus erythematosus, lung fibrosis, arteriosclerosis obliterans, arteriosclerosis, angina pectoris, myocardial infarction, Buerger disease, brain edema due to infectious disease, hemorrhage due to hemorrhagic virus (Ebola, dengue), acute respiratory distress syndrome and the like).

Examples of the packaging container include PTP, bottle, vial, syringe, blister pack and the like. The packaging container can be made of various materials such as glass, plastic and the like. The container may be packed up by the outer packaging made of paper which printed the contents and the like of the above-mentioned label.

The usage and dose of the compound (I) of the present invention or a pharmacologically acceptable salt thereof, and the aforementioned other drug contained in the kit of the present invention can be determined by referring to the aforementioned description of the administration method and the dose.

EXAMPLES

The present invention is described in detail in the following using Reference Examples, Examples, Experimental Examples, and Formulation Examples; however, the present invention is not limited to the following Examples and Experimental Examples. In addition, the reagents and materials to be used are commercially available unless otherwise specified. Furthermore, the "room temperature" shows a temperature of 15-30° C., unless otherwise specified. The ratio shown in the mixed solvent indicates the volume ratio unless otherwise specified. Unless otherwise specified, % shows mass %.

The abbreviations used in the following Reference Examples and Examples have the following meanings.
HPLC: high performance liquid chromatography
ESI: electro-spray ionization
APCI: atmospheric pressure chemical ionization
HATU: 1-[bis(dimethylamino)methylene]-1H-1,2,3-triazolo[4,5-b]pyridinium 3-oxide hexafluorophosphate
XPhos-Pd-G2: chloro(2-dicyclohexylphosphino-2',4',6'-triisopropyl-1,1'-biphenyl) [2-(2'-amino-1,1'-biphenyl)]palladium(II) (tetrahydrofuran adduct)

Reference Example 1

(1-1) Benzyl 3-[(di-tert-butoxy phosphoryl)oxy] azetidine-1-carboxylate (Reference Example compound 1-1)

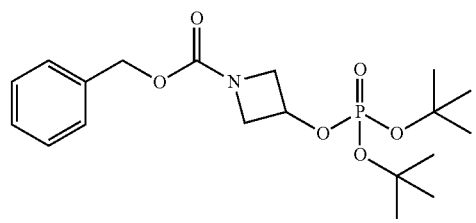 [SMILES: CC(C)(C)OP(=O)(OC1CN(C(=O)OCc2ccccc2)C1)OC(C)(C)C]

To a mixed solution of benzyl 3-hydroxyazetidine-1-carboxylate (4.00 g) in dichloromethane (38 mL) and acetonitrile (19 mL) was added under ice-cooling 1H-tetrazole (2.70 g) and di-tert-butyl N,N-diisopropyl phosphoramidite (9.14 mL), and the mixture was stirred at room temperature for 3 hr. tert-Butyl hydroperoxide (70% aqueous solution, 9.25 mL) was added, and the mixture was stirred at room temperature for 4 hr. To the reaction mixture was added saturated aqueous sodium thiosulfate solution, and the mixture was extracted with ethyl acetate. The organic layer was washed with saturated aqueous sodium hydrogen carbonate solution and saturated brine, dried over anhydrous sodium sulfate. The desiccant was filtered off, and the filtrate was concentrated under reduced pressure. The obtained residue was purified by silica gel column chromatography (hexane:ethyl acetate=60:40-40:60) to give the title compound (6.00 g) as a colorless oil.

MS (APCI) m/z: 417.1 (M+NH$_4$)$^+$.

(1-2) Benzyl 3-[(di-tert-butoxyphosphoryl)oxy]azetidine-1-carboxylate (Reference Example compound 1)

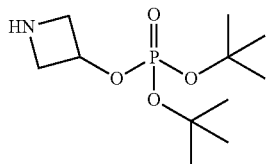

To a solution of Reference Example compound 1-1 (3.68 g) in ethanol (31 mL) was added 7.5% palladium carbon (368 mg), and the mixture was stirred under a hydrogen atmosphere at room temperature for one day and night. The insoluble material in the reaction mixture was filtered off with diatomaceous earth, and the filtrate was concentrated under reduced pressure. The obtained residue was purified by silica gel column chromatography (chloroform: methanol=100:0-80:20) to give the title compound (1.89 g) as a pale-yellow oil.

MS (APCI) m/z: 266.0 (M+H)$^+$

Reference Example 2 tert-Butyl 3-{[bis(benzyloxy)phosphoryl]oxy}azetidine-1-carboxylate (Reference Example compound 2)

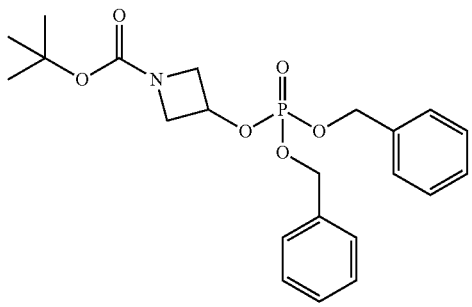 [SMILES: CC(C)(C)OC(=O)N1CC(OP(=O)(OCc2ccccc2)OCc2ccccc2)C1]

To a mixed solution of tert-butyl 3-hydroxyazetidine-1-carboxylate (5.00 g) in dichloromethane (58 mL) and acetonitrile (29 mL) were added under ice-cooling 1H-tetrazole (4.04 g) and dibenzyl N,N-diisopropyl phosphoramidite (14.5 mL), and the mixture was stirred at room temperature for 2 hr. tert-Butyl hydroperoxide (70% aqueous solution, 13.8 mL) was added, and the mixture was stirred at room temperature for 2 hr. To the reaction mixture was added saturated aqueous sodium thiosulfate solution, and the mixture was extracted with chloroform. The organic layer was washed with saturated brine, and dried over anhydrous sodium sulfate. The desiccant was filtered off, and the filtrate was concentrated under reduced pressure. The obtained residue was purified twice by silica gel column chromatography (hexane:ethyl acetate=30:70-45:55) to give the title compound (12.4 g) as a colorless oil.

MS (APCI) m/z: 334.3 (M-Boc)$^+$.

Reference Example 3 tert-Butyl (3R)-3-{[bis(benzyloxy)phosphoryl]oxy}pyrrolidine-1-carboxylate (Reference Example compound 3)

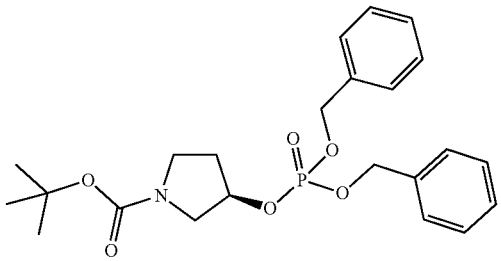 [SMILES: CC(C)(C)OC(=O)N1CC[C@@H](OP(=O)(OCc2ccccc2)OCc2ccccc2)C1]

tert-Butyl (3R)-3-hydroxypyrrolidine-1-carboxylate (3.00 g) was dissolved in dichloromethane (30 mL) and acetonitrile (10 mL), under ice-cooling, 1H-tetrazole (2.24 g) was added, dibenzyl N,N-diisopropyl phosphoramidite (5.8 mL) was added dropwise, and the mixture was stirred at room temperature for 2.5 hr. Under ice-cooling, tert-butyl hydroperoxide (5.8 mL) was added dropwise, and the mixture was stirred at room temperature for 1 hr. Under ice-cooling, 10% aqueous sodium metabisulfite solution (40 mL) was added, and the mixture was stirred at room temperature for 10 min. To the reaction mixture was added ethyl acetate, and the mixture was extracted, washed with water, saturated aqueous sodium hydrogen carbonate solution, and saturated brine, and dried over anhydrous sodium sulfate. The solvent was evaporated under reduced pressure. The residue was purified by silica gel column chromatography (hexane:ethyl acetate=60:40-34:66) to give the title compound (5.23 g) as a pale-yellow oil. MS (APCI) m/z: 447.9[M+H]$^+$

Reference Example 4

(4-1) Benzyl (3R)-3-[(di-tert-butoxyphosphoryl)oxy]pyrrolidine-1-carboxylate (Reference Example compound 4-1)

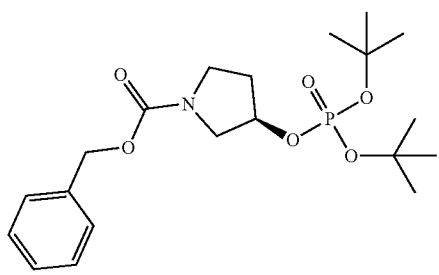 [SMILES: CC(C)(C)OP(=O)(O[C@@H]1CCN(C(=O)OCc2ccccc2)C1)OC(C)(C)C]

To a mixed solution of (R)-1-carbobenzoxy-3-pyrrolidinol (4.50 g) in dichloromethane (41 mL) and acetonitrile (20 mL) were added under ice-cooling 1H-tetrazole (2.85 g) and di-tert-butyl N,N-diisopropyl phosphoramidite (9.63 mL), and the mixture was stirred at room temperature for 2 hr. Under ice-cooling, tert-butyl hydroperoxide (70% aqueous solution, 9.75 mL) was added, and the mixture was stirred at room temperature for 2 hr. Water was added to the reaction mixture, and the mixture was extracted with ethyl acetate. The organic layer was dried over anhydrous sodium sulfate, the desiccant was filtered off, and the filtrate was concentrated under reduced pressure. The obtained residue was purified by silica gel column chromatography (hexane:ethyl acetate=55:45-30:70) to give the title compound (5.93 g) as a colorless oil.

MS (APCI) m/z: 414.0 (M+H)$^+$.

(4-2) Di-tert-butyl (3R)-pyrrolidin-3-yl phosphate (Reference Example compound 4)

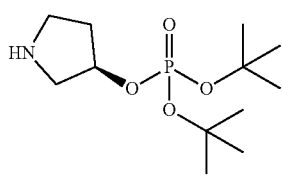 [SMILES: CC(C)(C)OP(=O)(O[C@@H]1CCNC1)OC(C)(C)C]

To a solution of Reference Example compound 4-1 (4.85 g) in ethanol (39 mL) was added 7.5% palladium carbon (485 mg), and the mixture was stirred under a hydrogen atmosphere at room temperature for one day and night. After filtering off the insoluble material in the reaction mixture with diatomaceous earth, the filtrate was concentrated under reduced pressure. The obtained residue was purified by silica gel column chromatography (chloroform:methanol=100:0-80:20) to give the title compound (2.11 g) as a pale-yellow oil.

MS (APCI) m/z: 280.1 (M+H)$^+$

Reference Example 5

3-(3-Decyloxy)propionic acid (Reference Example compound 5)

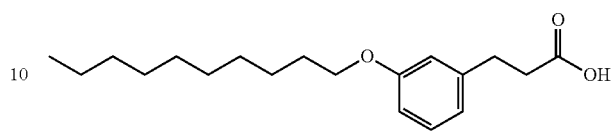

To a solution of 3-(3-hydroxyphenyl)propionic acid (4.0 g) in N,N-dimethylformamide (48.1 mL) was added under ice-cooling sodium hydride (1.9 g), and the mixture was stirred at room temperature for 20 min. A solution of 1-bromodecane (4.98 mL) in N,N-dimethylformamide (5.0 mL) was added dropwise, and the mixture was stirred at 80° C. for 1 hr. The reaction mixture was cooled with ice, 1N hydrochloric acid was added, and the precipitated solid was collected by filtration and washed with hexane to give the title compound (4.9 g) as a white solid.

MS(ESI) m/z: 305.4 (M−H)$^-$

Reference Example 6

(6-1) 2-[(4-Methoxyphenyl)methylamino]ethanol (Reference Example compound 6-1)

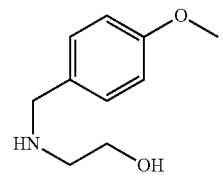

To a solution of 2-aminoethanol (1.50 g) in methanol (82 mL) was added 4-methoxybenzaldehyde (3.50 g), and the mixture was stirred at 60° C. for 2 hr. After cooling to 0° C., sodium borohydride (930 mg) was added thereto, and the mixture was stirred at room temperature for 1 hr. The reaction mixture was concentrated under reduced pressure, and the obtained residue was purified by silica gel column chromatography (chloroform/methanol=100:0-93:7) to give the title compound (3.71 g) as a colorless oil. MS(ESI) m/z: 182.1[M+H]$^+$

(6-2) tert-Butyl N-(2-hydroxyethyl)-N-[(4-methoxyphenyl)methyl]carbamate (Reference Example compound 6-2)

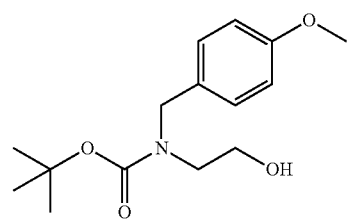 [SMILES: COc1ccc(CN(CCO)C(=O)OC(C)(C)C)cc1]

Reference Example compound 6-1 (3.40 g) was dissolved in acetonitrile (17 mL), N,N-diisopropylethylamine (1.13 mL) was added dropwise, a solution of di-tert-butyl dicarbonate (4.08 g) in acetonitrile (17 mL) was added dropwise, and the mixture was stirred at room temperature for 2 hr. The solvent was evaporated under reduced pressure, water was added, and the mixture was extracted with chloroform, washed with saturated brine, and dried over anhydrous sodium sulfate. The solvent was evaporated under reduced pressure to give an unpurified product (1.41 g) of the title compound as a colorless oil.

MS(ESI) m/z: 282.2[M+H]$^+$ (6-3) tert-Butyl N-{2-[(dibenzyloxyphosphoryl)oxy]ethyl}-N-[(4-methoxyphenyl)methyl]carbamate (Reference Example compound 6)

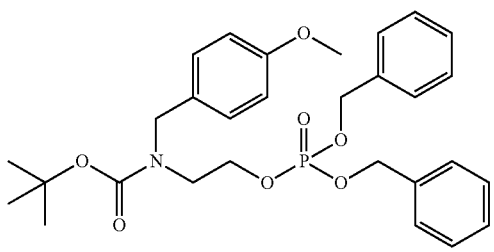 [SMILES: COc1ccc(CN(CCOP(=O)(OCc2ccccc2)OCc2ccccc2)C(=O)OC(C)(C)C)cc1]

To a mixed solution of Reference Example compound 6-2 (2.38 g) in dichloromethane (23.8 mL) and acetonitrile (9.52 mL) were added under ice-cooling 1H-tetrazole (711 mg) and dibenzyl N,N-diisopropylphosphoramidite (3.78 mL), and the mixture was stirred at room temperature for 1 hr. After cooling to 0° C., 30% aqueous hydrogen peroxide (1.04 mL) was added dropwise, and the mixture was stirred at room temperature for 1 hr. Under ice-cooling, saturated aqueous sodium thiosulfate solution (10 mL) was added. The mixture was stirred at room temperature for 10 min, extracted with ethyl acetate, washed successively with saturated aqueous sodium hydrogen carbonate and saturated brine, dried over anhydrous sodium sulfate and filtered. The solvent was evaporated. The obtained residue was purified by silica gel column chromatography (hexane:ethyl acetate=70:30-50:50) to give the title compound (4.37 g) as a colorless oil.

MS(ESI) m/z: 542.3[M+H]$^+$

Reference Example 7

(7-1) Benzyl {2-[(di-tert-butoxyphosphoryl)oxy]ethyl}carbamate (Reference Example compound 7-1)

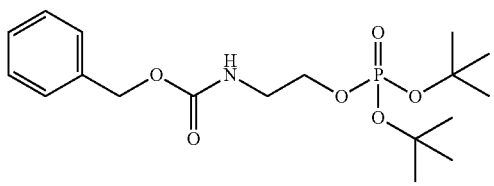 [SMILES: CC(C)(C)OP(=O)(OCCNC(=O)OCc1ccccc1)OC(C)(C)C]

To a mixed solution of benzyl (2-hydroxyethyl)carbamate (4.00 g) in dichloromethane (41 mL) and acetonitrile (20 mL) were added under ice-cooling 1H-tetrazole (2.87 g) and di-tert-butyl N,N-diisopropylphosphoramidite (9.70 mL), and the mixture was stirred at room temperature for 2 hr. tert-butyl hydroperoxide (70% aqueous solution, 9.82 mL) was added thereto, and the mixture was stirred at room temperature for 1 hr. To the reaction mixture was added saturated aqueous sodium thiosulfate solution, and the mixture was extracted with ethyl acetate. The organic layer was washed with saturated brine, and dried over anhydrous sodium sulfate. The desiccant was filtered off, and the filtrate was concentrated under reduced pressure. The obtained residue was purified by silica gel column chromatography (hexane:ethyl acetate=55:45-30:70) purified to give the title compound (5.26 g) as a colorless oil.

MS (APCI) m/z: 387.8 (M+H)$^+$.

(7-2) 2-Aminoethyl di-tert-butyl phosphate (Reference Example compound 7-2)

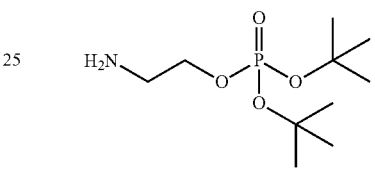

To a solution of Reference Example compound 7-1 (5.25 g) in ethanol (34 mL) was added 7.5% palladium carbon (525 mg), and the mixture was stirred under a hydrogen atmosphere at room temperature for one day and night. After filtering off the insoluble material in the reaction mixture with diatomaceous earth, the filtrate was concentrated under reduced pressure to give the title compound (3.42 g) as a pale-yellow oil.

MS (APCI) m/z: 253.9 (M+H)$^{+cl}$ (7-3) di-tert-Butyl 2-[(4-methoxybenzyl)amino]ethyl phosphate (Reference Example compound 7)

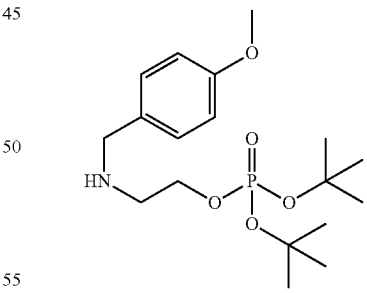

To a solution of Reference Example compound 7-2 (1.33 g) in ethanol (18 mL) was added p-anisaldehyde (751 mg), and the mixture was stirred at room temperature for 1 hr. Sodium borohydride (199 mg) was added thereto, and the mixture was stirred at room temperature for 1 hr. The reaction mixture was concentrated under reduced pressure. The obtained residue was purified by silica gel column chromatography (chloroform:methanol=100:0-93:7) to give the title compound (1.42 g) as a colorless oil. MS (APCI) m/z: 374.1 (M+H)$^+$.

Reference Example 8

(8-1) 7-Octyn-1-yl 4-methylbenzenesulfonate (Reference Example compound 8-1)

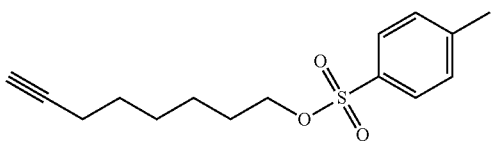 [SMILES: C#CCCCCCCOS(=O)(=O)c1ccc(C)cc1]

To a solution of 7-octyn-1-ol (5.0 g) in dichloromethane (40 mL) were added pyridine (6.4 mL) and p-toluenesulfonyl chloride (11.3 mL) at 0° C., and the mixture was stirred at the same temperature for 3 hr. Water was added to the reaction mixture, and the mixture was extracted with diethylether. The organic layer was washed with 1N hydrochloric acid, aqueous sodium hydrogen carbonate solution, and saturated brine, and dried over anhydrous sodium sulfate. The solvent was evaporated, and the obtained residue was purified by silica gel column chromatography (hexane:ethyl acetate=95:5-80:20) to give the title compound (10.7 g) as a colorless oil.
MS(ESI) m/z: 281.3 (M+H)$^+$

(8-2) 8-Nonynenitrile (Reference Example compound 8-2)

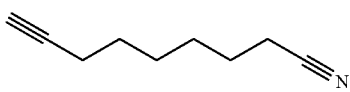

To a solution of Reference Example compound 8-1 (10.7 g) in dimethyl sulfoxide (38 mL) was added sodium cyanide (2.6 g), and the mixture was stirred with heating at 90° C. for 2 hr. The reaction mixture was cooled to room temperature, and poured into aqueous sodium hydrogen carbonate solution. Diethyl ether and water were added thereto, and the mixture was stirred and extracted with diethylether. The organic layer was washed with aqueous sodium hydrogen carbonate solution and saturated brine, and dried over anhydrous sodium sulfate. The solvent was evaporated and the obtained residue was purified by silica gel column chromatography (hexane:ethyl acetate=90:10-70:30) to give the title compound (3.7 g) as a colorless oil.
MS (APCI) m/z: 136.0 (M+H)$^+$

(8-3) 8-Nonynoic acid (Reference Example compound 8)

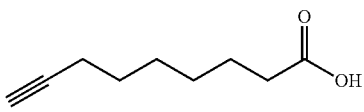

To a mixed solution of Reference Example compound 8-2 (3.7 g) in ethanol (14 mL) and water (4.6 mL) was added 1N aqueous sodium hydroxide solution (55 mL) and the mixture was stirred with heating at 90° C. for 15 hr. After cooling to room temperature, the reaction mixture was poured into ice water, and acidified by adding 6N hydrochloric acid (9.5 mL), and extracted with diethyl ether. The organic layer was washed with saturated brine, and dried over anhydrous sodium sulfate. The solvent was evaporated under reduced pressure to give the title compound (3.6 g) as a pale-yellow oil.
MS (APCI) m/z: 152.8 (M−H)$^−$

Example 1

(1-1) Methyl 3-[4-(nonyloxy)phenyl]propanoate (Example compound 1-1)

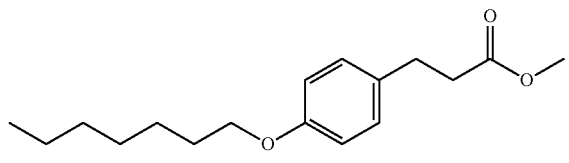 [SMILES: CCCCCCCOc1ccc(CCC(=O)OC)cc1]

Methyl-3-(4-hydroxyphenyl)propanoate (3.00 g) was dissolved in N,N-dimethylformamide (55.5 mL), 1-bromononane (3.90 mL), tetrabutylammonium iodide (1845 mg) and cesium carbonate (6238 mg) were added, and the mixture was stirred at 70° C. for 1 hr. The mixture was allowed to cool to room temperature, water was added to the reaction mixture, and the mixture was extracted with ethyl acetate, washed with water and saturated brine, and dried over anhydrous sodium sulfate. The solvent was evaporated under reduced pressure. The residue was purified by silica gel column chromatography (hexane:ethyl acetate=100:0-88:12) to give the title compound (4.94 g) as a white powder.
MS (APCI) m/z: 307.0[M+H]$^+$

(1-2) 3-(4-Nonyloxy)propionic acid (Example compound 1-2)

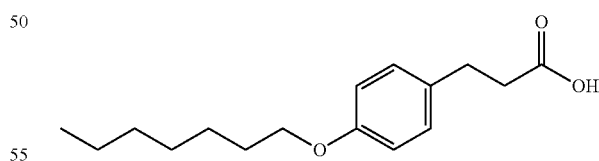

Example compound 1-1 (4.94 g) was dissolved in methanol (26.9 mL) and tetrahydrofuran (26.9 mL), 2N aqueous sodium hydroxide solution (26.6 mL) was added dropwise, and the mixture was stirred at 60° C. for 40 min. The solvent was evaporated under reduced pressure, water (75 mL) and methanol (20 mL) were added, and 1N hydrochloric acid (53 mL) was added dropwise under ice-cooling. Acetonitrile (20 mL) was added thereto, and sonicated, and the precipitated solid was washed with water to give the title compound (4.66 g) as a white powder. MS (APCI) m/z: 291.0[M−H]$^−$ (1-3) Dibenzyl 1-{3-[4-(nonyloxy)phenyl]propanoyl}azetidin-3-yl phosphate (Example compound 1-3)

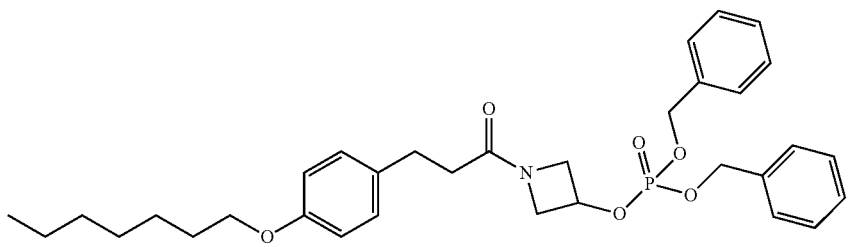 [SMILES: CCCCCCCOc1ccc(CCC(=O)N2CC(OP(=O)(OCc3ccccc3)OCc3ccccc3)C2)cc1]

Reference Example compound 2 (667 mg) was dissolved in acetonitrile (23.7 mL), trifluoroacetic acid (2.36 mL) was added dropwise under ice-cooling, and the mixture was stirred at room temperature for 5.5 hr. Under ice-cooling, trifluoroacetic acid (2.36 mL) was added thereto, and the mixture was stirred for 4.5 hr. The solvent was evaporated under reduced pressure, acetonitrile was added, and the solvent was evaporated under reduced pressure. This operation was repeated three times. The obtained residue was dissolved in N,N-dimethylformamide (4 mL), and added dropwise to a mixed solution of Example compound 1-2 (300 mg), N,N-dimethylformamide (2 mL), N,N-diisopropylethylamine (0.533 mL), and N,N,N',N'-tetramethyl-O-(7-azabenzotriazol-1-yl)uronium hexafluorophosphate (HATU) (585 mg), and the mixture was stirred at room temperature for 8.5 hr. The reaction mixture was diluted with ethyl acetate, water was added, and the mixture was extracted with ethyl acetate, washed with water and saturated brine, and dried over anhydrous sodium sulfate. The solvent was evaporated under reduced pressure. The residue was purified by silica gel column chromatography (ethyl acetate:methanol=100:0-91:9) to give the title compound (250 mg) as a colorless oil. MS (APCI) m/z: 608.0[M+H]$^+$ (1-4) 1-{3-[4-(Nonyloxy)phenyl]propanoyl}azetidin-3-yl dihydrogen phosphate ammonium salt (Example compound 1)

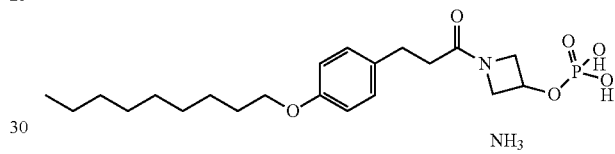

Example compound 1-3 (232 mg) was dissolved in ethanol (3.82 mL), 10% palladium carbon (93 mg) was added, and the mixture was stirred under a hydrogen atmosphere at room temperature for 100 min, and the reaction mixture was filtered.

The filtrate was concentrated, and the obtained residue was purified by preparative HPLC (10 mM aqueous ammonium carbonate solution-acetonitrile), and the obtained fraction was lyophilized to give the title compound (80 mg) as a white powder. MS (APCI) m/z: 428.3[M+H]$^+$ Example 2

(2-1) 1-{3-[3-(Decyloxy)phenyl]propanoyl}azetidin-3-yl dihydrogen phosphate ammonium salt (Example compound 2)

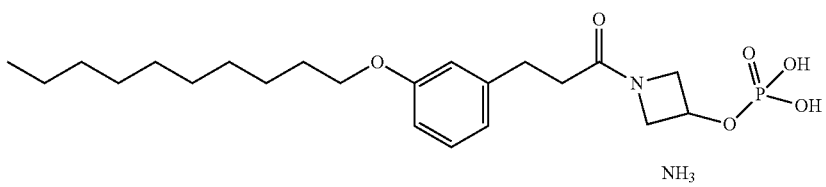

In Example 1, the reaction and treatment similar to those in (1-3)-(1-4) were performed using Reference Example compound 5 instead of Example compound 1-2 to give the title compound (91 mg) as a white powder. MS (APCI) m/z: 442.3[M+H]$^+$

Example 3

(3-1) 1-{3-[3-(Undecyloxy)phenyl]propanoyl}azetidin-3-yl dihydrogen phosphate ammonium salt (Example compound 3)

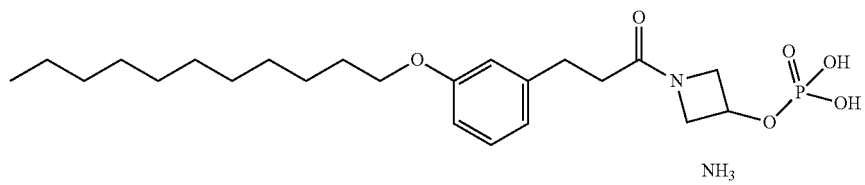

In Example 1, the reaction and treatment similar to those in (1-1)-(1-4) were performed using methyl-3-(3-hydroxyphenyl)propanoate instead of methyl-3-(4-hydroxyphenyl)propanoate to give the title compound (105 mg) as a white powder. MS (APCI) m/z: 456.3[M+H]$^+$

Example 4

(4-1) [4-(1-Undecyn-1-yl)phenyl]acetic acid (Example compound 4-1)

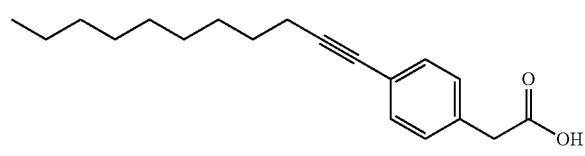 [SMILES: CCCCCCCCCC#Cc1ccc(CC(=O)O)cc1]

A mixture of 2-(4-iodophenyl)acetic acid (2.01 g), tetrahydrofuran (23.6 mL), 1-undecyne (900 mg), N,N-diisopropylethylamine (4.09 mL), copper iodide (I) (563 mg), and dichloropalladium triphenylphosphine (415 mg) was stirred at 80° C. for 15 hr. After filtering off the insoluble material in the reaction mixture with diatomaceous earth, the filtrate was concentrated under reduced pressure. The obtained residue was purified by silica gel column chromatography (hexane:ethyl acetate=100:00-20:80) to give a crudely purified product (1.13 g) of the title compound as a brown solid. MS (APCI) m/z: 304.0[M+NH$_4$]$^+$ (4-2) 2-(4-Undecylphenyl)acetic acid (Example compound 4-2)

A suspension of Example compound 4-1 (1.13 g), ethanol (19.7 mL), 10% palladium carbon (600 mg) was stirred under a hydrogen atmosphere at room temperature for 3 hr. After filtering off the insoluble material in the reaction mixture with diatomaceous earth, the filtrate was concentrated under reduced pressure. The obtained residue was purified by silica gel column chromatography (hexane:ethyl acetate=100:0-50:50), hexane was added and the precipitated solid was collected by filtration to give the title compound (746 mg) as a pale-yellow solid. MS (APCI) m/z: 308.1[M+NH$_4$]$^+$ (4-3) Dibenzyl 1-[(4-undecylphenyl)acetyl]azetidin-3-yl phosphate (Example compound 4-3)

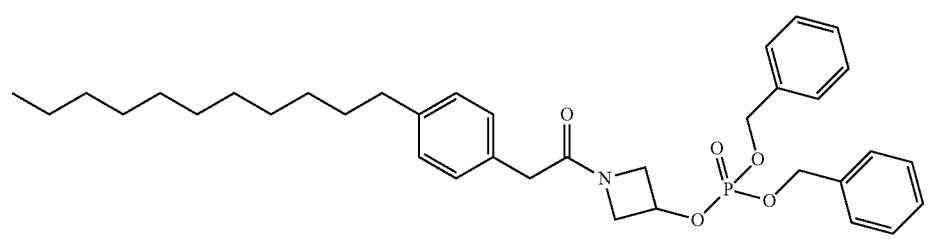 [SMILES: CCCCCCCCCCCc1ccc(CC(=O)N2CC(OP(=O)(OCc3ccccc3)OCc3ccccc3)C2)cc1]

To a solution of Reference Example compound 2 (350 mg) in acetonitrile (4.0 mL) was slowly added under ice-cooling trifluoroacetic acid (0.618 mL), and the mixture was stirred at room temperature for 2 hr. Under ice-cooling, trifluoroacetic acid (0.618 mL) was further added thereto, and the mixture was stirred at room temperature for 2 hr. Under ice-cooling, N,N-dimethylformamide (4.0 mL), and N,N-diisopropylethylamine (2.23 mL) were added, then Example compound 4-2 (187 mg) and HATU (294 mg) were added, and the mixture was stirred under ice-cooling for 2 hr. To the reaction mixture were added ethyl acetate and water, and the mixture was extracted with ethyl acetate, washed with water and saturated brine, and dried over anhydrous sodium sulfate. The solvent was evaporated under reduced pressure. The obtained residue was purified by preparative HPLC (10 mM aqueous ammonium carbonate solution-acetonitrile) to give the title compound (144 mg) as a pale-yellow oil. MS (APCI) m/z: 606.5[M+H]$^+$ (4-4) 1-[(4-Undecylphenyl)acetyl]azetidin-3-yl dihydrogen phosphate (Example compound 4)

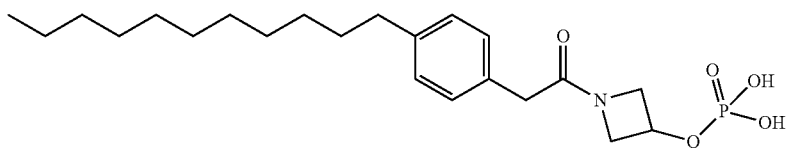 [SMILES: CCCCCCCCCCCc1ccc(CC(=O)N2CC(OP(=O)(O)O)C2)cc1]

A suspension of Example compound 4-3 (140 mg), 10% palladium carbon (70 mg), methanol (2.3 mL) was stirred under a hydrogen atmosphere at room temperature for 4 hr. The reaction mixture was passed through a syringe filter to remove palladium carbon and washed with tetrahydrofuran, and the filtrate was concentrated. To the obtained residue were added methanol and acetonitrile, and the precipitated solid was collected by filtration to give the title compound (70 mg) as a white solid.
MS (APCI) m/z: 426.3[M+H]$^+$ Example 5

(5-1) 1-[3-(4-Octylphenyl)propanoyl]azetidin-3-yl dihydrogen phosphate (Example compound 5)

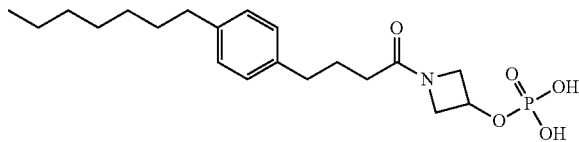 [SMILES: CCCCCCCc1ccc(CCCC(=O)N2CC(OP(=O)(O)O)C2)cc1]

In Example 4, the reaction and treatment similar to those in (4-1)-(4-4) were performed using 3-(4-iodophenyl)propanoic acid instead of 2-(4-iodophenyl)acetic acid and 1-octyne instead of 1-undecyne to give the title compound (12 mg) as a white solid. MS (APCI) m/z: 398.2[M+H]$^+$ Example 6

(6-1) 1-[4-(4-Heptylphenyl)butanoyl]azetidin-3-yl dihydrogen phosphate (Example compound 6)

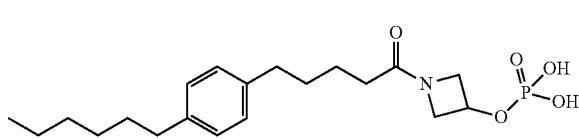 [SMILES: CCCCCCc1ccc(CCCCC(=O)N2CC(OP(=O)(O)O)C2)cc1]

In Example 4, the reaction and treatment similar to those in (4-1)-(4-4) were performed using 4-(4-iodophenyl)butanoic acid instead of 2-(4-iodophenyl)acetic acid and 1-heptyne instead of 1-undecyne to give the title compound (60 mg) as a white solid. MS (APCI) m/z: 398.2[M+H]$^+$ Example 7

(7-1) 1-[5-(4-Hexylphenyl)pentanoyl]azetidin-3-yl dihydrogen phosphate (Example compound 7)

In Example 4, the reaction and treatment similar to those in (4-1)-(4-4) were performed using 4-(4-iodophenyl)pentanoic acid instead of 2-(4-iodophenyl)acetic acid and 1-hexyne instead of 1-undecyne to give the title compound (62 mg) as a white solid. MS (APCI) m/z: 398.3[M+H]$^+$

Example 8

(8-1) 1-{3-[4-(Octyloxy)phenyl]propanoyl}azetidin-3-yl dihydrogen phosphate ammonium salt (Example compound 8)

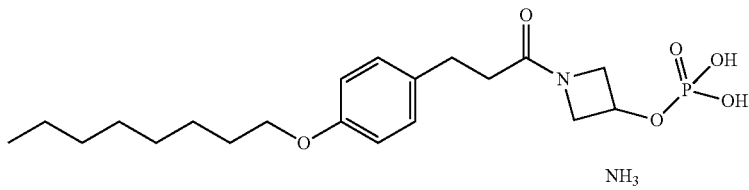

In Example 1, the reaction and treatment similar to those in (1-1)-(1-4) were performed using 1-bromooctane instead of 1-bromononane to give the title compound (81 mg) as a white powder. MS (APCI) m/z: 414.3[M+H]$^+$

Example 9

(9-1) 1-{3-[4-(Decyloxy)phenyl]propanoyl}azetidin-3-yl dihydrogen phosphate ammonium salt (Example compound 9)

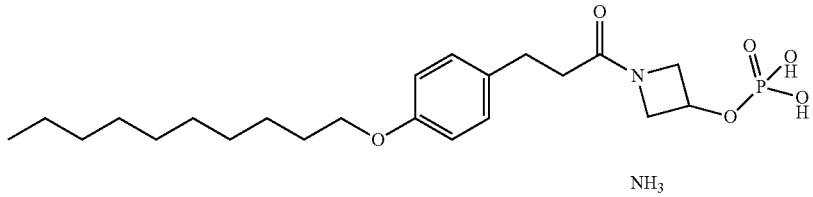

In Example 1, the reaction and treatment similar to those in (1-1)-(1-4) were performed using 1-bromodecane instead of 1-bromononane to give the title compound (94 mg) as a white powder. MS (APCI) m/z: 442.3[M+H]$^+$

Example 10

(10-1) Methyl 10-(4-methylphenyl)-10-oxadecanoate (Example compound 10-1)

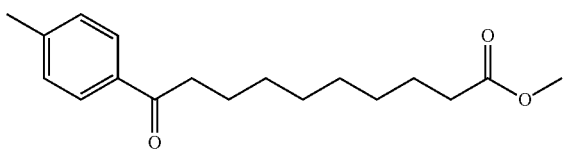

To a suspension of trichloroaluminum (2.27 g) and dichloromethane (42.6 mL) was added under ice-cooling methyl 10-chloro-10-oxadecanoate (2.0 g), and the mixture was stirred at room temperature for 15 min. Toluene (1.36 mL) was added dropwise under ice-cooling. Thereafter, the mixture was stirred at room temperature for 3 hr. The reaction mixture was poured into ice water, extracted with chloroform, successively washed with saturated aqueous sodium hydrogen carbonate solution and saturated brine, and dried over anhydrous sodium sulfate. The solvent was evaporated. The obtained residue was purified by NH silica gel column chromatography (hexane:ethyl acetate=100:0-85:15) to give the title compound (1.58 g) as a white solid.

MS (APCI) m/z: 291.2[M+H]$^+$

(10-2) 10-(4-Methylphenyl)-10-oxadecanoic acid (Example compound 10-2)

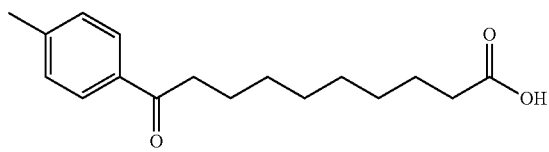 [SMILES: Cc1ccc(C(=O)CCCCCCCCC(=O)O)cc1]

To a solution of Example compound 10-1 (1.58 g) and methanol (10 mL) were added 1N aqueous sodium hydroxide solution (10.9 mL) and tetrahydrofuran (10 mL), and the mixture was stirred at room temperature for 4 hr. Under ice-cooling, to the reaction mixture were added 1N hydrochloric acid and ice water, and the precipitated solid was collected by filtration to give the title compound (1.45 g) as a white solid.

MS (APCI) m/z: 275.2[M+H]⁻

(10-3) 10-(4-Methylphenyl)decanoic acid (Example compound 10-3)

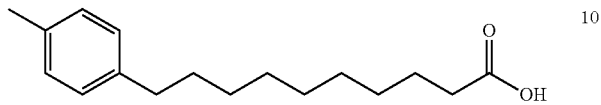

To a solution of Example compound 10-2 (1.45 g) and trifluoroacetic acid (14.5 mL) was added under ice-cooling triethylsilane (2.51 mL), and the mixture was stirred at room temperature for 3 hr. Ice water was added to the reaction mixture under ice-cooling. To the precipitated solid was added methanol, and the mixture was washed with sonicating in suspension, collected by filtration, and dried under reduced pressure to give the title compound (1.18 g) as a white solid.

MS (APCI) m/z: 261.2[M+H]⁻

(10-4) Dibenzyl 1-[10-(4-methylphenyl)decanoyl]azetidin-3-yl phosphate (Example compound 10-4)

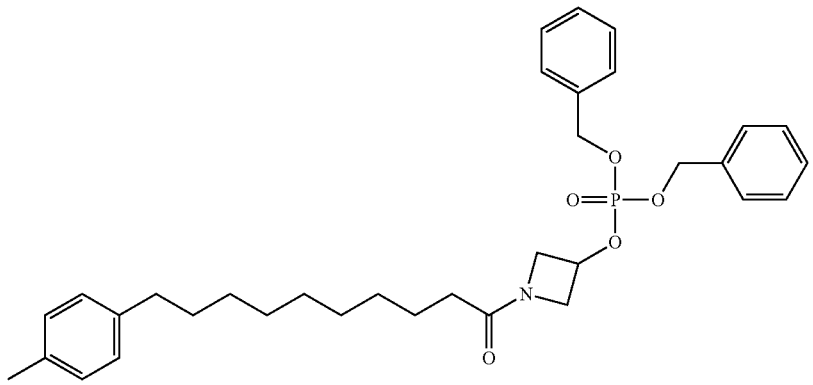 [SMILES: Cc1ccc(CCCCCCCCCC(=O)N2CC(OP(=O)(OCc3ccccc3)OCc3ccccc3)C2)cc1]

To a solution of Reference Example compound 2 (240 mg) in dichloromethane (1.8 mL) was added under ice-cooling trifluoroacetic acid (0.848 mL), and the mixture was stirred under ice-cooling for 1.5 hr. Under ice-cooling, to the reaction mixture were added dichloromethane (4.0 mL) and N,N-diisopropylethylamine (3.81 mL), and then N,N-dimethylformamide (2 mL), Example compound 10-3 (72 mg), and HATU (125 mg) were added, and the mixture was stirred under ice-cooling for 1 hr. To the reaction mixture were added dichloromethane and water, and the mixture was extracted with dichloromethane, washed with saturated brine, and dried over anhydrous sodium sulfate. The solvent was evaporated under reduced pressure. The obtained residue was purified by preparative HPLC (10 mM aqueous ammonium carbonate solution-acetonitrile) to give the title compound (110 mg) as a yellow oil. MS (APCI) m/z: 578.4[M+H]⁺

(10-5) 1-[10-(4-Methylphenyl)decanoyl]azetidin-3-yl dihydrogen phosphate (Example compound 10)

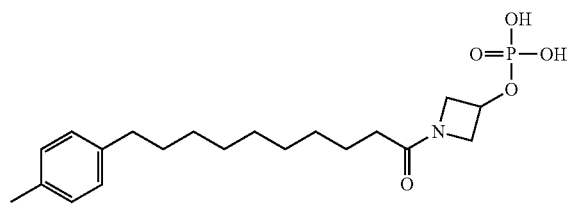 [SMILES: Cc1ccc(CCCCCCCCCC(=O)N2CC(OP(=O)(O)O)C2)cc1]

A suspension of Example compound 10-4 (105 mg), 10% palladium carbon (60 mg), and ethanol (3 mL) was stirred under a hydrogen atmosphere at room temperature for 2 hr. The reaction mixture was passed through a syringe filter to remove palladium carbon, washed with tetrahydrofuran, and the filtrate was concentrated. To the obtained residue were added tetrahydrofuran and acetonitrile and the precipitated solid was collected by filtration to give the title compound (63 mg) as a white solid. MS(ESI) m/z: 398.3[M+H]$^+$ Example 11

(11-1) 1-(11-Phenylundecanoyl)azetidin-3-yl dihydrogen phosphate (Example compound 11)

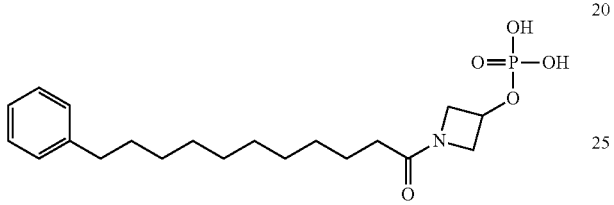

In Example 4, the reaction and treatment similar to those in (4-1)-(4-4) were performed using iodophenyl instead of 2-(4-iodophenyl)acetic acid and 10-undecynoic acid instead of 1-undecyne to give the title compound (218 mg) as a white solid.

MS(ESI) m/z: 398.3[M+H]$^+$

Example 12

(12-1) Dibenzyl {3-[(tert-butoxycarbonyl)amino]propyl}phosphonate (Example compound 12-1)

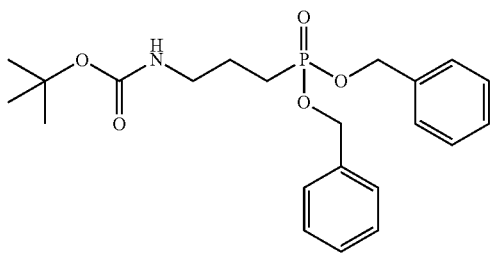 [SMILES: CC(C)(C)OC(=O)NCCCP(=O)(OCc1ccccc1)OCc1ccccc1]

To a solution of dibenzyl phosphite (2.20 g) in N,N-dimethylformamide (28 mL) was added sodium hydride (336 mg), and the mixture was stirred at room temperature for 1 hr.

tert-Butyl N-(3-bromopropyl)carbamate (2.00 g) was added thereto, and the mixture was stirred at 80° C. for 3 hr. Water was added to the reaction mixture, and the mixture was extracted with ethyl acetate. The organic layer was washed with water and brine, and dried over sodium sulfate. The desiccant was filtered off, and the filtrate was concentrated under reduced pressure. The obtained residue was purified by silica gel column chromatography (hexane:ethyl acetate=50:50-20:80) to give the title compound (2.76 g) as a colorless oil.

MS(ESI) m/z: 320.1[M-Boc+H]$^+$ (12-2) Dibenzyl (3-{[(4-methoxyphenyl)methyl]amino}propyl)phosphonate (Example compound 12-2)

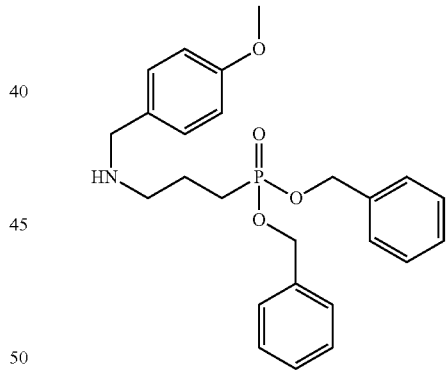

To a solution of Example compound 12-1 (1.37 g) in dichloromethane (16.3 mL) was added under ice-cooling trifluoroacetic acid (1.25 mL), and the mixture was stirred at the same temperature for 1 hr. Under ice-cooling, methanol (16.3 mL) and N,N-diisopropylethylamine (2.83 mL) were added, then 4-methoxybenzaldehyde (0.42 mL) was added thereto, and the mixture was stirred at room temperature for 2 hr. The reaction mixture was concentrated under reduced pressure, and the obtained residue was purified by silica gel column chromatography (chloroform:methanol=100:0-90:10) to give the title compound (247 mg) as a yellow oil.

MS(ESI) m/z: 440.4[M+H]$^+$ (12-3) Dibenzyl [3-({3-[3-(decyloxy)phenyl]propanoyl}[(4-methoxyphenyl)methyl]amino)propyl] phosphonate (Example compound 12-3)

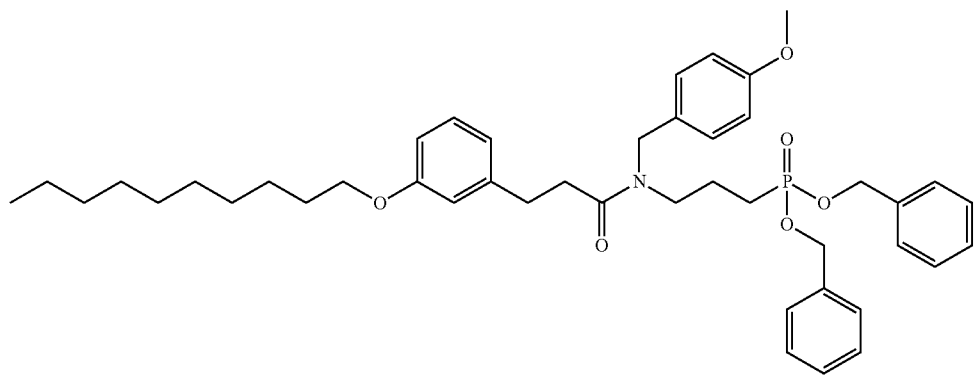 [SMILES: CCCCCCCCCCOc1cccc(CCC(=O)N(CCCP(=O)(OCc2ccccc2)OCc2ccccc2)Cc2ccc(OC)cc2)c1]

To a mixture of Example compound 12-2 (220 mg), N,N-dimethylformamide (5.0 mL), N,N-diisopropylethylamine (0.26 mL), and Reference Example compound 5 (153 mg) was added HATU (285 mg), and the mixture was stirred at room temperature for 4 hr. To the reaction mixture were added saturated aqueous sodium hydrogen carbonate solution and chloroform, and the mixture was stirred. The organic layer was separated by a Phase-separator (registered trade mark) and concentrated under reduced pressure. The obtained residue was purified by silica gel column chromatography (hexane:ethyl acetate=60:40-30:70) to give the title compound (330 mg) as a colorless oil.

(12-4) [3-({3-[3-(Decyloxy)phenyl]propanoyl}[(4-methoxyphenyl)methyl]amino)propyl]phosphonic acid ammonium salt (Example compound 12)

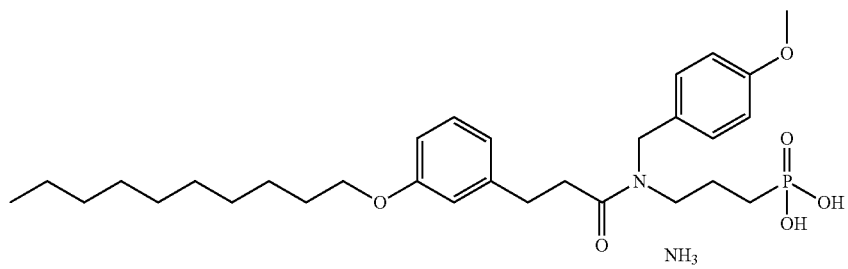

Example compound 12-4 (330 mg) was dissolved in ethanol (4.4 mL), 7.5% palladium carbon (64 mg) was added, and the mixture was stirred under a hydrogen atmosphere at room temperature for 3 hr, and filtered. The filtrate was concentrated, and the obtained residue was purified by preparative HPLC (10 mM aqueous ammonium carbonate solution-acetonitrile) to give the title compound (165 mg) as a colorless oil. MS (APCI) m/z: 548.2[M+H]$^+$ Example 13

(13-1) 1-{4-[3-(Undecyloxy)phenyl]pyridin-2-yl}azetidin-3-yl dihydrogen phosphate ammonium salt (Example compound 13)

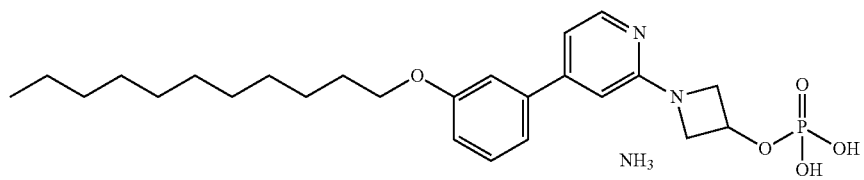

To a solution of Example compound 133-2 (150 mg) in N-methylpyrrolidone (4.3 mL) were added Reference Example compound 1 (139 mg) and 1,8-diazabicyclo[5.4.0]undec-7-ene (0.198 mL), and the mixture was stirred at 100° C. for 6 hr. To the reaction mixture was added saturated aqueous ammonium chloride solution, and the mixture was extracted with ethyl acetate. The organic layer was dried over sodium sulfate, the desiccant was filtered off, and the filtrate was concentrated under reduced pressure. To the obtained residue were added dichloromethane (4.4 mL) and trifluoroacetic acid (0.45 mL), and the mixture was stirred at room temperature for 2 hr. The reaction mixture was concentrated under reduced pressure. The obtained residue was purified by preparative HPLC (10 mM aqueous ammonium carbonate solution-acetonitrile) to give the title compound (21 mg) as a pale-yellow viscous oil.
MS (APCI) m/z: 477.3[M+H]$^+$ Example 14

(14-1) 3-(Undecyloxy)benzonitrile (Example compound 14-1)

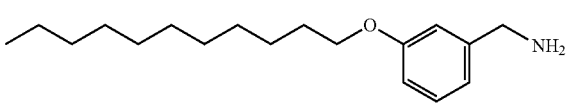

A mixture of 3-hydroxybenzonitrile (500 mg), 1-bromoundecane (1.12 mL), cesium carbonate (3.42 g), and N,N-dimethylformamide (8.4 mL) was stirred at 70° C. for one day and night. Water was added to the reaction mixture, and the mixture was extracted with diethyl ether. The organic layer was washed with water and saturated brine, and dried over anhydrous sodium sulfate. The desiccant was filtered off, and the filtrate was concentrated under reduced pressure. The obtained residue was purified by silica gel column chromatography (hexane:ethyl acetate=100:0-90:10) to give the title compound (1.09 g) as a colorless oil.
MS (APCI) m/z: 247.3 (M+H)$^+$.

(14-2) 1-[3-(Undecyloxy)phenyl]methanamine (Example compound 14-2)

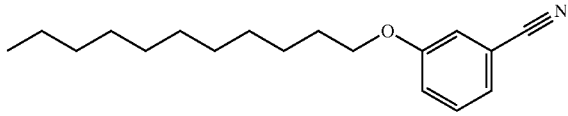 [SMILES: CCCCCCCCCCCOc1cccc(C#N)c1]

To a solution of Example compound 14-1 (650 mg) and nickel chloride (II) hexahydrate (113 mg) in methanol (11.9 mL) was added under ice-cooling sodium borohydride (540 mg) by small portions, and the mixture was stirred at the same temperature for 3 hr. Under ice-cooling, diethylenetriamine (0.77 mL) was added to quench the reaction. Saturated aqueous sodium hydrogen carbonate solution was added, and the mixture was extracted with ethyl acetate. The organic layer was dried over sodium sulfate, the desiccant was filtered off, and the filtrate was concentrated under reduced pressure. The obtained residue was purified by silica gel column chromatography (chloroform:methanol=100:0-90:10) to give the title compound (545 mg) as a colorless solid. MS (APCI) m/z: 278.2 (M+H)$^+$.

(1({[3-(Undecyloxy)phenyl]methyl}carbamoyl)azetidin-3-yl dihydrogen phosphate ammonium salt (Example compound 14)

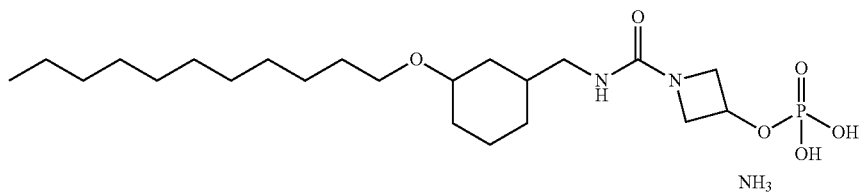

To a solution of Example compound 14-2 (162 mg) in N,N-dimethylformamide (1.9 mL) was added under ice-cooling 1,1'-carbonyldiimidazole (95 mg), and the mixture was stirred at the same temperature for 2 hr. Under ice-cooling, a solution of Reference Example compound 1 (170 mg) in N,N-diisopropylethylamine (0.12 mL) was added thereto, and the mixture was stirred at room temperature overnight. Water was added to the reaction mixture, and the mixture was extracted with ethyl acetate. The organic layer was dried over anhydrous sodium sulfate, the desiccant was filtered off, and the filtrate was concentrated under reduced pressure. To the obtained residue were added dichloromethane (5.8 mL) and trifluoroacetic acid (0.58 mL), and the mixture was stirred at room temperature for 2 hr and concentrated under reduced pressure. The obtained residue was purified by preparative HPLC (10 mM aqueous ammonium carbonate solution-acetonitrile) to give the title compound (205 mg) as a white solid.
MS (APCI) m/z: 457.3 (M+H)$^+$

Example 15

(1-[8-(4-Propylphenyl)octanoyl]azetidin-3-yl dihydrogen phosphate (Example compound 15)

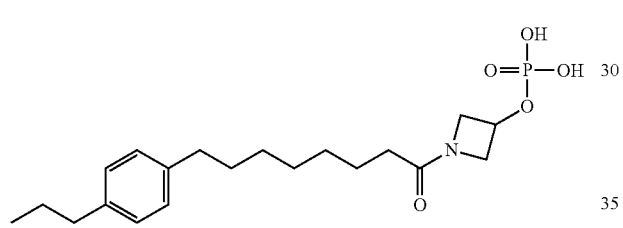

In Example 10, the reaction and treatment similar to those in (10-1), (10-3)-(10-5) were performed using propanoyl chloride instead of methyl 10-chloro-10-oxadecanoate and 8-phenyloctanoic acid instead of toluene to give the title compound (68 mg) as a white solid. MS(ESI) m/z: 398.3 [M+H]$^+$

Example 16

(16-1) 9-(4-Acetylphenyl)nonanoic acid (Example compound 16-1)

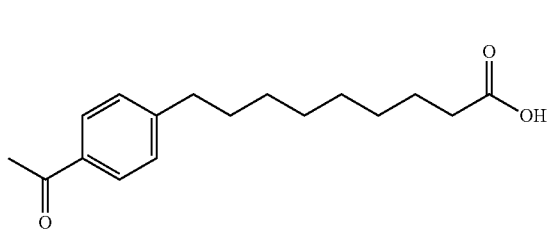 [SMILES: CC(=O)c1ccc(CCCCCCCCC(=O)O)cc1]

To a suspension of trichloroaluminum (6.83 g) and dichloromethane (64 mL) was added under ice-cooling acetylchloride (2.01 mL) and the mixture was stirred at room temperature for 10 min. A solution of 9-phenylnonanoic acid (3.00 g) in dichloromethane (15 mL) was added dropwise thereto, and the mixture was stirred for 3 hr. The reaction mixture was poured into ice water, extracted with chloroform, and dried over anhydrous sodium sulfate. Insoluble material was filtered off with diatomaceous earth and the filtrate was concentrated under reduced pressure. To the obtained residue were added water (150 mL), methanol (5 mL), and 4N aqueous sodium hydroxide solution (10 mL) and the mixture was stirred. Ice water (50 mL) and 1N hydrochloric acid (50 mL) were added, and the precipitated solid was collected by filtration to give the title compound (2.74 g) as a white solid. MS (APCI) m/z: 275.2[M−H]$^−$ (16-2) 9-(4-Ethylphenyl)nonanoic acid (Example compound 16-2)

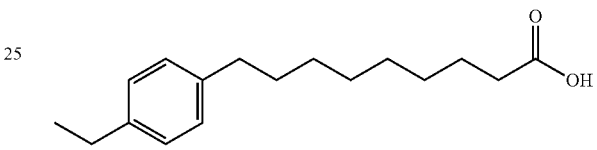

To a solution of Example compound 16-1 (2.74 g) in trifluoroacetic acid (27.5 mL) was added under ice-cooling triethylsilane (4.77 mL), and the mixture was stirred at room temperature for 2 hr. The reaction mixture was concentrated, ice water was added, and the mixture was extracted with ethyl acetate, and dried over anhydrous sodium sulfate. The solvent was evaporated under reduced pressure. To the precipitated solid was added diethyl ether, and the mixture was washed with sonicating in suspension, collected by filtration, and dried under reduced pressure to give the title compound (2.06 g) as a white solid. MS (APCI) m/z: 261.1[M−H]$^−$ (16-3) 9-(4-Ethylphenyl)-1-(3-hydroxyazetidin-1-yl) nonan-1-one (Example compound 16-3)

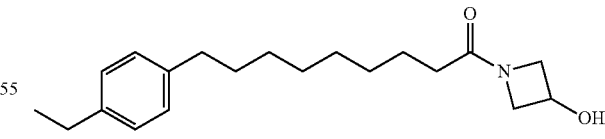

Example compound 16-2 (1.30 g) and azetidin-3-ol hydrochloride (0.65 mg) were dissolved in N,N-dimethylformamide (19.8 mL), N,N-diisopropylethylamine (1.71 mL) and HATU (2.26 g) were added, and the mixture was stirred at room temperature for 1 hr. To the reaction mixture was added water (20 mL) at 0° C., and the precipitated solid was collected by filtration and azeotropically distilled with toluene to give the title compound (1.43 g) as a white solid. MS(ESI) m/z: 318.3 (M+H)$^+$ (16-4) Dibenzyl 1-[9-(4-ethylphenyl)nonanoyl]azetidin-3-yl phosphate (Example compound 16-4)

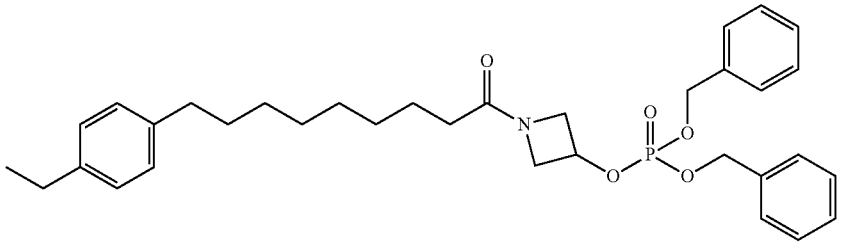 [SMILES: CCc1ccc(CCCCCCCCC(=O)N2CC(OP(=O)(OCc3ccccc3)OCc3ccccc3)C2)cc1]

Example compound 16-3 (980 mg) was suspended in dichloromethane (9.8 mL) and acetonitrile (3.9 mL), 1H-tetrazole (238 mg) and dibenzyl N,N-diisopropylphosphoramidite (1.27 mL) were added at 0° C., and the mixture was stirred at room temperature for 1 hr. After cooling to 0° C., 30% aqueous hydrogen peroxide (0.35 mL) was added thereto, and the mixture was stirred at room temperature for 1 hr. To the reaction mixture was added saturated aqueous sodium thiosulfate solution (10 mL) at 0° C., and the mixture was stirred at room temperature for 10 min. The mixture was extracted with ethyl acetate, washed with saturated aqueous sodium hydrogen carbonate solution and saturated brine, and dried over anhydrous sodium sulfate. The solvent was evaporated under reduced pressure. The obtained residue and crudely purified product (750 mg) were combined and purified by silica gel column chromatography (hexane:ethyl acetate=60:40-40:60) to give the title compound (1.95 g) as a colorless viscous oil. MS(ESI) m/z: 578.6 (M+H)$^+$ (16-5) 1-[9-(4-Ethylphenyl)nonanoyl]azetidin-3-yl dihydrogen phosphate (Example compound 16)

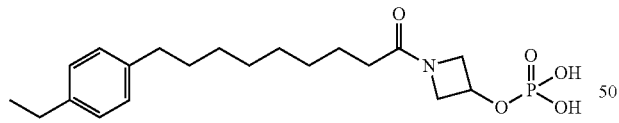

Example compound 16-4 (1.95 g) was dissolved in methanol (16.9 mL), palladium carbon (585 mg) was added, and the mixture was stirred under a hydrogen atmosphere at room temperature for 20 hr. After nitrogen purge, the reaction mixture was passed through a syringe filter to remove palladium carbon, and rinsed with methanol. After evaporation of the solvent, the obtained solid and crudely purified product (140 mg) were combined, suspended in acetonitrile (10 mL), heated to 80° C., and dissolved in ethanol (1 mL). After allowing to cool to room temperature, the precipitated solid was collected by filtration, and washed with acetonitrile:ethanol=10:1 to give the title compound (1.10 g) as a white powder. MS(ESI) m/z: 398.3 (M+H)$^+$ Example 17

(17-1) 5-(4-Methylphenyl)-4-pentyn-1-ol (Example compound 17-1)

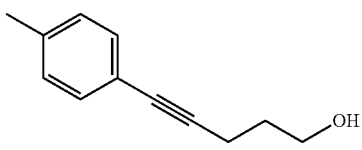

1-Iodo-4-methylbenzene (3.00 g) was dissolved in N,N-diisopropylethylamine (48 mL), and 4-pentyn-1-ol (1.54 mL), copper iodide (I) (86 mg) and dichlorobis(triphenylphosphine)palladium(II) (319 mg) were added thereto. After a degassing operation, the mixture was stirred under a nitrogen atmosphere at room temperature for 3 hr. The reaction mixture was filtered, and the filtrate was concentrated. The obtained residue was purified by silica gel column chromatography (hexane:ethyl acetate=75:25-50:50) to give the title compound (2.34 g) as a brown powder. MS (APCI) m/z: 175.1[M+H]$^+$ (17-2) 5-(4-Methylphenyl)pentan-1-ol (Example compound 17-2)

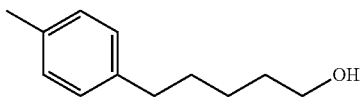

Example compound 17-1 (2.26 g) was dissolved in ethanol (43.3 mL), 10% palladium carbon (453 mg) was added, and the mixture was stirred under a hydrogen atmosphere at room temperature for 15.5 hr. The reaction mixture was filtered. The filtrate was concentrated, and the obtained residue was purified by silica gel column chromatography (hexane:ethyl acetate=70:30-50:50) to give the title compound (2.22 g) as a brown oil. MS (APCI) m/z: 196.1[M+NH$_4$]$^+$ (17-3) Methyl 3-(4-{[5-(4-methylphenyl)pentyl]oxy}phenyl)propanoate (Example compound 17-3)

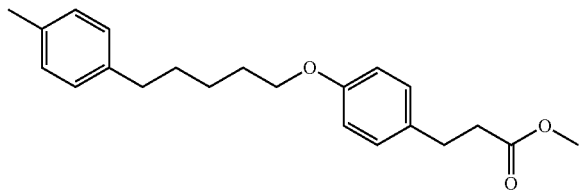

Example compound 17-2 (1.00 g) was dissolved in tetrahydrofuran (18.7 mL), triphenylphosphine (2.21 g) was added, then diisopropyl azodicarboxylate (3.82 mL) was added dropwise thereto under ice-cooling, and the mixture was stirred at room temperature for 19.5 hr. The solvent was evaporated under reduced pressure, and the residue was purified by silica gel column chromatography (hexane:ethyl acetate=90:10-80:20) to give the title compound (496 mg) as a white powder.

MS (APCI) m/z: 341.0[M+H]$^+$ (17-4) 3-(4-{[5-(4-Methylphenyl)pentyl]oxy}phenyl)propanoic acid (Example compound 17-4)

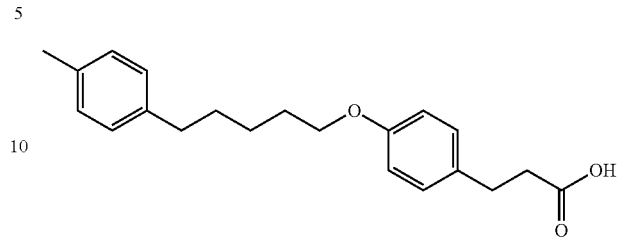

Example compound 17-3 (488 mg) was dissolved in methanol (2.39 mL) and tetrahydrofuran (2.39 mL), and 2N aqueous sodium hydroxide solution (2.37 mL) were added dropwise, and the mixture was stirred at 60° C. for 30 min. The solvent was evaporated under reduced pressure. Water (5 mL), methanol (2 mL) and acetonitrile (2 mL) were added to the residue, 1N hydrochloric acid (5 mL) was added dropwise thereto under ice-cooling, and the mixture was sonicated. Then, the precipitated solid was washed with water to give the title compound (396 mg) as a white powder. MS (APCI) m/z: 344.2[M+NH$_4$]$^+$ (17-5) 1-[3-(4-{[5-(4-Methylphenyl)pentyl]oxy}phenyl)propanoyl]azetidin-3-yl dihydrogen phosphate ammonium salt (Example compound 17)

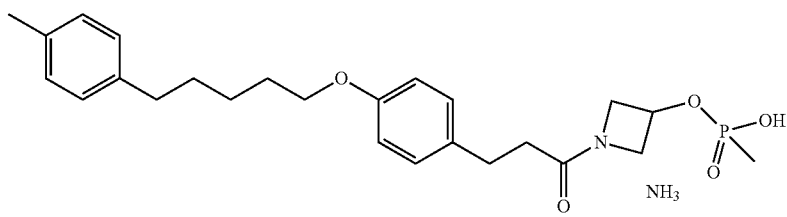

In Example 1, the reaction and treatment similar to those in (1-3)-(1-4) were performed using Example compound 17-4 instead of Example compound 1-2 to give the title compound (64 mg) as a white powder. MS (APCI) m/z: 462.3[M+H]+

Example 18

(18-1) Dibenzyl (3R)-1-{3-[3-(decyloxy)phenyl] propanoyl}pyrrolidin-3-yl phosphate (Example compound 18-1)

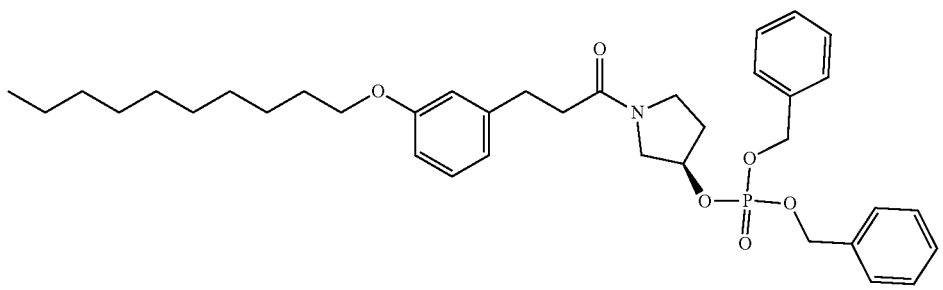 [SMILES: CCCCCCCCCCOc1cccc(CCC(=O)N2CC[C@@H](OP(=O)(OCc3ccccc3)OCc3ccccc3)C2)c1]

Reference Example compound 3 (370 mg) was dissolved in dichloromethane (2.07 mL), trifluoroacetic acid (1.27 mL) was added dropwise under ice-cooling, and the mixture was stirred under ice-cooling for 1 hr. Under ice-cooling, N,N-diisopropylethylamine (3.56 mL) was added, then, N,N-dimethylformamide (2.0 mL), Reference Example compound 5 (140 mg), and HATU (261 mg) were added thereto, and the mixture was stirred at room temperature for 85 min. The reaction mixture was diluted with ethyl acetate, water was added, and the mixture was extracted with ethyl acetate, washed with water and saturated brine, and dried over anhydrous sodium sulfate. The solvent was evaporated under reduced pressure. The residue was purified by silica gel column chromatography (ethyl acetate:methanol=100:0-95:5) to give the title compound (251 mg) as a pale-yellow oil. MS (APCI) m/z: 636.4[M+H]+

(18-2) (3R)-1-{3-[3-(Decyloxy)phenyl] propanoyl}pyrrolidin-3-yl dihydrogen phosphate ammonium salt (Example compound 18)

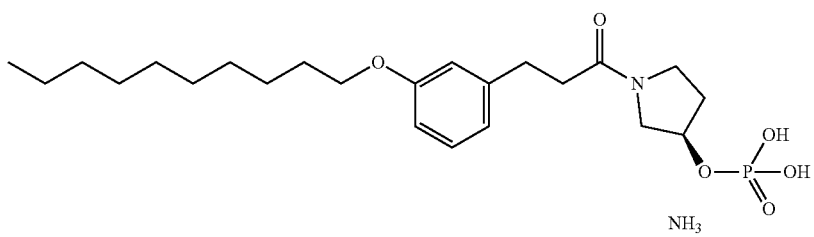

Example compound 18-1 (243 mg) was dissolved in methanol (3.82 mL), 10% palladium carbon (80 mg) was added, and the mixture was stirred under a hydrogen atmosphere at room temperature for 3 hr and filtered. The filtrate was concentrated, and the obtained residue was purified by preparative HPLC (10 mM aqueous ammonium carbonate solution-acetonitrile) to give the title compound (139 mg) as a white powder. MS (APCI) m/z: 456.4[M+H]$^+$ Example 19

(19-1) Dibenzyl (3R)-1-{3-[3-(undecyloxy)phenyl]propanoyl}pyrrolidin-3-yl phosphate (Example compound 19-1)

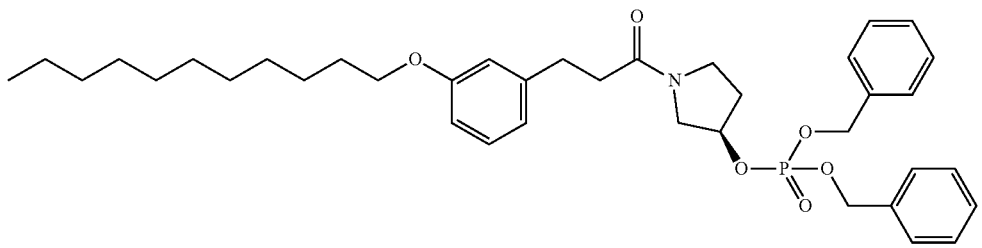 [SMILES: CCCCCCCCCCCOc1cccc(CCC(=O)N2CC[C@@H](OP(=O)(OCc3ccccc3)OCc3ccccc3)C2)c1]

Reference Example compound 3 (370 mg) was dissolved in dichloromethane (2.07 mL), trifluoroacetic acid (1.27 mL) was added dropwise under ice-cooling, and the mixture was stirred under ice-cooling for 1 hr. Under ice-cooling, N,N-diisopropylethylamine (3.56 mL) was added, then, N,N-dimethylformamide (2 mL), Example compound 3-2 (147 mg), and HATU (262 mg) were added thereto, and the mixture was stirred at room temperature for 100 min. The reaction mixture was diluted with ethyl acetate, water was added, and the mixture was extracted with ethyl acetate, washed with water and saturated brine, and dried over anhydrous sodium sulfate. The solvent was evaporated under reduced pressure. The residue was purified by silica gel column chromatography (ethyl acetate:methanol=100:0-95:5) to give the title compound (230 mg) as a pale-yellow oil. MS (APCI) m/z: 650.4[M+H]$^+$ (19-2) (3R)-1-{3-[3-(Undecyloxy)phenyl]propanoyl}pyrrolidin-3-yl dihydrogen phosphate ammonium salt (Example compound 19)

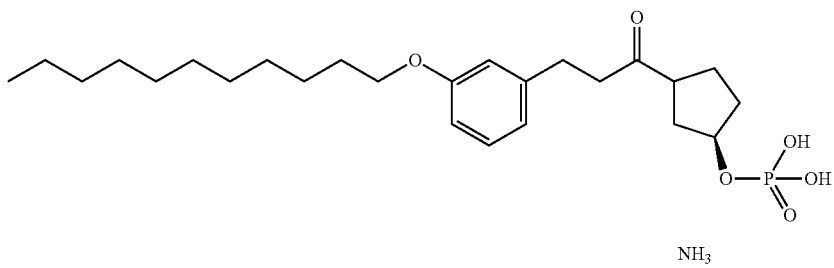

Example compound 19-1 (222 mg) was dissolved in methanol (3.42 mL), 10% palladium carbon (111 mg) was added, and the mixture was stirred under a hydrogen atmosphere at room temperature for 3 hr and filtered. The filtrate was concentrated, and the obtained residue was purified by preparative HPLC (10 mM aqueous ammonium carbonate solution-acetonitrile) to give the title compound (131 mg) as a white powder. MS (APCI) m/z: 470.4[M+H]+

Example 20

(20-1) (3R)-1-{3-[4-(Nonyloxy)phenyl]propanoyl}pyrrolidin-3-yl dihydrogen phosphate ammonium salt (Example compound 20)

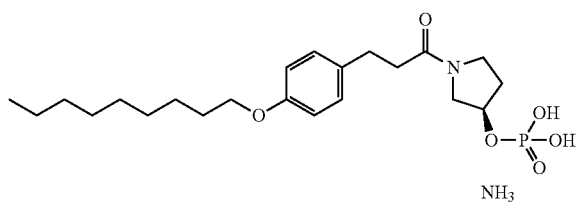

In Example 18, the reaction and treatment similar to those in (18-1)-(18-2) were performed using Example compound 1-2 instead of Reference Example compound 5 to give the title compound (141 mg) as a white powder. MS (APCI) m/z: 442.4[M+H]+

Example 21

(21-1) 1-(10-Phenyldecanoyl)azetidin-3-yl dihydrogen phosphate (Example compound 21)

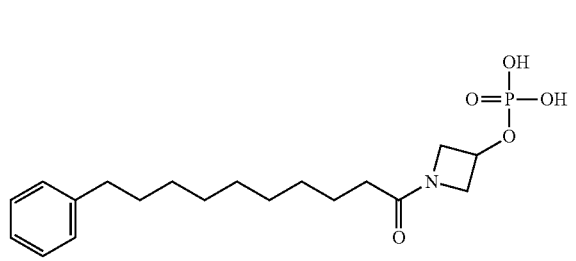 [SMILES: O=C(CCCCCCCCCc1ccccc1)N1CC(OP(=O)(O)O)C1]

In Example 4, the reaction and treatment similar to those in (4-3)-(4-4) were performed using 10-phenyldecanoic acid instead of Example compound 4-2 to give the title compound (104 mg) as a white solid. MS(ESI) m/z: 384.3[M+H]+

Example 22

(22-1) 1-(3-{4-[2-(4-Methylphenyl)ethoxy]phenyl}propanoyl)azetidin-3-yl dihydrogen phosphate ammonium salt (Example compound 22)

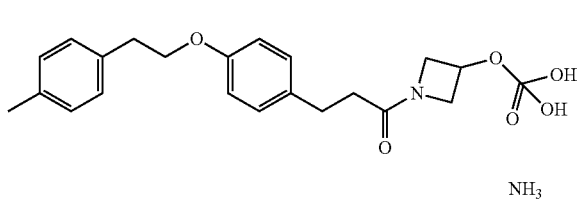

In Example 1, the reaction and treatment similar to those in (1-1)-(1-4) were performed using 1-(2-bromoethyl)-4-methylbenzene instead of 1-bromononane to give the title compound (138 mg) as a white powder. MS (APCI) m/z: 418.1[M−H]−

Example 23

(23-1) 1-(11-Phenylundecanoyl)pyrrolidin-3-yl dihydrogen phosphate (Example compound 23)

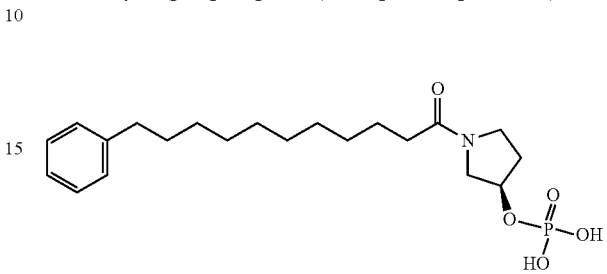

In Example 4, the reaction and treatment similar to those in (4-3)-(4-4) were performed using 10-phenyldecanoic acid instead of Example compound 4-2 and Reference Example compound 3 instead of Reference Example compound 2 to give the title compound (101 mg) as a white solid. MS(ESI) m/z: 412.3[M+H]+

Example 24

(24-1) (3R)-1-[9-(4-Ethylphenyl)nonanoyl]pyrrolidin-3-yl dihydrogen phosphate ammonium salt (Example compound 24)

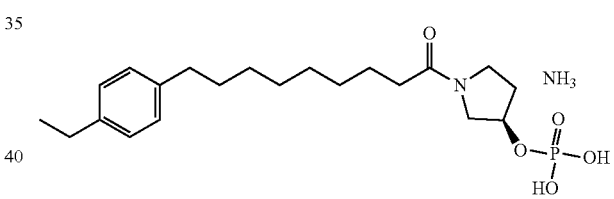

In Example 1, the reaction and treatment similar to those in (1-3)-(1-4) were performed using Example compound 16-2 instead of Example compound 1-2 and Reference Example compound 3 instead of Reference Example compound 2 to give the title compound (92 mg) as a colorless oil. MS(ESI) m/z: 412.3[M+H]+

Example 25

(25-1) (3R)-1-[10-(4-Mthylphenyl)decanoyl]pyrrolidin-3-yl dihydrogen phosphate ammonium salt (Example compound 25)

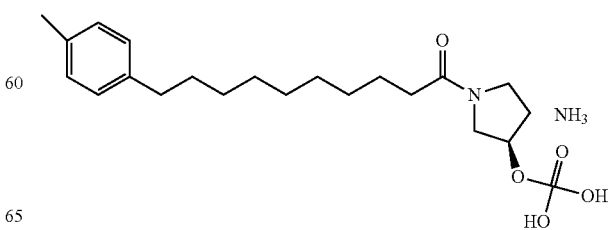

In Example 1, the reaction and treatment similar to those in (1-3)-(1-4) were performed using Example compound 10-3 instead of Example compound 1-2 and Reference Example compound 3 instead of Reference Example compound 2 to give the title compound (115 mg) as a white solid.
MS(ESI) m/z: 412.3[M+H]$^+$ Example 26

(26-1) Methyl 4-[(4-octyloxy)phenyl]butanoate (Example compound 26-1)

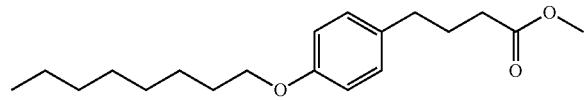 [SMILES: CCCCCCCCOc1ccc(CCCC(=O)OC)cc1]

To a suspension of methyl 4-(4-hydroxyphenyl)butanoate (350 mg), potassium carbonate (383 mg), and N,N-dimethylformamide (6.0 mL) was added 1-bromooctane (0.329 mL), and the mixture was stirred at room temperature for 24 hr. Water was added to the reaction mixture, and the mixture was extracted with ethyl acetate, washed with water and saturated brine, and dried over anhydrous sodium sulfate. The solvent was evaporated under reduced pressure to give the title compound (560 mg) as a yellow liquid.
MS (APCI) m/z: 324.1[M+NH$_4$]$^+$ (26-2) 4-[4-(Octyloxy)phenyl]butanoic acid (Example compound 26-2)

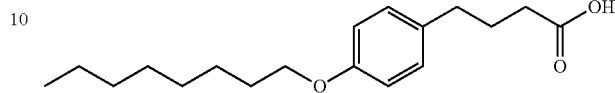

To a solution of Example compound 26-1 (560 mg) and methanol (3 mL) were added 1N aqueous sodium hydroxide solution (3.6 mL) and tetrahydrofuran (4 mL), and the mixture was stirred at room temperature for 3 hr. Under ice-cooling, to the reaction mixture were added 1N hydrochloric acid and water, and the precipitated solid was collected by filtration to give the title compound (220 mg) as a white solid.
MS (APCI) m/z: 291.1[M−H]$^-$ (26-3) Dibenzyl 1-{4-[4-(octyloxy)phenyl] butanoyl}azetidin-3-yl phosphate (Example compound 26-3)

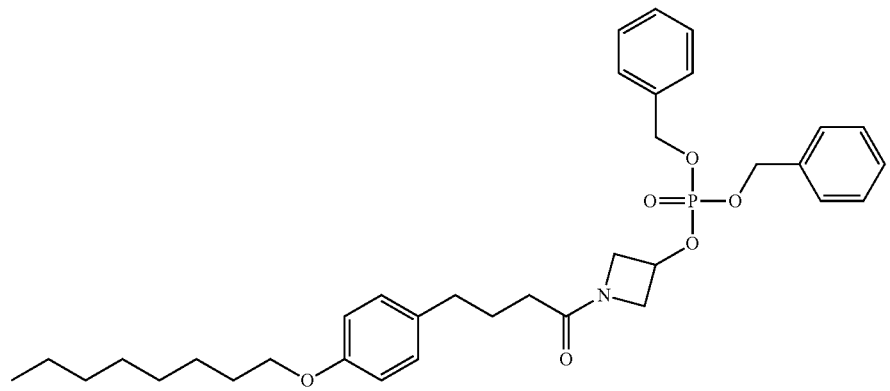 [SMILES: CCCCCCCCOc1ccc(CCCC(=O)N2CC(OP(=O)(OCc3ccccc3)OCc3ccccc3)C2)cc1]

To a solution of Reference Example compound 2 (400 mg) in dichloromethane (3.1 mL) was added under ice-cooling trifluoroacetic acid (1.43 mL), and the mixture was stirred under ice-cooling for 1 hr. Under ice-cooling, to the reaction mixture were added dichloromethane (6 mL) and N,N-diisopropylethylamine (6.4 mL), and Example compound 26-2 (158 mg) and HATU (246 mg) were added, and the mixture was stirred under ice-cooling for 1 hr. To the reaction mixture were added dichloromethane and water, and the mixture was extracted with dichloromethane, washed with saturated brine, and dried over anhydrous sodium sulfate. The solvent was evaporated under reduced pressure. The obtained residue was purified by preparative HPLC (10 mM aqueous ammonium carbonate solution-acetonitrile) to give the title compound (194 mg) as a pale-yellow oil. MS (APCI) m/z: 608.5[M+H]$^+$ (26-4) 1-{4-[4-(Octyloxy)phenyl]butanoyl}azetidin-3-yl dihydrogen phosphate (Example compound 26)

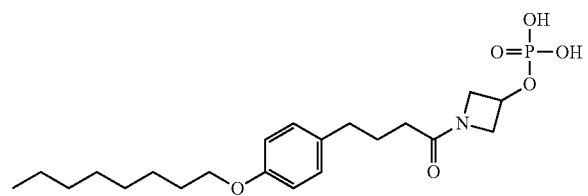 [SMILES: CCCCCCCCOc1ccc(CCCC(=O)N2CC(OP(=O)(O)O)C2)cc1]

A suspension of Example compound 26-3 (190 mg), 10% palladium carbon (60 mg), and ethanol (3 mL) was stirred under a hydrogen atmosphere at room temperature for 90 min. The reaction mixture was passed through a syringe filter to remove palladium carbon, washed with tetrahydrofuran, and the filtrate was concentrated. To the obtained residue were added tetrahydrofuran and acetonitrile, and the precipitated solid was collected by filtration to give the title compound (112 mg) as a white solid. MS (APCI) m/z: 428.3[M+H]$^+$ Example 27

(27-1) (3R)-1-[5-(4-Hexylphenyl)pentanoyl]pyrrolidin-3-yl dihydrogen phosphate ammonium salt (Example compound 27)

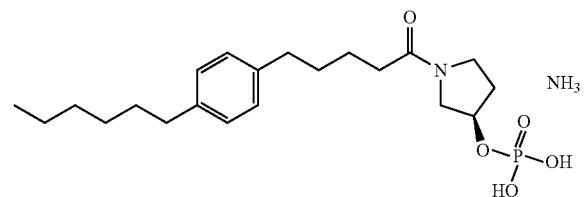

In Example 4, the reaction and treatment similar to those in (4-1)-(4-4) were performed using 4-(4-iodophenyl)pentanoic acid instead of 2-(4-iodophenyl)acetic acid, 1-hexyne instead of 1-undecyne, and Reference Example compound 3 instead of Reference Example compound 2, and the obtained residue was purified by preparative HPLC (10 mM aqueous ammonium carbonate solution-acetonitrile) to give the title compound (93 mg) as a colorless oil. MS (APCI) m/z: 412.4[M+H]$^+$ Example 28

(28-1) tert-Butyl (2-{[bis(benzyloxy)phosphoryl]oxy}ethyl)carbamate (Example compound 28-1)

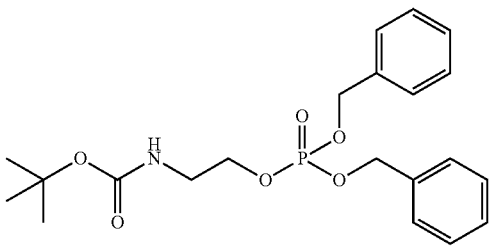 [SMILES: CC(C)(C)OC(=O)NCCOP(=O)(OCc1ccccc1)OCc1ccccc1]

To a suspension of tert-butyl (2-hydroxyethyl)carbamate (5.0 g), dichloromethane (50 mL), and 1H-tetrazole (4.34 g) was added acetonitrile (25 mL), and dibenzyl N,N-diisopropyl phosphoramidite (20.8 mL) was added, and the mixture was stirred at room temperature for 3 hr. Under ice-cooling, tert-butyl hydroperoxide (70% aqueous solution, 12.4 mL) was added thereto, and the mixture was stirred for 1 hr. The reaction mixture was concentrated, hexane was added to the residue, and insoluble material was filtered off and the mother liquor was concentrated under reduced pressure. The obtained residue was purified by silica gel column chromatography (ethyl acetate:hexane=100:0-40:60) to give the title compound (10.47 g) as a white solid. MS (APCI) m/z: 422.0[M+H]$^+$ (28-2) tert-Butyl (2-{[bis(benzyloxy)phosphoryl]oxy}ethyl)propylcarbamate (Example compound 28-2)

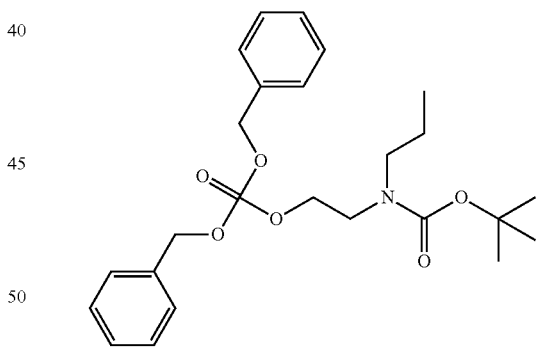

Sodium hydride was dissolved in N,N-dimethylformamide (2 mL), a solution of Example compound 28-1 (350 mg) in N,N-dimethylformamide (2 mL) was added dropwise under ice-cooling, and the mixture was stirred under ice-cooling for 20 min. Under ice-cooling, 1-iodopropane (2 mL) was added dropwise thereto, and the mixture was stirred at room temperature for 90 min. Under ice-cooling, water was added to the reaction mixture, and the mixture was extracted with ethyl acetate, washed with saturated brine, and dried over anhydrous sodium sulfate. The solvent was evaporated under reduced pressure. The residue was purified by silica gel column chromatography (hexane:ethyl acetate=75:25-50:50) to give the title compound (210 mg) as a pale-yellow oil.

MS (APCI) m/z: 464.0[M+H]+

(28-3) Dibenzyl 2-[{3-[3-(decyloxy)phenyl]propanoyl}(propyl)amino]ethyl phosphate (Example compound 28-3)

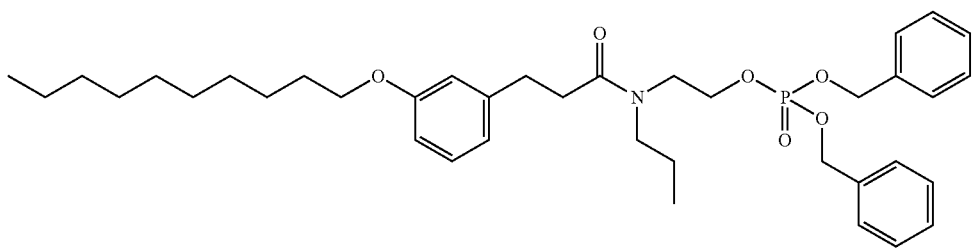 [SMILES: CCCCCCCCCCOc1cccc(CCC(=O)N(CCC)CCOP(=O)(OCc2ccccc2)OCc2ccccc2)c1]

Example compound 28-2 (390 mg) was dissolved in dichloromethane (2.1 mL), and trifluoroacetic acid (1.29 mL) was added dropwise under ice-cooling, and the mixture was stirred under ice-cooling for 1 hr. Under ice-cooling, N,N-diisopropylethylamine (3.63 mL) was added, then, N,N-dimethylformamide (2 mL), Reference Example compound 5 (143 mg), and HATU (266 mg) were added thereto, and the mixture was stirred at room temperature for 3 hr. The reaction mixture was diluted with ethyl acetate, water was added, and the mixture was extracted with ethyl acetate, washed with water and saturated brine, and dried over anhydrous sodium sulfate. The solvent was evaporated under reduced pressure. The residue was purified by silica gel column chromatography (hexane:ethyl acetate=60:40-40:60) to give the title compound (222 mg) as a pale-yellow oil. MS (APCI) m/z: 652.1[M+H]+

(28-4) 2-[{3-[3-(Decyloxy)phenyl]propanoyl}(propyl)amino]ethyl dihydrogen phosphate ammonium salt (Example compound 28)

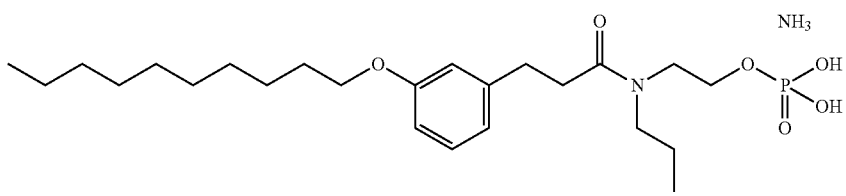

Example compound 28-3 (213 mg) was dissolved in methanol (3.27 mL), 10% palladium carbon (106 mg) was added, and the mixture was stirred under a hydrogen atmosphere at room temperature for 200 min, and filtered. The filtrate was concentrated, and the obtained residue was purified by preparative HPLC (10 mM aqueous ammonium carbonate solution-acetonitrile) to give the title compound (52 mg) as a colorless oil. MS (APCI) m/z: 472.2[M+H]$^+$ Example 29

(29-1) 4-{4-[2-(4-Methylphenyl)ethyl]phenyl}butanoic acid (Example compound 29-1)

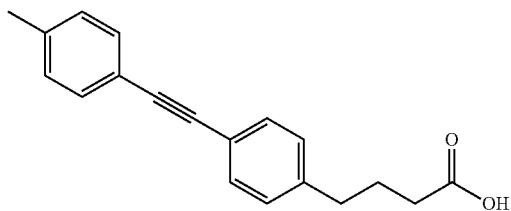 [SMILES: Cc1ccc(C#Cc2ccc(CCCC(=O)O)cc2)cc1]

A mixture of 4-(4-bromophenyl)butyric acid (2.00 g), 4-ethynyltoluene (1.04 g), bis(triphenylphosphine)palladium(II) dichloride (484 mg), copper iodide (I) (263 mg), and triethylamine (6.89 mL) was stirred at 60° C. for one day and night. To the reaction mixture was added 1N hydrochloric acid, and the mixture was extracted with ethyl acetate. The organic layer was dried over anhydrous sodium sulfate, the desiccant was filtered off, and the filtrate was concentrated under reduced pressure. The obtained residue was purified by silica gel column chromatography (hexane:ethyl acetate=25:75-0:100) and purified again by silica gel column chromatography (hexane:ethyl acetate=50:50-25:75). The residue was washed with diisopropyl ether to give the title compound (484 mg) as a colorless solid. MS(ESI) m/z: 277.3 (M−H)$^-$.

(29-2) Dibenzyl (3R)-1-(4-{4-[2-(methylphenyl)ethyl]phenyl}butanoyl)pyrrolidin-3-yl phosphate (Example compound 29-2)

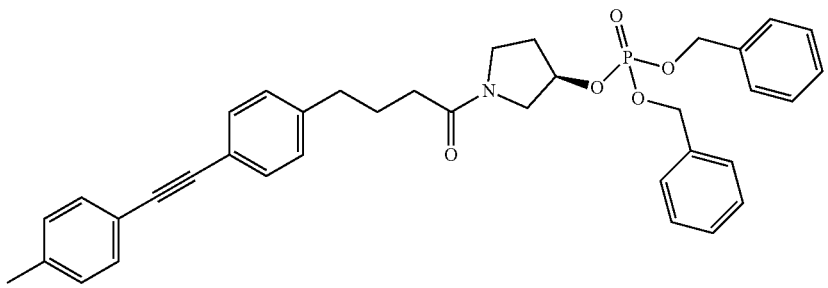 [SMILES: Cc1ccc(C#Cc2ccc(CCCC(=O)N3CC[C@@H](OP(=O)(OCc4ccccc4)OCc4ccccc4)C3)cc2)cc1]

To a solution of Reference Example compound 3 (600 mg) in dichloromethane (3.2 mL) was added under ice-cooling trifluoroacetic acid (1.3 mL), and the mixture was stirred at the same temperature for 1 hr. The reaction mixture was concentrated under reduced pressure. To the residue were added N,N-diisopropylethylamine (3.6 mL), N,N-dimethylformamide (2.7 mL), Example compound 29-1 (300 mg), and HATU (615 mg), and the mixture was stirred at room temperature overnight. Water was added to the reaction mixture, and the mixture was extracted with ethyl acetate. The organic layer was washed with water and saturated brine, and dried over anhydrous sodium sulfate. The desiccant was filtered off, and the filtrate was concentrated under reduced pressure. The obtained residue was purified by silica gel column chromatography (chloroform-methanol=100:0-94:6) and purified again by preparative HPLC (10 mM aqueous ammonium carbonate solution-acetonitrile) to give the title compound (541 mg) as a pale-yellow viscous oil. MS (APCI) m/z: 608.4 (M+H)+

(29-3) (3R)-1-(4-{4-[2-(4-Methylphenyl)ethyl]phenyl}butanoyl)pyrrolidin-3-yl dihydrogen phosphate ammonium salt (Example compound 29)

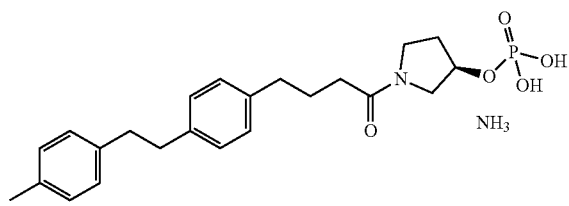

To a solution of Example compound 29-2 (284 mg) in ethanol (4.7 mL) was added 7.5% palladium carbon (28 mg), and the mixture was stirred under a hydrogen atmosphere at room temperature for 6 hr. After filtering off the insoluble material in the reaction mixture with diatomaceous earth, the filtrate was concentrated under reduced pressure. The obtained residue was purified by preparative HPLC (10 mM aqueous ammonium carbonate solution-acetonitrile) to give the title compound (151 mg) as a colorless solid. MS(ESI) m/z: 432.3 (M+H)+

Example 30

(30-1) {8-[(cis)-2-Octylcyclopropyl]octanoic acid (Example compound 30-1)

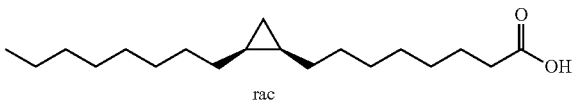 [SMILES: CCCCCCCC[C@H]1C[C@H]1CCCCCCCC(=O)O]

To a solution of 2,4,6-trichlorophenol (1.40 g) in dichloromethane (17.7 mL) was added diethyl zinc (1.00 mol/L toluene solution, 7.08 mL) at −50° C., and the mixture was stirred at the same temperature for 15 min. Diiodomethane (0.57 mL) was added thereto, and the mixture was further stirred at the same temperature for 15 min. Oleic acid (500 mg) was added, and the mixture was stirred for one day and night while gradually raising the temperature to room temperature. To the reaction mixture was added 1N hydrochloric acid, and the mixture was extracted with chloroform. The organic layer was dried over anhydrous sodium sulfate, the desiccant was filtered off, and the filtrate was concentrated under reduced pressure. The obtained residue was purified by silica gel column chromatography (chloroform:methanol=100:0-94:6) to give the title compound (522 mg) as a yellow oil.

MS(ESI) m/z: 295.4 (M−H)−.

(30-2) Di-tert-butyl (3R)-1-{8-[(cis)octylcyclopropyl]octanoyl}pyrrolidin-3-yl phosphate (Example compound 30-2)

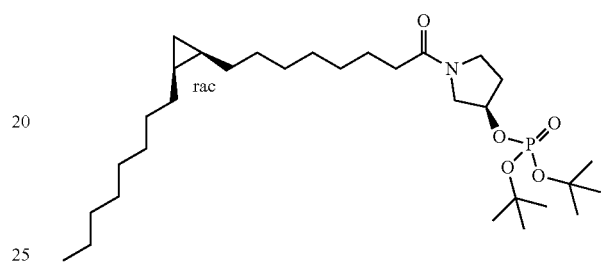

To a solution of Example compound 30-1 (150 mg) in N,N-dimethylformamide (5.1 mL) was added N,N-diisopropylethylamine (0.26 mL), Reference Example compound 4 (155 mg), and HATU (289 mg), and the mixture was stirred at room temperature overnight. Water was added to the reaction mixture, and the mixture was extracted with ethyl acetate. The organic layer was dried over anhydrous sodium sulfate, the desiccant was filtered off, and the filtrate was concentrated under reduced pressure. The obtained residue was purified by silica gel column chromatography (chloroform:methanol=100:0-95:5) to give the title compound (238 mg) as a yellow oil.

MS (APCI) m/z: 558.1 (M+H)+

(30-3) (3R)-1-{8-[(cis)-2-Octylcyclopropyl]octanoyl}pyrrolidin-3-yl dihydrogen phosphate ammonium salt (Example compound 30)

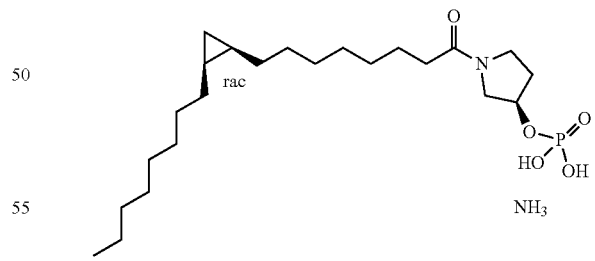

To a solution of Example compound 30-2 (230 mg) in dichloromethane (4.1 mL) was added trifluoroacetic acid (0.41 mL), and the mixture was stirred at room temperature for 2 hr. The reaction mixture was concentrated under reduced pressure. The obtained residue was purified by preparative HPLC (10 mM aqueous ammonium carbonate solution-acetonitrile) to give the title compound (145 mg) as a colorless solid.

MS (APCI) m/z: 446.5 (M+H)+

Example 31

(31-1) 3-[3-(4-Phenylbutoxy)phenyl]propionic acid (Example compound 31-1)

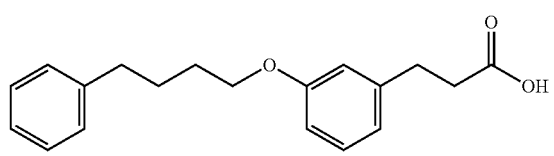 [SMILES: O=C(O)CCc1cccc(OCCCCc2ccccc2)c1]

In Example 1, the reaction and treatment similar to those in (1-1)-(1-2) were performed using methyl 3-(3-hydroxyphenyl)propanoate instead of methyl 3-(4-hydroxyphenyl)propanoate and 4-bromobutylbenzene instead of 1-bromononane to give the title compound (188 mg) as a colorless oil. MS(ESI) m/z: 297.1 (M−H)⁻

(31-2) (3R)-1-{3-[3-(4-Phenylbutoxy)phenyl]propanoyl}pyrrolidin-3-yl dihydrogen phosphate ammonium salt (Example compound 31)

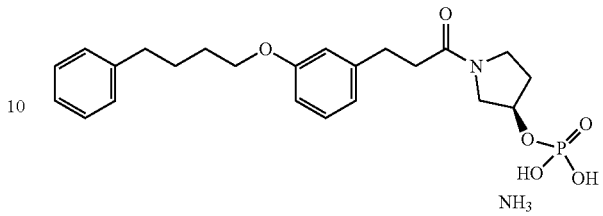

In Example 30, the reaction and treatment similar to those in (30-2)-(30-3) were performed using Example compound 31-11 instead of Example compound 30-1 to give the title compound (240 mg) as a colorless viscous oil.
MS (APCI) m/z: 448.4 (M+H)⁺

Example 32

(32-1) 2-[{3-[3-(Decyloxy)phenyl]propanoyl}(ethyl)amino]ethyl dihydrogen phosphate ammonium salt (Example compound 32)

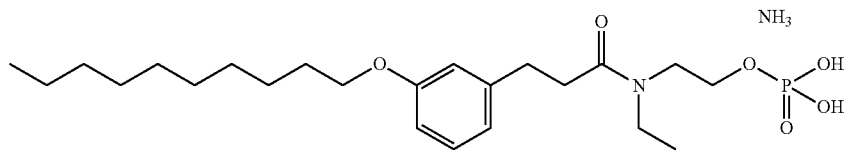

In Example 28, the reaction and treatment similar to those in (28-1), (28-3)-(28-4) were performed using tert-butyl ethyl(2-hydroxyethyl)carbamate instead of tert-butyl (2-hydroxyethyl)carbamate to give the title compound (69 mg) as a pale-yellow oil. MS (APCI) m/z: 458.2[M+H]⁺

Example 33

(33-1) tert-Butyl (2-hydroxymethyl)(2-methylpropyl)carbamate (Example compound 33-1)

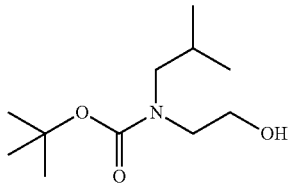

2-(Isobutylamino)ethanol hydrochloride (1.00 g) was dissolved in acetonitrile (5 mL), N,N-diisopropylethylamine (1.13 mL) was added dropwise, a solution of di-tert-butyl dicarbonate (1420 mg) in acetonitrile (5 mL) was added dropwise, and the mixture was stirred at room temperature for 4.5 hr. The solvent was evaporated under reduced pressure, water was added, and the mixture was extracted with chloroform, washed with saturated brine, and dried over anhydrous sodium sulfate. The solvent was evaporated under reduced pressure. The residue was purified by silica gel column chromatography (hexane:ethyl acetate=65:35-50:50) to give the title compound (1.41 g) as a colorless oil. MS (APCI) m/z: 217.9[M+H]⁺

(33-2) 2-[{3-[3-(Decyloxy)phenyl]propanoyl}(2-methylpropyl)amino]ethyl dihydrogen phosphate ammonium salt (Example compound 33)

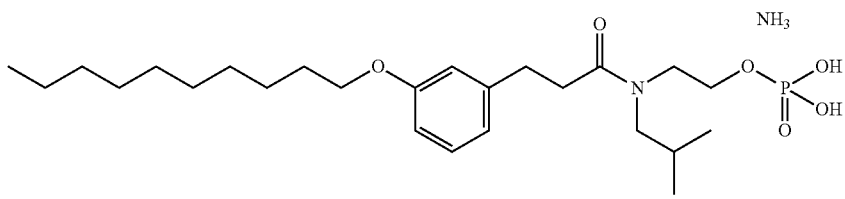

In Example 28, the reaction and treatment similar to those in (28-1), (28-3)-(28-4) were performed using Example compound 33-1 instead of tert-butyl (2-hydroxyethyl)carbamate to give the title compound (84 mg) as a colorless oil. MS (APCI) m/z: 486.4[M+H]⁺

Example 34

(34-1) Benzyl 4-pentynoate (Example compound 34-1)

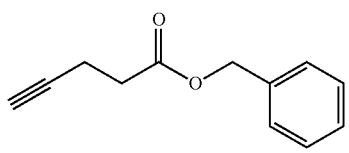

A mixture of 4-pentynoic acid (2.00 g), benzyl bromide (2.67 mL), potassium carbonate (5.64 g), and N,N-dimethylformamide (20 mL) was stirred at room temperature for one day and night. Water was added to the reaction mixture, and the mixture was extracted with ethyl acetate. The organic layer was washed with water and saturated brine, and dried over anhydrous sodium sulfate. The desiccant was filtered off, and the filtrate was concentrated under reduced pressure. The obtained residue was purified by silica gel column chromatography (hexane:ethyl acetate=95:5-85:15) to give the title compound (3.72 g) as a colorless oil.

MS (APCI) m/z: 189.2 (M+H)⁺.

(34-2) 1-Iodo-3-(octyloxy)benzene (Example compound 34-2)

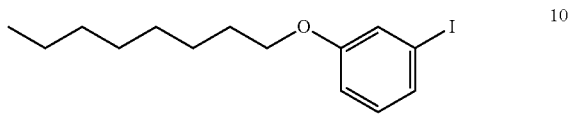

A mixture of 3-iodophenol (1.50 g), 1-bromooctane (1.30 mL), potassium carbonate (2.36 g), and N,N-dimethylformamide (14 mL) was stirred at 60° C. for one day and night. Water was added to the reaction mixture, and the mixture was extracted with diethyl ether. The organic layer was dried over anhydrous sodium sulfate, the desiccant was filtered off, and the filtrate was concentrated under reduced pressure. The obtained residue was purified by silica gel column chromatography (hexane:ethyl acetate=100:0-99:1) to give the title compound (2.18 g) as a colorless oil.

(34-3) Benzyl 5-[3-(octyloxy)phenyl]-4-pentynoate (Example compound 34-3)

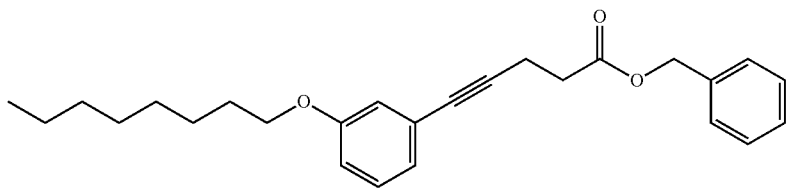 [SMILES: CCCCCCCCOc1cccc(C#CCCC(=O)OCc2ccccc2)c1]

A mixture of Example compound 34-2 (300 mg), Example compound 34-1 (204 mg), bis(triphenylphosphine)palladium(II) dichloride (63 mg), copper iodide (I) (17 mg), and triethylamine (3.01 mL) was stirred at 70° C. for one day and night. To the reaction mixture was added saturated aqueous ammonium chloride solution, and the mixture was extracted with ethyl acetate. The organic layer was washed with 1N hydrochloric acid and saturated brine, and dried over anhydrous sodium sulfate. The desiccant was filtered off, and the filtrate was concentrated under reduced pressure. The obtained residue was purified by silica gel column chromatography (hexane:ethyl acetate=100:0-90:10) to give the title compound (341 mg) as a colorless oil. MS (APCI) m/z: 393.4 (M+H)$^+$.

(34-4) 5-[(3-Octyloxy)phenyl]pentanoic acid (Example compound 34-4)

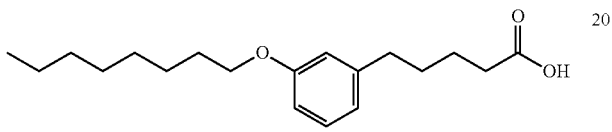

To a solution of Example compound 34-3 (341 mg) in ethanol (8.7 mL) was added 7.5% palladium carbon (34 mg), and the mixture was stirred under a hydrogen atmosphere at room temperature for one day and night. After filtering off the insoluble material in the reaction mixture with diatomaceous earth, the filtrate was concentrated under reduced pressure to give the title compound (313 mg) as a pale-yellow oil.

MS (APCI) m/z: 305.2 (M−H)$^−$ (34-5) Dibenzyl 1 {5-[3-(octyloxy)phenyl]pentanoyl}azetidin-3-yl phosphate (Example compound 34-5)

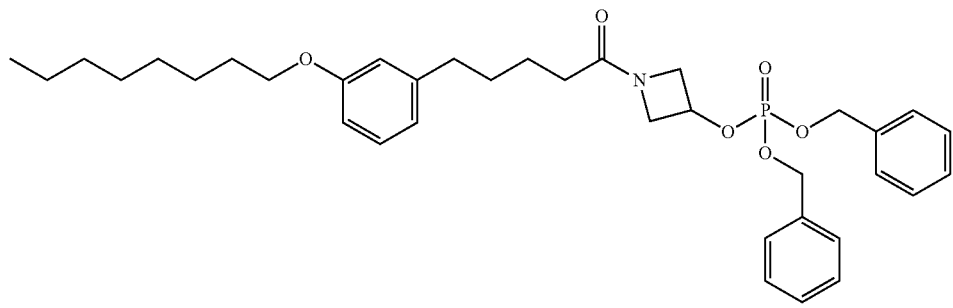 [SMILES: CCCCCCCCOc1cccc(CCCCC(=O)N2CC(OP(=O)(OCc3ccccc3)OCc3ccccc3)C2)c1]

To a solution of Reference Example compound 2 (440 mg) in dichloromethane (2.2 mL) was added under ice-cooling trifluoroacetic acid (0.89 mL), and the mixture was stirred at the same temperature for 2 hr. Under ice-cooling, N,N-diisopropylethylamine (2.9 mL), N,N-dimethylformamide (2.2 mL), Example compound 34-4 (270 mg), and HATU (503 mg) were added, and the mixture was stirred at room temperature for 3 hr. Water was added to the reaction mixture, and the mixture was extracted with ethyl acetate. The organic layer was washed with water and saturated brine, and dried over anhydrous sodium sulfate. The desiccant was filtered off, and the filtrate was concentrated under reduced pressure. The obtained residue was purified by preparative HPLC (10 mM aqueous ammonium carbonate solution-acetonitrile) to give the title compound (98 mg) as a pale-yellow oil. MS (APCI) m/z: 622.5 (M+H)$^+$ (34-6) 1-{5-[3-(Octyloxy)phenyl]pentanoyl}azetidin-3-yl dihydrogen phosphate ammonium salt (Example compound 34)

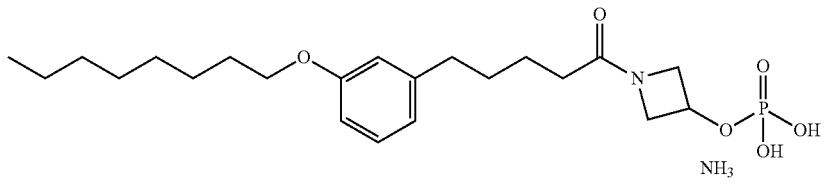

To a solution of Example compound 34-5 (98 mg) in ethanol (1.6 mL) was added 7.5% palladium carbon (10 mg), and the mixture was stirred under a hydrogen atmosphere at room temperature for 5 hr. After filtering off the insoluble material in the reaction mixture with diatomaceous earth, the filtrate was concentrated under reduced pressure. The obtained residue was purified by preparative HPLC (10 mM aqueous ammonium carbonate solution-acetonitrile) to give the title compound (51 mg) as a colorless solid. MS (APCI) m/z: 442.5 (M+H)$^+$ Example 35

(35-1) 1-{5-[3-(Hexyloxy)phenyl]pentanoyl}azetidin-3-yl dihydrogen phosphate ammonium salt (Example compound 35)

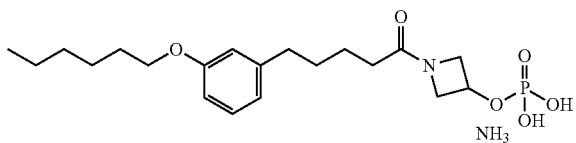

In Example 34, the reaction and treatment similar to those in (34-2)-(34-6) were performed using 1-bromohexane instead of 1-bromooctane to give the title compound (185 mg) as a colorless solid. MS (APCI) m/z: 414.4 (M+H)$^+$ Example 36

(36-1) 9-(4-Ethylphenyl)-N-(2-hydroxyethyl)-N-(2-methoxyethyl)nonanamide (Example compound 36-1)

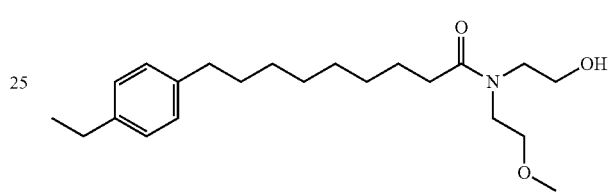

Example compound 16-2 (200 mg) was dissolved in N,N-dimethylformamide (1.81 mL), and N,N-diisopropylethylamine (0.396 mL), and HATU (435 mg) were added, then, a solution of 2-[(2-methoxyethyl)amino]ethan-1-ol (109 mg) in N,N-dimethylformamide (2 mL) was added dropwise thereto, and the mixture was stirred at room temperature for 14 hr. The reaction mixture was diluted with ethyl acetate, water was added, and the mixture was extracted with ethyl acetate, washed with saturated brine, and dried over anhydrous sodium sulfate. The solvent was evaporated under reduced pressure. The residue was purified by silica gel column chromatography (hexane:ethyl acetate=67:33-50:50) to give the title compound (153 mg) as a pale-yellow oil. MS (APCI) m/z: 364.4[M+H]$^+$ (36-2) Dibenzyl 2-{[9-(4-ethylphenyl)nonanoyl](2-methoxyethyl)amino}ethyl phosphate (Example compound 36-2)

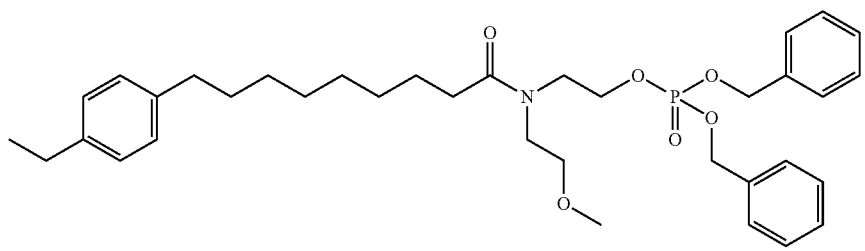 [SMILES: CCc1ccc(CCCCCCCCC(=O)N(CCOC)CCOP(=O)(OCc2ccccc2)OCc2ccccc2)cc1]

Example compound 36-1 (135 mg) was dissolved in dichloromethane (2 mL) and acetonitrile (0.809 mL), 1H-tetrazole (52 mg) was added under ice-cooling, then dibenzyl N,N-diisopropyl phosphoramidite (0.276 mL) was added dropwise thereto, and the mixture was stirred at room temperature for 130 min. Under ice-cooling, tert-butyl hydroperoxide (0.13 mL) was added dropwise to the mixture, and the mixture was stirred at room temperature for 1 hr. Under ice-cooling, saturated aqueous sodium thiosulfate solution (3 mL) was added, and the mixture was stirred at room temperature for 10 min. To the reaction mixture was added ethyl acetate, and the mixture was extracted with ethyl acetate, washed with saturated aqueous sodium hydrogen carbonate solution and saturated brine, and dried over anhydrous sodium sulfate. The solvent was evaporated under reduced pressure. The residue was purified by silica gel column chromatography (hexane:ethyl acetate=50:50-25:75) to give the title compound (130 mg) as a colorless oil.
MS (APCI) m/z: 624.4[M+H]$^+$ (36-3) 2-{[9-(4-Ethylphenyl)nonanoyl](2-methoxyethyl)amino}ethyl dihydrogen phosphate ammonium salt (Example compound 36)

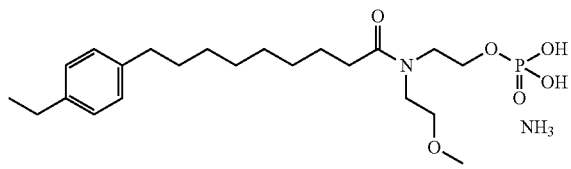

Example compound 36-2 (124 mg) was dissolved in methanol (3 mL), 10% palladium carbon (62 mg) was added, and the mixture was stirred under a hydrogen atmosphere at room temperature for 220 min and filtered. The filtrate was concentrated, the obtained residue was purified by preparative HPLC (10 mM aqueous ammonium carbonate solution-acetonitrile) to give the title compound (52 mg) as a colorless oil.
MS (APCI) m/z: 444.2[M+H]$^+$ Example 37

(37-1) 2-{[3-(Benzyloxy)benzyl]amino}ethanol (Example compound 37-1)

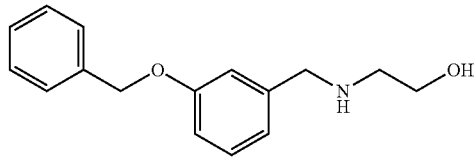 [SMILES: OCCNCc1cccc(OCc2ccccc2)c1]

2-Aminoethanol (1.00 g) was dissolved in methanol (10 mL) and dichloromethane (2 mL), 3-benzyloxybenzaldehyde (3.51 g), and acetic acid (0.946 mL) were added, and the mixture was stirred at 60° C. for 2 hr. To the mixed solution was added sodium triacetoxyborohydride (5.21 g) under ice-cooling, and the mixture was stirred at room temperature for 3 hr. To the reaction mixture was added 1M aqueous sodium hydroxide solution, and the mixture was extracted with ethyl acetate, washed with saturated brine, and dried over anhydrous sodium sulfate. The solvent was evaporated under reduced pressure. The residue was purified by silica gel column chromatography (chloroform:methanol=100:0-90:10) to give the title compound (3.91 g) as a yellow oil. MS(ESI) m/z: 258.2[M+H]$^+$ (37-2) 2-[{3-[3-(Decyloxy)phenyl]propanoyl}(3-hydroxybenzyl)amino]ethyl dihydrogen phosphate ammonium salt (Example compound 37)

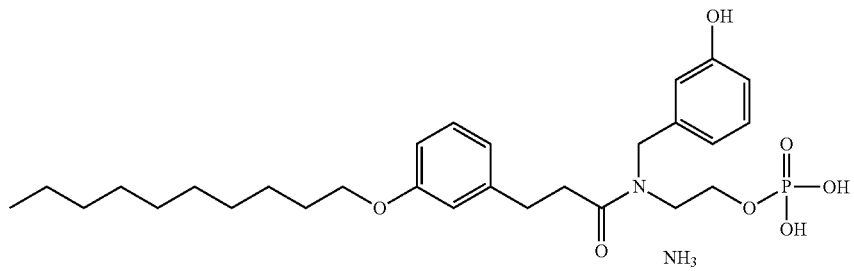

In Example 36, the reaction and treatment similar to those in (36-1)-(36-3) were performed using Reference Example compound 5 instead of Example compound 16-2 and Example compound 37-1 instead of 2-[(2-methoxyethyl)amino]ethan-1-ol to give the title compound (229 mg) as a colorless oil.

MS (APCI) m/z: 536.3[M+H]$^+$

Example 38

(38-1) (3R)-1-[9-(4-Ethylphenyl)nonanoyl]piperidin-3-yl dihydrogen phosphate ammonium salt (Example compound 38)

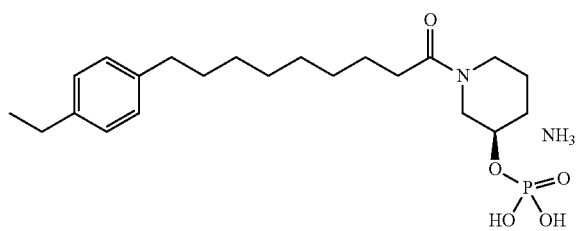

In Example 36, the reaction and treatment similar to those in (36-1)-(36-3) were performed using (3R)-piperidin-3-ol hydrochloride instead of 2-[(2-methoxyethyl)amino]ethan-1-ol to give the title compound (310 mg) as a colorless oil.

MS (APCI) m/z: 426.4[M+H]$^+$

Example 39

(39-1) 2-{[3-(Benzyloxy)propyl]amino}ethanol (Example compound 39-1)

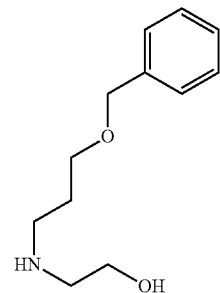 [SMILES: OCCNCCCOCc1ccccc1]

1-Bromo-3-benzyloxypropane (1.50 g) was dissolved in ethanol (14.7 mL), 2-aminoethanol (1.98 mL) and sodium iodide (98 mg) were added, and the mixture was stirred at 90° C. for 1 hr. The mixture was allowed to cool to room temperature, and the solvent was evaporated under reduced pressure. To the obtained residue was added saturated aqueous ammonium chloride solution, and the mixture was back extracted with ethyl acetate. 4N Aqueous sodium hydroxide solution was added to the aqueous layer under cooling at 0° C. to adjust to pH 9-10, and the mixture was extracted with ethyl acetate, and dried over anhydrous magnesium sulfate. The solvent was evaporated under reduced pressure to give the title compound (1.06 g) as a pale-yellow oil. MS (APCI) m/z: 210.2[M+H]$^+$

(39-2) N-[3-(Benzyloxy)propyl]-3-[3-(decyloxy)phenyl]-N-(2-hydroxyethyl)propanamide (Example compound 39-2)

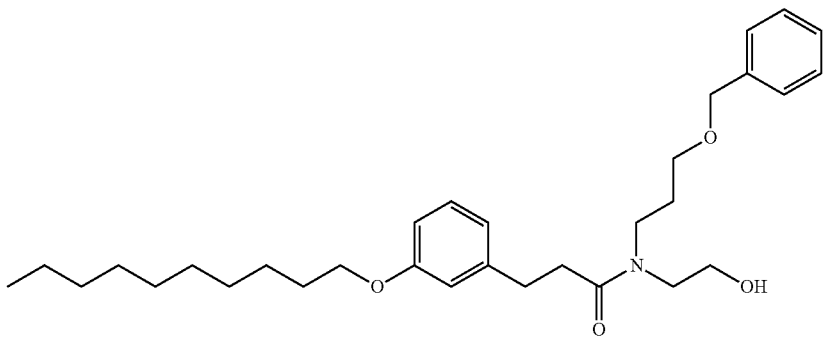 [SMILES: CCCCCCCCCCOc1cccc(CCC(=O)N(CCO)CCCOCc2ccccc2)c1]

Reference Example compound 5 (200 mg) was dissolved in N,N-dimethylformamide (1.35 mL), and N,N-diisopropylethylamine (0.339 mL), and HATU (372 mg) were added. A solution of Example compound 39-1 (164 mg) in N,N-dimethylformamide (3 mL) was added dropwise thereto, and the mixture was stirred at room temperature for 12.5 hr. The reaction mixture was diluted with ethyl acetate, water was added, and the mixture was extracted with ethyl acetate, washed with saturated brine, and dried over anhydrous sodium sulfate. The solvent was evaporated under reduced pressure. The residue was purified by silica gel column chromatography (hexane:ethyl acetate=50:50-25:75) to give the title compound (quant.) as a pale-yellow oil.

MS (APCI) m/z: 498.5[M+H]$^+$ (39-3) Dibenzyl 2-[{3-[3-(decyloxy)phenyl]propanoyl}(3-hydroxypropyl)amino]ethyl phosphate (Example compound 39-3)

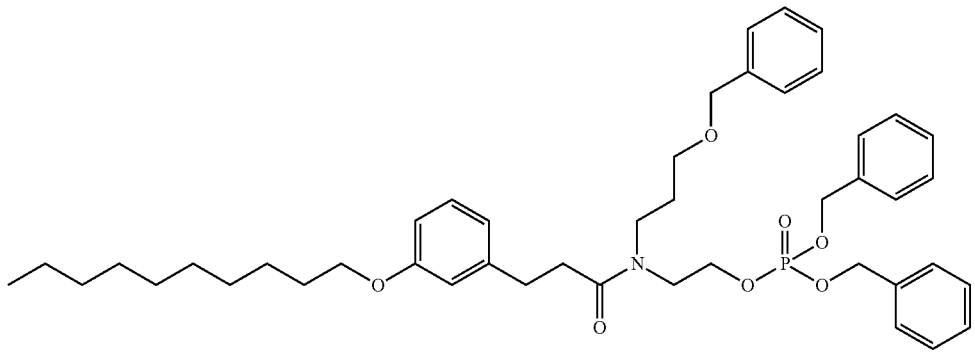 [SMILES: CCCCCCCCCCOc1cccc(CCC(=O)N(CCCOCc2ccccc2)CCOP(=O)(OCc2ccccc2)OCc2ccccc2)c1]

Example compound 39-2 (335 mg) was dissolved in dichloromethane (3.35 mL) and acetonitrile (1.34 mL), 1H-tetrazole (94.3 mg) was added under ice-cooling, dibenzyl N,N-diisopropyl phosphoramidite (0.502 mL) was added dropwise, and the mixture was stirred at room temperature for 200 min. Under ice-cooling, tert-butyl hydroperoxide (0.24 mL) was added dropwise, and the mixture was stirred at room temperature for 70 min. Under ice-cooling, saturated aqueous sodium thiosulfate solution (5 mL) was added to the mixture, and the mixture was stirred at room temperature for 10 min. To the reaction mixture was added ethyl acetate and the mixture was extracted with ethyl acetate, washed with saturated aqueous sodium hydrogen carbonate solution and saturated brine, and dried over anhydrous sodium sulfate. The solvent was evaporated under reduced pressure. The residue was purified by silica gel column chromatography (hexane:ethyl acetate=60:40-20:80) to give the title compound (252 mg) as a colorless oil.

MS (APCI) m/z: 758.2[M+H]$^+$ (39-4) 2-[{3-[3-(Decyloxy)phenyl]propanoyl}(3-hydroxypropyl)amino]ethyl dihydrogen phosphate ammonium salt (Example compound 39)

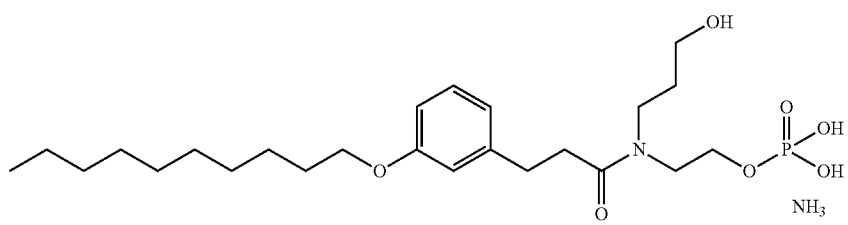

Example compound 39-3 (226 mg) was dissolved in methanol (2.98 mL), 10% palladium carbon (113 mg) was added, and the mixture was stirred under a hydrogen atmosphere at room temperature for 3.5 hr. The reaction mixture was filtered, and the filtrate was concentrated. The obtained residue was purified by preparative HPLC (10 mM aqueous ammonium carbonate solution-acetonitrile) to give the title compound (85 mg) as a colorless oil. MS (APCI) m/z: 488.3[M+H]$^+$ Example 40

(40-1) 2-[{3-[3-(Decyloxy)phenyl]propanoyl}(2-phenylethyl)amino]ethyl dihydrogen phosphate ammonium salt (Example compound 40)

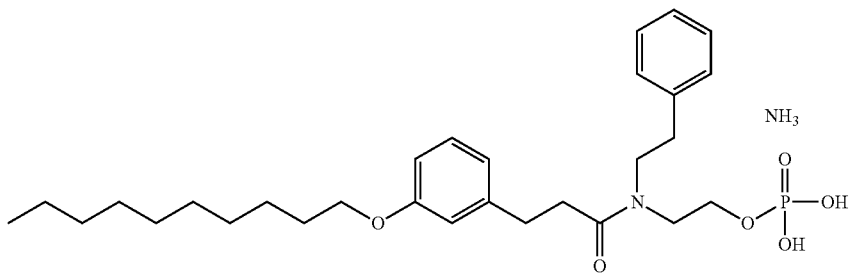

In Example 36, the reaction and treatment similar to those in (36-1)-(36-3) were performed using Reference Example compound 5 instead of Example compound 16-2 and 2-(2-phenylethylamino)ethanol instead of 2-[(2-methoxyethyl)amino]ethan-1-ol to give the title compound (103 mg) as a colorless oil. MS (APCI) m/z: 534.3[M+H]$^+$ Example 41

(41-1) 2-{[4-(Benzyloxy)butyl]amino}ethanol (Example compound 41-1)

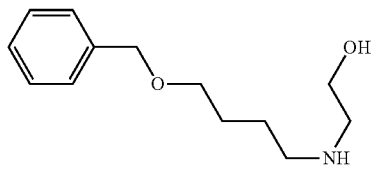 [SMILES: OCCNCCCCOCc1ccccc1]

4-Benzyloxy-1-bromobutane (1.60 g) was dissolved in ethanol (14.8 mL), and 2-aminoethanol (1.99 mL) and sodium iodide (99 mg) were added, and the mixture was stirred at 90° C. for 1 hr. The mixture was allowed to cool to room temperature, and the solvent was evaporated under reduced pressure. To the obtained residue was added saturated aqueous ammonium chloride solution, and the mixture was back extracted with ethyl acetate. 10N Aqueous sodium hydroxide solution was added to the aqueous layer under cooling at 0° C. to adjust to pH 9-10, and the mixture was extracted with ethyl acetate, and dried over anhydrous magnesium sulfate. The solvent was evaporated under reduced pressure to give the title compound (1.28 g) as a pale-yellow oil. MS (APCI) m/z: 224.3[M+H]$^+$ (41-2) 2-[{3-[3-(Decyloxy)phenyl]propanoyl}(4-hydroxybutyl)amino]ethyl dihydrogen phosphate ammonium salt (Example compound 41)

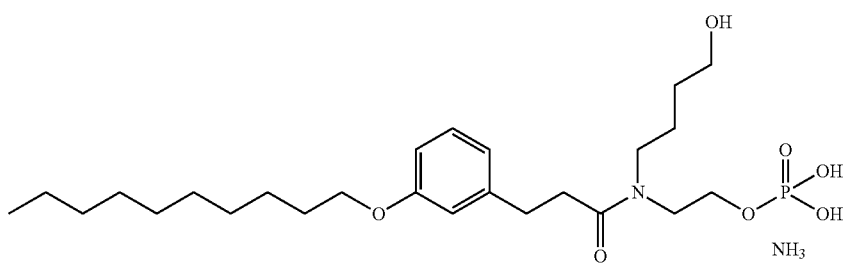

In Example 36, the reaction and treatment similar to those in (36-1)-(36-3) were performed using Reference Example compound 5 instead of Example compound 16-2 and Example compound 41-1 instead of 2-[(2-methoxyethyl)amino]ethan-1-ol to give the title compound (129 mg) as a colorless oil.

MS (APCI) m/z: 502.3[M+H]$^+$

Example 42

(42-1) 7-Octynoic acid (Example compound 42-1)

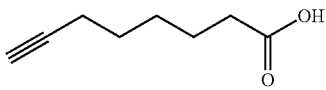

To a solution of lithium acetylide ethylenediamine complex (7.08 g) and dimethyl sulfoxide (12.8 mL) was added dropwise under ice-cooling a solution of 6-bromohexanoic acid (5.00 g) in dimethyl sulfoxide (25.6 mL), and the mixture was stirred at room temperature for 2 hr. To the reaction mixture was slowly added ice water, and the mixture was stirred for a while, acidified with concentrated hydrochloric acid, and extracted with chloroform. The organic layer was dried over anhydrous sodium sulfate, the desiccant was filtered off, and the filtrate was concentrated under reduced pressure. The obtained residue was purified by silica gel column chromatography (hexane:ethyl acetate=95:5-70:30) to give the title compound (3.24 g) as a yellow oil. MS (APCI) m/z: 139.0[M−H]$^-$ (42-2) Benzyl 7-octynoate (Example compound 42-2)

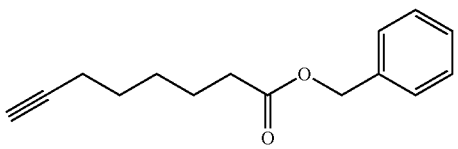 [SMILES: C#CCCCCCC(=O)OCc1ccccc1]

A mixture of Example compound 42-1 (3.24 g), benzyl bromide (3.02 mL), potassium carbonate (6.38 g), and N,N-dimethylformamide (23 mL) was stirred at room temperature for one day and night. Water was added to the reaction mixture, and the mixture was extracted with diethyl ether. The organic layer was washed with water and saturated brine, and dried over anhydrous sodium sulfate. The desiccant was filtered off, and the filtrate was concentrated under reduced pressure. The obtained residue was purified by silica gel column chromatography (hexane:ethyl acetate=100:0-93:7) to give the title compound (4.81 g) as a colorless oil.

MS (APCI) m/z: 231.2 (M+H)$^+$.

(42-3) Benzyl 8-(2-chlorophenyl)-7-octynoate (Example compound 42-3)

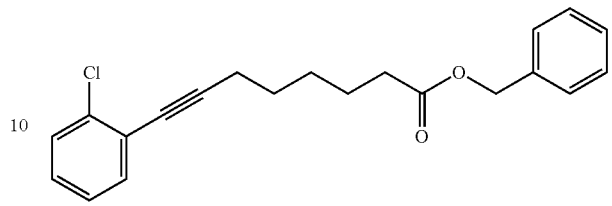

A mixture of 1-chloro-2-iodobenzene (518 mg), Example compound 42-2 (500 mg), bis(triphenylphosphine)palladium(II) dichloride (152 mg), copper iodide (I) (41 mg), and triethylamine (7.24 mL) was stirred at room temperature for one day and night. To the reaction mixture was added saturated aqueous ammonium chloride solution, and the mixture was extracted with ethyl acetate. The organic layer was washed with 1N hydrochloric acid and saturated brine, and dried over anhydrous sodium sulfate. The desiccant was filtered off, and the filtrate was concentrated under reduced pressure. The obtained residue was purified by silica gel column chromatography (hexane:ethyl acetate=100:0-90:10) to give the title compound (588 mg) as a colorless oil.

MS (APCI) m/z: 341.2 (M+H)$^+$.

(42-4) 8-(2-Octylphenyl)octanoic acid (Example compound 42-4)

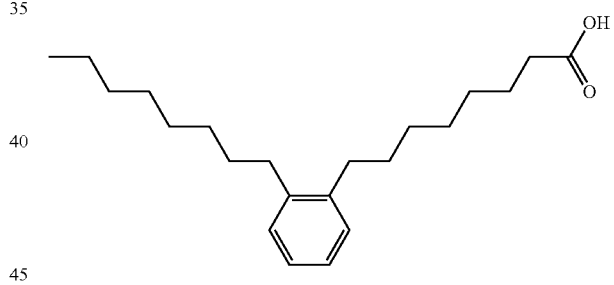

A mixture of Example compound 42-3 (280 mg), trans-1-octenylboronic acid pinacol ester (294 mg), chloro(2-dicyclohexylphosphino-2',4',6'-triisopropyl-1,1'-biphenyl)[2-(2'-amino-1,1'-biphenyl)]palladium(II) (XPhos-Pd-G2) (65 mg), tripotassium phosphate (523 mg), and tetrahydrofuran (8.22 mL) was stirred at 60° C. overnight. After filtering off the insoluble material in the reaction mixture with diatomaceous earth, the filtrate was concentrated under reduced pressure. The obtained residue was purified by silica gel column chromatography (hexane:ethyl acetate=100:0-90:10) to give a crudely purified product as a yellow oil. To a solution of the obtained yellow oil in ethanol (8.2 mL) was added 7.5% palladium carbon (41 mg), and the mixture was stirred under a hydrogen atmosphere at room temperature for 3 hr. The insoluble material in the reaction mixture was filtered off with diatomaceous earth, and the filtrate was concentrated under reduced pressure. The obtained residue was purified by preparative HPLC (10 mM aqueous ammonium carbonate solution-acetonitrile) to give the title compound (34 mg) as an orange oil. MS(ESI) m/z: 331.4 (M+H)$^-$.

(42-5) 1-[8-(2-Octylphenyl)octanoyl]azetidin-3-yl dihydrogen phosphate ammonium salt (Example compound 42)

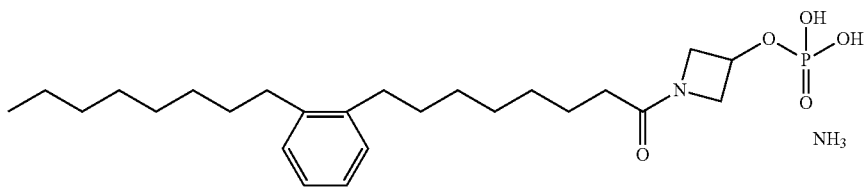

To a solution of Example compound 42-4 (34 mg) in N,N-dimethylformamide (1.0 mL) were added N,N-diisopropylethylamine (0.052 mL), Reference Example compound 1 (32 mg), and HATU (153 mg), and the mixture was stirred at room temperature overnight.

Water was added to the reaction mixture, and the mixture was extracted with ethyl acetate. The organic layer was dried over anhydrous sodium sulfate, the desiccant was filtered off, and the filtrate was concentrated under reduced pressure. The obtained residue was purified by silica gel column chromatography (chloroform:methanol=100:0-96:4). To the obtained crudely purified product were added dichloromethane (1.0 mL) and trifluoroacetic acid (0.10 mL), and the mixture was stirred at room temperature for 4 hr. The reaction mixture was concentrated under reduced pressure. The obtained residue was purified by preparative HPLC (10 mM aqueous ammonium carbonate solution-acetonitrile) to give the title compound (33 mg) as a yellow viscous oil. MS (APCI) m/z: 468.5 (M+H)+

Example 43

(43-1) Benzyl 8-(3-chlorophenyl)-7-octynoate (Example compound 43-1)

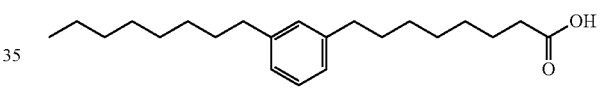

A mixture of 1-chloro-3-iodobenzene (400 mg), Example compound 42-2 (497 mg), bis(triphenylphosphine)palladium(II) dichloride (122 mg), copper iodide (I) (33 mg), and triethylamine (5.79 mL) was stirred at room temperature for one day and night. To the reaction mixture was added saturated aqueous ammonium chloride solution, and the mixture was extracted with ethyl acetate. The organic layer was washed with 1N hydrochloric acid and saturated brine, and dried over anhydrous sodium sulfate. The desiccant was filtered off, and the filtrate was concentrated under reduced pressure. The obtained residue was purified by silica gel column chromatography (hexane:ethyl acetate=100:0-90:10) to give the title compound (601 mg) as a colorless oil.

MS (APCI) m/z: 341.3 (M+H)+.

(43-2) 8-(3-Octylphenyl)octanoic acid (Example compound 43-2)

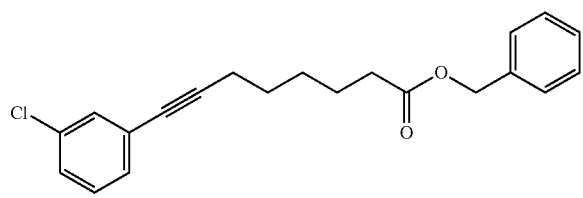 [SMILES: O=C(CCCCCC#Cc1cccc(Cl)c1)OCc1ccccc1]

A mixture of Example compound 43-1 (300 mg), trans-1-octenylboronic acid pinacol ester (231 mg), chloro(2-dicyclohexylphosphino-2',4',6'-triisopropyl-1,1'-biphenyl)[2-(2'-amino-1,1'-biphenyl)]palladium(II) (XPhos-Pd-G2) (35 mg), tripotassium phosphate (374 mg), tetrahydrofuran (8.8 mL), and water (2.9 mL) was stirred at 60° C. overnight. After filtering off the insoluble material in the reaction mixture with diatomaceous earth, the filtrate was concentrated under reduced pressure. To the obtained residue were again added trans-1-octenylboronic acid pinacol ester (231 mg), chloro(2-dicyclohexylphosphino 2',4',6'-triisopropyl-1,1'-biphenyl) [2-(2'-amino-1,1'-biphenyl)]palladium(II) (XPhos-Pd-G2) (35 mg), tripotassium phosphate (374 mg), and tetrahydrofuran (8.8 mL), and the mixture was stirred at 60° C. overnight. After filtering off the insoluble material in the reaction mixture with NH silica-diatomaceous earth, the filtrate was concentrated under reduced pressure. The obtained residue was purified by silica gel column chromatography ((hexane:ethyl acetate=100:0-90:10) to give a crudely purified product as a yellow oil. To a solution of the obtained yellow oil in ethanol (8.8 mL) was added 7.5% palladium carbon (45 mg) and the mixture was stirred under a hydrogen atmosphere at room temperature for 3 hr. The insoluble material in the reaction mixture was filtered off with diatomaceous earth, and the filtrate was concentrated under reduced pressure. The obtained residue was purified by silica gel column chromatography (chloroform:methanol=100:0-92:8) to give the title compound (197 mg) as a pale-yellow oil.

(43-3) 1-[8-(3-Octylphenyl)octanoyl]azetidin-3-yl dihydrogen phosphate ammonium salt (Example compound 43)

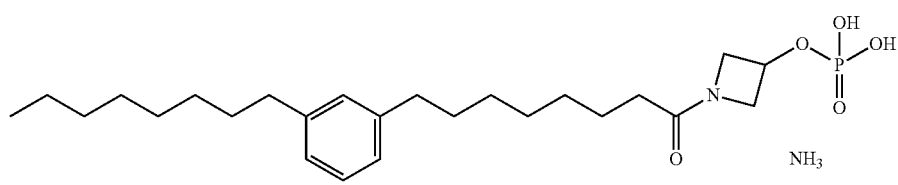

To a solution of Example compound 43-2 (197 mg) in N,N-dimethylformamide (5.9 mL) were added N,N-diisopropylethylamine (0.308 mL), Reference Example compound 1 (189 mg) and HATU (338 mg), and the mixture was stirred at room temperature overnight. Water was added to the reaction mixture, and the mixture was extracted with ethyl acetate. The organic layer was dried over anhydrous sodium sulfate, the desiccant was filtered off, and the filtrate was concentrated under reduced pressure. The obtained residue was purified by silica gel column chromatography (chloroform:methanol=100:0-96:4). To the obtained crudely purified product were added dichloromethane (5.9 mL) and trifluoroacetic acid (0.59 mL), and the mixture was stirred at room temperature for 6 hr. The reaction mixture was concentrated under reduced pressure. The obtained residue was purified by preparative HPLC (10 mM aqueous ammonium carbonate solution-acetonitrile) to give the title compound (92 mg) as a yellow viscous oil. MS (APCI) m/z: 468.5 $(M+H)^+$

Example 44

(44-1) 2-[{3-[3-(Decyloxy)phenyl]propanoyl}(4-hydroxybenzyl)amino]ethyl dihydrogen phosphate ammonium salt (Example compound 44)

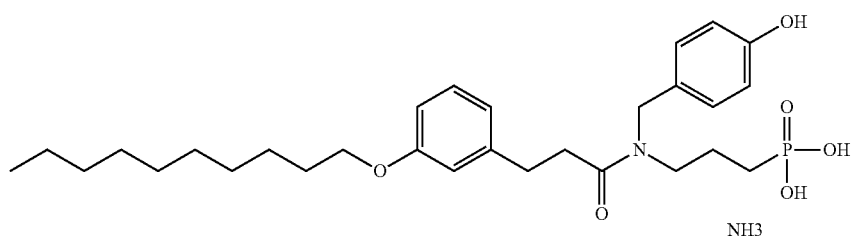

In Example 37, the reaction and treatment similar to those in (37-1)-(37-2) were performed using 4-benzyloxybenzaldehyde instead of 3-benzyloxybenzaldehyde to give the title compound (168 mg) as a colorless oil.

MS (APCI) m/z: 536.3[M+H]$^+$

Example 45

(45-1) 3-[(2-{[tert-Butyl(dimethyl)silyl]oxy}ethyl)amino]propan-1-ol (Example compound 45-1)

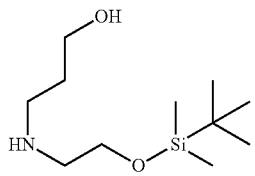

(2-Bromoethoxy)(tert-butyl)dimethylsilane (2.08 g) was dissolved in acetonitrile (27.9 mL), 3-amino-1-propanol (11.5 mL) was added, and the mixture was stirred at 95° C. for 1 hr. After allowing to cool to room temperature, water was added thereto, and the mixture was extracted with ethyl acetate, washed with saturated brine, and dried over anhydrous sodium sulfate. The solvent was evaporated under reduced pressure. The residue was purified by silica gel column chromatography (chloroform:methanol=100:0-80:20) to give the title compound (1.78 g) as a colorless oil. MS (APCI) m/z: 234.3[M+H]$^+$ (45-2) N-(2-{[tert-Butyl(dimethyl)silyl]oxy}ethyl)-3-[3-(decyloxy)phenyl]-N-(3-hydroxypropyl)propanamide (Example compound 45-2)

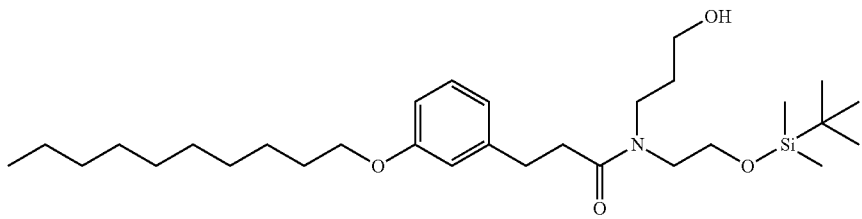 [SMILES: CCCCCCCCCCOc1cccc(CCC(=O)N(CCCO)CCO[Si](C)(C)C(C)(C)C)c1]

Reference Example compound 5 (400 mg) was dissolved in N,N-dimethylformamide (4.7 mL), N,N-diisopropylethylamine (0.678 mL) and HATU (745 mg) were added, and a solution of Example compound 45-1 (366 mg) in N,N-dimethylformamide (4.0 mL) was added dropwise thereto, and the mixture was stirred at room temperature for 15 hr. The reaction mixture was diluted with ethyl acetate, water was added, and the mixture was extracted with ethyl acetate, washed with saturated brine, and dried over anhydrous sodium sulfate. The solvent was evaporated under reduced pressure. The residue was purified by silica gel column chromatography (hexane:ethyl acetate=65:35-34:66) to give the title compound (624 mg) as a pale-brown oil.

MS (APCI) m/z: 522.6[M+H]$^+$ (45-3) N-(2-{[tert-Butyl(dimethyl)silyl]oxy}ethyl)-3-[3-(decyloxy)phenyl]-N-(3-methoxypropyl)propanamide (Example compound 45-3)

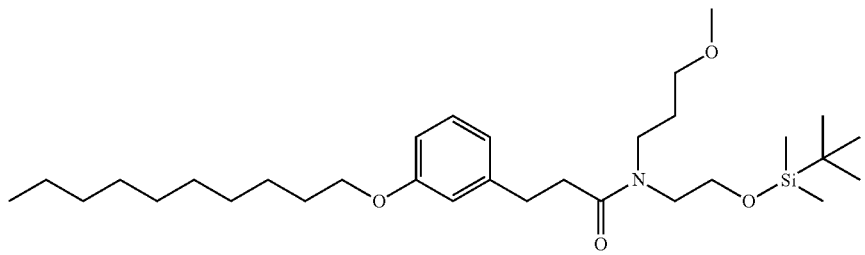 [SMILES: CCCCCCCCCCOc1cccc(CCC(=O)N(CCCOC)CCO[Si](C)(C)C(C)(C)C)c1]

Sodium hydride (35 mg) was dissolved in N,N-dimethylformamide (1.74 mL), a solution of Example compound 45-2 (300 mg) in N,N-dimethylformamide (4 mL) was added dropwise under ice-cooling, and the mixture was stirred under ice-cooling for 20 min. Under ice-cooling, iodomethane (0.107 mL) was added dropwise to the mixture, and the mixture was stirred at room temperature for 3 hr. Under ice-cooling, sodium hydride (35 mg), and iodomethane (0.107 mL) were added thereto, and the mixture was stirred at room temperature for 14 hr. Under ice-cooling, water was added to the mixture, and the mixture was extracted with ethyl acetate, washed with saturated brine, and dried over anhydrous sodium sulfate. The solvent was evaporated under reduced pressure. The residue was purified by silica gel column chromatography (hexane:ethyl acetate=75:25-60:40) to give the title compound (224 mg) as a pale-yellow oil. MS (APCI) m/z: 536.5[M+F]$^+$ (45-4) 3-[3-(Decyloxy)phenyl]-N-(2-hydroxyethyl)-N-[3-(methoxy)propyl]propanamide (Example compound 45-4)

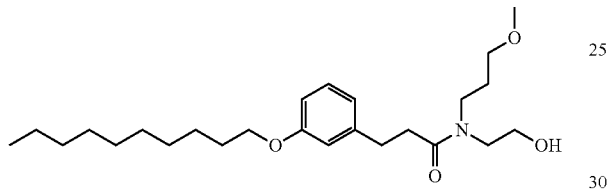

Example compound 45-3 (216 mg) was dissolved in tetrahydrofuran (4.04 mL), tetrabutylammonium fluoride (0.606 mL) was added dropwise under ice-cooling, and the mixture was stirred at room temperature for 1 hr. The solvent was evaporated under reduced pressure, and the residue was purified by silica gel column chromatography (hexane:ethyl acetate=25:75-0:100) to give the title compound (quant.) as a colorless oil. MS (APCI) m/z: 422.5[M+H]$^+$ (45-5) Dibenzyl 2-[{3-[3-(decyloxy)phenyl]propanoyl}(3-methoxypropyl)amino]ethyl phosphate (Example compound 45-5)

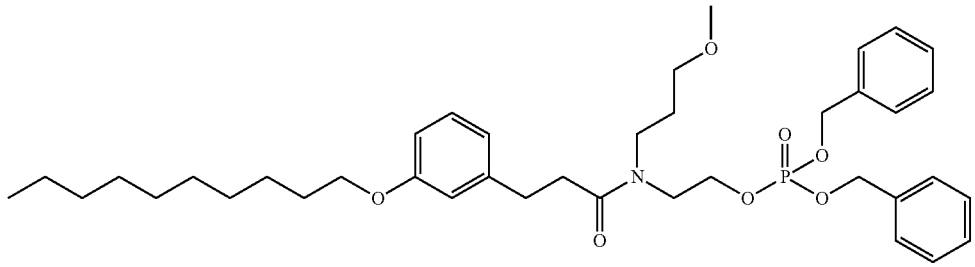 [SMILES: CCCCCCCCCCOc1cccc(CCC(=O)N(CCCOC)CCOP(=O)(OCc2ccccc2)OCc2ccccc2)c1]

Example compound 45-4 (162 mg) was dissolved in dichloromethane (1.62 mL) and acetonitrile (0.647 mL), 1H-tetrazole (54 mg) was added under ice-cooling, then, dibenzyl N,N-diisopropyl phosphoramidite (0.286 mL) was added dropwise, and the mixture was stirred at room temperature for 1 hr. Under ice-cooling, tert-butyl hydroperoxide (0.14 mL) was added dropwise thereto, and the mixture was stirred at room temperature for 1 hr. Under ice-cooling, saturated aqueous sodium thiosulfate solution (5 mL) was added to the mixture, and the mixture was stirred at room temperature for 10 min. To the reaction mixture was added ethyl acetate and, after extraction, and the mixture was washed with saturated aqueous sodium hydrogen carbonate solution and saturated brine, and dried over anhydrous sodium sulfate. The solvent was evaporated under reduced pressure. The residue was purified by silica gel column chromatography (hexane:ethyl acetate=50:50-15:85) to give the title compound (159 mg) as a colorless oil.

MS (APCI) m/z: 682.2[M+H]$^+$ (45-6) 2-[{3-[3-(Decyloxy)phenyl]propanoyl}(3-methoxypropyl)amino]ethyl dihydrogen phosphate ammonium salt (Example compound 45)

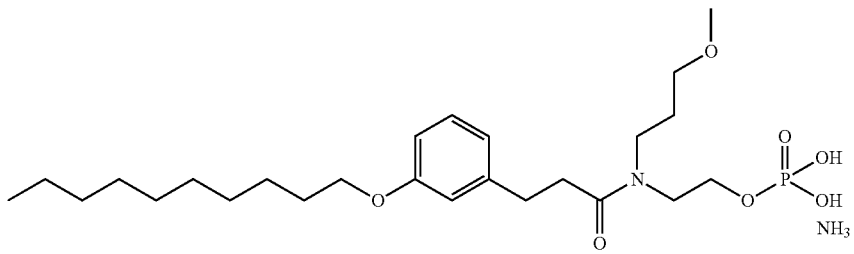

Example compound 45-5 (152 mg) was dissolved in methanol (3 mL), 10% palladium carbon (76 mg) was added, and the mixture was stirred under a hydrogen atmosphere at room temperature for 3.5 hr, and filtered. The filtrate was concentrated, and the obtained residue was purified by preparative HPLC (10 mM aqueous ammonium carbonate solution-acetonitrile) to give the title compound (75 mg) as a colorless oil.

MS (APCI) m/z: 502.3[M+H]$^+$

Example 46

(46-1) N-(2-{[tert-Butyl(dimethyl)silyl]oxy}ethyl)-3-[3-(decyloxy)phenyl]-N-(2-hydroxyethyl)propanamide (Example compound 46-1)

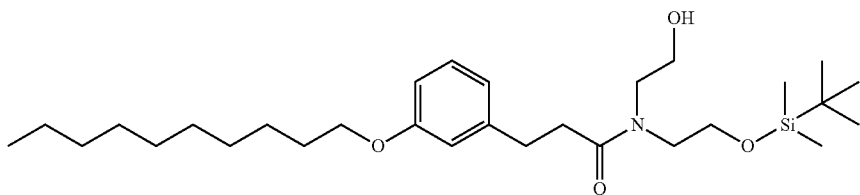 [SMILES: CCCCCCCCCCOc1cccc(CCC(=O)N(CCO)CCO[Si](C)(C)C(C)(C)C)c1]

In Example 45, the reaction and treatment similar to those in (45-1)-(45-2) were performed using 2-aminoethanol instead of 3-amino-1-propanol to give the title compound (633 mg) as a pale-yellow oil. MS (APCI) m/z: 508.5[M+H]$^+$ (46-2) N-(2-{[tert-Butyl(dimethyl)silyl]oxy}ethyl)-3-[3-(decyloxy)phenyl]-N-(2-oxyethyl)propanamide (Example compound 46-2)

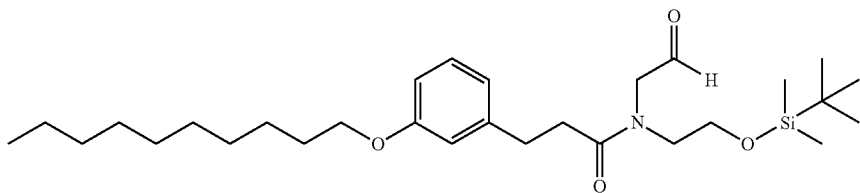 [SMILES: CCCCCCCCCCOc1cccc(CCC(=O)N(CC=O)CCO[Si](C)(C)C(C)(C)C)c1]

Example compound 46-1 (582 mg) was dissolved in dichloromethane (4.58 mL), iodobenzene diacetate (553 mg) and 9-azanoradamantane N-oxyl (nor-AZADO, 7 mg) were added, and the mixture was stirred at room temperature for 95 min. Diiodobenzene diacetate (553 mg) and nor-AZADO (7 mg) were added to the mixture, and the mixture was stirred for 3.5 hr. To the reaction mixture were added saturated aqueous sodium hydrogen carbonate solution and 20% aqueous sodium thiosulfate solution, and the mixture was stirred for 30 min. After extraction with chloroform, the mixture was washed with saturated brine, and dried over anhydrous sodium sulfate. The solvent was evaporated under reduced pressure. The residue was purified by silica gel column chromatography (hexane:ethyl acetate=75:25-60:40) to give the title compound (406 mg) as a colorless oil. MS (APCI) m/z: 506.6[M+H]$^+$ (46-3) N-(2-{[tert-Butyl(dimethyl)silyl]oxy}ethyl)-3-[3-(decyloxy)phenyl]-N-[2-(dimethylamino)ethyl]propanamide (Example compound 46-3)

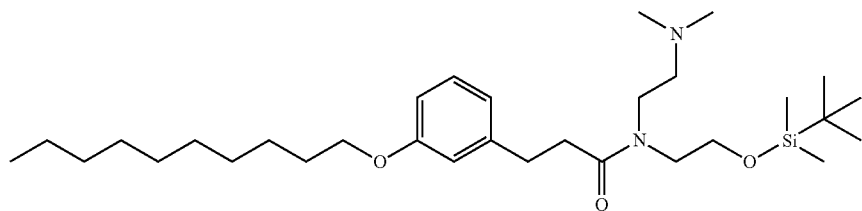 [SMILES: CCCCCCCCCCOc1cccc(CCC(=O)N(CCO[Si](C)(C)C(C)(C)C)CCN(C)C)c1]

Example compound 46-2 (388 mg) was dissolved in dichloromethane (3.84 mL), and 2M dimethylamine-tetrahydrofuran solution (1.151 mL) and acetic acid (0.044 mL) were added, and the mixture was stirred at room temperature for 10 min. Under ice-cooling, sodium tri(acetoxy)borohydride (407 mg) was added thereto, and the mixture was stirred at room temperature for 19.5 hr. Under ice-cooling, 1N aqueous sodium hydroxide solution was added dropwise to the mixture, and the mixture was extracted with ethyl acetate, washed with saturated brine, and dried over anhydrous sodium sulfate. The solvent was evaporated under reduced pressure. The residue was purified by silica gel column chromatography (chloroformmethanol=100:0-85:15) to give the title compound (383 mg) as a colorless oil. MS (APCI) m/z: 535.7[M+H]$^+$ (46-4) 3-[3-(Decyloxy)phenyl]-N-[2-(dimethylamino)ethyl]-N-(2-hydroxyethyl)propanamide (Example compound 46-4)

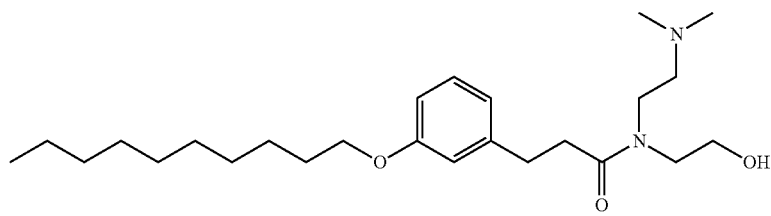 [SMILES: CCCCCCCCCCOc1cccc(CCC(=O)N(CCO)CCN(C)C)c1]

Example compound 46-3 (370 mg) was dissolved in tetrahydrofuran (6.92 mL), tetrabutylammonium fluoride (1.04 mL) was added dropwise under ice-cooling, and the mixture was stirred at room temperature for 1 hr. The solvent was evaporated under reduced pressure, and the residue was purified by NH silica gel column chromatography (hexane: ethyl acetate=10:90-0:100) to give the title compound (173 mg) as a colorless oil. MS (APCI) m/z: 421.5[M+H]$^+$ (46-5) Di-tert-butyl 2-({3-[3-(decyloxy)phenyl]propanoyl}[2-(dimethylamino)ethyl]amino)ethyl phosphate (Example Compound 46-5)

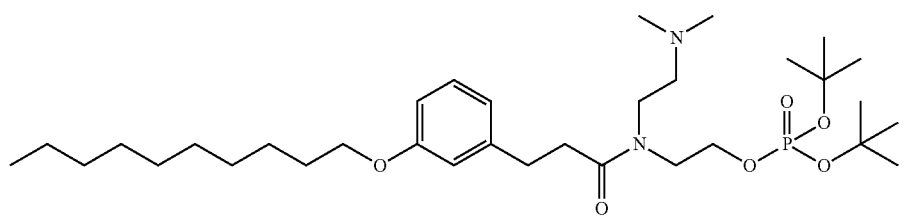 [SMILES: CCCCCCCCCCOc1cccc(CCC(=O)N(CCOP(=O)(OC(C)(C)C)OC(C)(C)C)CCN(C)C)c1]

Example compound 46-4 (164 mg) was dissolved in dichloromethane (1.64 mL) and acetonitrile (0.657 mL), and 1H-tetrazole (54.7 mg) was added under ice-cooling, di-tert-butyl N,N-diisopropyl phosphoramidite (0.259 mL) was added dropwise, and the mixture was stirred at room temperature for 70 min. Under ice-cooling, tert-butyl hydroperoxide (0.14 mL) was added dropwise thereto, and the mixture was stirred at room temperature for 1 hr. Under ice-cooling, thioanhydrous sodium sulfate aqueous solution (5 mL) was added to the mixture, and the mixture was stirred at room temperature for 10 min. To the reaction mixture was added ethyl acetate and extracted, and the organic layer was washed with saturated aqueous sodium hydrogen carbonate solution and saturated brine, and dried over anhydrous sodium sulfate. The solvent was evaporated under reduced pressure. The residue was purified by NH silica gel column chromatography (ethyl acetate:methanol=100:0-95:5) to give the title compound (quant.) as a colorless oil.

MS (APCI) m/z: 613.5[M+H]$^+$ (46-6) 2-({3-[3-(Decyloxy)phenyl]propanoyl}[2-(dimethylamino)ethyl]amino)ethyl dihydrogen phosphate ammonium salt (Example compound 46)

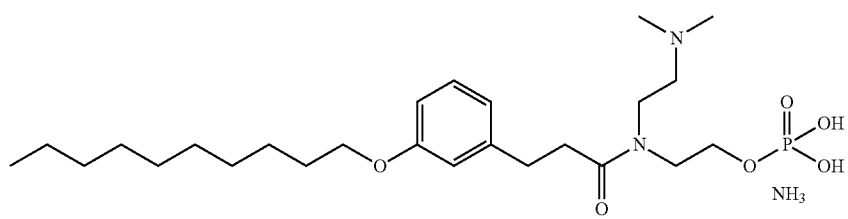

Example compound 46-5 (336 mg) was dissolved in dichloromethane (6.0 mL), trifluoroacetic acid (0.598 mL) was added dropwise under ice-cooling, and the mixture was stirred at room temperature for 2 hr. The solvent was evaporated under reduced pressure, diethyl ether was added, and the solvent was evaporated under reduced pressure. This evaporation operation was repeated 3 times, and the obtained residue was purified by preparative HPLC (10 mM aqueous ammonium carbonate solution-acetonitrile) to give the title compound (115 mg) as a colorless oil. MS (APCI) m/z: 501.4[M+H]$^+$ Example 47

(47-1) N-[2-(Benzyloxy)ethyl]-3-[3-(decyloxy)phenyl]-N-(4-hydroxybutyl)propanamide (Example compound 47-1)

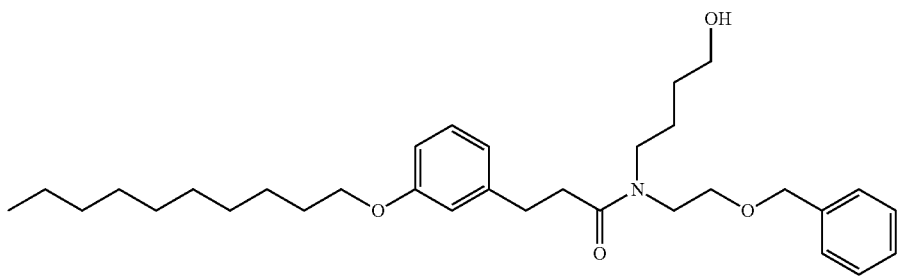 [SMILES: CCCCCCCCCCOc1cccc(CCC(=O)N(CCCCO)CCOCc2ccccc2)c1]

In Example 39, the reaction and treatment similar to those in (39-1)-(39-2) were performed using [(2-bromoethyl)oxy]methyl}benzene instead of 1-bromo-3-benzyloxypropane and 4-amino-1-butanol instead of 2-aminoethanol to give the title compound (738 mg) as a pale-yellow oil. MS (APCI) m/z: 512.6[M+H]$^+$ (47-2) N-[2-(Benzyloxy)ethyl]-3-[3-(decyloxy)phenyl]-N-(4-methoxybutyl)propanamide (Example compound 47-2)

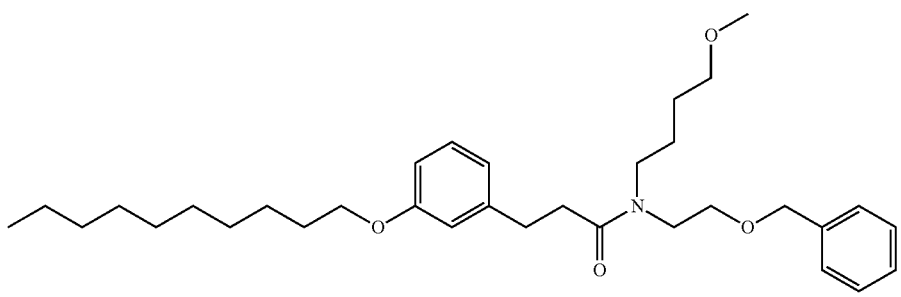 [SMILES: CCCCCCCCCCOc1cccc(CCC(=O)N(CCCCOC)CCOCc2ccccc2)c1]

In Example 45, the reaction and treatment similar to those in (45-3) were performed using Example compound 47-1 instead of Example compound 45-2 to give the title compound (331 mg) as a pale-yellow oil. MS (APCI) m/z: 526.6[M+H]$^+$ (47-3) 3-[3-(Decyloxy)phenyl]-N-(2-hydroxyethyl)-N-[4-(methoxy)butyl]propanamide (Example compound 47-3)

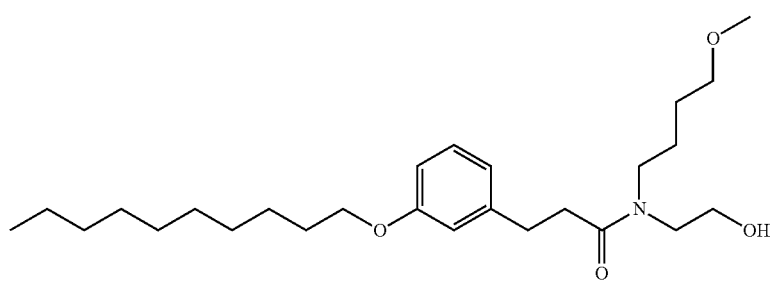 [SMILES: CCCCCCCCCCOc1cccc(CCC(=O)N(CCO)CCCCOC)c1]

Example compound 47-2 (309 mg) was dissolved in methanol (3.92 mL), 10% palladium carbon (93 mg) was added, and the mixture was stirred under a hydrogen atmosphere at room temperature for 1.5 hr and filtered. The filtrate was concentrated to give the title compound (quant.) as a colorless oil. MS (APCI) m/z: 436.6[M+H]$^+$ (47-4) 2-[{3-[3-(Decyloxy)phenyl]propanoyl}(4-methoxybutyl)amino]ethyl dihydrogen phosphate ammonium salt (Example compound 47)

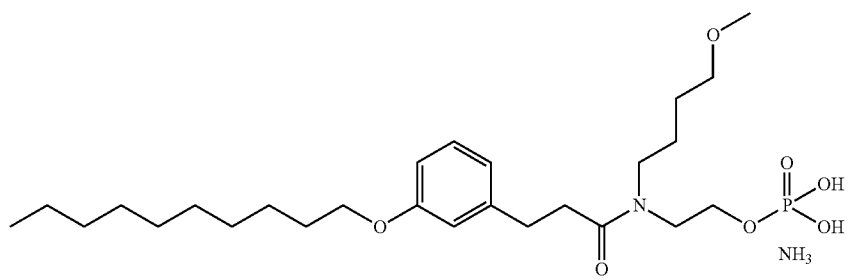

In Example 45, the reaction and treatment similar to those in (45-5)-(45-6) were performed using Example compound 47-3 instead of Example compound 45-4 to give the title compound (151 mg) as a colorless oil. MS (APCI) m/z: 516.1[M+H]⁺

Example 48

(48-1) Methyl 3-(undecyloxy)benzoate (Example compound 48-1)

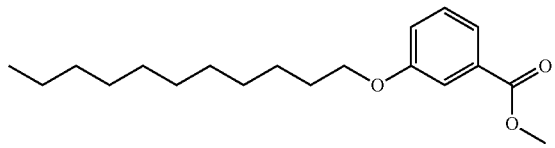 [SMILES: CCCCCCCCCCCOc1cccc(C(=O)OC)c1]

A mixture of methyl 3-hydroxybenzoate (600 mg), 1-bromoundecane (0.968 mL), cesium carbonate (2.57 g), and N,N-dimethylformamide (13 mL) was stirred at room temperature for one day and night. Water was added to the reaction mixture, and the mixture was extracted with diethyl ether. The organic layer was washed with water and saturated brine, and dried over anhydrous sodium sulfate. The desiccant was filtered off, and the filtrate was concentrated under reduced pressure. The obtained residue was purified by silica gel column chromatography (hexane:ethyl acetate=100:0-95:5), and purified again by silica gel column chromatography (hexane:chloroform=100:0-70:30) to give the title compound (1.07 g) as a colorless oil. MS (APCI) m/z: 307.4 (M+H)⁺.

(48-2) [3-(Undecyloxy)phenyl]methanol (Example compound 48-2)

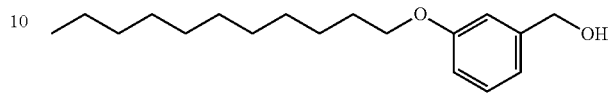

To a solution of Example compound 48-1 (16.3 mL) was added under ice-cooling lithium aluminum hydride (124 mg), and the mixture was stirred at room temperature for 4 hr. To the reaction mixture were sequentially added water (0.1 mL), 1N aqueous sodium hydroxide solution (0.1 mL), water (0.3 mL), and celite, and the mixture was stirred at room temperature overnight. After filtering off the insoluble material in the reaction mixture with diatomaceous earth, the filtrate was concentrated under reduced pressure to give the title compound (434 mg) as a colorless solid. MS (APCI) m/z: 279.3 (M+H)⁺

(48-3) 3-(Undecyloxy)benzyl 3-[(di-tert-butoxy phosphoryl)oxy]azetidine-1-carboxylate (Example compound 48-3)

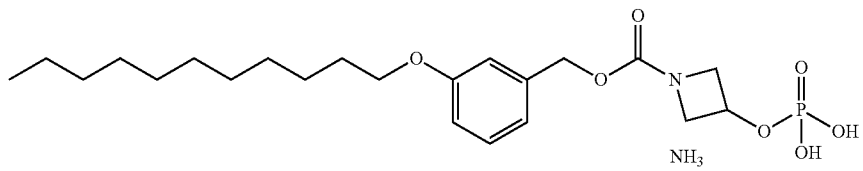

To a solution of Example compound 48-2 (1.8 mL) was added under ice-cooling 1,1'-carbonyldiimidazole (87 mg), and the mixture was stirred at the same temperature for 3 hr. Under ice-cooling, a solution of Reference Example compound 1 (157 mg) in N,N-dimethylformamide (1.8 mL) and triethylamine (0.090 mL) were added thereto, and the mixture was stirred at room temperature overnight. Water was added to the reaction mixture, and the mixture was extracted with ethyl acetate. The organic layer was dried over anhydrous sodium sulfate, the desiccant was filtered off, and the filtrate was concentrated under reduced pressure. The obtained residue was purified by silica gel column chromatography (hexane:ethyl acetate=85:15-60:40) to give the title compound (172 mg) as a colorless viscous oil.
MS (APCI) m/z: 587.0 (M+NH₄)⁺

(48-4) 3-(Undecyloxy)benzyl 3-(phosphonooxy)azetidine-1-carboxylate ammonium salt (Example compound 48)

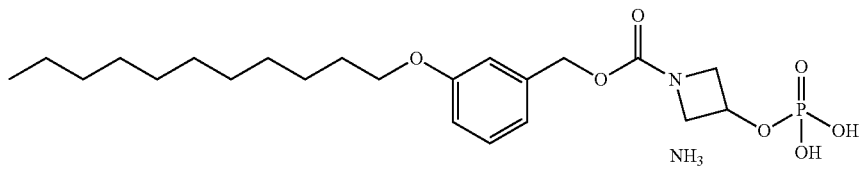

To a solution of Example compound 48-3 (172 mg) in dichloromethane (3.0 mL) was added trifluoroacetic acid (0.30 mL), and the mixture was stirred at room temperature for 2 hr. The reaction mixture was concentrated under reduced pressure. The obtained residue was purified by preparative HPLC (10 mM aqueous ammonium carbonate solution-acetonitrile) to give the title compound (125 mg) as a colorless solid.
MS (APCI) m/z: 457.9 (M+H)⁺

Example 49

(49-1) Methyl 9-(4-methylphenyl)-8-nonenoate (Example compound 49-1)

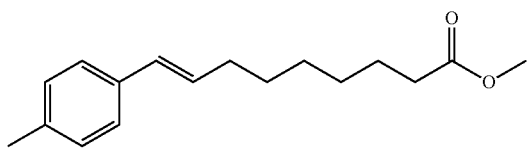

Methyl 8-nonenoate (100 mg) was dissolved in N,N-dimethylformamide (2 mL), 1-iodo-4-methylbenzene (209 mg), potassium carbonate (221 mg), tetrabutylammonium chloride (148 mg), and dichloro bis(triphenylphosphine)palladium(II) (75 mg) were added at room temperature, and the mixture was stirred at 120° C. for 18 hr. To the reaction mixture was added under ice-cooling saturated brine, and the mixture was extracted with ethyl acetate, washed with 1N hydrochloric acid, and dried over anhydrous sodium sulfate. The solvent was evaporated and the residue was purified by silica gel column chromatography (hexane:ethyl acetate=100:0-90:10) to give a crudely purified product (201 mg) of the title compound as a yellow oil.
MS (APCI) m/z: 261.1[M+H]⁺

(49-2) 9-(4-Methylphenyl)nonanoic acid (Example compound 49-2)

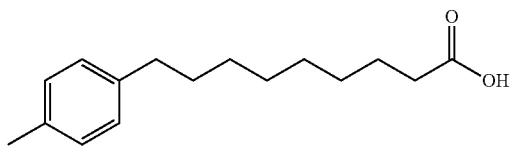 [SMILES: Cc1ccc(CCCCCCCCC(=O)O)cc1]

Example compound 49-1 (200 mg) was dissolved in methanol (2 mL), palladium carbon (80 mg) was added at room temperature, and the mixture was stirred under a hydrogen atmosphere at room temperature for 6 hr. After completion of the reaction, membrane filter filtration was perfoLmed, the filtrate was concentrated, and the residue was purified by silica gel column chromatography (hexane:ethyl acetate=95:5) to give a colorless oil (130 mg). The obtained oil (130 mg) was dissolved in methanol (5 mL), 1N aqueous sodium hydroxide solution (1.98 mL) was added at room temperature, and the mixture was stirred at room temperature for 16 hr. After completion of the reaction, 1N hydrochloric acid was added, and the aqueous layer was extracted with ethyl acetate, washed with water, and dried over anhydrous sodium sulfate. The solvent was evaporated to give an unpurified product (100 mg) of the title compound as a colorless oil. MS (APCI) m/z: 247.0[M−H]⁻

(49-3) 1-[9-(4-Methylphenyl)nonanoyl]azetidin-3-yl dihydrogen phosphate ammonium salt (Example compound 49)

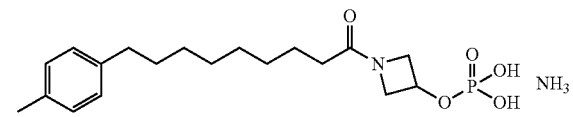

In Example 1, the reaction and treatment similar to those in (1-3)-(1-4) were performed using Example compound 49-2 instead of Example compound 1-2 to give the title compound (55 mg) as a colorless oil. MS (APCI) m/z: 384.2[M+H]⁺

Example 50

(50-1) 2-[{3-[3-(Decyloxy)phenyl]propanoyl}(5-hydroxypentyl)amino]ethyl dihydrogen phosphate ammonium salt (Example compound 50)

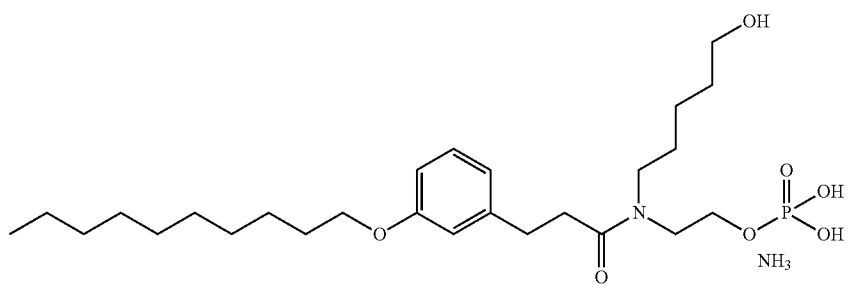

In Example 39, the reaction and treatment similar to those in (39-1)-(39-4) were performed using {[(5-bromopentyl)oxy]methyl}benzene instead of 1-bromo-3-benzyloxypropane to give the title compound (156 mg) as a colorless oil. MS (APCI) m/z: 516.1[M+H]$^+$ Example 51

(51-1) 2-[{3-[3-(Decyloxy)phenyl]propanoyl}(6-hydroxyhexyl)amino]ethyl dihydrogen phosphate ammonium salt (Example compound 51)

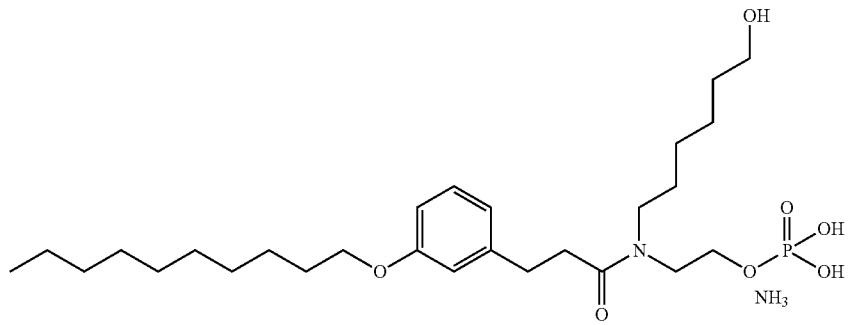

In Example 39, the reaction and treatment similar to those in (39-1)-(39-4) were performed using {[(6-bromohexyl)oxy]methyl}benzene instead of 1-bromo-3-benzyloxypropane to give the title compound (101 mg) as a white powder. MS (APCI) m/z: 530.1[M+H]$^+$ Example 52

(52-1) 2-[{3-[3-(Decyloxy)phenyl]propanoyl}(5-methoxypentyl)amino]ethyl dihydrogen phosphate ammonium salt (Example compound 52)

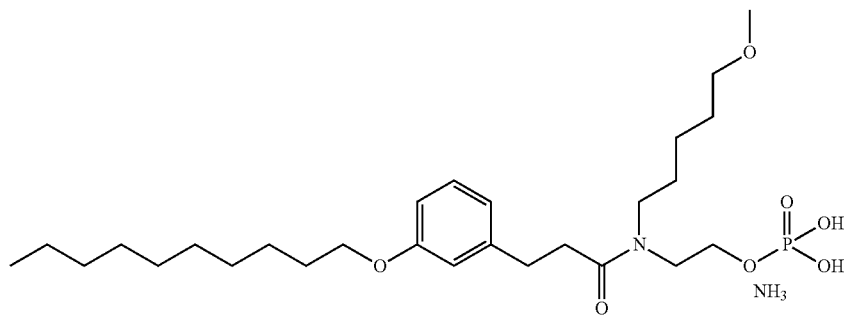

In Example 47, the reaction and treatment similar to those in (47-1)-(47-4) were performed using 5-amino-1-pentanol instead of 4-amino-1-butanol to give the title compound (179 mg) as a colorless oil. MS (APCI) m/z: 530.1[M+H]+

Example 53

(53-1) 2-[{3-[3-(Decyloxy)phenyl]propanoyl}(6-methoxyhexyl)amino]ethyl dihydrogen phosphate ammonium salt (Example compound 53)

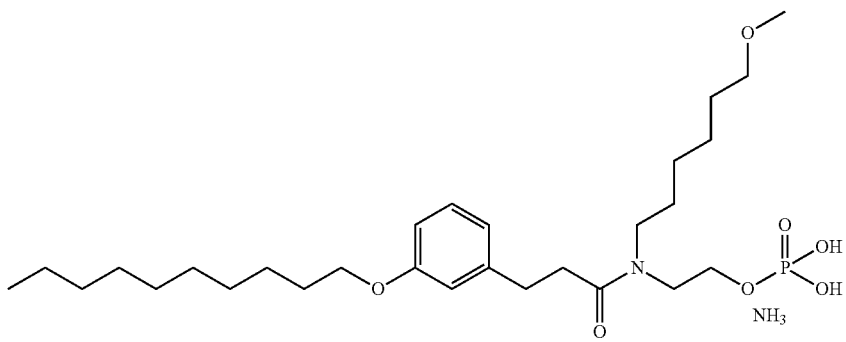

In Example 47, the reaction and treatment similar to those in (47-1)-(47-4) were performed using 6-amino-1-hexanol instead of 4-amino-1-butanol to give the title compound (141 mg) as a white powder. MS (APCI) m/z: 544.1[M+H]+

Example 54

(54-1) 2-[{3-[3-(Decyloxy)phenyl]propanoyl}(4-methoxybenzyl)amino]ethyl dihydrogen phosphate ammonium salt (Example compound 54)

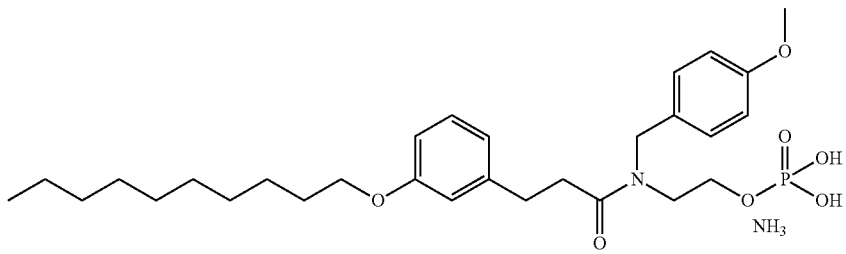

In Example 36, the reaction and treatment similar to those in (36-1)-(36-3) were performed using 2-[(4-methoxybenzyl)amino]ethanol instead of 2-[(2-methoxyethyl)amino]ethan-1-ol to give the title compound (172 mg) as a pale-yellow oil. MS (APCI) m/z: 550.1[M+H]$^+$ Example 55

(55-1) 2-[{3-[3-(Decyloxy)phenyl]propanoyl}(propan-2-yl)amino]ethyl dihydrogen phosphate ammonium salt (Example compound 55)

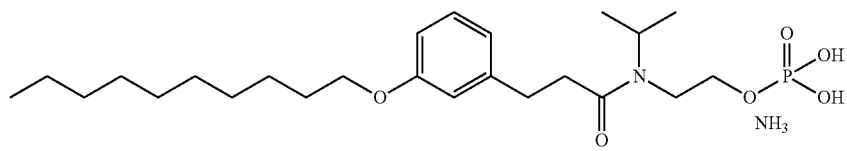

In Example 36, the reaction and treatment similar to those in (36-1)-(36-3) were performed using 2-(isopropylamino)ethanol instead of 2-[(2-methoxyethyl)amino]ethan-1-ol to give the title compound (52 mg) as a pale-yellow oil. MS (APCI) m/z: 472.1[M+H]$^+$ Example 56

(56-1) 2-[(Pyridin-3-ylmethyl)amino]ethanol (Example compound 56-1)

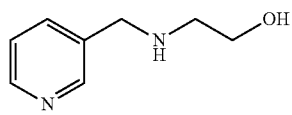

2-Aminoethanol (400 mg) was dissolved in methanol (10 mL), 3-pyridine carbaldehyde (702 mg) was added, and the mixture was stirred at 60° C. for 2 hr. To the mixed solution was added sodium borohydride (248 mg) under ice-cooling, and the mixture was stirred at 60° C. for 5 hr. The reaction mixture was cooled to room temperature, and evaporated under reduced pressure. The residue was purified by silica gel column chromatography (chloroform:methanol=100:0-95:5) to give the title compound (936 mg) as a pale-yellow oil. MS (APCI) m/z: 153.2[M+H]$^+$ (56-2) 2-[{3-[3-(Decyloxy)phenyl]propanoyl}(pyridin-3-yl methyl)amino]ethyl dihydrogen phosphate ammonium salt (Example compound 56)

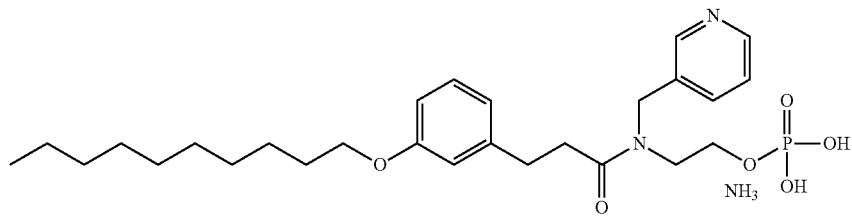

In Example 36, the reaction and treatment similar to those in (36-1)-(36-3) were performed using Example compound 56-1 instead of 2-[(2-methoxyethyl)amino]ethan-1-ol to give the title compound (151 mg) as a colorless oil.

MS (APCI) m/z: 521.3[M+H]$^+$

Example 57

(57-1) 2-[(1,3-Thiazol-2-ylmethyl)amino]ethanol (Example compound 57-1)

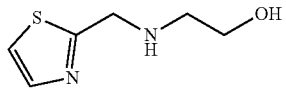

2-Aminoethanol (300 mg) was dissolved in methanol (9.8 mL), 3-thiazole carbaldehyde (556 mg) was added, and the mixture was stirred at 60° C. for 2 hr. To the mixed solution was added sodium borohydride (186 mg) under ice-cooling, and the mixture was stirred at 60° C. for 2 hr. The reaction mixture was allowed to cool to room temperature, and evaporated under reduced pressure. The residue was purified by silica gel column chromatography (chloroform:methanol=100:0-95:5) to give the title compound (721 mg) as a brown oil.

MS (APCI) m/z: 159.2[M+H]$^+$ (57-2) 2-[{3-[3-(Decyloxy)phenyl]propanoyl}(1,3-thiazol-2-ylmethyl)amino]ethyl dihydrogen phosphate ammonium salt (Example compound 57)

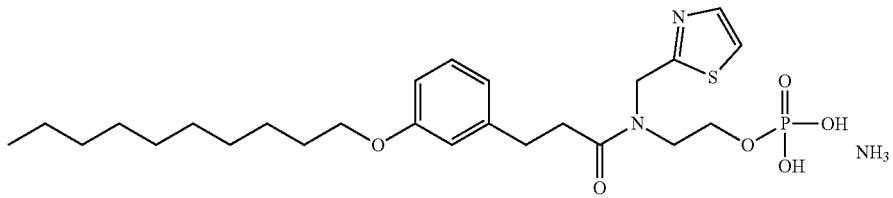

In Example 36, the reaction and treatment similar to those in (36-1)-(36-3) were performed using Example compound 57-1 instead of 2-[(2-methoxyethyl)amino]ethan-1-ol to give the title compound (52 mg) as a colorless oil.

MS (APCI) m/z: 527.2[M+H]$^+$

Example 58

(58-1) 2-[(Pyridin-4-yl methyl)amino]ethanol (Example compound 58-1)

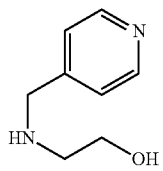

2-Aminoethanol (500 mg) was dissolved in ethanol (10 mL), 4-pyridine carbaldehyde (877 mg) was added, and the mixture was stirred at 60° C. for 2 hr. After allowing to cool to room temperature, sodium borohydride (310 mg) was added thereto under ice-cooling, and the mixture was stirred at room temperature for 1 hr, and was stirred at 60° C. for 25 min. After allowing to cool to room temperature, water was added, then, 1N aqueous sodium hydroxide solution was added to the mixture, and the mixture was extracted with chloroform, and dried over anhydrous sodium sulfate. The solvent was evaporated under reduced pressure. The residue was purified by NH silica gel column chromatography (ethyl acetate:methanol=100:0-80:20) to give the title compound (583 mg) as a colorless oil. MS (APCI) m/z: 153.0[M+H]$^+$ (58-2) 3-[3-(Decyloxy)phenyl]-N-(2-hydroxyethyl)-N-(pyridin-4-ylmethyl)propanamide (Example compound 58-2)

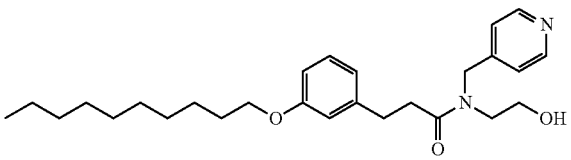 [SMILES: CCCCCCCCCCOc1cccc(CCC(=O)N(CCO)Cc2ccncc2)c1]

Reference Example compound 5 (250 mg) was dissolved in N,N-dimethylformamide (2.44 mL), and N,N-diisopropylethylamine (0.423 mL) and HATU (465 mg) were added. A solution of Example compound 58-1 (149 mg) in N,N-dimethylformamide (3 mL) was added dropwise thereto, and the mixture was stirred at room temperature for 14.5 hr. The reaction mixture was diluted with ethyl acetate, water was added, and the mixture was extracted with ethyl acetate, washed with saturated brine, and dried over anhydrous sodium sulfate. The solvent was evaporated under reduced pressure. The residue was purified by silica gel column chromatography (ethyl acetate:methanol=100:0-87:13) to give the title compound (292 mg) as a pale-yellow oil.

MS (APCI) m/z: 441.4[M+H]$^+$ (58-3) 2-[{3-[3-(Decyloxy)phenyl]propanoyl}(pyridin-4-yl methyl)amino]ethyl dihydrogen phosphate ammonium salt (Example compound 58)

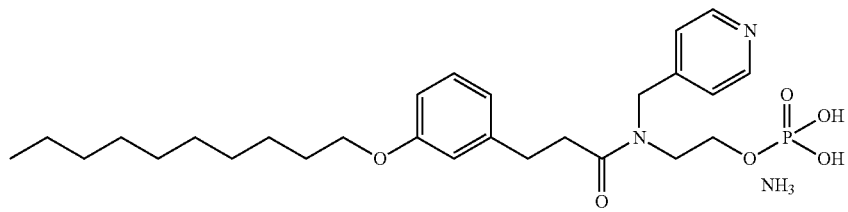

In Example 46, the reaction and treatment similar to those in (46-5)-(47-6) were performed using Example compound 58-2 instead of Example compound 46-4 to give the title compound (182 mg) as a colorless oil. MS (APCI) m/z: 521.3[M+H]$^+$ Example 59

(59-1) Benzyl 5-(4-iodophenyl)-4-pentynoate (Example compound 59-1)

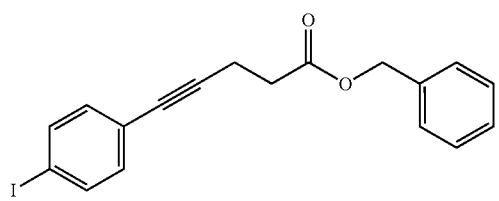 [SMILES: O=C(CCC#Cc1ccc(I)cc1)OCc1ccccc1]

A mixture of 1,4-diiodobenzene (3.94 g), Example compound 34-1 (750 mg), bis(triphenylphosphine)palladium(II) dichloride (140 mg), copper iodide (I) (38 mg), and triethylamine (13.3 mL) was stirred at 70° C. for one day and night. To the reaction mixture was added saturated aqueous ammonium chloride solution, and the mixture was extracted with diethyl ether. The organic layer was washed with 1N hydrochloric acid, and dried over anhydrous sodium sulfate. The desiccant was filtered off, and the filtrate was concentrated under reduced pressure. The obtained residue was purified by silica gel column chromatography (hexane:ethyl acetate=100:0-93:7) to give the title compound (893 mg) as a colorless oil.

MS (APCI) m/z: 407.9 (M+NH$_4$)$^+$.

(59-2) Benzyl 5-[4-(1-heptynyl)phenyl]-4-pentynoate (Example compound 59-2)

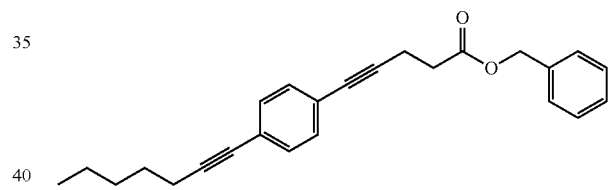

A mixture of Example compound 59-1 (300 mg), 1-heptyne (0.151 mL), bis(triphenylphosphine)palladium(II) dichloride (54.0 mg), copper iodide (I) (14.6 mg), and triethylamine (2.56 mL) was stirred at 70° C. for 6 hr. To the reaction mixture was added saturated aqueous ammonium chloride solution, and the mixture was extracted with diethyl ether. The organic layer was washed with 1N hydrochloric acid and saturated brine, and dried over anhydrous sodium sulfate. The desiccant was filtered off, and the filtrate was concentrated under reduced pressure. The obtained residue was purified by silica gel column chromatography (hexane:ethyl acetate=100:0-93:7) to give the title compound (250 mg) as a yellow solid.

MS (APCI) m/z: 376.0 (M+NH$_4$)$^+$.

(59-3) 5-(4-Heptylphenyl)pentanoic acid (Example compound 59-3)

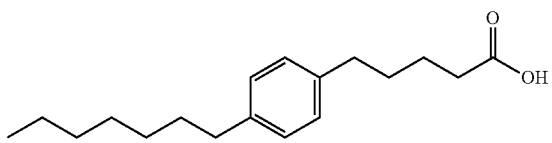 [SMILES: CCCCCCCc1ccc(CCCCC(=O)O)cc1]

To a solution of Example compound 59-2 (250 mg) in ethanol (7.0 mL) was added 7.5% palladium carbon (25 mg), and the mixture was stirred under a hydrogen atmosphere at room temperature for one day and night. After filtering off the insoluble material in the reaction mixture with diatomaceous earth, the filtrate was concentrated under reduced pressure. The obtained residue was purified by silica gel column chromatography (hexane:ethyl acetate=90:10-60:40) to give the title compound (161 mg) as a colorless solid.

MS (APCI) m/z: 275.1 (M−H)−

(59-4) 1-[5-(4-Heptylphenyl)pentanoyl]azetidin-3-yl dihydrogen phosphate ammonium salt (Example compound 59)

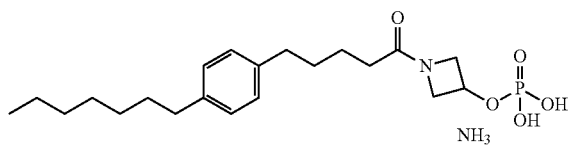

To a solution of Example compound 59-3 (158 mg) in N,N-dimethylformamide (5.7 mL) were added N,N-diisopropylethylamine (0.30 mL), Reference Example compound 1 (182 mg), and HATU (326 mg), and the mixture was stirred at room temperature overnight. Water was added to the reaction mixture, and the mixture was extracted with ethyl acetate. The organic layer was dried over anhydrous sodium sulfate, the desiccant was filtered off, and the filtrate was concentrated under reduced pressure. To the residue were added dichloromethane (5.7 mL) and trifluoroacetic acid (0.57 mL), and the mixture was stirred at room temperature for 3 hr. The reaction mixture was concentrated under reduced pressure. The obtained residue was purified by preparative HPLC (10 mM aqueous ammonium carbonate solution-acetonitrile) to give the title compound (244 mg) as a colorless solid.

MS (APCI) m/z: 412.2 (M+H)+

Example 60

(60-1) (8E)-9-[4-(Trifluoromethyl)phenyl]-8-nonenoic acid (Example compound 60-1)

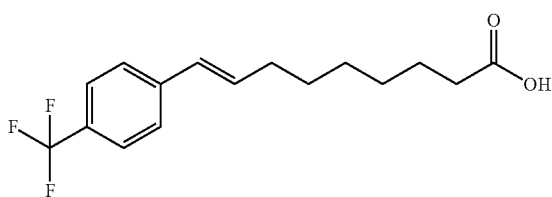 [SMILES: O=C(O)CCCCCC/C=C/c1ccc(C(F)(F)F)cc1]

8-Nonenoic acid (100 mg) was dissolved in N,N-dimethylformamide (3 mL), and 1-iodo-4-(trifluoromethyl)benzene (226 mg), potassium carbonate (265 mg), lithium chloride (35.2 mg), and dichloro bis(triphenylphosphine)palladium (II) (89.9 mg) were added at room temperature, and the mixture was stirred at 120° C. for 3 hr. To the reaction mixture was added under ice-cooling 1N hydrochloric acid, and the mixture was extracted with ethyl acetate, washed with saturated brine, and dried over anhydrous sodium sulfate. The solvent was evaporated and the residue was purified by silica gel column chromatography (hexane:ethyl acetate=90:10-60:40) to give a crudely purified product (186 mg) of the title compound as a yellow oil.

(60-2) 9-[4-(Trifluoromethyl)phenyl]nonanoic acid (Example compound 60-2)

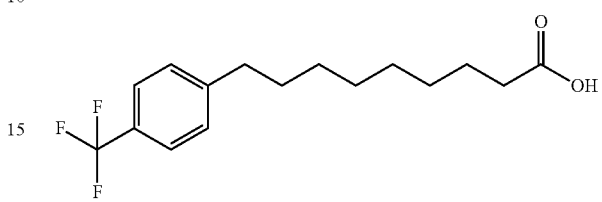

Example compound 60-1 (158 mg) was dissolved in methanol (5 mL), palladium carbon (32 mg) was added, and the mixture was stirred at room temperature for 6 hr. After completion of the reaction, membrane filter filtration was performed, and the filtrate was concentrated to give an unpurified product (160 mg) of the title compound as a colorless oil.

MS (APCI) m/z: 301.0[M+H]+

(60-3) 1-{9-[4-(Trifluoromethyl)phenyl]nonanoyl}azetidin-3-yl dihydrogen phosphate ammonium salt (Example compound 60)

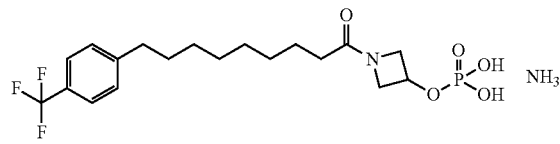

In Example 1, the reaction and treatment similar to those in (1-3)-(1-4) were performed using Example compound 60-2 instead of Example compound 1-2 to give the title compound (34 mg) as a colorless oil. MS (APCI) m/z: 438.1[M+H]+

Example 61

(61-1) 1-[5-(3-Heptylphenyl)pentanoyl]azetidin-3-yl dihydrogen phosphate ammonium salt (Example compound 61)

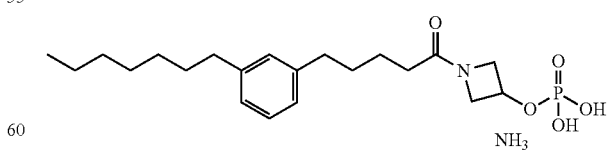

In Example 59, the reaction and treatment similar to those in (59-1)-(59-4) were performed using 1,3-diiodobenzene instead of 1,4-diiodobenzene to give the title compound (256 mg) as a colorless solid. MS (APCI) m/z: 412.2 (M+H)+

Example 62

(62-1) 1-[5-(3-Octylphenyl)pentanoyl]azetidin-3-yl dihydrogen phosphate ammonium salt (Example compound 62)

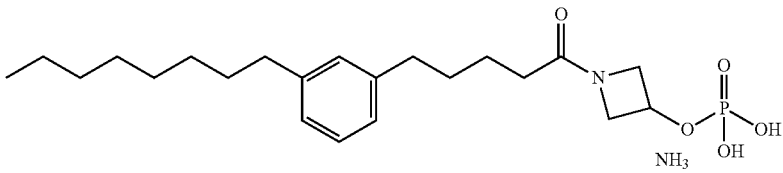

In Example 59, the reaction and treatment similar to those in (59-1)-(59-4) were performed using 1,3-diiodobenzene instead of 1,4-diiodobenzene and 1-octyne instead of 1-heptyne to give the title compound (250 mg) as a colorless solid. MS (APCI) m/z: 426.3 (M+H)⁺

Example 63

(63-1) 9-(3-Ethylphenyl)nonanoic acid (Example compound 63-1)

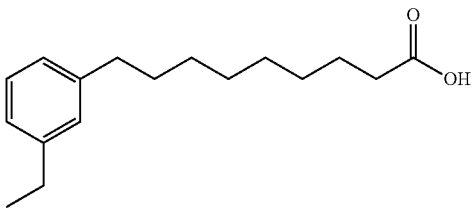 [SMILES: CCc1cccc(CCCCCCCCC(=O)O)c1]

In Example 60, the reaction and treatment similar to those in (60-1)-(60-2) were performed using 3-ethyliodobenzene instead of 1-iodo-4-(trifluoromethyl)benzene to give the title compound (289 mg) as a colorless oil. MS (APCI) m/z: 261.1[M=H]⁻

(63-2) 1-[9-(3-Ethylphenyl)nonanoyl]azetidin-3-yl dihydrogen phosphate (Example compound 63)

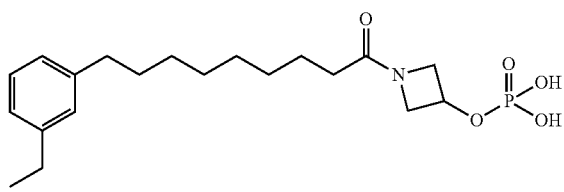 [SMILES: CCc1cccc(CCCCCCCCC(=O)N2CC(OP(=O)(O)O)C2)c1]

In Example 4, the reaction and treatment similar to those in (4-3)-(4-4) were performed using Example compound 63-1 instead of Example compound 4-2 to give the title compound (52 mg) as a colorless oil. MS (APCI) m/z: 398.2[M+H]⁺

Example 64

(64-1) 1-[5-(2-Octylphenyl)pentanoyl]azetidin-3-yl dihydrogen phosphate ammonium salt (Example compound 64)

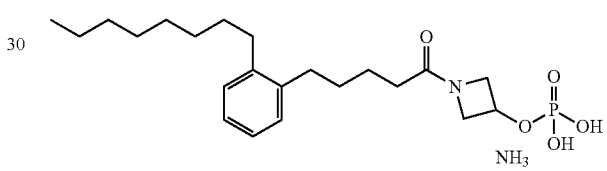

In Example 59, the reaction and treatment similar to those in (59-1)-(59-4) were performed using 1,2-diiodobenzene instead of 1,4-diiodobenzene and 1-octyne instead of 1-heptyne to give the title compound (98 mg) as a colorless solid. MS (APCI) m/z: 426.3 (M+H)⁺

Example 65

(65-1) 1-{9-[3-(Trifluoromethyl)phenyl]nonanoyl}azetidin-3-yl dihydrogen phosphate (Example compound 65)

In Example 60, the reaction and treatment similar to those in (60-1)-(60-2) were performed using 3-(trifluoromethyl)iodobenzene instead of 1-iodo-4-(trifluoromethyl)benzene to give the title compound (30 mg) as a colorless oil. MS (APCI) m/z: 438.2[M+14]⁺

Example 66

(66-1) 1 {9-[4-(Propan-2-yl)phenyl]nonanoyl}azetidin-3-yl dihydrogen phosphate (Example compound 66)

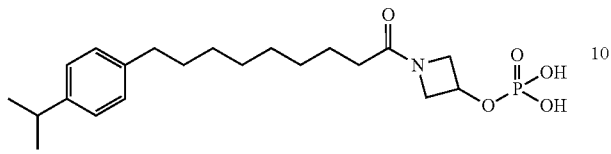

In Example 60, the reaction and treatment similar to those in (60-1)-(60-2) were performed using 4-isopropyliodobenzene instead of 1-iodo-4-(trifluoromethyl)benzene to give the title compound (36 mg) as a colorless oil. MS (APCI) m/z: 412.2[M+H]$^+$

Example 67

(67-1) 2-[{3-[3-(Decyloxy)phenyl]propanoyl}(4-fluorobenzyl)amino]ethyl dihydrogen phosphate ammonium salt (Example compound 67)

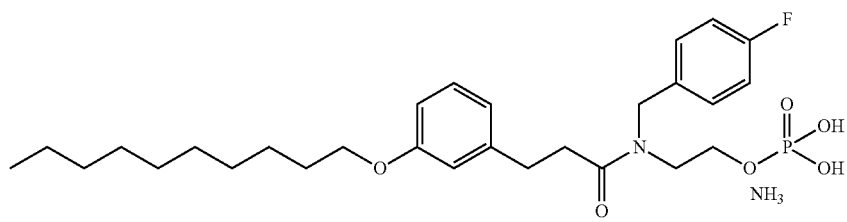

In Example 58, the reaction and treatment similar to those in (58-2)-(58-3) were performed using 2-[(4-fluorophenyl)methylamino]ethanol instead of Example compound 58-1 to give the title compound (125 mg) as a white powder. MS (APCI) m/z: 538.1[M+H]$^+$

Example 68

(68-1) 2-(Benzyl{3-[3-(decyloxy)phenyl]propanoyl}amino)ethyl dihydrogen phosphate ammonium salt (Example compound 68)

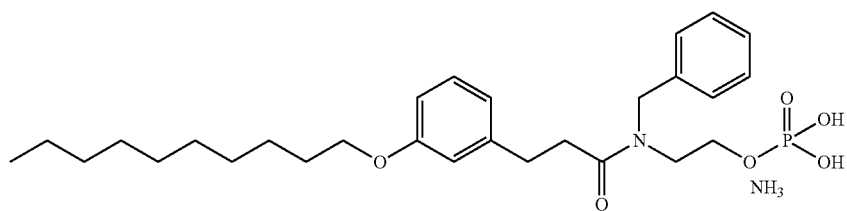

In Example 36, the reaction and treatment similar to those in (36-1)-(36-3) were performed using Reference Example compound 5 instead of Example compound 16-2 and 2-(benzylamino)ethanol instead of 2-[(2-methoxyethyl)amino]ethan-1-ol to give the title compound (181 mg) as a pale-yellow oil.

MS (APCI) m/z: 520.1[M+H]$^+$

Example 69

(69-1) [4-(Benzyloxy)phenyl]acetaldehyde (Example compound 69-1)

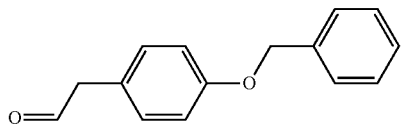

2-(4-Benzyloxyphenyl)ethanol (1000 mg) was dissolved in dichloromethane (29.2 mL), 1,1,1-tris(acetyloxy)-1,1-dihydro-1,2-benziodoxol-3-(1H)-one (2229 mg) was added, and the mixture was stirred at room temperature for 17 min. Under ice-cooling, to the reaction mixture was added saturated aqueous sodium thiosulfate solution (40 mL), and the mixture was stirred at room temperature for 10 min. The mixture was extracted with chloroform, washed with saturated aqueous sodium hydrogen carbonate solution and saturated brine, and dried over anhydrous sodium sulfate. The solvent was evaporated under reduced pressure. The residue was purified by silica gel column chromatography (hexane:ethyl acetate=90:10-65:35) to give the title compound (695 mg) as a white powder.

(69-2) 2-({3-[3-(Decyloxy)phenyl]propanoyl}[2-(4-hydroxyphenyl)ethyl]amino)ethyl dihydrogen phosphate ammonium salt (Example compound 69)

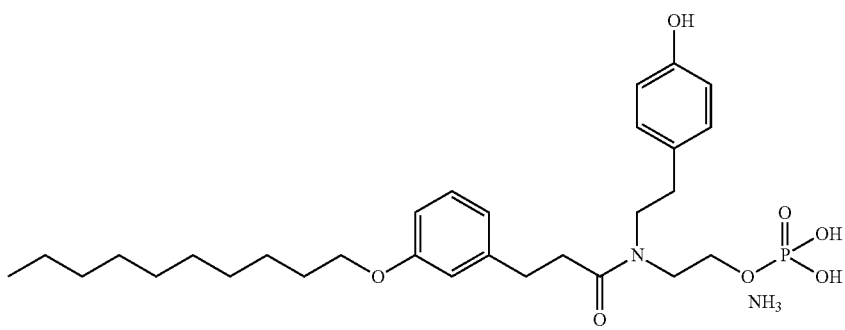

In Example 37, the reaction and treatment similar to those in (37-1)-(37-2) were performed using Example compound 69-1 instead of 3-benzyloxybenzaldehyde to give the title compound (143 mg) as a colorless oil. MS (APCI) m/z: 550.1[M+H]$^+$ Example 70

(70-1) Methyl 9-(4-butylphenyl)-9-oxononanoate (Example compound 70-1)

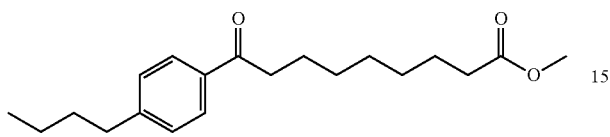

9-Methoxy-9-oxo-nonanoic acid (0.5 g) was dissolved in 1,2-dichloroethane (5 mL), thionyl chloride (0.4 mL) and N,N-dimethylformamide (0.01 mL) were added, and the mixture was stirred at 80° C. for 1 hr. Thionyl chloride (2 mL) and N,N-dimethylformamide (0.05 mL) were added thereto and the mixture was stirred at 80° C. for 2 hr. The solvent was evaporated under reduced pressure. To a solution of the residue in dichloromethane (4 mL) was added aluminum chloride (320 mg) at 0° C., and the mixture was stirred for 15 min, butylbenzene (0.37 mL) was added at the same temperature, and the mixture was stirred at room temperature for 2 hr. Since the reaction hardly proceeded, aluminum chloride (320 mg) was added at 0° C. and the mixture was stirred for 15 min. Anisole (0.37 mL) was added to the mixture at the same temperature, and the mixture was stirred at room temperature for 15 hr. The reaction mixture was slowly added dropwise to ice water, and the mixture was stirred for 1 hr, extracted with ethyl acetate, washed with saturated brine, and dried over anhydrous sodium sulfate. The solvent was evaporated under reduced pressure to give a crudely purified product (765 mg) of the title compound as a pale-yellow oil. MS (APCI) m/z: 319.1 (M+H)$^+$ (70-2) Methyl 9-(4-butylphenyl)nonanoate (Example compound 70-2)

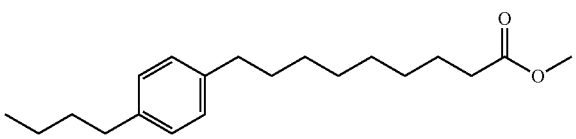 [SMILES: CCCCc1ccc(CCCCCCCCC(=O)OC)cc1]

To a solution of Example compound 70-1 (765 mg) in trifluoroacetic acid (8 mL) was added triethylsilane (1.5 mL) at 0° C. and the mixture was stirred at room temperature for 30 min. The solvent was evaporated under reduced pressure. To the residue were added ice water and aqueous sodium hydroxide solution, and the mixture was extracted with ethyl acetate, washed with saturated brine, and dried over anhydrous sodium sulfate. The solvent was evaporated under reduced pressure. The obtained residue was purified by silica gel column chromatography (hexane:ethyl acetate=95:5-85:15) to give the title compound (100 mg) as a colorless oil. MS (APCI) m/z: 305.0 (M+H)$^+$ (70-3) 9-(4-Butylphenyl)nonanoic acid (Example compound 70-3)

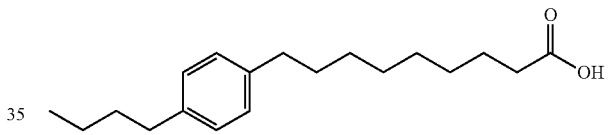

To a mixed solution of Example compound 70-2 (0.8 mL) and tetrahydrofuran (0.8 mL) was added 1N aqueous sodium hydroxide solution (0.66 mL), and the mixture was stirred at room temperature for 4 hr. To the reaction mixture were added 1N hydrochloric acid (0.7 mL) and water (1 mL), and the mixture was extracted with ethyl acetate, washed with saturated brine, and dried over anhydrous sodium sulfate. The solvent was evaporated under reduced pressure to give the title compound (70 mg) as a pale-yellow solid. MS (APCI) m/z: 289.1 (M=H)$^-$ (70-4) 1-[9-(4-Butylphenyl)nonanoyl]azetidin-3-yl dihydrogen phosphate ammonium salt (Example compound 70)

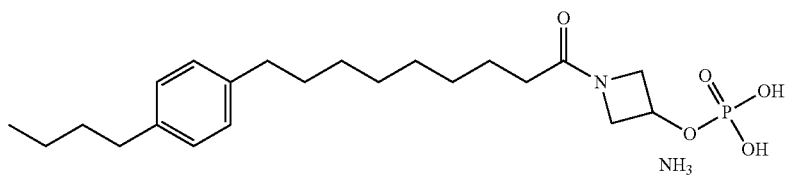

To a solution of Reference Example compound 2 (160 mg) in dichloromethane (1.2 mL) was added trifluoroacetic acid (0.55 mL) at 0° C. and the mixture was stirred for 1 hr. Dichloromethane (0.8 mL), N,N-diisopropylethylamine (2.49 mL), Example compound 70-3 (70 mg) and HATU (110 mg) were added to the mixture at the same temperature and the mixture was stirred for 2 hr. Water was added to the reaction mixture, and the mixture was extracted with dichloromethane, washed with saturated brine, and dried over anhydrous sodium sulfate. The solvent was evaporated under reduced pressure and the obtained residue was dissolved in methanol (2.5 mL). Palladium carbon (45 mg) was added, and the mixture was stirred under a hydrogen atmosphere at room temperature for 10 hr. After nitrogen purge, the reaction mixture was passed through a syringe filter to remove palladium carbon, and rinsed with methanol. The solvent was evaporated, and the obtained residue was purified by preparative HPLC (10 mM aqueous ammonium carbonate solution-acetonitrile) to give the title compound (29 mg) as a colorless viscous oil. MS(ESI) m/z: 426.3 (M+H)$^+$ Example 71

(71-1) 1-[5-(2-Nonylphenyl)pentanoyl]azetidin-3-yl dihydrogen phosphate ammonium salt (Example compound 71)

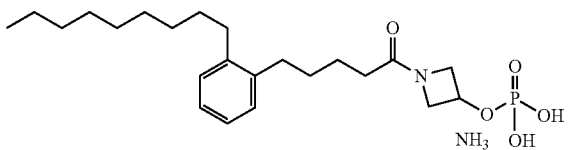

In Example 59, the reaction and treatment similar to those in (59-1)-(59-4) were performed using 1,2-diiodobenzene instead of 1,4-diiodobenzene and 1-nonyne instead of 1-heptyne to give the title compound (74 mg) as an orange viscous oil.

MS (APCI) m/z: 440.3 (M+H)$^+$

Example 72

(72-1) N-(4{[(2-Hydroxyethyl)amino]methyl}phenyl)methanesulfonamide (Example compound 72-1)

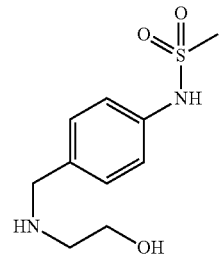 [SMILES: CS(=O)(=O)Nc1ccc(CNCCO)cc1]

2-Aminoethanol (368 mg) was dissolved in methanol (24 mL), N-(4-formylphenyl)methanesulfonamide (1200 mg) was added, and the mixture was stirred at 60° C. for 100 min. After allowing to cool to room temperature, 10% palladium carbon (600 mg) was added thereto, and the mixture was stirred under a hydrogen atmosphere at room temperature for 230 min and filtered. The filtrate was concentrated to give the title compound (quant.) as an orange oil. MS (APCI) m/z: 245.0[M+H]$^+$ (72-2) 2-({3-[3-(Decyloxy)phenyl]propanoyl}{4-[(methylsulfonyl)amino]benzy}amino)ethyl dihydrogen phosphate ammonium salt (Example compound 72)

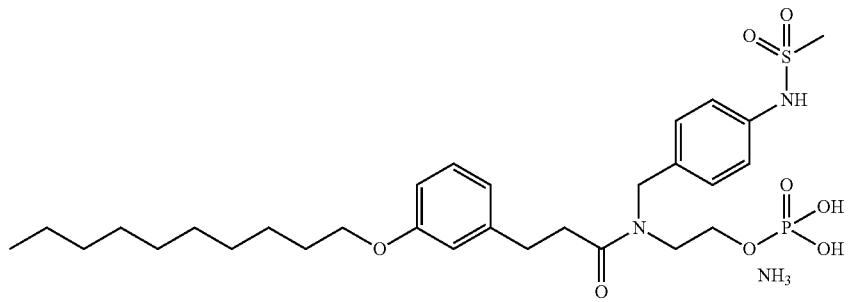

In Example 36, the reaction and treatment similar to those in (36-1)-(36-3) were performed using Reference Example compound 5 instead of Example compound 16-2 and Example compound 72-1 instead of 2-[(2-methoxyethyl)amino]ethan-1-ol to give the title compound (114 mg) as a colorless oil.

MS (APCI) m/z: 611.2[M−H]⁻

Example 73

(73-1) 2-[(4-Aminobenzyl){3-[3-(decyloxy)phenyl]propanoyl}amino]ethyl dihydrogen phosphate ammonium salt (Example compound 73)

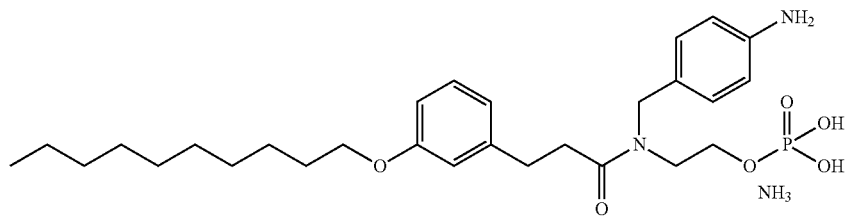

In Example 58, the reaction and treatment similar to those in (58-1)-(58-3) were performed using tert-butyl (4-formylphenyl)carbamate instead of 4-pyridine carbaldehyde to give the title compound (230 mg) as a pale-yellow oil.

MS (APCI) m/z: 533.2[M−H]⁻

Example 74

(74-1) 9-[4-(Trifluoromethoxy)phenyl]-8-nonynoic acid (Example compound 74-1)

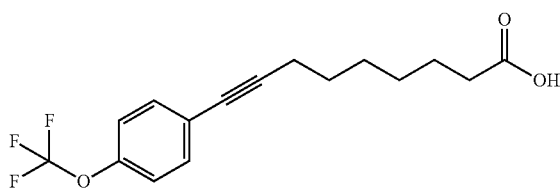 [SMILES: O=C(O)CCCCCCC#Cc1ccc(OC(F)(F)F)cc1]

A mixture of Reference Example compound 8 (200 mg), 1-iodo-4-(trifluoromethoxy)benzene (410 mg), copper iodide (I) (123 mg), dichloro palladium triphenylphosphine (27 mg), N,N-diisopropylethylamine (0.90 mL) and tetrahydrofuran (5.2 mL) was stirred at 60° C. for 3 hr. To the reaction mixture was added 1N hydrochloric acid, and the mixture was extracted with ethyl acetate, washed with saturated brine, and dried over anhydrous sodium sulfate. The solvent was evaporated under reduced pressure. The residue was purified by silica gel column chromatography (hexane:ethyl acetate=80:20-60:40) to give the title compound (320 mg) as an orange oil.

MS(ESI) m/z: 313.3 (M−H)⁻

(74-2) Dibenzyl 1-{9-[4-(trifluoromethoxy)phenyl]-8-nonynoyl}azetidin-3-yl phosphate (Example compound 74-2)

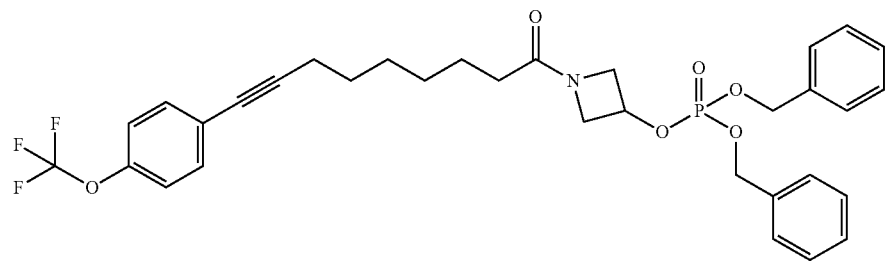 [SMILES: O=C(CCCCCCC#Cc1ccc(OC(F)(F)F)cc1)N1CC(OP(=O)(OCc2ccccc2)OCc2ccccc2)C1]

To a solution of Reference Example compound 2 (248 mg) in dichloromethane (5.7 mL) was added trifluoroacetic acid (0.88 mL) at 0° C. and the mixture was stirred for 1 hr. N,N-diisopropylethylamine (2.64 mL), Example compound 74-1 (120 mg) and HATU (436 mg) were added thereto at the same temperature, and the mixture was stirred for 1 hr. Water was added to the reaction mixture, and the mixture was extracted with ethyl acetate, washed with saturated brine, and dried over anhydrous sodium sulfate. The solvent was evaporated under reduced pressure. The obtained residue was purified by preparative HPLC (10 mM aqueous ammonium carbonate solution-acetonitrile) to give the title compound (140 mg) as a colorless oil.

MS(ESI) m/z: 630.5 (M+H)+

(74-3) 1-{9-[4-(Trifluoromethoxy)phenyl]nonanoyl}azetidin-3-yl dihydrogen phosphate (Example compound 74)

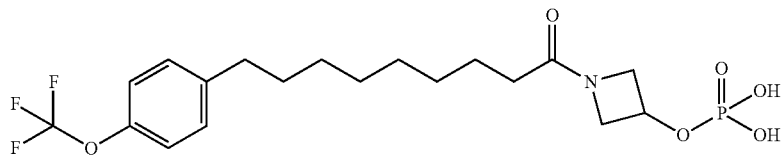 [SMILES: O=C(CCCCCCCCc1ccc(OC(F)(F)F)cc1)N1CC(OP(=O)(O)O)C1]

Example compound 74-2 (140 mg) was dissolved in methanol (2.2 mL), palladium carbon (70 mg) was added, and the mixture was stirred under a hydrogen atmosphere at room temperature for 5 hr. After nitrogen purge, the reaction mixture was passed through a syringe filter to remove palladium carbon, and rinsed with methanol. The solvent was evaporated to give the title compound (87 mg) as a colorless viscous oil.

MS (APCI) m/z: 454.2 (M+H)+

Example 75

(75-1) tert-Butyl(3-iodophenoxy)diphenylsilane (Example compound 75-1)

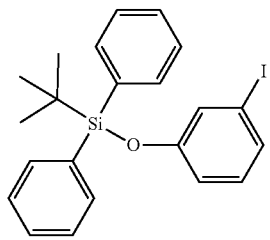 [SMILES: CC(C)(C)[Si](Oc1cccc(I)c1)(c1ccccc1)c1ccccc1]

A mixture of 2-iodophenol (10.0 g), tert-butyldiphenylchlorosilane (12.4 mL), imidazole (6.19 g), and N,N-dimethylformamide (45.5 mL) was stirred at 70° C. for 3 hr. Water was added to the reaction mixture, and the mixture was extracted with diethyl ether. The organic layer was washed with water and saturated brine, and dried over anhydrous sodium sulfate. The desiccant was filtered off, and the filtrate was concentrated under reduced pressure. The obtained residue was purified by silica gel column chromatography (hexane only) to give the title compound (19.5 g) as a colorless oil.

MS (APCI) m/z: 475.8 (M+NH4)+.

(75-2) Benzyl 5-(3-{[tert-butyl(diphenyl)silyl]oxy}phenyl)-4-pentynoate (Example compound 75-2)

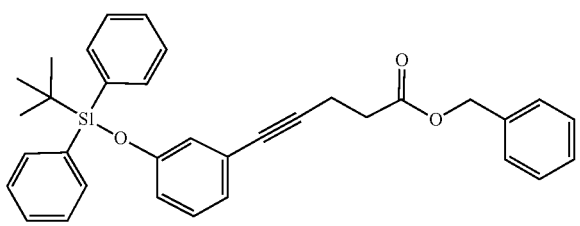

A mixture of Example compound 75-1 (9.74 g), Example compound 34-1 (4.00 g), bis(triphenylphosphine)palladium (II) dichloride (746 mg), copper iodide (I) (202 mg), and triethylamine (42.5 mL) was stirred at 70° C. for one day and night. To the reaction mixture was added saturated aqueous ammonium chloride solution, and the mixture was extracted with diethyl ether. The organic layer was washed with 1N hydrochloric acid and saturated brine, and dried over anhydrous sodium sulfate. The desiccant was filtered off, and the filtrate was concentrated under reduced pressure. The obtained residue was purified by silica gel column chromatography (hexane:ethyl acetate=100:0-90:10) to give the title compound (8.61 g) as a yellow oil. MS (APCI) m/z: 536.1 (M+NH4)+.

(75-3) 5-(3-{[tert-Butyl(diphenyl)silyl]oxy}phenyl)-4-pentynoic acid (Example compound 75-3)

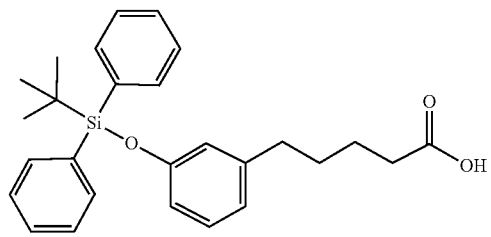 [SMILES: CC(C)(C)[Si](Oc1cccc(CCCCC(=O)O)c1)(c1ccccc1)c1ccccc1]

To a solution of Example compound 75-2 (8.61 g) in ethanol (55.3 mL) was added 7.5% palladium carbon (861 mg), and the mixture was stirred under a hydrogen atmosphere at room temperature for one day and night. After filtering off the m insoluble material in the reaction mixture with diatomaceous earth, the filtrate was concentrated under reduced pressure. The obtained residue was purified by silica gel column chromatography (hexane:ethyl acetate=80:20-60:40) to give the title compound (7.98 g) as a colorless oil.

MS (APCI) m/z: 431.2 (M−H)⁻

(75-4) 5-(3-{[tert-Butyl(diphenyl)silyl]oxy}phenyl)-1-(3-hydroxyazetidin)-1-yl)pentan-1-one (Example compound 75-4)

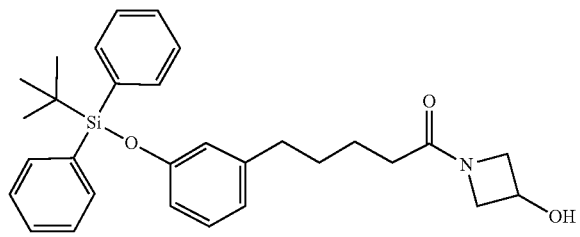 [SMILES: CC(C)(C)[Si](Oc1cccc(CCCCC(=O)N2CC(O)C2)c1)(c1ccccc1)c1ccccc1]

To a solution of Example compound 75-3 (7.98 g) in N,N-dimethylformamide (46.1 mL) were added N,N-diisopropylethylamine (12.8 mL), 3-hydroxyazetidine hydrochloride (2.42 g) and HATU (14.4 g), and the mixture was stirred at room temperature overnight. Water was added to the reaction mixture, and the mixture was extracted with diethyl ether. The organic layer was washed with water and saturated brine, and dried over anhydrous sodium sulfate. The desiccant was filtered off, and the filtrate was concentrated under reduced pressure. The obtained residue was purified by silica gel column chromatography (hexane:ethyl acetate=40:60-0:100) to give the title compound (6.82 g) as a yellow oil.

MS (APCI) m/z: 488.1 (M+H)⁺

(75-5) Di-tert-butyl 1-[5-(3-{[tert-butyl(biphenyl)silyl]oxy}phenyl)pentanoy]azetidin-3-yl phosphate (Example compound 75-5)

MR⁷R¹

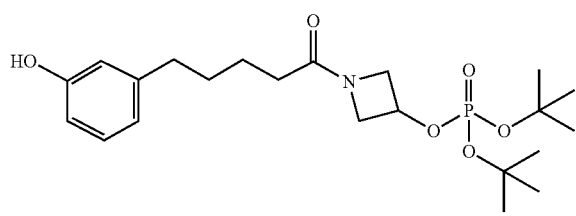 [SMILES: CC(C)(C)OP(=O)(OC1CN(C(=O)CCCCc2cccc(O)c2)C1)OC(C)(C)C]

To a mixed solution of Example compound 75-4 in dichloromethane (28.0 mL) and acetonitrile (14.0 mL) were added under ice-cooling 1H-tetrazole (1.96 g) and di-tert-butyl N,N-diisopropyl phosphoramidite (6.62 mL), and the mixture was stirred at room temperature for 3 hr. tert-Butyl hydroperoxide (70% aqueous solution, 6.70 mL) was added thereto, and the mixture was stirred at room temperature for 4 hr. To the reaction mixture was added saturated aqueous sodium thiosulfate solution, and the mixture was extracted with ethyl acetate. The organic layer was washed with saturated brine, and dried over anhydrous sodium sulfate. The desiccant was filtered off, and the filtrate was concentrated under reduced pressure. The obtained residue was purified by silica gel column chromatography (hexane:ethyl acetate=20:80-0:100) to give the title compound (6.68 g) as a colorless viscous oil.

MS (APCI) m/z: 679.9 (M+H)⁺

(75-6) Di-tert-butyl 1-[5-(3-hydroxyphenyl)pentanoyl]azetidin-3-yl phosphate (Example compound 75-6)

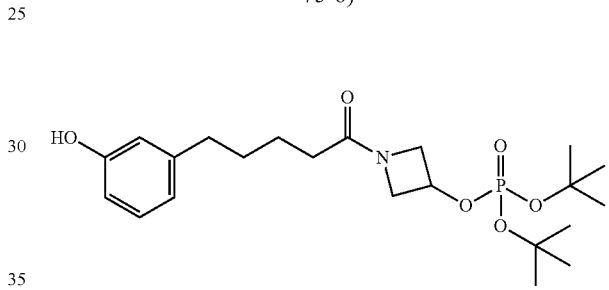

To a solution of Example compound 75-5 (5.30 g) in tetrahydrofuran (39.0 mL) was added tetrabutylammonium fluoride (about 1 mol/L tetrahydrofuran solution, 23.4 mL), and the mixture was stirred at room temperature for one day and night. Water was added to the reaction mixture, and the mixture was extracted with ethyl acetate. The organic layer was washed with water and saturated brine, and dried over anhydrous sodium sulfate. The desiccant was filtered off, and the filtrate was concentrated under reduced pressure. The obtained residue was purified by silica gel column chromatography (chloroform:methanol=100:0-90:10) to give the title compound (3.16 g) as a yellow oil. MS (APCI) m/z: 458.8 (M+NH₄)⁺

(75-7) 1-{5-[3-(3-Phenylpropyloxy)phenyl]pentanoyl}azetidin-3-yl dihydrogen phosphate ammonium salt (Example compound 75)

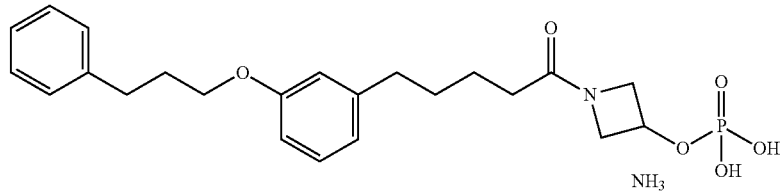

To a solution of Example compound 75-6 (190 mg) in N,N-dimethylformamide (4.3 mL) were added sodium hydride (60%, 17.2 mg) and (3-bromopropyl)benzene (94.3 mg), and the mixture was stirred at room temperature for 3 hr. Water was added to the reaction mixture, and the mixture was extracted with ethyl acetate. The organic layer was washed with saturated brine, and dried over anhydrous sodium sulfate. The desiccant was filtered off, and the filtrate was concentrated under reduced pressure. To the residue were added dichloromethane (4.3 mL) and trifluoroacetic acid (0.86 mL), and the mixture was stirred at room temperature for 3 hr. The reaction mixture was concentrated under reduced pressure. The obtained residue was purified by preparative HPLC (10 mM aqueous ammonium carbonate solution-acetonitrile) to give the title compound (181 mg) as a yellow viscous oil. MS (APCI) m/z: 448.3 (M+H)$^+$ Example 76

(76-1) Benzyl 5-hexynoate (Example compound 76-1)

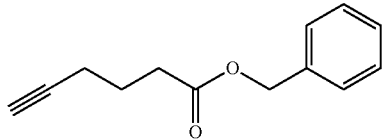

A mixture of 5-hexynoic acid (5.50 g), benzyl bromide (6.42 mL), potassium carbonate (13.6 g), and N,N-dimethylformamide (49 mL) was stirred at room temperature for one day and night. Water was added to the reaction mixture, and the mixture was extracted with diethyl ether. The organic layer was washed with water and saturated brine, and dried over anhydrous sodium sulfate. The desiccant was filtered off, and the filtrate was concentrated under reduced pressure. The obtained residue was purified by silica gel column chromatography (hexane:ethyl acetate=100:0-90:10) to give the title compound (10.38 g) as a colorless oil. MS (APCI) m/z: 203.0 (M+H)$^+$ (76-2) 1-[6-(3-Hexylphenyl)hexanoyl]azetidin-3-yl dihydrogen phosphate ammonium salt (Example compound 76)

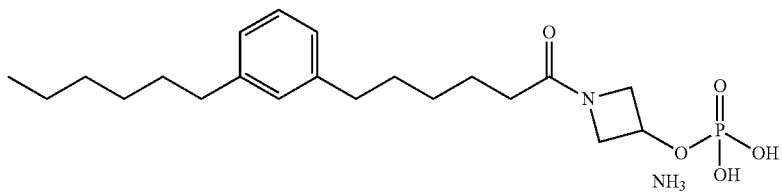

In Example 59, the reaction and treatment similar to those in (59-1)-(59-4) were performed using 1,3-diiodobenzene instead of 1,4-diiodobenzene, Example compound 76-1 instead of Example compound 34-1, and 1-hexyne instead of 1-heptyne to give the title compound (55 mg) as a colorless viscous oil.

MS (APCI) m/z: 412.3 (M+H)+

Example 77

(77-1) 1-[6-(3-Heptylphenyl)hexanoyl]azetidin-3-yl dihydrogen phosphate ammonium salt (Example compound 77)

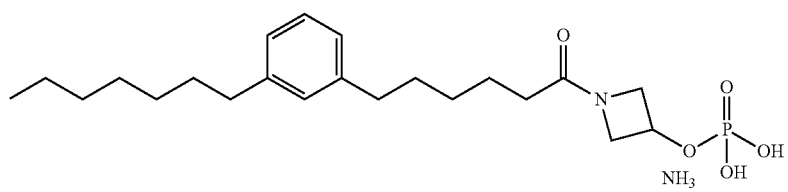

In Example 59, the reaction and treatment similar to those in (59-1)-(59-4) were performed using 1,3-diiodobenzene instead of 1,4-diiodobenzene and Example compound 76-1 instead of Example compound 34-1 to give the title compound (100 mg).

MS (APCI) m/z: 426.3 (M+H)+

Example 78

(78-1) 1-{5-[3-(4-Phenylbutoxy)phenyl]pentanoyl}azetidin-3-yl dihydrogen phosphate ammonium salt (Example compound 78)

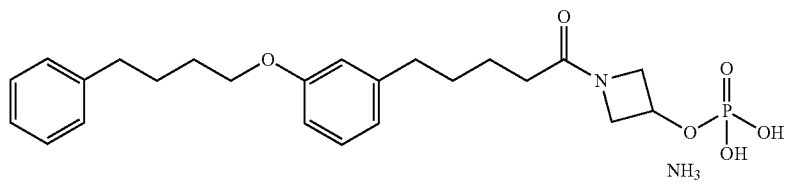

In Example 75, the reaction and treatment similar to those in (75-7) were performed using (4-bromobutyl)benzene instead of (3-bromopropyl)benzene to give the title compound (414 mg). MS (APCI) m/z: 462.3 (M+H)+

Example 79

(79-1) 1-(5-{3-[5-(Phenylpentyl)oxy]phenyl}pentanoyl)azetidin-3-yl dihydrogen phosphate ammonium salt (Example compound 79)

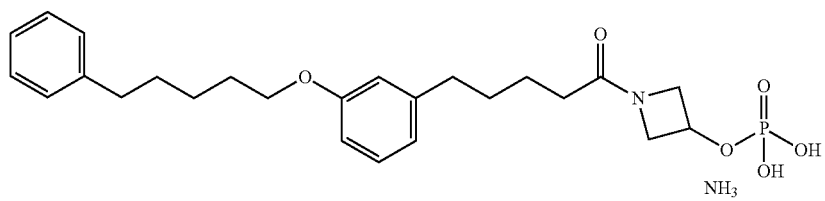

In Example 75, the reaction and treatment similar to those in (75-7) were performed using (5-bromopentyl)benzene instead of (3-bromopropyl)benzene to give the title compound (416 mg). MS (APCI) m/z: 476.3 (M+H)+

Example 80

(80-1) 1-[9-(4-Propylphenyl)nonanoyl]azetidin-3-yl dihydrogen phosphate ammonium salt (Example compound 80)

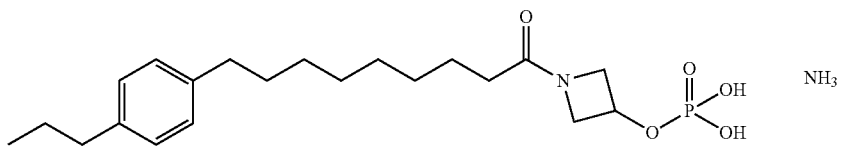

In Example 60, the reaction and treatment similar to those in (60-1)-(60-2) were performed using 1-iodo-4-propylbenzene instead of 1-iodo-4-(trifluoromethoxy)benzene and the obtained residue was purified by preparative HPLC (10 mM aqueous ammonium carbonate solution-acetonitrile) to give the title compound (75 mg) as a colorless oil.
MS (APCI) m/z: 412.3[M+H]+

Example 81

(81-1) 2-({3-[3-(Decyloxy)phenyl]propanoyl}[4-(methoxymethyl)benzyl]amino)ethyl dihydrogen phosphate ammonium salt (Example compound 81)

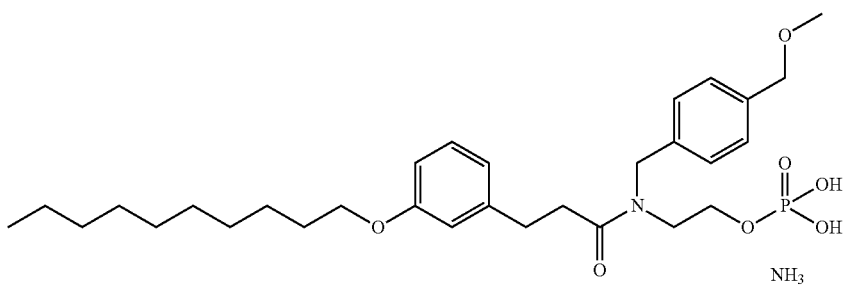

In Example 58, the reaction and treatment similar to those in (58-1)-(58-3) were performed using 4-(methoxymethyl)benzaldehyde instead of 4-pyridine carbaldehyde to give the title compound (264.1 mg) as a colorless oil.
MS (APCI) m/z: 564.0[M+H]+

Example 82

(82-1) Methyl 9-(4-bromophenyl)-9-oxo-nonanoate (Example compound 82-1)

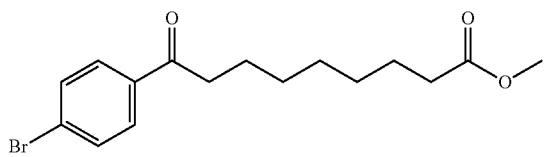 [SMILES: COC(=O)CCCCCCCC(=O)c1ccc(Br)cc1]

9-Methoxy-9-oxo-nonanoic acid (3.00 g) was dissolved in 1,2-dichloroethane (29.7 mL), thionyl chloride (3.25 mL) and N,N-dimethylformamide (0.12 mL) were added and the mixture was stirred at 80° C. for 1 hr. The solvent was evaporated under reduced pressure. To a solution of the residue in dichloromethane (24.8 mL) was added aluminum chloride (1.98 g) at 0° C. and the mixture was stirred for 15 min. Bromobenzene (1.57 mL) was added at the same temperature and the mixture was stirred at room temperature for 2 hr. Since the reaction hardly proceeded, aluminum chloride (0.99 g) was added at 0° C. and the mixture was stirred for 15 min. Bromobenzene (0.78 mL) was added at the same temperature, and the mixture was stirred at room temperature for 15 hr. Aluminum chloride (0.99 g) was further added at 0° C. and the mixture was stirred for 15 min. Bromobenzene (0.78 mL) was added at the same temperature and the mixture was stirred at room temperature for 3 hr. The reaction mixture was slowly added dropwise to ice water, and the mixture was stirred for 1 hr, extracted with chloroform, washed with saturated brine, and dried over anhydrous sodium sulfate. The solvent was evaporated under reduced pressure. The obtained residue was purified by basic silica gel column chromatography (hexane:ethyl acetate=1:1) to give the title compound (4.99 g) as a pale-yellow oil. MS(ESI) m/z: 341.2, 343.2 (M+H)⁺

(82-2) 9-(4-Bromophenyl)nonanoic acid (Example compound 82-2)

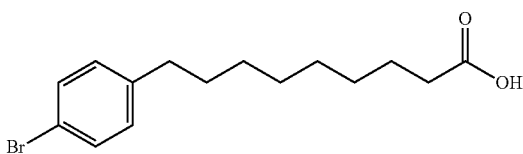 [SMILES: O=C(O)CCCCCCCCc1ccc(Br)cc1]

To a solution of Example compound 82-1 (4.99 g) in methanol (29.2 mL) were added 1N aqueous sodium hydroxide solution (29.2 mL), tetrahydrofuran (14.6 mL), and the mixture was stirred at room temperature for 4 hr. 1N hydrochloric acid (30 mL) was added thereto under ice-cooling, and the mixture was extracted with ethyl acetate, and dried over anhydrous sodium sulfate. The solvent was evaporated under reduced pressure. The obtained residue was added to trifluoroacetic acid (48.7 mL) solution, triethylsilane (7.01 mL) was added to the mixture under ice-cooling, and the mixture was stirred at room temperature for 1 hr. The solvent was evaporated and the obtained residue was poured into ice water and the mixture was stirred for 1 hr, extracted with ethyl acetate, washed with saturated brine, and dried over anhydrous sodium sulfate. The solvent was evaporated under reduced pressure. The obtained residue was purified by silica gel column chromatography (hexane:ethyl acetate=90:10-65:35) to give the title compound (0.42 g) as a white solid.

MS (APCI) m/z: 311.0, 313.0[M+H]⁻

(82-3) 9-(Biphenyl-4-yl)nonanoic acid (Example compound 82-3)

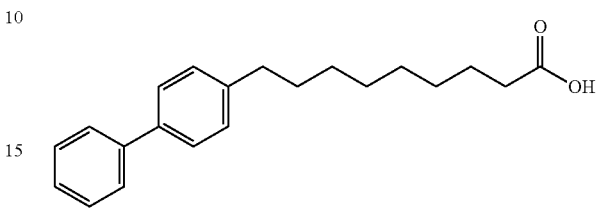

To a solution of Example compound 82-2 (100 mg) in 1,4-dioxane (1.6 mL) were added phenylboronic acid pinacol ester (78 mg), 2N aqueous potassium phosphate solution (0.64 mL), and XPhos-Pd-G2 (25 mg) under a nitrogen atmosphere, and the mixture was stirred at 100° C. for 2 hr. To the reaction mixture was added 1N hydrochloric acid, and the mixture was extracted with ethyl acetate, washed with saturated brine, and dried over anhydrous sodium sulfate. The solvent was evaporated under reduced pressure. The obtained residue was purified by silica gel column chromatography (hexane:ethyl acetate=70:30-50:50) to give the title compound (97 mg) as a white solid.

MS(ESI) m/z: 309.2 (M−H)⁻

(82-4) Dibenzyl 1-[9-(biphenyl-4-yl)nonanoyl]azetidin-3-yl phosphate (Example compound 82-4)

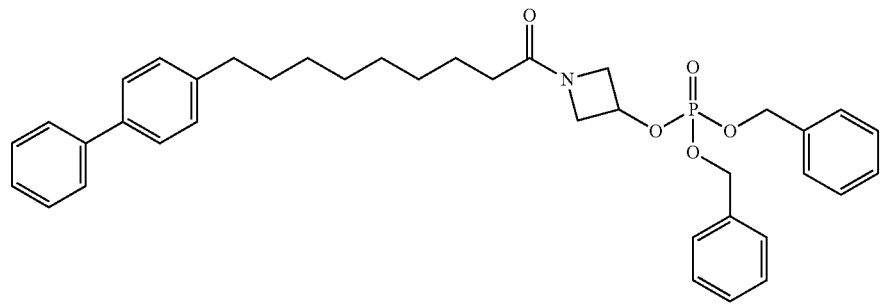 [SMILES: O=C(CCCCCCCCc1ccc(-c2ccccc2)cc1)N1CC(OP(=O)(OCc2ccccc2)OCc2ccccc2)C1]

To a solution of Reference Example compound 2 (210 mg) in dichloromethane (4.9 mL) was added under ice-cooling trifluoroacetic acid (0.75 mL), and the mixture was stirred for 1 hr. N,N-diisopropylethylamine (2.23 mL) was added dropwise to the reaction mixture under ice-cooling, a solution of Example compound 82-3 (108 mg) in dichloromethane (1 mL) and HATU (175 mg) were added thereto, and the mixture was stirred for 1 hr under ice-cooling. To the reaction mixture was added saturated brine, and the mixture was extracted with ethyl acetate, and dried over anhydrous sodium sulfate. The solvent was evaporated under reduced pressure. The obtained residue was purified by preparative HPLC (10 mM aqueous ammonium carbonate solution-acetonitrile) to give the title compound (140 mg) as a colorless oil. MS(ESI) m/z: 626.6[M+H]$^+$ (82-5) 1-[9-(Biphenyl-4-yl)nonanoyl]azetidin-3-yl dihydrogen phosphate (Example compound 82)

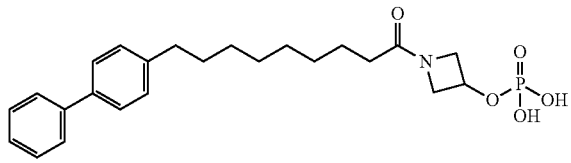 [SMILES: O=C(CCCCCCCCc1ccc(-c2ccccc2)cc1)N1CC(OP(=O)(O)O)C1]

A suspension of Example compound 82-4 (140 mg), palladium carbon (70 mg), methanol (1.5 mL) was stirred under a hydrogen atmosphere at room temperature for 20 hr. The reaction mixture was passed through a filter for removing Pd, rinsed with methanol, and the filtrate was concentrated. The obtained solid was washed with sonicating in suspension in methanol to give the title compound (83 mg) as a white solid.
MS (APCI) m/z: 446.2 (M+H)$^+$ Example 83

(83-1) 4-({[tert-Butyl(biphenyl)silyl]oxy}methyl)benzaldehyde (Example compound 83-1)

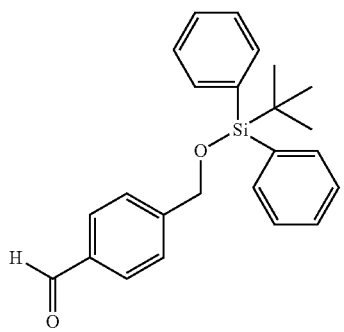 [SMILES: CC(C)(C)[Si](OCc1ccc(C=O)cc1)(c1ccccc1)c1ccccc1]

4-(Hydroxymethyl)benzaldehyde (1.20 g) was dissolved in dichloromethane (30 mL), imidazole (1.44 g) was added under ice-cooling, tert-butylchlorodiphenylsilane (2.75 mL) was added dropwise thereto, and the mixture was stirred at room temperature for 75 min. Under ice-cooling, water was added to the reaction mixture, and the mixture was extracted with ethyl acetate, washed with saturated brine, and dried over anhydrous sodium sulfate. The solvent was evaporated under reduced pressure. The residue was purified by silica gel column chromatography (hexane:ethyl acetate=100:0-87:13) to give the title compound (quant.) as a white powder.
MS (APCI) m/z: 375.1[M+H]$^+$ (83-2) 2-({3-[3-(Decyloxy)phenyl]propanoyl}[4-(hydroxymethyl)benzyl]amino)ethyl dihydrogen phosphate ammonium salt (Example compound 83)

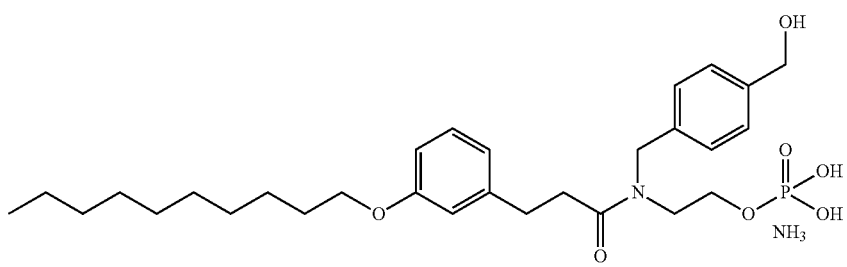

In Example 58, the reaction and treatment similar to those in (58-1)-(58-3) were performed using Example compound 83-1 instead of 4-pyridine carbaldehyde to give the title compound (169 mg) as a colorless oil. MS (APCI) m/z: 550.1[M+H]$^+$

Example 84

(84-1) 9-(4-tert-Butylphenyl)-8-nonynoic acid (Example compound 84-1)

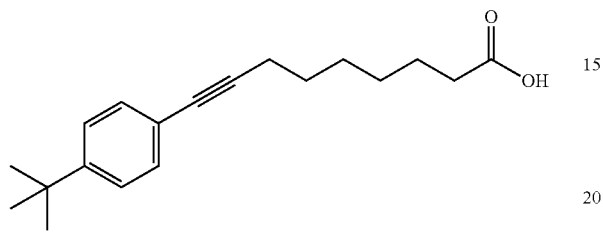

A mixture of Reference Example compound 8 (150 mg), 1-tert-butyl-4-iodobenzene (0.207 mL), copper iodide (I) (28 mg), dichloropalladium triphenylphosphine (41 mg), N,N-diisopropylethylamine (0.67 mL) and tetrahydrofuran (3.9 mL) was stirred at 60° C. for 3 hr. To the reaction mixture was added 1N hydrochloric acid, and the mixture was extracted with ethyl acetate, washed with saturated brine, and dried over anhydrous sodium sulfate. The solvent was evaporated under reduced pressure. The residue was purified by silica gel column chromatography (hexane:ethyl acetate=75:25-55:45) to give the title compound (140 mg) as a brown solid.
MS(ESI) m/z: 287.3 (M+H)$^+$

(84-2) Dibenzyl {1-[9-(4-tert-butylphenyl)-8-nonynoyl}azetidin-3-yl phosphate (Example compound 84-2)

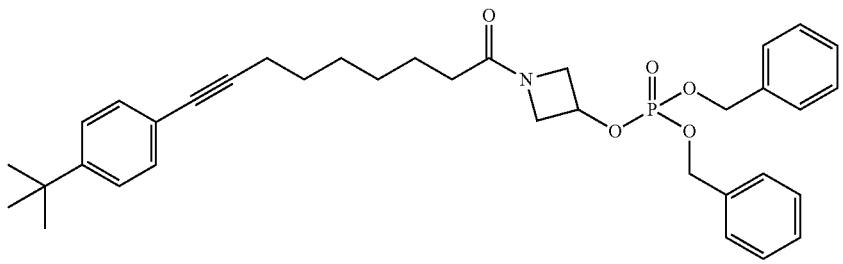 [SMILES: CC(C)(C)c1ccc(C#CCCCCCCC(=O)N2CC(OP(=O)(OCc3ccccc3)OCc3ccccc3)C2)cc1]

To a solution of Reference Example compound 2 (159 mg) in dichloromethane (3.7 mL) was added trifluoroacetic acid (0.56 mL) at 0° C. and the mixture was stirred for 1 hr. N,N-diisopropylethylamine (1.69 mL), Example compound 84-1 (70 mg) and HATU (279 mg) were added thereto at the same temperature, and the mixture was stirred for 1 hr. Water was added to the reaction mixture, and the mixture was extracted with ethyl acetate, washed with saturated brine, and dried over anhydrous sodium sulfate. The solvent was evaporated under reduced pressure. The obtained residue was purified by preparative HPLC (10 mM aqueous ammonium carbonate solution-acetonitrile) to give the title compound (89 mg) as a colorless oil.
MS(ESI) m/z: 602.6 (M+H)$^+$

(84-3) 1-[9-(4-tert-Butylphenyl)nonanoyl]azetidin-3-yl dihydrogen phosphate (Example compound 84)

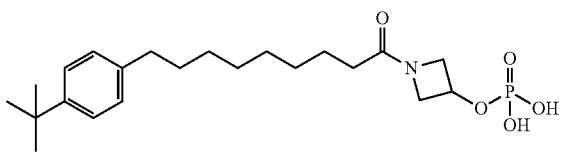 [SMILES: CC(C)(C)c1ccc(CCCCCCCCC(=O)N2CC(OP(=O)(O)O)C2)cc1]

Example compound 84-2 (86 mg) was dissolved in methanol (1.4 mL), palladium carbon (43 mg) was added,

Example 85

(85-1) 9-(4-Bromo-3-fluorophenyl)-8-nonynoic acid (Example compound 85-1)

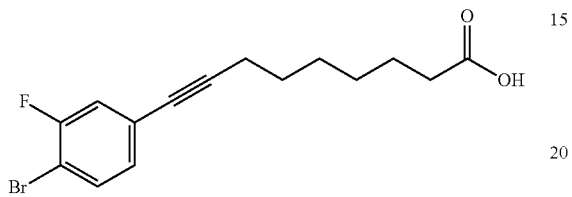

In Example 74, the reaction and treatment similar to those in (74-1) were performed using 1-bromo-2-fluoro-4-iodobenzene instead of 1-iodo-4-(trifluoromethoxy)benzene to give the title compound (589 mg) as an orange solid.
MS(ESI) m/z: 327.0, 325.0 (M+H)$^+$

(85-2) 9-(4-Ethenyl-3-fluorophenyl)-8-nonynoic acid (Example compound 85-2)

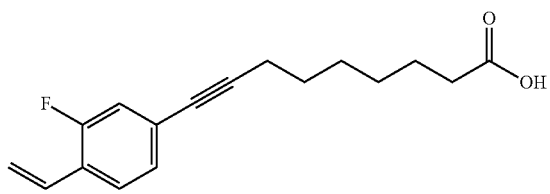 [SMILES: C=Cc1ccc(C#CCCCCCCC(=O)O)cc1F]

In Example 82, the reaction and treatment similar to those in (82-3) were performed using Example compound 85-1 instead of Example compound 82-2 and vinylboronic acid pinacol ester instead of phenylboronic acid pinacol ester to give the title compound (137 mg) as a white solid.
MS(ESI) m/z: 275.2 (M+H)$^+$

(85-3) 1-[9-(4-Ethyl-3-fluorophenyl)nonanoyl]azetidin-3-yl dihydrogen phosphate (Example compound 85)

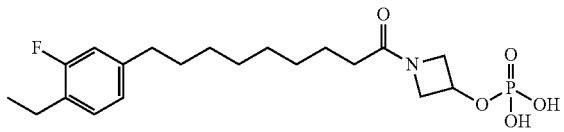 [SMILES: CCc1ccc(CCCCCCCCC(=O)N2CC(OP(=O)(O)O)C2)cc1F]

In Example 74, the reaction and treatment similar to those in (74-2)-(74-3) were performed using Example compound 85-2 instead of Example compound 74-1 to give the title compound (51 mg) as a colorless viscous oil.
MS (APCI) m/z: 416.2 (M+H)$^+$

Example 86

(86-1) 2-[{3-[3-(Decyloxy)phenyl]propanoyl}(4-ethoxybenzyl)amino]ethyl dihydrogen phosphate ammonium salt (Example compound 86)

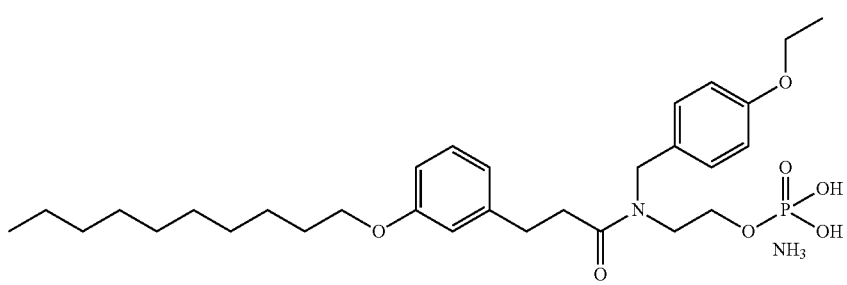

In Example 56, the reaction and treatment similar to those in (56-1)-(56-2) were performed using 4-ethoxybenzaldehyde instead of 3-pyridine carbaldehyde to give the title compound (195 mg) as a colorless viscous oil.

MS (APCI) m/z: 564 (M+H)+

Example 87

(87-1) 9-(4-Cyclopropylphenyl)nonanoic acid (Example compound 87-1)

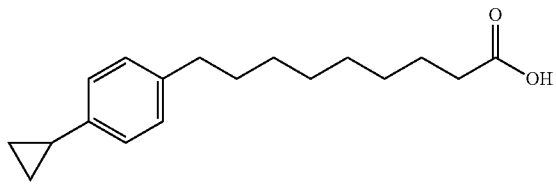 [SMILES: O=C(O)CCCCCCCCc1ccc(C2CC2)cc1]

To a solution of Example compound 82-2 (200 mg) in 1,4-dioxane (4.3 mL) were added cyclopropylboronic acid pinacol ester (215 mg), 2N aqueous potassium phosphate solution (1.28 mL), and XPhos-Pd-G2 (50 mg) under a nitrogen atmosphere, and the mixture was stirred at 100° C. for 2 hr. Furthermore, cyclopropylboronic acid pinacol ester (107 mg), 2N aqueous potassium phosphate solution (0.64 mL), and XPhos-Pd-G2 (50 mg) were added thereto, and the mixture was stirred at 100° C. for 2 days. To the reaction mixture was added 1N hydrochloric acid, and the mixture was extracted with ethyl acetate, washed with saturated brine, and dried over anhydrous sodium sulfate. The solvent was evaporated under reduced pressure. The obtained residue was purified by silica gel column chromatography (hexane:ethyl acetate=70:30-40:60) to give a crudely purified product (82 mg) of the title compound as a yellow solid. MS(ESI) m/z: 273.3 (M−H)−

(87-2) 1-[9-(4-Cyclopropylphenyl)nonanoyl]azetidin-3-yl dihydrogen phosphate ammonium salt (Example compound 87)

To a solution of Example compound 87-1 (75 mg) in N,N-dimethylformamide (2.7 mL) were added N,N-diisopropylethylamine (0.106 mL), Reference Example compound 1 (87 mg) and HATU (156 mg), and the mixture was stirred at room temperature for 2 hr.

Water was added to the reaction mixture, and the mixture was extracted with ethyl acetate. The organic layer was dried over anhydrous sodium sulfate, the desiccant was filtered off, and the filtrate was concentrated under reduced pressure. To the obtained residue were added dichloromethane (2.7 mL) and trifluoroacetic acid (0.27 mL), and the mixture was stirred at room temperature for 3 hr. The reaction mixture was concentrated under reduced pressure. The obtained residue was purified by preparative HPLC (10 mM aqueous ammonium carbonate solution-acetonitrile) to give the title compound (44 mg) as a colorless viscous oil. MS (APCI) m/z: 410.2 (M+H)+

Example 88

(88-1) 1-{5-[3-(4-Cyclohexylbutoxy)phenyl]pentanoyl}azetidin yl dihydrogen phosphate ammonium salt (Example compound 88)

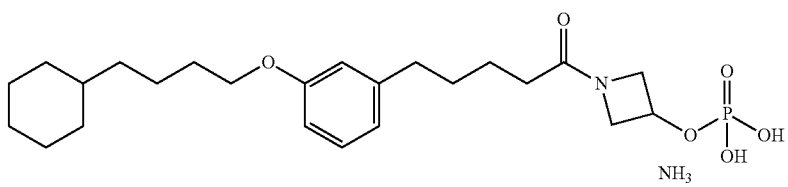

In Example 75, the reaction and treatment similar to those in (75-7) were performed using (4-bromobutyl)cyclohexane instead of (3-bromopropyl)benzene to give the title compound (141 mg). MS (APCI) m/z: 468.3 (M+H)

Example 89

(89-1) 1-{9-[2-Fluoro-4-(trifluoro)phenyl]nonanoyl}azetidin-3-yl dihydrogen phosphate ammonium salt (Example compound 89)

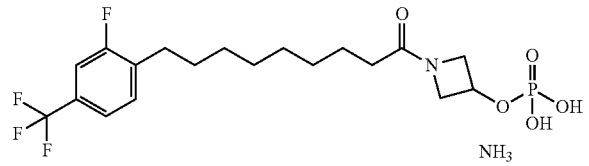

In Example 59, the reaction and treatment similar to those in (59-2)-(59-4) were performed using 1-iodo-4-(trifluoromethoxy)benzene instead of Example compound 59-1 and Reference Example compound 8 instead of 1-heptyne to give the title compound (71 mg) as a colorless viscous oil. MS (APCI) m/z: 456.2 (M+H)$^+$ Example 90

(90-1) 1-{5-[3-(2-Cyclohexylethoxy)phenyl]pentanoyl}azetidin-3-yl dihydrogen phosphate ammonium salt (Example compound 90)

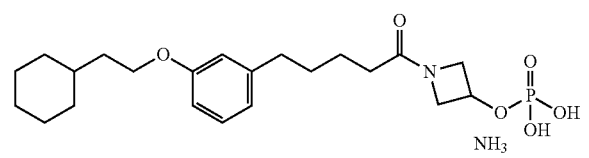

In Example 75, the reaction and treatment similar to those in (75-7) were performed using (2-bromoethyl)cyclohexane instead of (3-bromopropyl)benzene to give the title compound (140 mg). MS (APCI) m/z: 440.3 (M+H)$^+$ Example 91

(91-1) 1-(5-{3-[(6,6,6-Trifluorohexyl)oxy]phenyl}pentanoyl)azetidin-3-yl dihydrogen phosphate ammonium salt (Example compound 91)

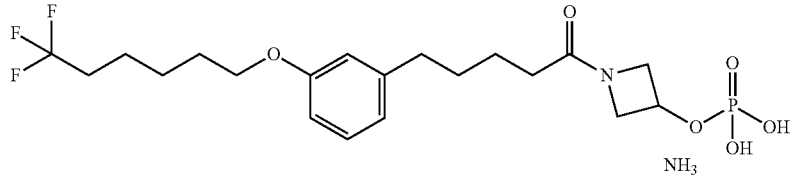

In Example 75, the reaction and treatment similar to those in (75-7) were performed using 1-bromo-6,6,6-trifluorohexane instead of (3-bromopropyl)benzene to give the title compound (51 mg). MS (APCI) m/z: 468.2 (M+H)$^+$ Example 92

(92-1) 1-{9-[3-Fluoro-4-(trifluoro)phenyl]nonanoyl}azetidin-3-yl dihydrogen phosphate (Example compound 92)

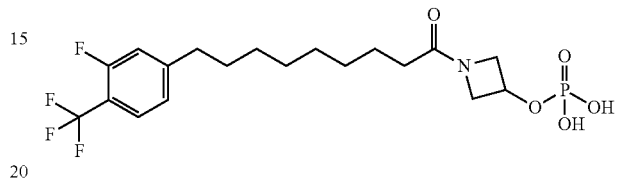

In Example 74, the reaction and treatment similar to those in (74-1)-(74-3) were performed using 2-fluoro-4-iodobenzene trifluoride instead of 1-iodo-4-(trifluoromethoxy)benzene to give the title compound (91 mg) as a white solid. MS(ESI) m/z: 275 (M+H)$^+$ Example 93

(93-1) 9-[(4-Cyclohexen-1-yl)phenyl]nonanoic acid (Example compound 93-1)

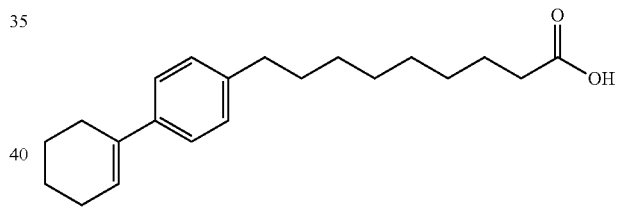

To a solution of Example compound 82-2 (143 mg) in 1,4-dioxane (2.3 mL) were added 1-cyclohexen-1-ylboronic acid (115 mg), 2N aqueous potassium phosphate solution (0.91 mL), and XPhos-Pd-G2 (36 mg) under a nitrogen atmosphere, and the mixture was stirred at 100° C. for 3 hr. To the reaction mixture was added 1N hydrochloric acid, and the mixture was extracted with ethyl acetate, washed with saturated brine, and dried over anhydrous sodium sulfate. The solvent was evaporated under reduced pressure. The obtained residue was purified by silica gel column chromatography (hexane:ethyl acetate=75:25-60:40) to give the title compound (126 mg) as a white solid.
MS (APCI) m/z: 315.2 (M+H)$^+$ (93-2) Dibenzyl 1-{9-[(4-cyclohexen-1-yl)phenyl]nonanoyl}azetidin-3-yl phosphate (Example Compound 93-2)

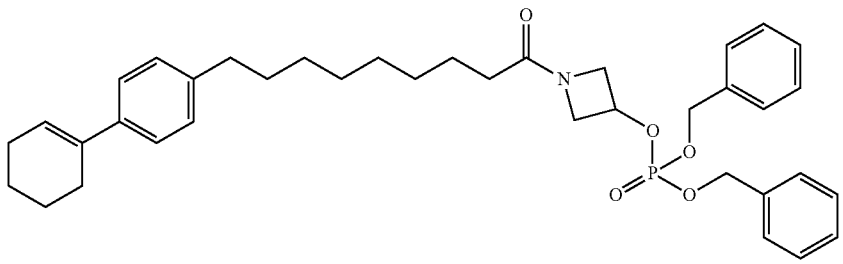 [SMILES: O=C(CCCCCCCCc1ccc(C2=CCCCC2)cc1)N1CC(OP(=O)(OCc2ccccc2)OCc2ccccc2)C1]

To a solution of Reference Example compound 2 (144 mg) in dichloromethane (3.3 mL) was added trifluoroacetic acid (0.51 mL) at 0° C. and the mixture was stirred for 1 hr. N,N-diisopropylethylamine (1.54 mL), Example compound 93-1 (70 mg) and HATU (254 mg) were added thereto at the same temperature, and the mixture was stirred for 1 hr. Water was added to the reaction mixture, and the mixture was extracted with ethyl acetate, washed with saturated brine, and dried over anhydrous sodium sulfate. The solvent was evaporated under reduced pressure. The obtained residue was purified by preparative HPLC (10 mM aqueous ammonium carbonate solution-acetonitrile) to give the title compound (100 mg) as a colorless oil.
MS(ESI) m/z: 630.6 (M+H)+

(93-3) 1-[9-(4-Cyclohexylphenyl)nonanoyl]azetidin-3-yl dihydrogen phosphate (Example compound 93)

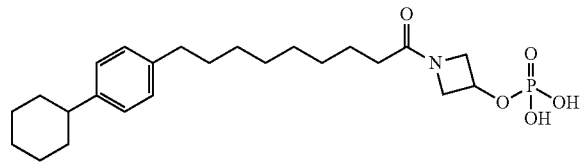 [SMILES: O=C(CCCCCCCCc1ccc(C2CCCCC2)cc1)N1CC(OP(=O)(O)O)C1]

Example compound 93-2 (98 mg) was dissolved in methanol (1.0 mL), palladium carbon (29 mg) was added, and the mixture was stirred under a hydrogen atmosphere at room temperature for 20 hr. After nitrogen purge, the reaction mixture was passed through a syringe filter to remove palladium carbon, and rinsed with methanol. The solvent was evaporated to give the title compound (87 mg) as a colorless viscous oil.
MS (APCI) m/z: 452.4 (M+H)+

Example 94

(94-1) tert-Butyl (4-formylphenyl)methylcarbamate (Example compound 94-1)

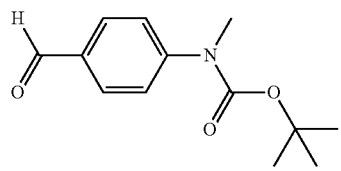 [SMILES: CN(C(=O)OC(C)(C)C)c1ccc(C=O)cc1]

tert-Butyl(4-formylphenyl)carbamate (2.00 g) was dissolved in N,N-dimethylformamide (18.4 mL), sodium hydride (470 mg) was added under ice-cooling, and the mixture was stirred at room temperature for 30 min. Under ice-cooling, methyliodide (0.844 mL) was added dropwise thereto, and the mixture was stirred at room temperature for 2 hr. Under ice-cooling, water was added to the mixture, and the mixture was extracted with ethyl acetate and dried over anhydrous sodium sulfate. The solvent was evaporated under reduced pressure. The residue was purified by silica gel column chromatography (hexane:ethyl acetate=95:5-80:20) to give the title compound (1.82 g) as a colorless oil. MS (APCI) m/z: 235.9[M+H]+

(94-2) 2-[{3-[3-(Decyloxy)phenyl]propanoyl}[4-(methylamino)benzyl]amino] ethyl dihydrogen phosphate ammonium salt (Example compound 94)

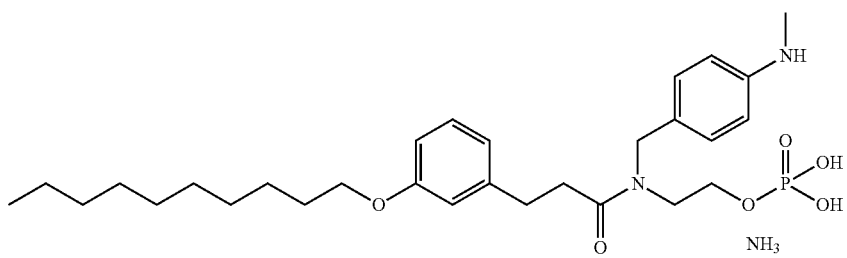

In Example 58, the reaction and treatment similar to those in (58-1)-(58-3) were performed using Example compound 94-1 instead of 4-pyridine carbaldehyde to give the title compound (237 mg) as a white oil. MS (APCI) m/z: 547.5[M−H]⁻

Example 95

(95-1) 2-[{3-[3-(Decyloxy)phenyl]propanoyl}(3-methoxybenzyl)amino]ethyl dihydrogen phosphate ammonium salt (Example compound 95)

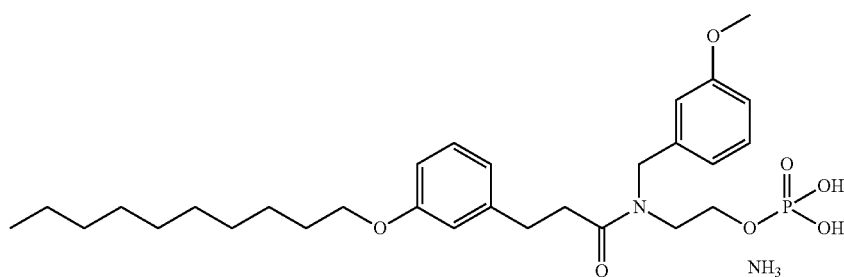

In Example 56, the reaction and treatment similar to those in (56-1)-(56-2) were performed using 3-methoxybenzaldehyde instead of 3-pyridine carbaldehyde to give the title compound (240 mg) as a colorless oil.
MS (APCI) m/z: 550.2[M+H]⁺

Example 96

(96-1) 2-({3-[3-(Decyloxy)phenyl]propanoyl}[(6-methoxypyridin-3-yl)methyl]amino)ethyl dihydrogen phosphate ammonium salt (Example compound 96)

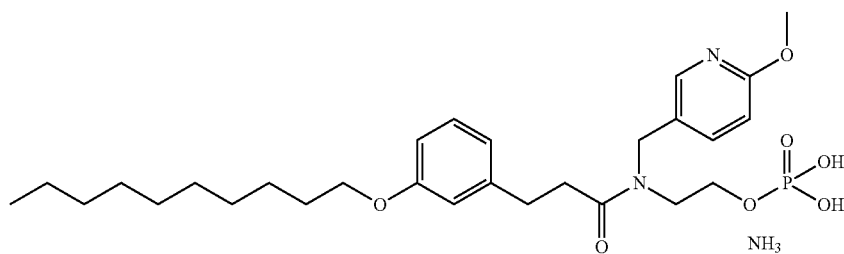

In Example 58, the reaction and treatment similar to those in (58-1)-(58-3) were performed using 6-methoxy pyridine carbaldehyde instead of 4-pyridine carbaldehyde to give the title compound (165 mg) as a colorless oil.

MS (APCI) m/z: 551.4[M+H]$^+$

Example 97

(97-1) 3-[3-(Hexyloxy)phenyl]propyl-3-(phosphonooxy)azetidine-1-carboxylate ammonium salt (Example compound 97)

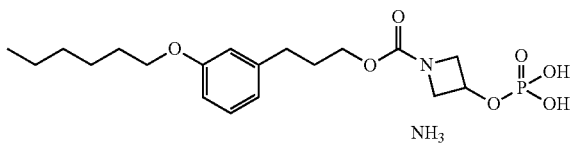

In Example 48, the reaction and treatment similar to those in (48-1)-(48-4) were performed using methyl 3-(3-hydroxyphenyl)propionate instead of methyl 3-hydroxybenzoate, and 1-bromohexane instead of 1-bromoundecane to give the title compound (92 mg) as a colorless solid. MS (APCI) m/z: 416.2 (M+H)$^+$ Example 98

(98-1) Benzyl 5-[4-bromo-2-(trifluoromethyl)phenyl]-4-pentynoate (Example compound 98-1)

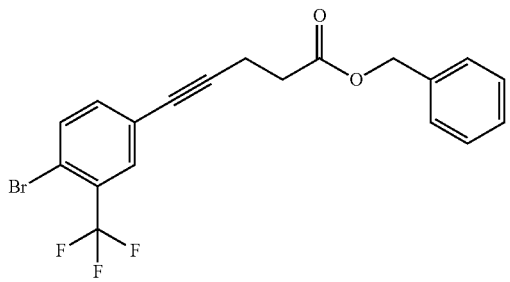 [SMILES: O=C(CCC#Cc1ccc(Br)c(C(F)(F)F)c1)OCc1ccccc1]

A mixture of 1-bromo-4-iodo-2-(trifluoromethyl)benzene (1.19 g), Example compound 34-1 (600 mg), bis(triphenylphosphine)palladium(II) dichloride (112 mg), copper iodide (I) (30 mg) and triethylamine (15.9 mL) was stirred at room temperature for one day and night. To the reaction mixture was added saturated aqueous ammonium chloride solution, and the mixture was extracted with diethyl ether. The organic layer was washed with 1N hydrochloric acid and saturated brine, and dried over anhydrous sodium sulfate. The desiccant was filtered off, and the filtrate was concentrated under reduced pressure. The obtained residue was purified by silica gel column chromatography (hexane:ethyl acetate=95:5-85:15) to give the title compound (1.02 g) as a yellow oil.

MS (APCI) m/z: 428.0, 429.9 (M+NH$_4$)$^+$ (98-2) Benzyl 5-{4-[(1E)-1-hepten-1-yl]-3-(trifluoromethyl)pentyl}-4-pentynoate (Example compound 98-2)

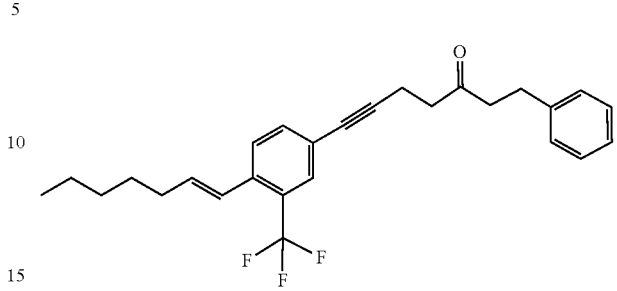

A mixture of Example compound 98-1 (200 mg), trans-1-heptenylboronic acid pinacol ester (131 mg), XPhos-Pd-G2 (19.1 mg), tripotassium phosphate (207 mg), tetrahydrofuran (4.9 mL), and water (2.4 mL) was stirred at 60° C. for 2 hr. To the reaction mixture were added saturated brine solution and ethyl acetate, and the organic layer was separated by a Phase-separator (registered trade mark) and concentrated under reduced pressure. The obtained residue was purified twice by NH silica gel column chromatography (hexane:ethyl acetate=100:0-90:10) and purified again by silica gel column chromatography (hexane:ethyl acetate=100:0-90:10) to give the title compound (163 mg) as a yellow oil. MS (APCI) m/z: 446.1 (M+NH$_4$)$^+$ (98-3) 5-[4-Heptyl-3-(trifluoromethyl)phenyl]pentanoic acid (Example compound 98-3)

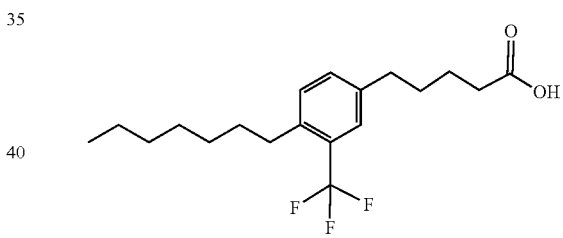

To a solution of Example compound 98-2 (158 mg) in ethanol (3.7 mL) was added 7.5% palladium carbon (32 mg), and the mixture was stirred under a hydrogen atmosphere at room temperature for one day and night. After filtering off the insoluble material in the reaction mixture with diatomaceous earth, the filtrate was concentrated under reduced pressure to give the title compound (136 mg) as a yellow oil.

MS (APCI) m/z: 343.1 (M−H)$^-$ (98-4) 1-{5-[4-Heptyl-3-(trifluoromethyl)phenyl]pentanoyl}azetidin-3-yl dihydrogen phosphate ammonium salt (Example compound 98)

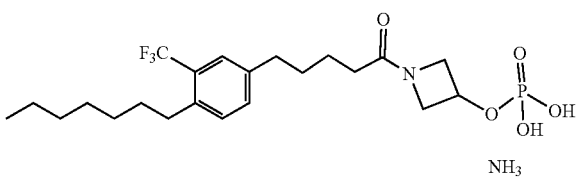

To a solution of Example compound 98-3 (122 mg) in N,N-dimethylformamide (3.5 mL) were added N,N-diisopropylethylamine (0.18 mL), Reference Example compound 1 (113 mg) and HATU (202 mg), and the mixture was stirred at room temperature overnight. The reaction mixture was purified by preparative HPLC (10 mM aqueous ammonium carbonate solution-acetonitrile). To the obtained residue were added dichloromethane (3.5 mL) and trifluoroacetic acid (0.71 mL), and the mixture was stirred at room temperature for 2 hr. The reaction mixture was concentrated under reduced pressure. The obtained residue was purified by preparative HPLC (10 mM aqueous ammonium carbonate solution-acetonitrile) to give the title compound (126 mg) as a colorless solid. MS (APCI) m/z: 480.3 (M+H)$^+$ Example 99

(99-1) 1-[5-(4-Heptyl-3-methoxyphenyl)pentanoyl]azetidin-3-yl dihydrogen phosphate ammonium salt (Example compound 99)

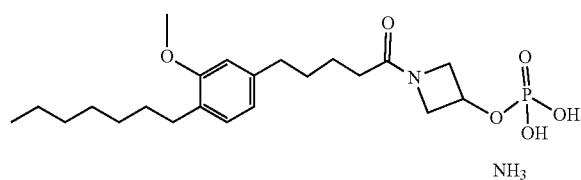

In Example 98, the reaction and treatment similar to those in (98-1)-(98-4) were performed using 1-bromo-4-iodo-2-methoxybenzene instead of 1-bromo-4-iodo-2-(trifluoromethyl)benzene to give the title compound (96 mg) as a colorless solid. MS (APCI) m/z: 442.4 (M+H)$^+$ Example 100

(100-1) 1-{5-[4-Heptyl-2-(trifluoromethyl)phenyl]pentanoyl}azetidin-3-yl dihydrogen phosphate ammonium salt (Example compound 100)

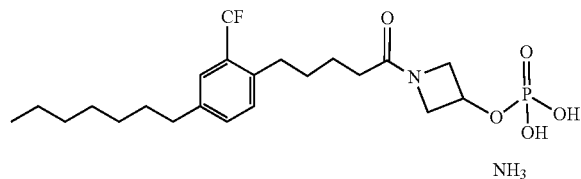

In Example 98, the reaction and treatment similar to those in (98-1)-(98-4) were performed using 4-bromo-1-iodo-3-(trifluoromethyl)benzene instead of 1-bromo-4-iodo-2-(trifluoromethyl)benzene to give the title compound (158 mg) as a colorless solid. MS (APCI) m/z: 480.3 (M+H)$^+$ Example 101

(101-1) Diethyl [2-(3-bromophenyl)ethyl]propanoate (Example compound 101-1)

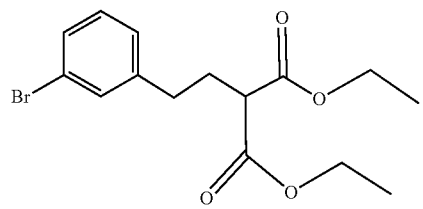 [SMILES: CCOC(=O)C(CCc1cccc(Br)c1)C(=O)OCC]

To a suspension of sodium hydride (60%, 1.52 g) in N,N-dimethylformamide (38 mL) was added diethyl malonate (6.07 g), and the mixture was stirred at room temperature for 1 hr. A solution of 3-bromo-1-(2-bromoethyl)benzene (10.0 g) in N,N-dimethylformamide (38 mL) was added thereto, and the mixture was stirred at room temperature for 5 hr. Water was added to the reaction mixture, and the mixture was extracted with diethyl ether. The organic layer was washed with water and saturated brine, and dried over anhydrous sodium sulfate. The desiccant was filtered off, and the filtrate was concentrated under reduced pressure. The obtained residue was purified by silica gel column chromatography (hexane:ethyl acetate=100:0-92:8) to give the title compound (8.73 g) as a colorless oil.
MS (APCI) m/z: 343.0 (M+H)$^+$.

(101-2) 4-(3-Bromophenyl)butanoic acid (Example compound 101-2)

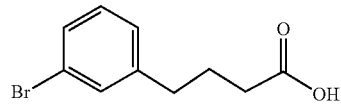 [SMILES: O=C(O)CCCc1cccc(Br)c1]

A mixture of Example compound 101-1 (8.73 g), 4N aqueous sodium hydroxide solution (25.4 mL), and ethanol (25 mL) was stirred with heating under reflux for 3 hr. The reaction mixture was concentrated under reduced pressure. A mixture of 4N hydrogen chloride aqueous solution (50.8 mL) and 1,4-dioxane (51 mL) was added to the residue, and the mixture was stirred with heating under reflux for one day and night. To the reaction mixture was added saturated brine, and the mixture was extracted with ethyl acetate. The organic layer was dried over anhydrous sodium sulfate, the desiccant was filtered off, and the filtrate was concentrated under reduced pressure. The obtained residue was purified by silica gel column chromatography (hexane:ethyl acetate=75:25-50:50) to give the title compound (3.35 g) as a colorless oil.
MS (APCI) m/z: 240.9,242.8 (M−H)$^-$ (101-3) 4-(3-Iodophenyl)butanoic acid (Example compound 101-3)

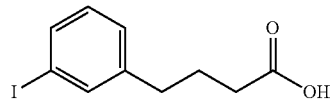 [SMILES: O=C(O)CCCc1cccc(I)c1]

To a solution of Example compound 101-2 (300 mg) in tetrahydrofuran (12.3 mL) was added dropwise n-butyllithium (1.60 mol/l, n-hexane solution, 1.93 mL) at −78° C., and the mixture was stirred at the same temperature for 15 min. Iodine (470 mg) was added thereto, and the mixture was stirred for 2 hr while gradually raising the temperature to room temperature. To the reaction mixture were added saturated aqueous sodium thiosulfate solution, 1N hydrochloric acid, and chloroform. The organic layer was separated by a Phase-separator (registered trade mark) and concentrated under reduced pressure. The obtained residue was purified by silica gel column chromatography (hexane:ethyl acetate=75:25-50:50) to give the title compound (231 mg) as a colorless oil.

MS (APCI) m/z: 288.8 (M−H)⁻

(101-4) 1-[4-(3-Octylphenyl)butanoyl]azetidin-3-yl dihydrogen phosphate (Example compound 101)

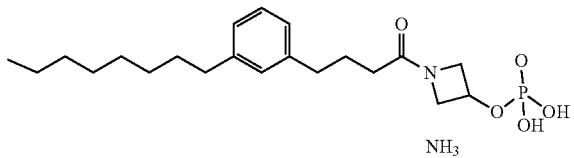

In Example 74, the reaction and treatment similar to those in (74-1)-(74-3) were performed using 1-octyne instead of Reference Example compound 8 and Example compound 101-3 instead of 1-iodo-4-(trifluoromethoxy)benzene, and the obtained residue was purified by preparative HPLC (10 mM aqueous ammonium carbonate solution-acetonitrile) to give the title compound (31 mg) as a colorless solid. MS (APCI) m/z: 412.4 (M+H)⁺

Example 102

(102-1) 9-(Propylphenyl)-9-nonynoic acid (Example compound 102-1)

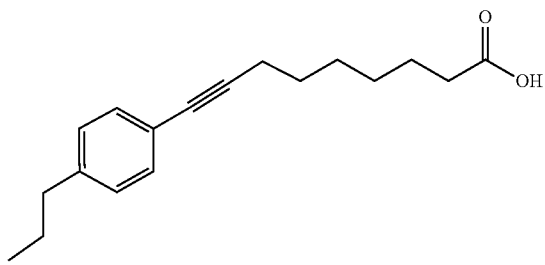 [SMILES: CCCc1ccc(C#CCCCCCCC(=O)O)cc1]

Reference Example compound 8 (3.60 g) was dissolved in tetrahydrofuran (10 mL), 1-iodo-4-propylbenzene (8.60 g), N,N-diisopropylethylamine (16 mL), copper iodide (I) (670 mg), and dichloro bis(triphenylphosphine)palladium (II) (980 mg) were added at room temperature, and the mixture was stirred at 60° C. for 4 hr. To the reaction mixture was added 1N hydrochloric acid under ice-cooling, and the mixture was extracted with ethyl acetate, washed with saturated brine, and dried over anhydrous sodium sulfate. The solvent was evaporated and the residue was purified by silica gel column chromatography (hexane:ethyl acetate=90:10-65:35) to give a crudely purified product (3.86 g) of the title compound as a brown oil.

MS (APCI) m/z: 271.0[M−H]⁻

(102-2) 9-(4-Propylphenyl)nonanoic acid (Example compound 102-2)

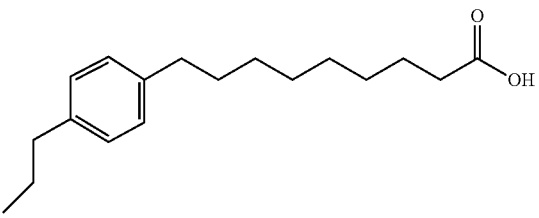 [SMILES: CCCc1ccc(CCCCCCCCC(=O)O)cc1]

Example compound 102-1 (3.42 g) was dissolved in methanol (50 mL), palladium carbon (1.36 g) was added, and the mixture was stirred at room temperature for 16 hr. After completion of the reaction, palladium carbon was filtered off with diatomaceous earth, and the filtrate was concentrated. The residue was purified by silica gel column chromatography (ethyl acetate:methanol=90:10-60:40) to give the title compound (2.12 g) as a brown oil. MS (APCI) m/z: 275.2[M−H]⁻

(102-3) 2-[(1,3-Thiazol-5-yl methyl)amino]ethanol (Example compound 102-3)

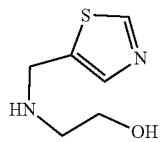

2-Aminoethanol (135 mg) was dissolved in methanol (7.4 mL), thiazole-5-carbaldehyde (250 mg) was added, and the mixture was stirred at 60° C. for 2 hr. After allowing to cool to room temperature, sodium borohydride (310 mg) was added thereto under ice-cooling, and the mixture was stirred at room temperature for 1.5 hr. The solvent was evaporated under reduced pressure, the obtained residue was purified by NH slica gel column chromatography (chloroform:methanol=100:0-90:10) to give the title compound (330 mg) as a pale-yellow oil.

MS (APCI) m/z: 158.9[M+H]⁺

(102-4) N-(2-Hydroxyethyl)-9-(4-propylphenyl)-N-(1,3-thiazol ylmethyl)nonanamide (Example compound 102-4)

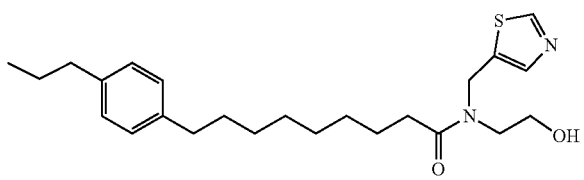 [SMILES: CCCc1ccc(CCCCCCCCC(=O)N(CCO)Cc2cncs2)cc1]

Example compound 102-1 (200 mg) was dissolved in N,N-dimethylformamide (2.2 mL), N,N-diisopropylethylamine (0.376 mL) and HATU (413 mg) were added, a solution of Example compound 102-3 (137 mg) in N,N-dimethylformamide (3 mL) was added dropwise, and the mixture was stirred at room temperature for 12.5 hr. The reaction mixture was diluted with ethyl acetate, water was added thereto, and the mixture was extracted with ethyl acetate, washed with saturated brine, and dried over anhydrous sodium sulfate. The solvent was evaporated under reduced pressure. The residue was purified by silica gel column chromatography (ethyl acetate:methanol=100:0-91:9) to give the title compound (quant.) as a colorless oil.

MS (APCI) m/z: 417.4[M+H]$^+$ (102-5) Di-tert-butyl 2-{[9-(4-propylphenyl)nonanoyl](1,3-thiazol-5-ylmethyl)amino}ethyl phosphate (Example compound 102-5)

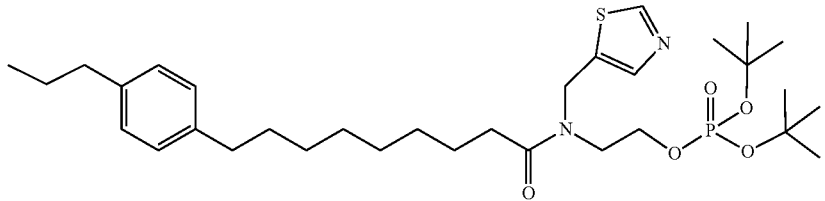 [SMILES: CCCc1ccc(CCCCCCCCC(=O)N(CCOP(=O)(OC(C)(C)C)OC(C)(C)C)Cc2cncs2)cc1]

Example compound 102-4 (302 mg) was dissolved in dichloromethane (3.0 mL) and acetonitrile (1.2 mL), 1H-tetrazole (101 mg) was added under ice-cooling, di-tert-butyl N,N-diisopropyl phosphoramidite (0.466 mL) was added dropwise, and the mixture was stirred at room temperature for 95 min. Under ice-cooling, tert-butyl hydroperoxide (0.26 mL) was added dropwise thereto, and the mixture was stirred at room temperature for 1 hr. Under ice-cooling, saturated aqueous sodium thiosulfate solution (5 mL) was added to the mixture, and the mixture was stirred at room temperature for 10 min. Ethyl acetate was added to the reaction mixture for extraction, and the mixture was washed with saturated aqueous sodium hydrogen carbonate solution and saturated brine, and dried over anhydrous sodium sulfate. The solvent was evaporated under reduced pressure. The residue was purified by silica gel column chromatography (ethyl acetate:methanol=100:0-95:5) to give the title compound (309 mg) as a colorless oil.

MS (APCI) m/z: 609.2[M+H]$^+$ (102-6) 2-{[9-(4-Propylphenyl)nonanoyl] (1,3-thiazol-5-ylmethyl)amino}ethyl dihydrogen phosphate ammonium salt (Example compound 102)

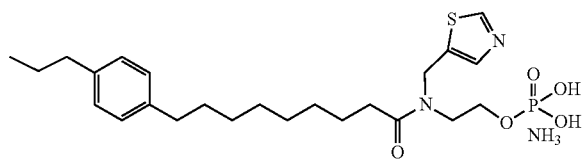

Example compound 102-5 (301 mg) was dissolved in dichloromethane (7.61 mL), trifluoroacetic acid (0.758 mL) was added dropwise under ice-cooling, and the mixture was stirred at room temperature for 140 min. The solvent was evaporated under reduced pressure, diethyl ether was added to the residue, and the solvent was evaporated under reduced pressure. This evaporation operation was repeated 3 times, and the obtained residue was purified by preparative HPLC (10 mM aqueous ammonium carbonate solution-acetonitrile) to give the title compound (176 mg) as a pale-yellow oil.

MS (APCI) m/z: 497.2[M+H]$^+$

Example 103

(103-1) Di-tert-butyl 2-{[4-(methylsulfamoyl)benzyl]amino}ethyl phosphate (Example compound 103-1)

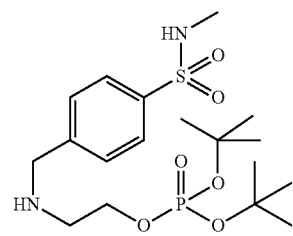 [SMILES: CNS(=O)(=O)c1ccc(CNCCOP(=O)(OC(C)(C)C)OC(C)(C)C)cc1]

Reference Example compound 7-2 (636 mg) was dissolved in methanol (8.37 mL), 4-formyl-N-methylbenzenesulfonamide (500 mg) was added, and the mixture was stirred at 60° C. for 2 hr. After allowing to cool to room temperature, sodium borohydride (95 mg) was added thereto under ice-cooling, and the mixture was stirred at room temperature for 85 min. Under ice-cooling, water was added to the mixture, and the solvent was evaporated under reduced pressure. The residue was purified by NH silica gel column chromatography (chloroform:methanol=100:0-95:5) to give the title compound (599 mg) as a colorless oil.

MS (APCI) m/z: 437.0[M+H]$^+$ (103-2) 2-({3-[3-(Decyloxy)phenyl]propanoyl}{4-[(methylsulfamoyl)benzyl]amino)ethyl dihydrogen phosphate ammonium salt (Example compound 103)

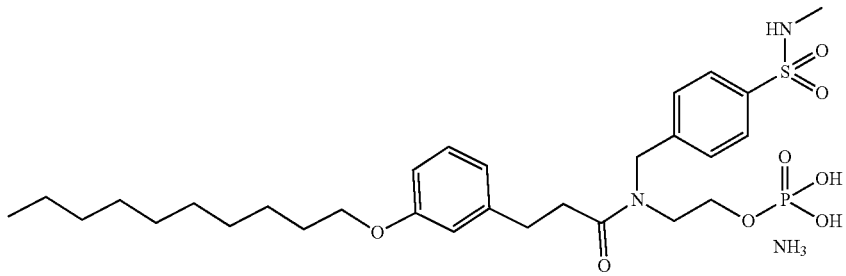

Reference Example compound 5 (170 mg) was dissolved in N,N-dimethylformamide (2.04 mL), N,N-diisopropylethylamine (0.288 mL) and HATU (316 mg) were added, a solution of Example compound 103-1 (339 mg) in N,N-dimethylformamide (3 mL) was added dropwise, and the mixture was stirred at room temperature for 15.5 hr. The reaction mixture was diluted with ethyl acetate, water was added thereto, and the mixture was extracted with ethyl acetate, washed with saturated brine, and dried over anhydrous sodium sulfate. The solvent was evaporated under reduced pressure. The residue was purified by silica gel column chromatography (hexane:ethyl acetate=20:80-0:100), the obtained compound was dissolved in dichloromethane (9 mL), trifluoroacetic acid (0.896 mL) was added dropwise under ice-cooling, and the mixture was stirred at room temperature for 2 hr. The solvent was evaporated under reduced pressure, diethyl ether was added to the residue, and the solvent was evaporated under reduced pressure. This evaporation operation was repeated 3 times, and the obtained residue was purified by preparative HPLC (10 mM aqueous ammonium carbonate solution-acetonitrile) to give the title compound (53 mg) as a white powder. MS (APCI) m/z: 613.0[M+H]$^+$ Example 104

(104-1) 2-{[9-(4-Propylphenyl)nonanoyl](pyrazin-4-ylmethyl)amino}ethyl dihydrogen phosphate ammonium salt (Example compound 104)

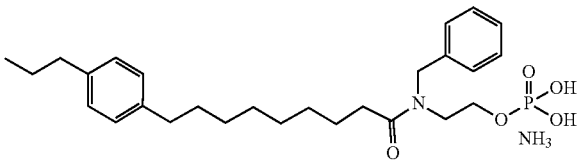

In Example 58, the reaction and treatment similar to those in (58-1)-(58-3) were performed using pyridazine carbaldehyde instead of 4-pyridine carbaldehyde to give the title compound (173 mg) as a pale-purple oil.
MS (APCI) m/z: 492.3[M+H]$^+$ Example 105

(105-1) 2-{(4-Methoxybenzyl)[9-(4-pentylphenyl)nonanoyl]amino}ethyl dihydrogen phosphate ammonium salt (Example compound 105)

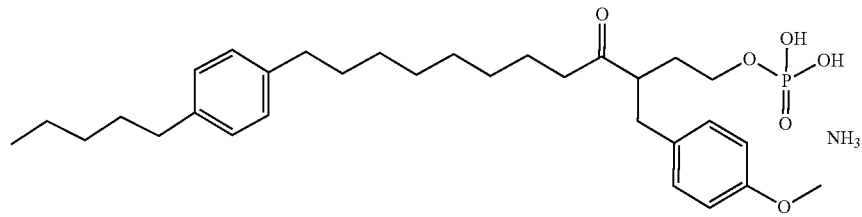

In Example 59, the reaction and treatment similar to those in (59-2)-(59-4) were performed using 1-iodo-4-pentylbenzene instead of Example compound 59-1, Reference Example compound 8 instead of 1-heptyne, and Reference Example compound 7 instead of Reference Example compound 1 to give the title compound (90 mg) as a colorless oil.

MS (APCI) m/z: 548.0[M+H]$^+$

Example 106

(106-1) Benzyl 5-(4-hydroxyphenyl)-4-pentynoate (Example compound 106-1)

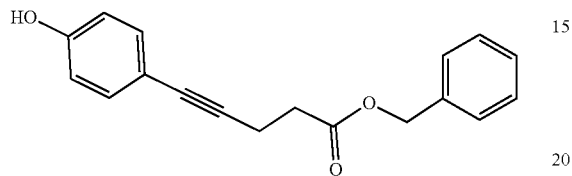

In Example 59, the reaction and treatment similar to those in (59-1) were performed using 4-iodophenol instead of 1,4-diiodobenzene to give the title compound (2.56 g) as a yellow oil. MS (APCI) m/z: 279.1[M−H]$^-$ (106-2) Benzyl 5-{4-[(5-phenylpentyl)oxy]phenyl}-4-pentynoate (Example compound 106-2)

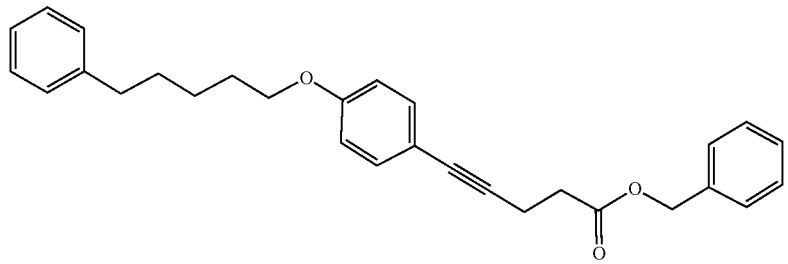 [SMILES: O=C(CCC#Cc1ccc(OCCCCCc2ccccc2)cc1)OCc1ccccc1]

A mixture of Example compound 106-1 (150 mg), 1-bromo-5-phenylpentane (0.108 mL), cesium carbonate (349 mg), and N,N-dimethylformamide (2.68 mL) was stirred at room temperature overnight. Water was added to the reaction mixture, and the mixture was extracted with diethyl ether. The organic layer was dried over anhydrous sodium sulfate, the desiccant was filtered off, and the filtrate was concentrated under reduced pressure. The obtained residue was purified by silica gel column chromatography (ethyl acetate:methanol=100:0-90:10) to give the title compound (201 mg) as a colorless solid.

MS (APCI) m/z: 427.4[M+H]$^+$ (106-3) 2-[(4-Methoxybenzyl)(5-{4-[(5-phenylpentyl)oxy]phenyl}pentanoyl)amino]ethyl dihydrogen phosphate ammonium salt (Example compound 106)

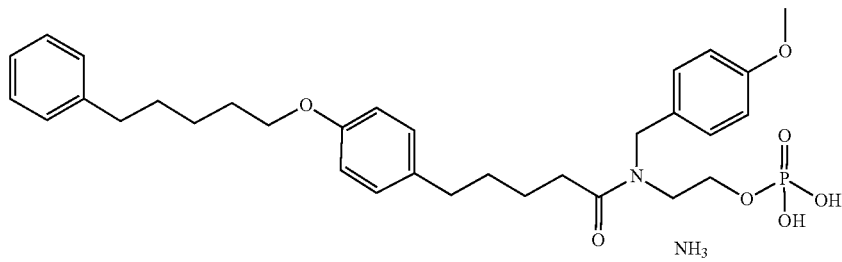

To a solution of Example compound 106-2 (195 mg) in ethanol (4.6 mL) was added 7.5% palladium carbon (39 mg), and the mixture was stirred under a hydrogen atmosphere at room temperature for one day and night. After filtering off the insoluble material in the reaction mixture with diatomaceous earth, the filtrate was concentrated under reduced pressure. The residue was dissolved in N,N-dimethylformamide (4.6 mL), and N,N-diisopropylethylamine (0.24 mL) HATU (261 mg), and Reference Example compound 7 (205 mg) were added, and the mixture was stirred at room temperature overnight. Water was added to the reaction mixture, and the mixture was extracted with ethyl acetate. The organic layer was washed with water and saturated brine, and dried over sodium sulfate. The desiccant was filtered off, and the filtrate was concentrated under reduced pressure. The obtained residue was purified by silica gel column chromatography (hexane:ethyl acetate=65:35-45:55). To a solution of the obtained solid (255 mg) in dichloromethane (3.7 mL) was added trifluoroacetic acid (0.73 mL) and the mixture was stirred at room temperature for 2 hr. The reaction mixture was concentrated under reduced pressure. The obtained residue was purified by preparative HPLC (10 mM aqueous ammonium carbonate solution-acetonitrile) to give the title compound (165 mg) as a colorless solid.

MS (APCI) m/z: 584.0 (M+H)$^+$

Example 107

(107-1) 2-[(4-Methoxybenzyl){5-[4-(4-phenylbutoxy)phenyl]pentanoyl}amino]ethyl dihydrogen phosphate ammonium salt (Example compound 107)

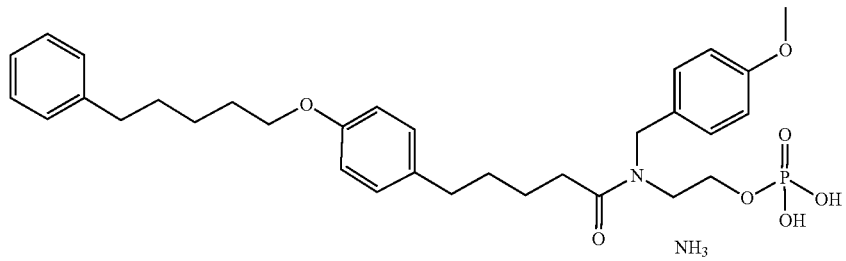

In Example 106, the reaction and treatment similar to those in (106-2)-(106-3) were performed using 1-bromo-4-phenylbutane instead of 1-bromo-5-phenylpentane to give the title compound (215 mg) as a colorless viscous oil.

MS (APCI) m/z: 570.0 (M+H)$^+$

Example 108

(108-1) Benzyl 5-(2-chloro-5-hydroxyphenyl)-4-pentynoate (Example compound 108-1)

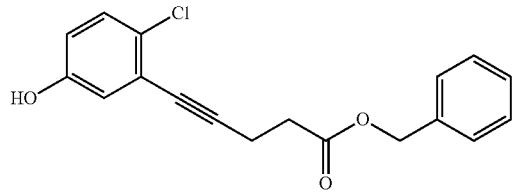 [SMILES: O=C(CCC#Cc1cc(O)ccc1Cl)OCc1ccccc1]

In Example 59, the reaction and treatment similar to those in (59-1) were performed using 4-chloro-3-iodophenol instead of 1,4-diiodobenzene to give the title compound (628 mg) as a yellow solid. MS (APCI) m/z: 312.9[M−H]$^-$ (108-2) Benzyl 5-(2-chloro-5-hydroxyphenyl)pentanoate (Example compound 108-2)

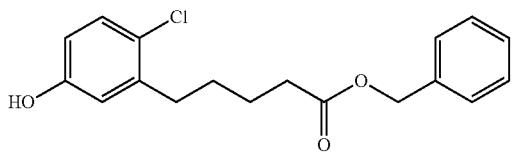 [SMILES: O=C(CCCCc1cc(O)ccc1Cl)OCc1ccccc1]

To a solution of Example compound 108-1 (620 mg) in tetrahydrofuran (6.5 mL) and methanol (6.5 mL) was added tris(triphenylphosphine)rhodium (I) chloride (91 mg), and the mixture was stirred under a hydrogen atmosphere at room temperature overnight. The reaction mixture was concentrated under reduced pressure. The obtained residue was purified by silica gel column chromatography (hexane:ethyl acetate=85:15-65:35) to give the title compound (489 mg) as a pale-yellow oil.

MS (APCI) m/z: 317.0[M−H]⁻

(108-3) Benzyl 5-[2-chloro-5-(4-phenylbutoxy)phenyl]pentanoate (Example compound 108-3)

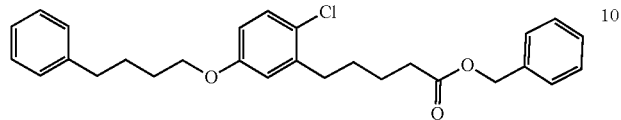

In Example 106, the reaction and treatment similar to those in (106-2) were performed using Example compound 108-2 instead of Example compound 106-1 and 1-bromo-4-phenylbutane instead of 1-bromo-5-phenylpentane to give the title compound (209 mg) as a colorless oil. MS (APCI) m/z: 468.2 (M+NH$_4$)⁺

(108-4) Di-tert-butyl 2-[{5-[2-chloro-5-(4-phenylbutoxy)phenyl]pentanoyl}(4-methoxybenzyl)amino]ethyl phosphate (Example compound 108-4)

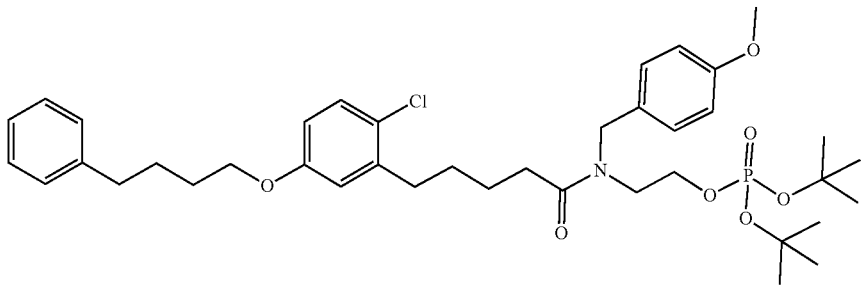 [SMILES: COc1ccc(CN(CCOP(=O)(OC(C)(C)C)OC(C)(C)C)C(=O)CCCCc2cc(OCCCCc3ccccc3)ccc2Cl)cc1]

To a mixed solution of Example compound 108-3 (200 mg) in ethanol (1.1 mL) and tetrahydrofuran (1.1 mL) was added 1N aqueous sodium hydroxide solution (1.77 mL), and the mixture was stirred at room temperature for 2 hr. To the reaction mixture were added 1N hydrochloric acid and chloroform, and the mixture was stirred. The organic layer was separated by a Phase-separator (registered trade mark), and concentrated under reduced pressure. To a solution of the residue in N,N-dimethylformamide (4.4 mL) were added N,N-diisopropylethylamine (0.23 mL), Reference Example compound 7 (199 mg) and HATU (253 mg), and the mixture was stirred at room temperature overnight. Water was added to the reaction mixture, and the mixture was extracted with ethyl acetate. The organic layer was washed with water and saturated brine, and dried over anhydrous sodium sulfate. The desiccant was filtered off, and the filtrate was concentrated under reduced pressure. The obtained residue was purified by silica gel column chromatography (hexane:ethyl acetate=45:55-20:80) to give the title compound (310 mg) as a yellow oil. MS (APCI) m/z: 715.9[M+H]⁺

(108-5) 2-[{5-[2-Chloro-5-(4-phenylbutoxy)phenyl]pentanoyl}(4-methoxybenzyl)amino]ethyl dihydrogen phosphate ammonium salt (Example compound 108)

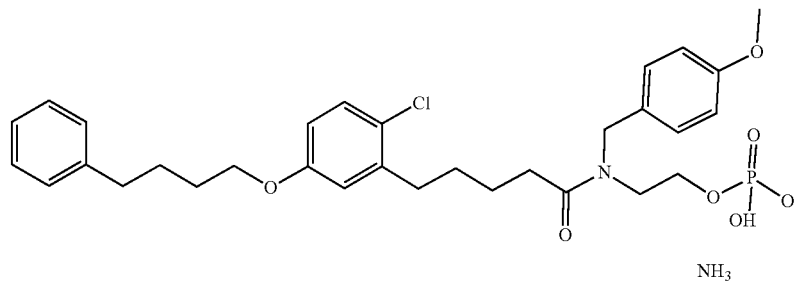

To a solution of Example compound 108-4 (305 mg) in dichloromethane (4.3 mL) was added trifluoroacetic acid (0.85 mL), and the mixture was stirred at room temperature for 2 hr. The reaction mixture was concentrated under reduced pressure. The obtained residue was purified by preparative HPLC (10 mM aqueous ammonium carbonate solution-acetonitrile) to give the title compound (222 mg) as a pale-yellow viscous oil.

MS (APCI) m/z: 604.0[M+H]+

Example 109

(109-1) 2-[{5-[2-Chloro-3-(4-phenylbutoxy)phenyl]pentanoyl}(4-methoxybenzyl)amino]ethyl dihydrogen phosphate ammonium salt (Example compound 109)

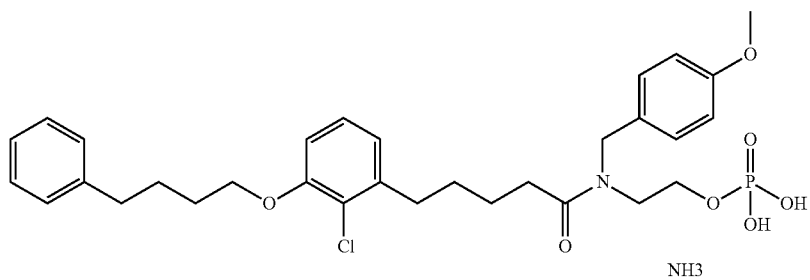

In Example 108, the reaction and treatment similar to those in (108-1)-(108-5) were performed using 2-chloro-3-iodophenol instead of 4-chloro-3-iodophenol to give the title compound (170 mg) as a pale-yellow viscous oil.

MS (APCI) m/z: 604.0[M+H]+

Example 110

(110-1) 2-[{5-[3-(5-Cyclohexylpentyl)phenyl]pentanoyl}(4-methoxybenzyl)amino]ethyl dihydrogen phosphate ammonium salt (Example compound 110)

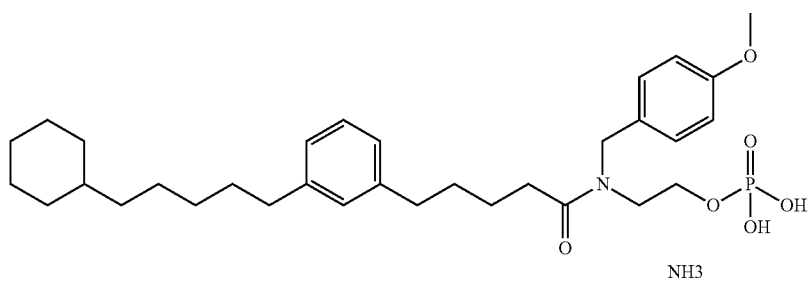

In Example 59, the reaction and treatment similar to those in (59-1)-(59-4) were performed using 1,3-diiodobenzene instead of 1,4-diiodobenzene, 4-pentyn-1-ylcyclohexane instead of 1-heptyne, and Reference Example compound 7 instead of Reference Example compound 1 to give the title compound (83 mg) as a colorless viscous oil. MS (APCI) m/z: 574.1[M+H]$^+$

Example 111

(111-1) 2-[{5-[4-(5-Cyclohexylpentyl)phenyl]pentanoyl}(4-methoxybenzyl)amino]ethyl dihydrogen phosphate ammonium salt (Example compound 111)

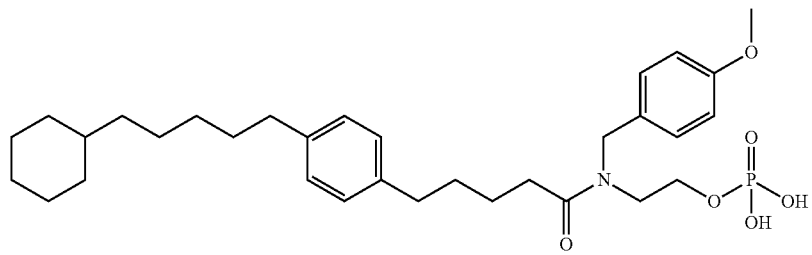

In Example 59, the reaction and treatment similar to those in (59-2)-(59-4) were performed using 4-pentyn-1-ylcyclohexane instead of 1-heptyne and Reference Example compound 7 instead of Reference Example compound 1 to give the title compound (99 mg) as a colorless viscous oil.

MS (APCI) m/z: 574.1[M+H]$^+$

Example 112

(112-1) 2-{[(2-Methoxypyridin-4-yl)methyl][9-(4-propylphenyl)nonanoyl]amino}ethyl dihydrogen phosphate ammonium salt (Example compound 112)

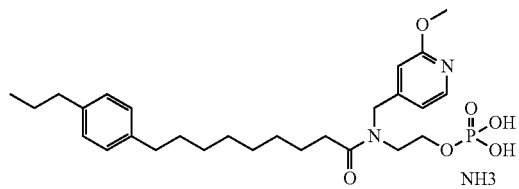

In Example 58, the reaction and treatment similar to those in (58-1)-(58-3) were performed using 2-methoxypyridine-4-carbaldehyde instead of 4-pyridine carbaldehyde to give the title compound (132 mg) as a colorless viscous oil.

MS (APCI) m/z: 521.2[M+H]$^+$

Example 113

(113-1) Benzyl 5-(3-hydroxyphenyl)-4-pentynoate (Example compound 113-1)

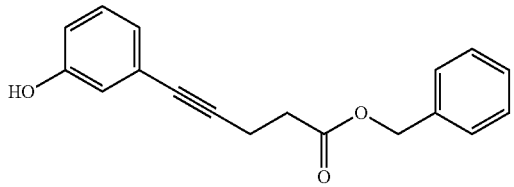 [SMILES: O=C(CCC#Cc1cccc(O)c1)OCc1ccccc1]

In Example 59, the reaction and treatment similar to those in (59-1) were performed using 3-iodophenol instead of 1,4-diiodobenzene to give the title compound (2.78 g) as a colorless solid. MS (APCI) m/z: 279.1[M–H]$^-$ (113-2) Benzyl 5-[3-(3-butyn-1-yl oxy)phenyl]-4-pentynoate (Example compound 113-2)

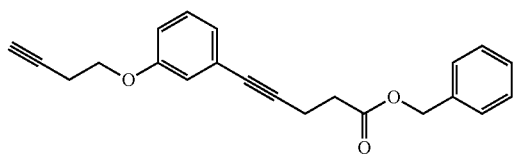 [SMILES: C#CCCOc1cccc(C#CCCC(=O)OCc2ccccc2)c1]

To a solution of Example compound 113-1 (848 mg) in tetrahydrofuran (7.56 mL) were sequentially added under ice-cooling 3-butyn-1-ol (0.23 mL), triphenylphosphine (1190 mg), and diisopropyl azodicarboxylate (2.39 mL), and the mixture was stirred at room temperature overnight.

Water was added to the reaction mixture, and the mixture was extracted with ethyl acetate. The organic layer was dried over anhydrous sodium sulfate, the desiccant was filtered off, and the filtrate was concentrated under reduced pressure. The obtained residue was purified by silica gel column chromatography (hexane:ethyl acetate=95:5-65:35) to give the title compound (163 mg) as a pale-yellow oil. MS (APCI) m/z: 333.1[M+H]$^+$ (113-3) 2-{(4-Methoxybenzyl)[5-(3-{4-[4-(trifluoromethoxy)phenyl]butoxy}phenyl)pentanoyl]amino}ethyl dihydrogen phosphate ammonium salt (Example compound 113)

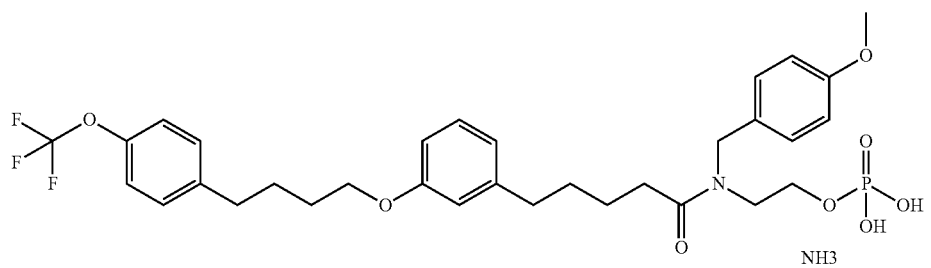

In Example 59, the reaction and treatment similar to those in (59-3)-(59-4) were performed using 1-iodo-4-(trifluoromethoxy)benzene instead of Example compound 59-1 and Example compound 113-2 instead of 1-heptyne, and Reference Example compound 7 instead of Reference Example compound 1 to give the title compound (86 mg) as a colorless viscous oil.

MS (APCI) m/z: 654.1[M+H]$^+$

Example 114

(114-1) 2-[4-(Trifluoromethoxy)phenyl]ethyl 4-methylbenzenesulfonate (Example compound 114-1)

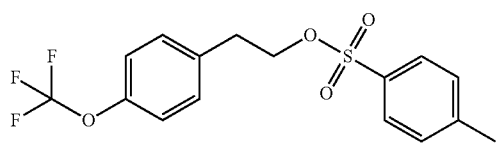 [SMILES: Cc1ccc(S(=O)(=O)OCCc2ccc(OC(F)(F)F)cc2)cc1]

To a solution of 2-{4-(trifluoromethoxy)phenyl}ethanol (400 mg) in dichloromethane (9.7 mL) were added triethylamine (0.549 mL), p-toluenesulfonyl chloride (0.329 mL) and N,N-dimethylaminopyridine (24 mg), and the mixture was stirred at room temperature overnight. To the reaction mixture were added water and diethyl ether, and the mixture was stirred. The organic layer was separated by a Phase-separator (registered trade mark), and concentrated under reduced pressure. The obtained residue was purified by silica gel column chromatography (hexane:ethyl acetate=95:5-80:20) to give the title compound (622 mg) as a colorless oil.

MS (APCI) m/z: 378.0[M+NH$_4$]$^+$ (114-2) 2-{(4-Methoxybenzyl)[5-(3-{2-[4-(trifluoromethoxy)phenyl]ethoxy}phenyl)pentanoyl]amino}ethyl dihydrogen phosphate ammonium salt (Example compound 114)

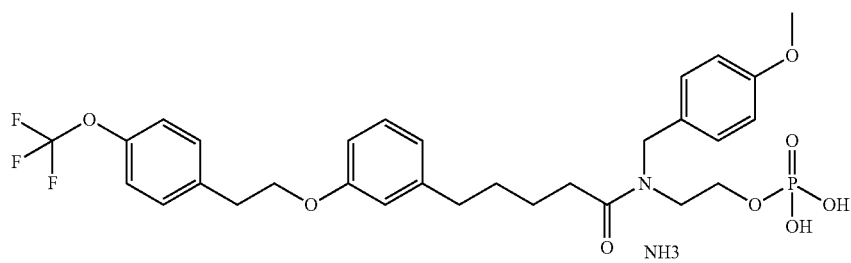

In Example 106, the reaction and treatment similar to those in (106-2)-(106-3) were performed using Example compound 113-1 instead of Example compound 106-1 and Example compound 114-1 instead of 1-bromo-5-phenylpentane to give the title compound (98 mg) as a colorless viscous oil.

MS (APCI) m/z: 626.0[M+H]$^+$

Example 115

(115-1) 2-{(4-Methoxybenzyl)[5-(4-{2-[4-(trifluoromethoxy)phenyl]ethoxy}phenyl)pentanoyl]amino}ethyl dihydrogen phosphate ammonium salt (Example compound 115)

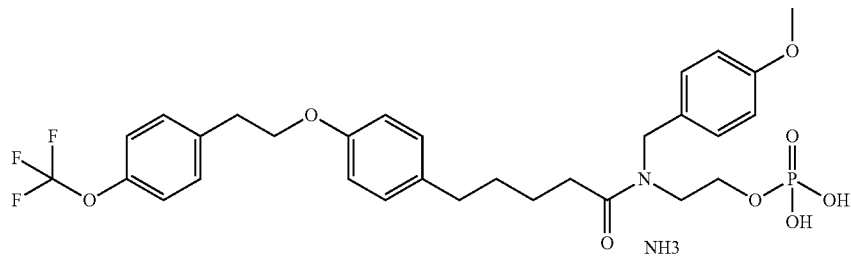

In Example 106, the reaction and treatment similar to those in (106-2)-(106-3) were performed using Example compound 114-1 instead of 1-bromo-5-phenylpentane to give the title compound (65 mg) as a colorless viscous oil.

MS (APCI) m/z: 626.0[M+H]$^+$

Example 116

(116-1) Ethyl (trans)-2-(4-bromophenyl)cyclopropanecarboxylate (Example compound 116-1A) and ethyl (cis)-2-(4-bromophenyl)cyclopropanecarboxylate (Example compound 116-1B)

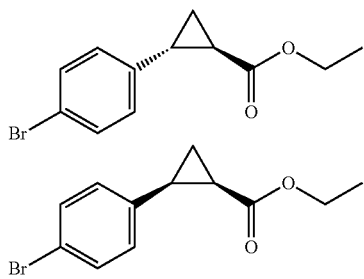

To a solution of 1-bromo-4-ethenylbenzene (5.00 g) in dichloromethane (54.6 mL) was added at room temperature rhodium (II) acetate (dimer) (241 mg), ethyl diazoacetate (6.76 mL) was added dropwise with a syringe pump over 1 hr, and the mixture was stirred at room temperature overnight. The reaction mixture was concentrated under reduced pressure. The obtained residue was purified by silica gel column chromatography (hexane:ethyl acetate-98:2-92:8) to give Example compound 116-1A (3.13 g) and Example compound 116-1B (3.18 g) as colorless oils. MS (APCI) m/z: 269.0[M+H]$^+$ (116-2) [(trans)-2-(4-Bromophenyl)cyclopropyl]methanol (Example compound 116-2)

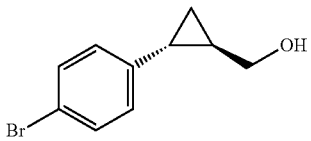 [SMILES: OC[C@@H]1C[C@H]1c1ccc(Br)cc1]

To a solution of Example compound 116-1A (1.50 g) in tetrahydrofuran (27.8 mL) was added under ice-cooling lithium aluminum hydride (423 mg), and the mixture was stirred at room temperature for 2 hr. To the reaction mixture were sequentially added water (0.4 mL), 1N aqueous sodium hydroxide solution (0.4 mL), and water (1.2 mL), and the mixture was stirred at room temperature overnight. The insoluble material in the reaction mixture was filtered off with diatomaceous earth, and the filtrate was concentrated under reduced pressure. The obtained residue was purified by silica gel column chromatography (hexane:ethyl acetate-75:25-55:45) to give the title compound (1.18 g) as a colorless oil.

(116-3) (trans)-2-(4-Bromophenyl)cyclopropanecarbaldehyde (Example compound 116-3)

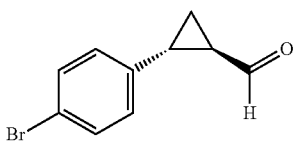 [SMILES: O=C[C@@H]1C[C@H]1c1ccc(Br)cc1]

4 Å molecular sieves (powder, 1.17 g) were dried under reduced pressure at 150° C. for 2 hr. To a solution of Example compound 116-2 (1.17 g) in dichloromethane (10.3 mL) and acetonitrile (5.15 mL) were sequentially added 4-methylmorpholine N-oxide (1.06 mL), dried 4 Å molecular sieves (powder, 1170 mg) and tetrapropylammonium perruthenate (90 mg), and the mixture was stirred at room temperature for 30 min. After filtering off the insoluble material in the reaction mixture with diatomaceous earth, the filtrate was concentrated under reduced pressure. The obtained residue was purified by silica gel column chromatography (hexane:ethyl acetate=85:15-65:35) to give the title compound (647 mg) as a colorless solid.

MS (APCI) m/z: 225.0[M+H]$^+$ (116-4) Ethyl (2E)-3-[(trans)-2-(4-bromophenyl) cyclopropyl]-2-propenoate (Example compound 116-4)

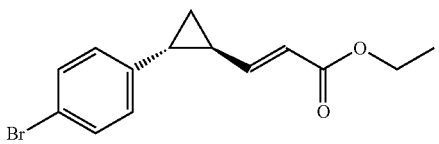 [SMILES: CCOC(=O)/C=C/[C@@H]1C[C@H]1c1ccc(Br)cc1]

To a solution of lithium chloride (36 mg) in acetonitrile (5.69 mL) were added under ice-cooling triethyl phosphonoacetate (0.678 mL) and 1,8-diazabicyclo[5.4.0]undec-7-ene (0.515 mL), and the mixture was stirred at room temperature for 30 min. Under ice-cooling, a solution of Example compound 116-3 (641 mg) in acetonitrile (5.69 mL) was added thereto, and the mixture was stirred at room temperature for 2 hr. Water was added to the reaction mixture, and the mixture was extracted with diethyl ether. The organic layer was washed with 1N hydrochloric acid and saturated brine, and dried over anhydrous sodium sulfate. The desiccant was filtered off, and the filtrate was concentrated under reduced pressure. The obtained residue was purified by silica gel column chromatography (hexane:ethyl acetate=98:2-88:12) to give the title compound (597 mg) as a colorless oil.

MS (APCI) m/z: 295.1[M+H]$^+$ (116-5) Ethyl (2E)-3-[(trans)-2-{4-[(1E)-1-hepten-1-yl]phenyl}cyclopropyl]-2-propenoate (Example compound 116-5)

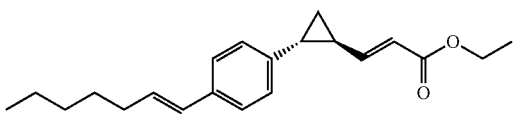 [SMILES: CCCCC/C=C/c1ccc([C@@H]2C[C@H]2/C=C/C(=O)OCC)cc1]

A mixture of Example compound 116-4 (120 mg), trans-1-heptenylboronic acid pinacol ester (109 mg), XPhos-Pd-G2 (32 mg), tripotassium phosphate (173 mg), tetrahydrofuran (2.0 mL) and water (1.0 mL) was stirred at 60° C. for 4 hr. Water was added to the reaction mixture, and the mixture was extracted with diethyl ether. The organic layer was dried over anhydrous sodium sulfate, the desiccant was filtered off, and the filtrate was concentrated under reduced pressure. The obtained residue was purified by silica gel column chromatography (hexane:ethyl acetate=100:0-90:10) to give the title compound (109 mg) as a yellow oil. MS (APCI) m/z: 313.0[M+H]$^+$ (116-6) (2E)-3-[(trans)-2-{4-[(1E)-1-Hepten-1-yl]phenyl}cyclopropyl]-2-propenoic acid (Example compound 116-6)

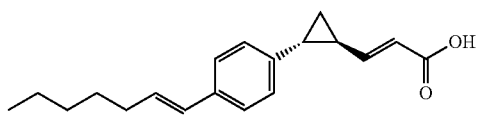 [SMILES: CCCCC/C=C/c1ccc([C@@H]2C[C@H]2/C=C/C(=O)O)cc1]

To a solution of Example compound 116-5 (105 mg) in ethanol (1.68 mL) and tetrahydrofuran (1.68 mL) was added 1N aqueous sodium hydroxide solution (1.34 mL), and the mixture was stirred at room temperature overnight. To the reaction mixture were added 1N hydrochloric acid and chloroform, and the mixture was stirred. The organic layer was separated by a Phase-separator (registered trade mark), and concentrated under reduced pressure. The obtained residue was purified by silica gel column chromatography (hexane:ethyl acetate=35:15-65:85) to give the title compound (82 mg) as a colorless oil.

MS (APCI) m/z: 283.1 [M−H]$^-$ (116-7) Di-tert-butyl 2-[{3-[(trans)-2-(4-heptylphenyl)cyclopropyl]propanoyl}(4-methoxybenzyl)amino}ethyl phosphate (Example compound 116-7)

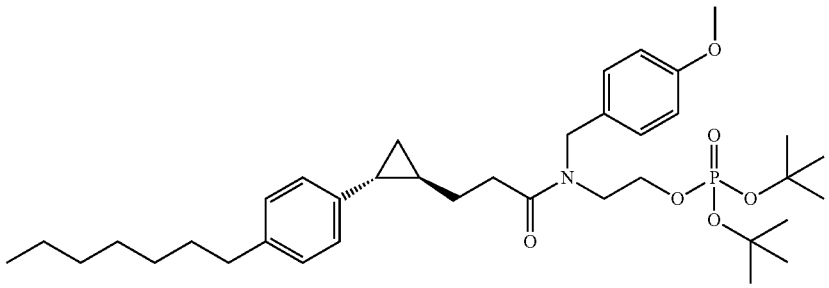 [SMILES: CCCCCCCc1ccc([C@@H]2C[C@H]2CCC(=O)N(CCOP(=O)(OC(C)(C)C)OC(C)(C)C)Cc2ccc(OC)cc2)cc1]

To a solution of Example compound 116-6 (77 mg) in ethyl acetate (2.7 mL) was added 5% rhodium-alumina (15 mg), and the mixture was stirred under a hydrogen atmosphere at room temperature for 3 hr. After filtering off the insoluble material in the reaction mixture with diatomaceous earth, the filtrate was concentrated under reduced pressure. To a solution of the obtained residue in N,N-dimethylformamide (2.7 mL) were added N,N-diisopropylethylamine (0.141 mL), Reference Example compound 7 (121 mg) and HATU (154 mg), and the mixture was stirred at room temperature for 3 hr. Water was added to the reaction mixture, ethyl acetate was added and the mixture was stirred. The organic layer was separated by a Phase-separator (registered trade mark), and concentrated under reduced pressure. The obtained residue was purified by silica gel column chromatography (hexane:ethyl acetate=50:50-25:75) to give the title compound (109 mg) as a colorless oil.

MS (APCI) m/z: 644.0[M+H]$^+$ (116-8) 2-[{3-[(trans)-2-(4-Heptylphenyl)cyclopropyl]propanoyl}(4-methoxybenzyl)amino]ethyl dihydrogen phosphate ammonium salt (Example compound 116)

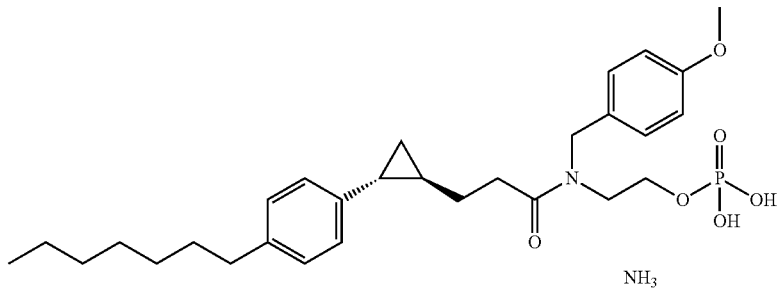

To a solution of Example compound 116-7 (102 mg) in dichloromethane (1.58 mL) was added trifluoroacetic acid (0.32 mL), and the mixture was stirred at room temperature for 2 hr. The reaction mixture was concentrated under reduced pressure. The obtained residue was purified by preparative HPLC (10 mM aqueous ammonium carbonate solution-acetonitrile) to give the title compound (43 mg) as a colorless viscous oil.

MS (APCI) m/z: 532.1[M+H]$^+$

Example 117

(117-1) 2-[{3-[(cis)-2-(4-Heptylphenyl)cyclopropyl]propanoyl}(4-methoxybenzyl)amino]ethyl dihydrogen phosphate ammonium salt (Example compound 117)

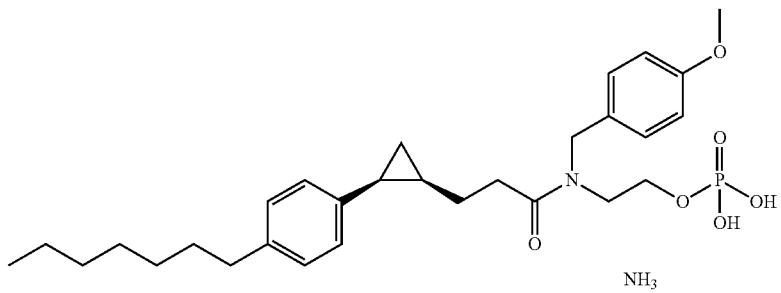

In Example 116, the reaction and treatment similar to those in (116-2)-(116-8) were performed using Example compound 116-1B instead of Example compound 116-1A to give the title compound (37 mg) as a colorless viscous oil. MS (APCI) m/z: 532.1[M+H]$^+$ Example 118

(118-1) 9-(4-Hexylphenyl)-8-nonynoic acid (Example compound 118-1)

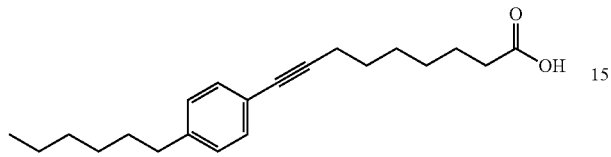

A mixture of Reference Example compound 8 (200 mg), 1-hexyl-4-iodobenzene (560 mg), copper iodide (I) (37 mg), dichloropalladium triphenylphosphine (55 mg), N,N-diisopropylethylamine (0.90 mL) and tetrahydrofuran (5.2 mL) was stirred at 60° C. for 5 hr. To the reaction mixture was added 1N hydrochloric acid, and the mixture was extracted with ethyl acetate, washed with saturated brine, and dried over anhydrous sodium sulfate. The solvent was evaporated under reduced pressure. The residue was purified by silica gel column chromatography (hexane:ethyl acetate=80:20-50:50) to give a crudely purified product (230 mg) of the title compound as a brown solid. MS(ESI) m/z: 313.4 (M−H)$^−$ (118-2) Methyl 9-(4-hexylphenyl)nonanoate (Example compound 118-2)

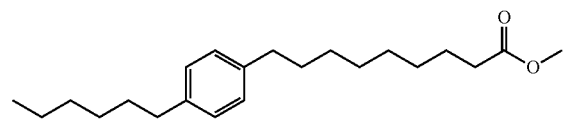 [SMILES: CCCCCCc1ccc(CCCCCCCCC(=O)OC)cc1]

To a solution of Example compound 118-1 (230 mg) in methanol (4.88 mL) was added palladium carbon (69 mg), and the mixture was stirred under a hydrogen atmosphere at room temperature for 2 days. After nitrogen purge, the reaction mixture was passed through a syringe filter to remove palladium carbon, rinsed with methanol, and the solvent was evaporated under reduced pressure to give the title compound (210 mg) as a yellow oil. MS (APCI) m/z: 333.2 (M+H)$^+$ (118-3) 9-(4-Hexylphenyl)nonanoic acid (Example compound 118-3)

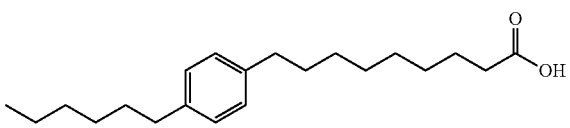 [SMILES: CCCCCCc1ccc(CCCCCCCCC(=O)O)cc1]

Example compound 118-2 (140 mg) was dissolved in methanol (1.4 mL), 1N aqueous sodium hydroxide solution (0.84 mL) was added, and the mixture was stirred at room temperature for 20 hr. After completion of the reaction, 1N hydrochloric acid (ca. 3 mL) was added to the mixture under ice-cooling, and the mixture was extracted with ethyl acetate, washed with saturated brine, and dried over anhydrous sodium sulfate. The solvent was evaporated to give the title compound (132 mg) as a colorless solid. MS(ESI) m/z: 317.4[M−H]$^−$ (118-4) Dibenzyl 1-[9-(4-hexylphenyl)nonanoyl] azetidin-3-yl phosphate (Example compound 118-4)

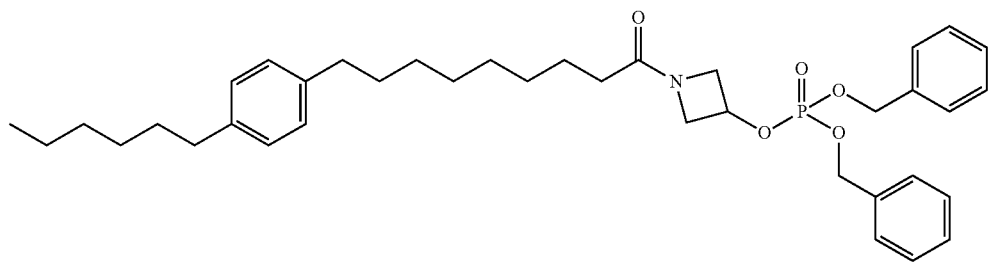 [SMILES: CCCCCCc1ccc(CCCCCCCCC(=O)N2CC(OP(=O)(OCc3ccccc3)OCc3ccccc3)C2)cc1]

To a solution of Reference Example compound 2 (248 mg) in dichloromethane (1.88 mL) was added trifluoroacetic acid (0.288 mL) under ice-cooling, and the mixture was stirred for 1 hr. N,N-diisopropylethylamine (0.87 mL) was added dropwise at the same temperature, and Example compound 118-4 (40 mg) and HATU (143 mg) were added thereto, and the mixture was stirred for 1 hr. Under ice-cooling, water was added to the reaction mixture, and the mixture was extracted with ethyl acetate, washed with saturated brine, and dried over anhydrous sodium sulfate. The solvent was evaporated under reduced pressure. The obtained residue was purified by silica gel column chromatography (hexane:ethyl acetate=50:50-30:70) to give the title compound (68 mg) as a colorless oil. MS(ESI) m/z: 634.4 (M+H)$^+$ (118-5) 1-[9-(4-Hexylphenyl)nonanoyl]azetidin-3-yl dihydrogen phosphate (Example compound 118)

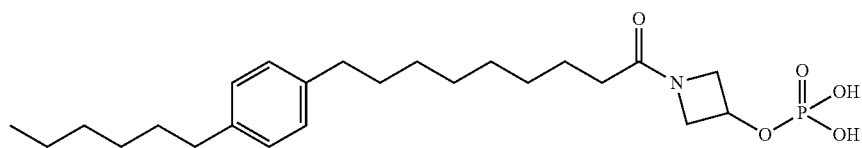 [SMILES: CCCCCCc1ccc(CCCCCCCCC(=O)N2CC(OP(=O)(O)O)C2)cc1]

Example compound 118-4 (64 mg) was dissolved in tetrahydrofuran (1.0 mL), 10% palladium carbon (32 mg) was added, and the mixture was stirred under a hydrogen atmosphere at room temperature for 5 hr. After completion of the reaction, membrane filter filtration was performed, and the filtrate was concentrated to give the title compound (45 mg) as a colorless viscous oil. MS (APCI) m/z: 454.3 [M+H]$^+$ Example 119

(119-1) 2-{(3,4-Dimethoxybenzyl)[9-(4-propylphenyl)nonanoyl]amino}ethyl dihydrogen phosphate ammonium salt (Example compound 119)

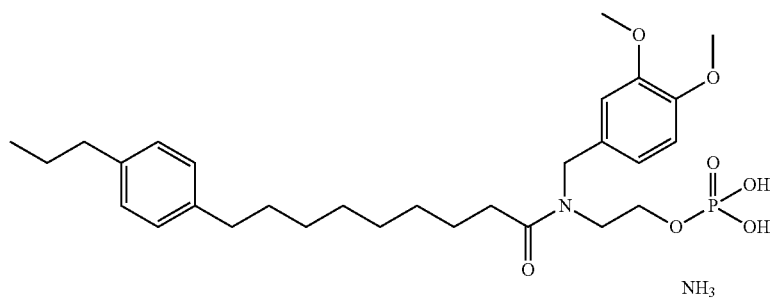

In Example 56, the reaction and treatment similar to those in (56-1)-(56-2) were performed using 3,4-dimethoxybenzaldehyde instead of 3-pyridine carbaldehyde, and Example compound 102-1 instead of Reference Example compound 5 to give the title compound (173 mg) as a white solid.
MS (APCI) m/z: 550.0[M+H]$^+$ Example 120

(120-1) Benzyl 5-{3-[2-(4-bromophenyl)ethoxy]phenyl}-4-pentynoate (Example compound 120-1)

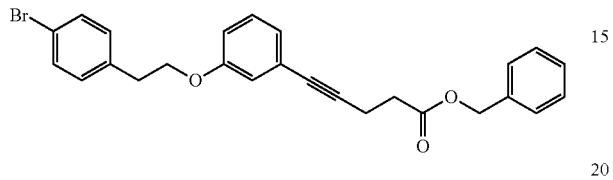

To a solution of Example compound 113-1 (600 mg), 2-(4-bromophenyl)ethanol (430 mg), triphenylphosphine (842 mg) in tetrahydrofuran (10.7 mL) was slowly added dropwise diisopropyl azodicarboxylate (1.69 mL), and the mixture was stirred at room temperature overnight. The reaction mixture was concentrated under reduced pressure, and the obtained residue was purified by silica gel column chromatography (hexane:ethyl acetate=95:5-85:15) to give the title compound (857 mg) as a colorless oil.
MS (APCI) m/z: 463.1[M+H]$^+$ (120-2) Benzyl 5-{3-[2-(biphenyl-4-yl)ethoxy]phenyl}-4-pentynoate (Example compound 120-2)

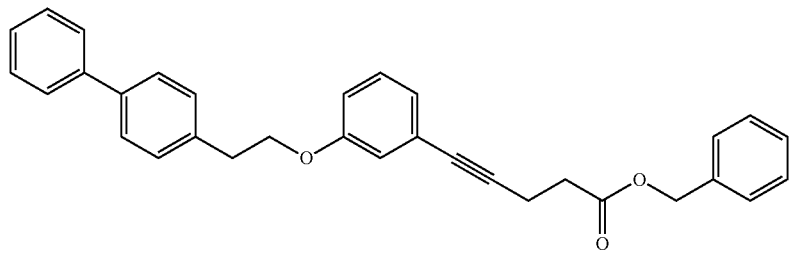 [SMILES: O=C(CCC#Cc1cccc(OCCc2ccc(-c3ccccc3)cc2)c1)OCc1ccccc1]

A mixture of Example compound 120-1 (200 mg), phenylboronic acid (63 mg), XPhos-Pd-G2 (34 mg), tripotassium phosphate (275 mg), tetrahydrofuran (4.3 mL) and water (2.15 mL) was stirred at 60° C. for 3 hr. To the reaction mixture were added saturated brine and diethyl ether, and the mixture was stirred. The organic layer was separated by a Phase-separator (registered trade mark), and concentrated under reduced pressure. The obtained residue was purified by silica gel column chromatography (hexane:ethyl acetate=100:0-90:10) to give the title compound (118 mg) as a pale-yellow oil.

MS (APCI) m/z: 478.1[M+NH$_4$]$^+$ (120-3) 2-[(5-{3-[2-(Biphenyl-4-yl)ethoxy]phenyl}pentanoyl) (4-methoxybenzyl)amino]ethyl dihydrogen phosphate ammonium salt (Example compound 120)

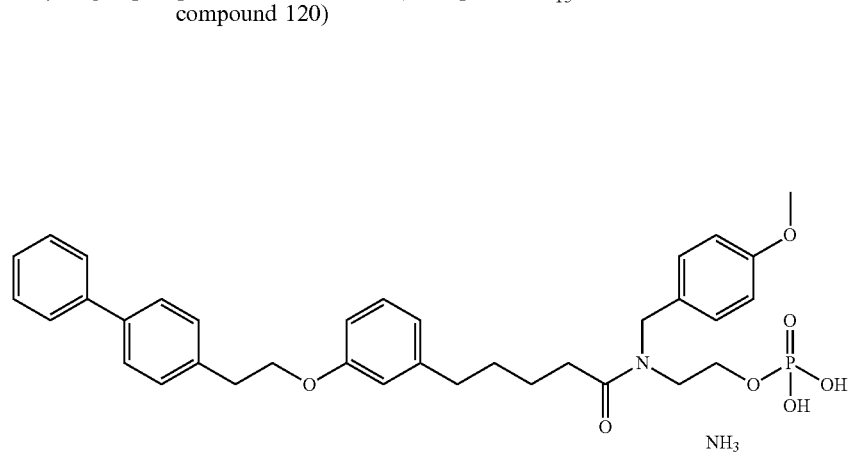

In Example 59, the reaction and treatment similar to those in (59-3)-(59-4) were performed using Example compound 120-2 instead of Example compound 59-2 and Reference Example compound 7 instead of Reference Example compound 1 to give the title compound (54 mg) as a pale-yellow viscous oil.

MS (APCI) m/z: 616.3[M−H]$^−$

Example 121

(121-1) 1-(3-Buten-1-yl)-4-iodobenzene (Example compound 121-1)

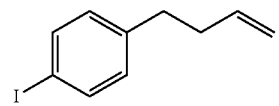

To allylmagnesium bromide (36.1 mL) was added under ice-cooling a solution of 4-iodobenzyl bromide (5.00 g) in tetrahydrofuran (8.4 mL), and the mixture was stirred at room temperature overnight. Water was added to the reaction mixture, and the mixture was extracted with ethyl acetate. The organic layer was dried over anhydrous sodium sulfate, the desiccant was filtered off, and the filtrate was concentrated under reduced pressure. The obtained residue was purified by silica gel column chromatography (hexane only) to give the title compound (4.34 g) as a colorless oil.

(121-2) Ethyl (trans)-2-[2-(4-iodophenyl) ethyl]cyclopropanecarboxylate (Example compound 121-2A) and ethyl (cis)-2-[2-(4-iodophenyl)ethyl]cyclopropanecarboxylate (Example compound 121-2B)

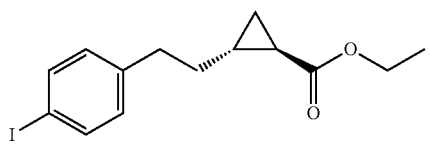

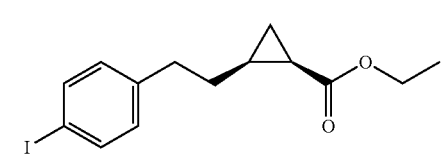

In Example 116, the reaction and treatment similar to those in (116-1) were performed using 1-(3-buten-1-yl)-4-iodobenzene instead of 1-bromo-4-ethenylbenzene to give Example compound 121-2A (2.57 g) and Example compound 121-2B (2.17 g) as colorless oils. MS (APCI) m/z: 345.0[M+H]$^+$ (121-3) 2-[{(trans)-2-[2-(4-Heptylphenyl)ethyl]cyclopropyl}carbonyl)(4-methoxybenzyl)amino]ethyl dihydrogen phosphate ammonium salt (Example compound 121)

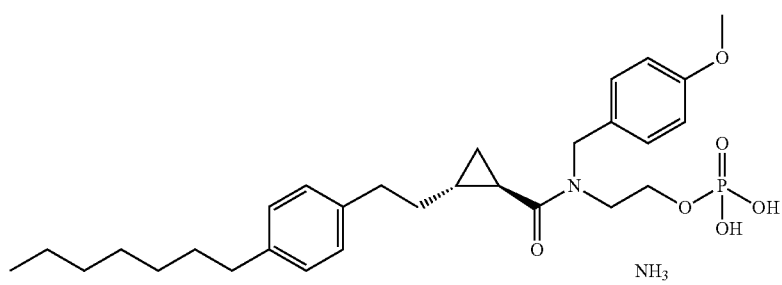

In Example 116, the reaction and treatment similar to those in (116-5)-(116-8) were performed using Example compound 121-2A instead of Example compound 116-4 to give the title compound (66 mg) as a pale-yellow viscous oil.
MS (APCI) m/z: 532.2[M+H]$^+$ Example 122

(122-1) 2-[({(cis)-2-[2-(4-Heptylphenyl)ethyl]cyclopropyl}carbonyl) (4-methoxybenzyl)amino]ethyl dihydrogen phosphate ammonium salt (Example compound 122)

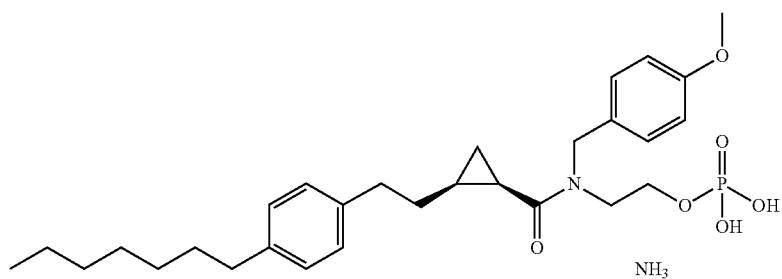

In Example 116, the reaction and treatment similar to those in (116-5)-(116-8) were performed using Example compound 121-2B instead of Example compound 116-4 to give the title compound (26 mg) as a pale-yellow viscous oil.
MS (APCI) m/z: 532.1[M+H]$^+$

Example 123

(123-1) 2-[(5-{4-[2-(Biphenyl-4-yl)ethoxy] phenyl}pentanoyl) (4-methoxybenzyl)amino]ethyl dihydrogen phosphate ammonium salt (Example compound 123)

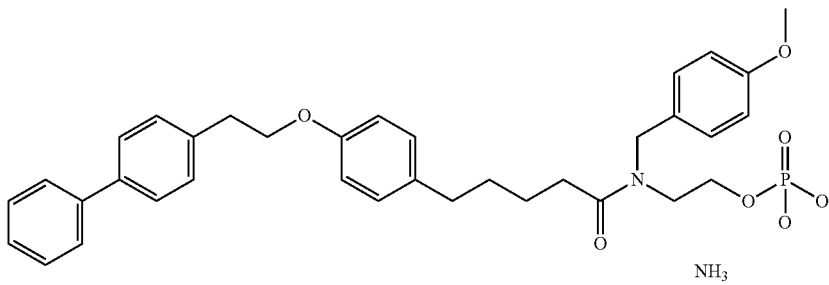

In Example 120, the reaction and treatment similar to those in (120-1)-(120-3) were performed using Example compound 106-1 instead of Example compound 113-1 to give the title compound (74 mg) as a colorless viscous oil.
MS (APCI) m/z: 616.3[M−H]$^-$

Example 124

(124-1) 2-[(5-{3-[4-(Biphenyl-4-yl)butoxy] phenyl}pentanoyl) (4-methoxybenzyl)amino]ethyl dihydrogen phosphate ammonium salt (Example compound 124)

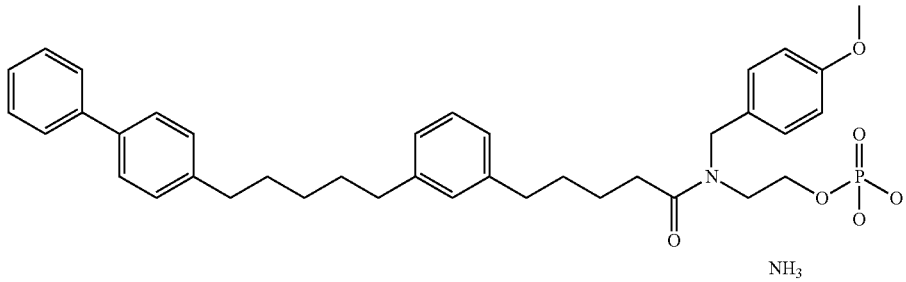

In Example 120, the reaction and treatment similar to those in (120-1)-(120-3) were performed using 4-(4-bromophenyl)butan-1-ol instead of 2-(4-bromophenyl)ethanol to give the title compound (30 mg) as a pale-yellow viscous oil.
MS (APCI) m/z: 644.3[M−H]⁻

Example 125

(125-1) 2-[(5-{4-[4-(Biphenyl-4-yl)butoxy] phenyl}pentanoyl) (4-methoxybenzyl)amino]ethyl dihydrogen phosphate ammonium salt (Example compound 125)

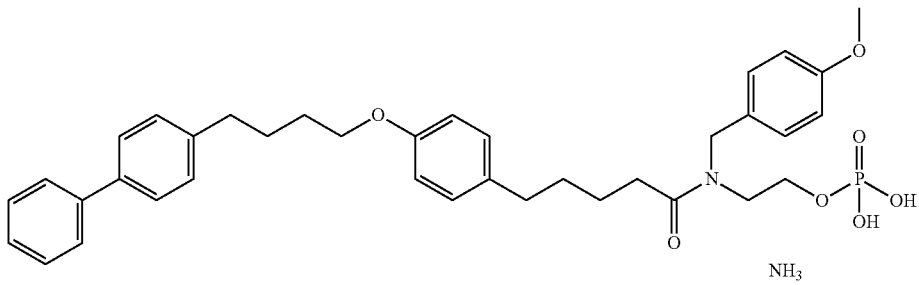

In Example 120, the reaction and treatment similar to those in (120-1)-(120-3) were performed using Example compound 106-1 instead of Example compound 113-1 and 4-(4-bromophenyl)butan-1-ol instead of 2-(4-bromophenyl)ethanol to give the title compound (22 mg) as a pale-yellow viscous oil.
MS (APCI) m/z: 644.3[M−H]⁻

Example 126

(126-1) 2-[{3-[3-(Decyloxy)phenyl]propanoyl}(isothiazol-5-ylmethyl)amino]ethyl dihydrogen phosphate ammonium salt (Example compound 126)

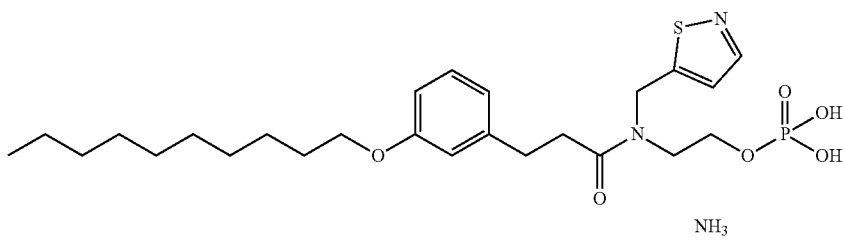

In Example 58, the reaction and treatment similar to those in (58-1)-(58-3) were performed using isoxazole-5-carbaldehyde instead of, 4-pyridine carbaldehyde to give the title compound (181 mg) as a pale-yellow viscous oil.
MS (APCI) m/z: 527.1[M+H]$^+$ Example 127

(127-1) 2-[{6-[3-(5-Cyclohexylpentyl)phenyl]hexanoyl}(4-methoxybenzyl)amino]ethyl dihydrogen phosphate ammonium salt (Example compound 127)

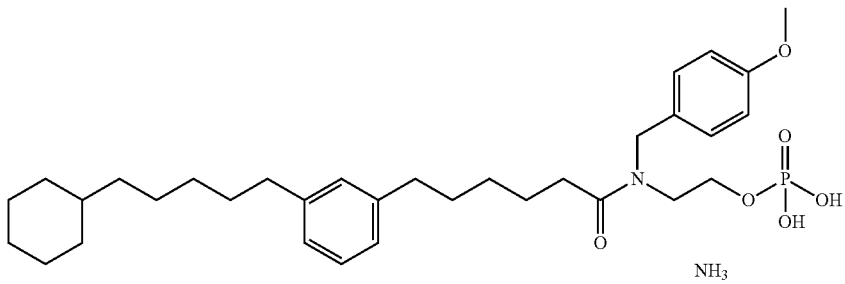

In Example 59, the reaction and treatment similar to those in (59-2)-(59-4) were performed using Example compound 76-1 instead of Example compound 59-1, 4-pentyn-1-yl cyclohexane instead of 1-heptyne, and Reference Example compound 7 instead of Reference Example compound 1 to give the title compound (15 mg) as a colorless viscous oil.
MS (APCI) m/z: 588.2[M+H]$^+$ Example 128

(128-1) 2-{[9-(4-Butylphenyl)nonanoyl](4-methoxybenzyl)amino}ethyl dihydrogen phosphate ammonium salt (Example compound 128)

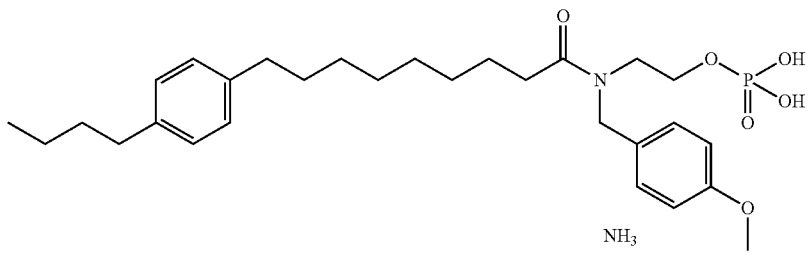

In Example 70, the reaction and treatment similar to those in (70-4) were performed using Reference Example compound 6 instead of Reference Example compound 2 to give the title compound (12 mg) as a colorless solid. MS (APCI) m/z: 534.1[M+H]$^+$ Example 129

(129-1) 2-[{6-[3-(4-Cyclohexylbutyl)phenyl]hexanoyl}(4-methoxybenzyl)amino]ethyl dihydrogen phosphate ammonium salt (Example compound 129)

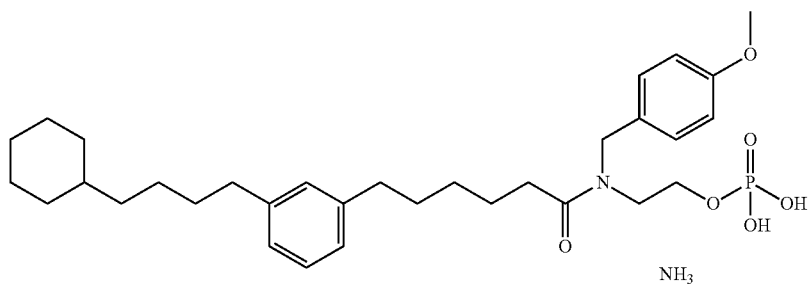

In Example 59, the reaction and treatment similar to those in (59-2)-(59-4) were performed using Example compound 76-1 instead of Example compound 59-1 and 3-butyn-1-yl cyclohexane instead of 1-heptyne, and Reference Example compound 7 instead of Reference Example compound 1 to give the title compound (46 mg) as a pale-yellow viscous oil.

MS(ESI) m/z: 572.6[M−H]$^-$

Example 130

(130-1) Ethyl (trans)-2-(3-bromophenyl)cyclopropanecarboxylate (Example compound 130-1A) and ethyl (cis)-2-(3-bromophenyl) cyclopropanecarboxylate (Example compound 130-1B)

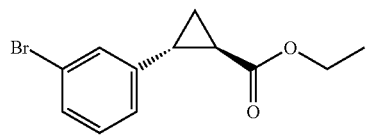

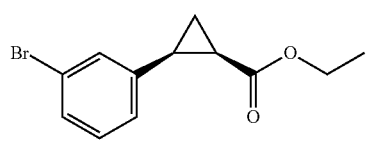

In Example 116, the reaction and treatment similar to those in (116-1) were performed using 1-bromo-3-ethenylbenzene instead of 1-bromo-4-ethenylbenzene to give Example compound 130-1A (4.49 g) and Example compound 130-1B (3.82 g) as colorless oils. MS (APCI) m/z: 269.0[M+H]$^+$ (130-2) Ethyl (trans)-2-(3-hydroxyphenyl)cyclopropane carboxylate (Example compound 130-2)

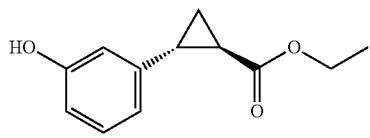

A mixture of Example compound 130-1A (350 mg), tetrahydroxydiborane (350 mg), XPhos-Pd-G2 (51 mg), potassium acetate (383 mg) and ethanol (13.0 mL) was stirred at 80° C. for 5 hr. To the reaction mixture were added water and ethyl acetate, and the mixture was stirred. The organic layer was separated by a Phase-separator (registered trade mark), and concentrated under reduced pressure. To the residue were added water (2.6 mL), ammonium hydrogen carbonate (103 mg) and 30% hydrogen peroxide (0.26 mL), and the mixture was stirred at room temperature overnight. To the reaction mixture were added saturated aqueous ammonium chloride solution and ethyl acetate, and the mixture was stirred. The organic layer was separated by a Phase-separator (registered trade mark), and concentrated under reduced pressure. The obtained residue was purified by silica gel column chromatography (hexane:ethyl acetate=80:20-60:40) to give the title compound (327 mg) as an orange oil.

MS (APCI) m/z: 204.9[M−H]$^-$

(130-3) (trans)-2-(3-Hydroxyphenyl)cyclopropanecarboxylic acid (Example compound 130-3)

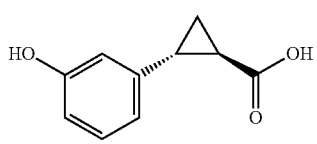 [SMILES: O=C(O)[C@@H]1C[C@H]1c1cccc(O)c1]

To a solution of Example compound 130-2 (320 mg) in ethanol (3.87 mL) and tetrahydrofuran (3.87 mL) was added 1N aqueous sodium hydroxide solution (6.21 mL), and the mixture was stirred at room temperature for 3 hr. To the reaction mixture were added saturated aqueous sodium hydrogen carbonate solution and chloroform, and the mixture was stirred. The organic layer was separated by a Phase-separator (registered trade mark), and concentrated under reduced pressure. The obtained residue was purified by silica gel column chromatography (hexane:ethyl acetate=100:0-90:10) to give the title compound (247 mg) as a pale-yellow oil.

MS (APCI) m/z: 176.8[M−H]$^{-}$

(130-4) Di-tert-butyl 2-[{[(trans)-2-(3-hydroxyphenyl)cyclopropyl]carbonyl}(4-methoxybenzyl)amino}ethyl phosphate (Example compound 130-4)

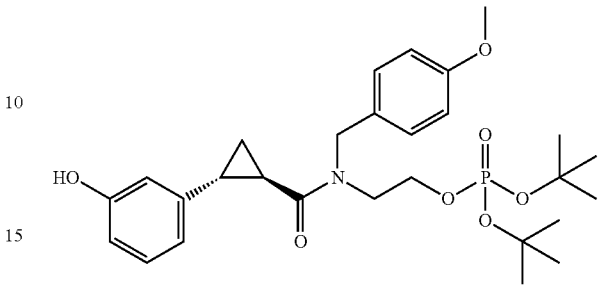

To a solution of Example compound 130-3 (120 mg) in N,N-dimethylformamide (6.7 mL) were added N,N-diisopropylethylamine (0.35 mL), Reference Example compound 7 (302 mg) and HATU (384 mg), and the mixture was stirred at room temperature overnight. To the reaction mixture were added water and ethyl acetate, and the mixture was stirred. The organic layer was separated by a Phase-separator (registered trade mark), and concentrated under reduced pressure. The obtained residue was purified by silica gel column chromatography (chloroform:methanol=100:0-90:10) to give the title compound (261 mg) as an orange oil.

MS (APCI) m/z: 534.0[M+H]$^{+}$

(130-5) Di-tert-butyl 2-[({(trans)-2-[3-(decyloxy)phenyl]cyclopropyl}carbonyl) (4-methoxybenzyl)amino]ethyl phosphate (Example compound 130-5)

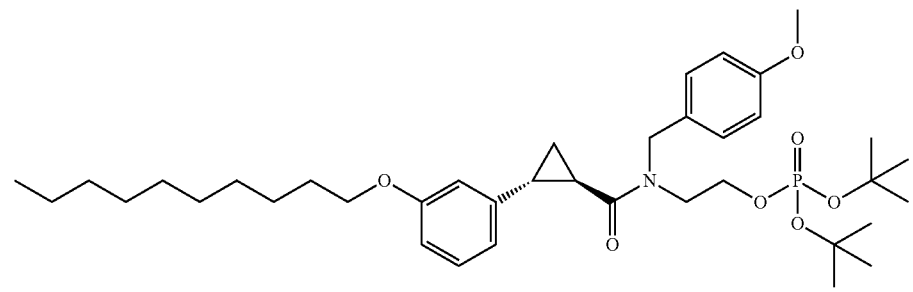 [SMILES: CCCCCCCCCCOc1cccc([C@@H]2C[C@H]2C(=O)N(CCOP(=O)(OC(C)(C)C)OC(C)(C)C)Cc2ccc(OC)cc2)c1]

A mixture of Example compound 130-4 (125 mg), 1-bromodecane (0.053 mL), cesium carbonate (153 mg) and N,N-dimethylformamide (2.34 mL) was stirred at room temperature overnight. To the reaction mixture were added water and ethyl acetate, and the mixture was stirred. The organic layer was separated by a Phase-separator (registered trade mark), and concentrated under reduced pressure. The obtained residue was purified by silica gel column chromatography (hexane:ethyl acetate=60:40-40:60) to give the title compound (73 mg) as a pale-yellow oil. MS (APCI) m/z: 674.0[M+H]$^+$ (130-6) 2-[({(trans)-2-[3-(Decyloxy)phenyl]cyclopropyl}carbonyl)(4-methoxybenzyl)amino]ethyl dihydrogen phosphate ammonium salt (Example compound 130)

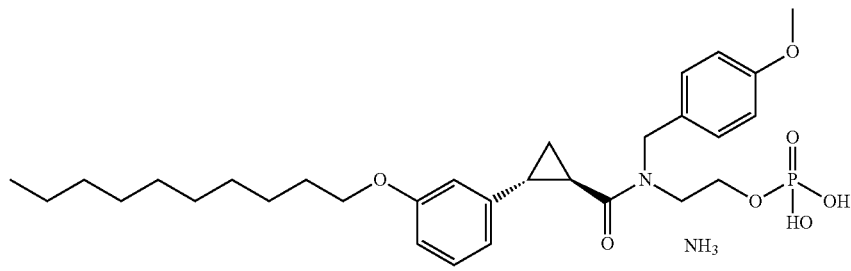

To a solution of Example compound 130-5 (68 mg) in dichloromethane (1.0 mL) was added trifluoroacetic acid (0.20 mL), and the mixture was stirred at room temperature for 1 hr. The reaction mixture was concentrated under reduced pressure. The obtained residue was purified by preparative HPLC (10 mM aqueous ammonium carbonate solution-acetonitrile) to give the title compound (26 mg) as a colorless solid.
MS(ESI) m/z: 560.6[M−H]$^−$ Example 131

(131-1) 2-[(4-Methoxybenzyl){[(trans)-2-{3-[(7-phenylheptyl)oxy]phenyl}cyclopropyl]carbonyl}amino]ethyl dihydrogen phosphate ammonium salt (Example compound 131)

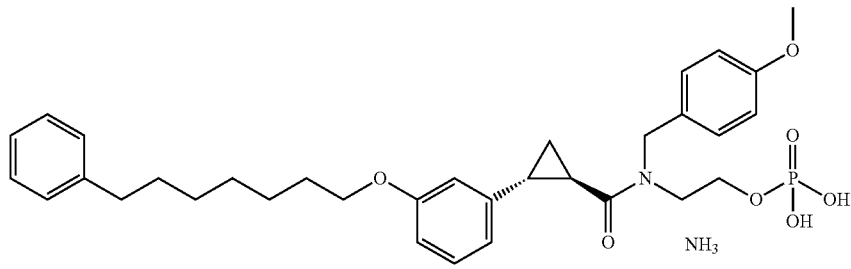

In Example 130, the reaction and treatment similar to those in (130-5)-(130-6) were performed using 1-bromo-7-phenylheptane instead of 1-bromodecane to give the title compound (22 mg) as a colorless oil. MS(ESI) m/z: 594.6 [M−H]⁻

Example 132

(132-1) 3-[3-(Decyloxy)phenyl]-1-(3-hydroxyazetidin-1-yl)propan-1-one (Example compound 132-1)

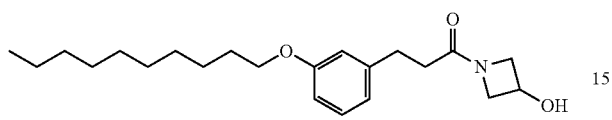

In Example 16, the reaction and treatment similar to those in (16-3) were performed using Reference Example compound 5 instead of Example compound 16-2 to give the title compound (589 mg) as a pale-yellow solid. MS (APCI) m/z: 362.3[M+H]⁺

(132-2) Diethyl {[(1-{3-[3-(decyloxy)phenyl]propanoyl}azetidin-3-yl)oxy]methyl}phosphonate (Example compound 132-2)

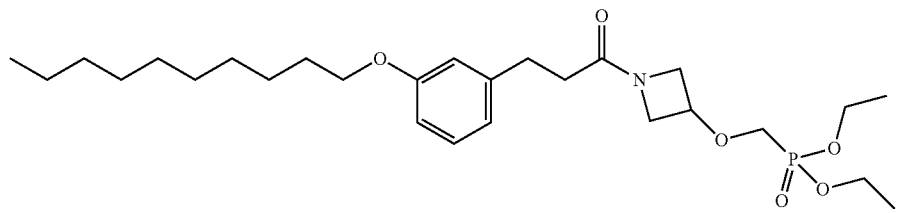 [SMILES: CCCCCCCCCCOc1cccc(CCC(=O)N2CC(OCP(=O)(OCC)OCC)C2)c1]

To a suspension of sodium hydride (50 mg) in tetrahydrofuran (8.3 mL) was added dropwise under ice-cooling a solution of Example compound 132-1 in tetrahydrofuran (3 mL), and the mixture was stirred for 20 min. Successively, a solution of (diethoxyphosphoryl)methyl trifluoromethanesulfonate (498 mg) in tetrahydrofuran (3 mL) was added dropwise thereto, and the mixture was stirred with ice-cooling for 40 min. Water was added to the reaction mixture, and the mixture was extracted with ethyl acetate, washed with saturated brine, dried over anhydrous sodium sulfate, and filtered. The solvent was evaporated under reduced pressure. The obtained residue was purified by silica gel column chromatography (ethyl acetate:methanol=100:0-89:11) to give the title compound (365 mg) as a colorless oil. MS (APCI) m/z: 512.4[M+H]⁺

(132-3) {[(1-{3-[3-(Decyloxy)phenyl]propanoyl}azetidin-3-yl)oxy]methyl}phosphonic acid ammonium salt (Example compound 132)

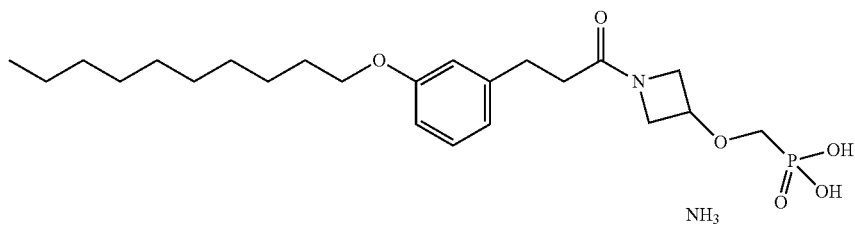

To Example compound 132-2 (357 mg) was added acetonitrile (3.5 mL), bromotrimethylsilane (922 mL) was added under ice-cooling, and the mixture was stirred at room temperature for 15 hr. Under ice-cooling, to the reaction mixture was added methanol (3 mL), and the mixture was stirred at room temperature for 30 min, and purified by preparative HPLC (10 mM aqueous ammonium carbonate solution-acetonitrile) to give the title compound (18 mg) as a pale-brown solid.

MS (APCI) m/z: 454.2[M−H]−

Example 133

(133-1) 1-Iodo-3-(undecyloxy)benzene (Example compound 133-1)

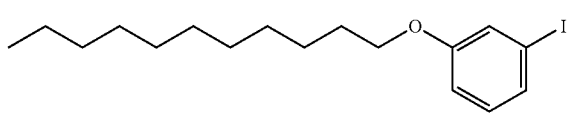 [SMILES: CCCCCCCCCCCOc1cccc(I)c1]

A mixture of 3-iodophenol (1.50 g), 1-bromoundecane (1.67 mL), cesium carbonate (4.44 g) and N,N-dimethylformamide (22.7 mL) was stirred at room temperature for 2 hr. Water was added to the reaction mixture, and the mixture was extracted with ethyl acetate. The organic layer was washed with saturated brine, and dried over anhydrous sodium sulfate. The desiccant was filtered off, and the filtrate was concentrated under reduced pressure. The obtained residue was purified by silica gel column chromatography (hexane:ethyl acetate=100:0-98:2) to give the title compound (2.66 g) as a colorless oil.

(133-2) 2-Fluoro-4-[3-(undecyloxy)phenyl]pyridine (Example compound 133-2)

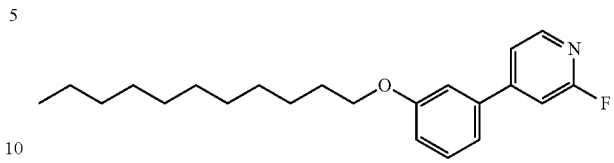

A mixture of Example compound 133-1 (800 mg), bis(pinacolato)diboron (651 mg), potassium acetate (629 mg), 1,1'-(diphenylphosphino)ferrocene-palladium (II) dichloromethane complex (87 mg) and 1,4-dioxane (12 mL) was stirred in a microwave reactor (Initiator, manufactured by Biotage) at 120° C. for 2 hr. To the mixture were added 4-bromo-2-fluoropyridine (527 mg), 1,1'-(diphenylphosphino)ferrocene-palladium (II) dichloromethane complex (87 mg), sodium carbonate (680 mg) and water (2.0 mL), and the mixture was stirred in a microwave reactor (Initiator, manufactured by Biotage) at 120° C. for 2 hr. Water was added to the reaction mixture, and the mixture was extracted with ethyl acetate. The organic layer was washed with saturated brine, and dried over anhydrous sodium sulfate. The desiccant was filtered off, and the filtrate was concentrated under reduced pressure. The obtained residue was purified by silica gel column chromatography (hexane:ethyl acetate=100:0-90:10) to give the title compound (342 mg) as a colorless oil.

MS (APCI) m/z: 344.2[M+H]+

(133-3) (2R)-1-({4-[3-(Undecyloxy)phenyl]pyridin-2-yl}amino)propan-2-ol (Example compound 133-3)

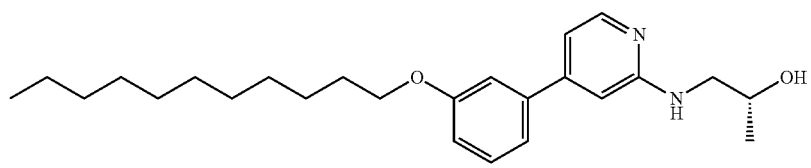 [SMILES: CCCCCCCCCCCOc1cccc(-c2ccnc(NC[C@@H](C)O)c2)c1]

To a solution of Example compound 133-2 (335 mg) in dimethylsulfoxide (3 mL) were added N,N-diisopropylethylamine (0.25 mL) and (2R)-1-aminopropan-2-ol (205 mg), and the mixture was stirred in a microwave reactor (Initiator, manufactured by Biotage) at 150° C. for 1 hr. To the reaction mixture was added N,N-diisopropylethylamine (0.084 mL), (2R)-1-aminopropan-2-ol (205 mg) was added, and the mixture was stirred in a microwave reactor at 150° C. for 1 hr. Furthermore, (2R)-1-aminopropan-2-ol (147 mg) was added to the mixture, and the mixture was stirred in a microwave reactor at 150° C. for 4 hr. Water was added to the reaction mixture, and the mixture was extracted with ethyl acetate. The organic layer was washed with saturated brine, and dried over anhydrous sodium sulfate. The desiccant was filtered off, and the filtrate was concentrated under reduced pressure. The obtained residue was purified by silica gel column chromatography (hexane:ethyl acetate=70:30-40:60) to give the title compound (189 mg) as a pale-yellow solid. MS (APCI) m/z: 399.3[M+H]$^+$ (133-4) Dibenzyl (2R)-1-({4-[3-(undecyloxy)phenyl]pyridin-2-yl}amino)propan-2-yl phosphate (Example compound 133-4)

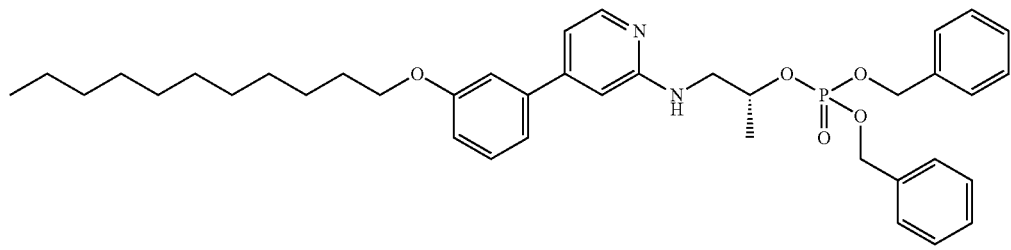 [SMILES: CCCCCCCCCCCOc1cccc(-c2ccnc(NC[C@@H](C)OP(=O)(OCc3ccccc3)OCc3ccccc3)c2)c1]

To a solution of Example compound 133-3 (184 mg) in dichloromethane solution (2 mL) and acetonitrile (0.5 mL) was added under ice-cooling 1H-tetrazole (65 mg), dibenzyl N,N-diisopropyl phosphoramidite (319 mg) was added dropwise, and the mixture was stirred at room temperature for 6 hr. The reaction mixture was ice-cooled, 30% aqueous hydrogen peroxide (0.095 mL) was added dropwise, and the mixture was stirred at room temperature for 1 hr. Under ice-cooling, saturated aqueous sodium thiosulfate solution (1 mL) was added thereto, and the mixture was stirred at room temperature. Then, water was added to the mixture, and the mixture was extracted with ethyl acetate, washed successively with saturated aqueous sodium hydrogen carbonate and saturated brine, dried over anhydrous sodium sulfate, and filtered. The solvent was evaporated, and the obtained residue was purified by silica gel column chromatography (hexane:ethyl acetate=70:30-40:60) to give the title compound (329 mg) as a pale-yellow oil.
MS (APCI) m/z: 659.4[M+H]$^+$ (133-5) (2R)-1-({4-[3-(Undecyloxy)phenyl]pyridin-2-yl}amino)propan-2-yl dihydrogen phosphate (Example compound 133)

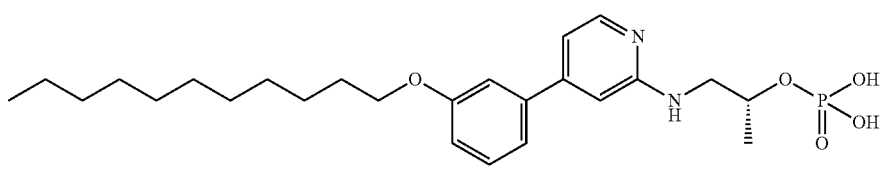 [SMILES: CCCCCCCCCCCOc1cccc(-c2ccnc(NC[C@@H](C)OP(=O)(O)O)c2)c1]

To a solution of Example compound 133-4 (323 mg) in methanol (5 mL) was added 10% palladium carbon (162 mg), and the mixture was stirred under a hydrogen atmosphere at room temperature for 4 hr. After filtering off the insoluble material in the reaction mixture with diatomaceous earth, the filtrate was concentrated under reduced pressure. After washing with sonicating in suspension in a mixed solvent of dimethylformamide and diethyl ether, the solid was collected by filtration to give the title compound (117 mg) as a white solid.

MS (APCI) m/z: 479.3[M+H]$^+$

Example 134

(134-1) 4,4,5,5-Tetramethyl-2-[3-(undecyloxy)phenyl]-1,3,2-dioxaborolane (Example compound 134-1)

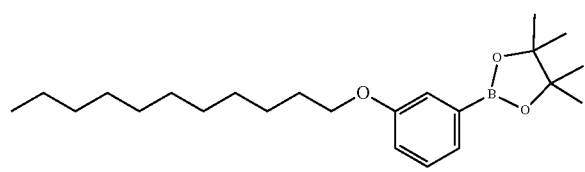 [SMILES: CCCCCCCCCCCOc1cccc(B2OC(C)(C)C(C)(C)O2)c1]

A mixture of 3-(4,4,5,5-tetramethyl-1,3,2-dioxaboran-2-yl)phenol (4.70 g), 1-bromoundecane (4.76 mL), cesium carbonate (13.9 g) and N,N-dimethylformamide (42.71 mL) was stirred at room temperature overnight. Water was added to the reaction mixture, and the mixture was extracted with diethyl ether. The organic layer was washed with water and saturated brine, and dried over sodium sulfate. The desiccant was filtered off, and the filtrate was concentrated under reduced pressure. The obtained residue was purified by NH silica gel column chromatography (hexane:ethyl acetate=100:0-90:10) to give the title compound (5.78 g) as a colorless oil.

MS (APCI) m/z: 375.3[M+H]$^+$ (134-2) 2-Chloro-4-[3-(undecyloxy)phenyl]pyrimidine (Example compound 134-2)

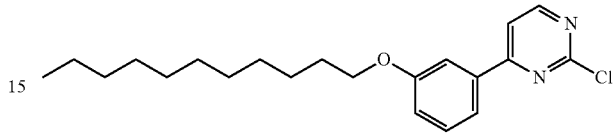

A mixture of Example compound 134-1 (1.65 g), dichloropyridine (657 mg), 1,1'-(diphenylphosphino)ferrocene-palladium (II) dichloromethane complex (180 mg), sodium carbonate (1.40 g), 1,4-dioxane (22 mL), and water (7.34 mL) was stirred at 100° C. for 3 hr. To the reaction mixture was added saturated brine, and the mixture was extracted with ethyl acetate. The organic layer was dried over sodium sulfate. The desiccant was filtered off, and the filtrate was concentrated under reduced pressure. The obtained residue was purified by silica gel column chromatography (hexane:ethyl acetate=100:0-88:12) to give the title compound (1.11 g) as a white solid.

MS(ESI) m/z: 361.3[M+H]$^+$ (134-3) (2R)-1-({4-[3-(Undecyloxy)phenyl]pyrimidin-2-yl}amino)propan-2-ol (Example compound 134-3)

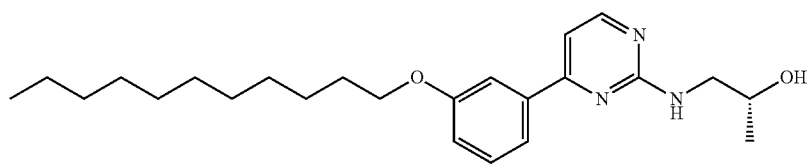 [SMILES: CCCCCCCCCCCOc1cccc(-c2ccnc(NC[C@@H](C)O)n2)c1]

To a solution of Example compound 134-2 (200 mg) in N-methylpyrrolidone (3.0 mL) were added N,N-diisopropylethylamine (0.144 mL) and (2R)-1-aminopropan-2-ol (62 mg), and the mixture was stirred in a microwave reactor (Initiator, manufactured by Biotage) at 120° C. for 1 hr. Water was added to the reaction mixture, and the mixture was extracted with ethyl acetate. The organic layer was washed with saturated brine, and dried over anhydrous sodium sulfate. The desiccant was filtered off, and the filtrate was concentrated under reduced pressure. The obtained residue was purified by silica gel column chromatography (hexane:ethyl acetate=70:30-40:60) to give the title compound (163 mg) as a white solid.

MS(ESI) m/z: 400.4[M+H]$^+$ (134-4) (2R)-1-({4-[3-(Undecyloxy)phenyl]pyrimidinyl}amino)propan-2-yl dihydrogen phosphate (Example compound 134)

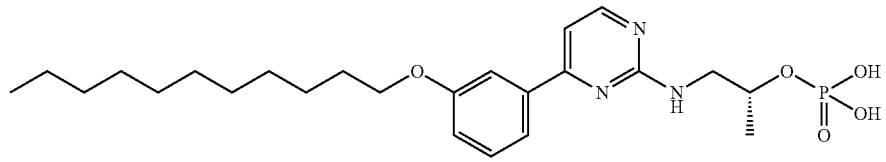 [SMILES: CCCCCCCCCCCOc1cccc(-c2ccnc(NC[C@@H](C)OP(=O)(O)O)n2)c1]

Example compound 134-3 (160 mg) was dissolved in dichloromethane (2.0 mL) and acetonitrile (0.5 mL), 1H-tetrazole (56 mg) was added under ice-cooling, di-tert-butyl N,N-diisopropyl phosphoramidite (0.253 mL) was added dropwise, and the mixture was stirred at room temperature for 2 hr. Under ice-cooling, tert-butyl hydroperoxide (0.15 mL) was added dropwise thereto, and the mixture was stirred at room temperature for 1 hr. Under ice-cooling, 10% thioanhydrous sodium sulfate aqueous solution (1 mL) was added to the mixture, and the mixture was extracted with water and ethyl acetate, washed with saturated brine, and dried over anhydrous sodium sulfate. The solvent was evaporated under reduced pressure. The residue was purified by silica gel column chromatography (hexane:ethyl acetate=70:30-40:60). The obtained colorless oil (198 mg) was dissolved in dichloromethane (4.0 mL), trifluoroacetic acid (0.256 mL) was added dropwise under ice-cooling, and the mixture was stirred at room temperature for 2 hr. The solvent was evaporated under reduced pressure, diethyl ether was added to the precipitated solid, and the mixture was washed with sonicating in suspension, collected by filtration, and dried under reduced pressure to give the title compound (86 mg) as a pale-yellow solid. MS (APCI) m/z: 480.4[M+H]$^+$ Example 135

(135-1) (2R)-1-({4-[3-(Undecyloxy)phenyl]pyrimidin-2-yl}oxy)propan-2-ol (Example compound 135-1)

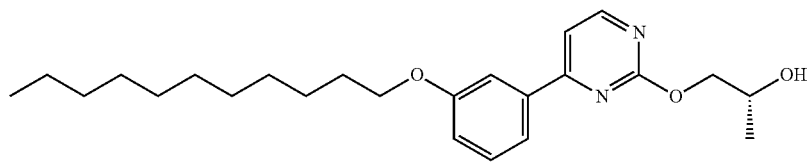 [SMILES: CCCCCCCCCCCOc1cccc(-c2ccnc(OC[C@@H](C)O)n2)c1]

To a solution of (R)-(−)-1,2-propanediol (38 mg) in N,N-dimethylformamide (2.1 mL) was added sodium hydride (20 mg), and the mixture was stirred at room temperature for 15 min. To the reaction mixture was added Example compound 134-2 (150 mg), and the mixture was stirred at room temperature overnight. Water was added to the reaction mixture, and the mixture was extracted with ethyl acetate. The organic layer was dried over sodium sulfate, the desiccant was filtered off, and the filtrate was concentrated under reduced pressure. The obtained residue was purified by silica gel column chromatography (hexane:ethyl acetate=80:20-50:50) to give the title compound (99 mg) as a colorless oil. MS(ESI) m/z: 401.5[M+H]$^+$ (135-2) (2R)-1-({4-[3-(Undecyloxy)phenyl]pyrimidin-2-yl}oxy)propan-2-yl dihydrogen phosphate ammonium salt (Example compound 135)

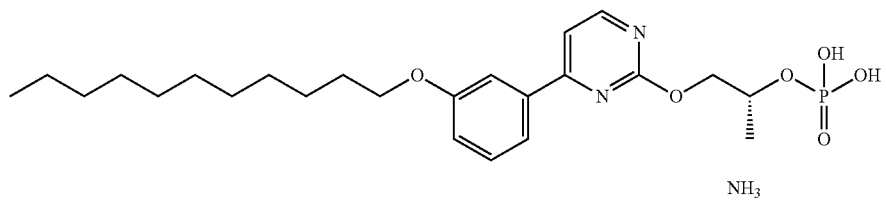

In Example 36, the reaction and treatment similar to those in (36-2)-(36-3) were performed using Example compound 135-1 instead of Example compound 36-1 to give the title compound (50 mg) as a white solid. MS(ESI) m/z: 481.4 [M+H]$^+$ Example 136

(136-1) 4-[3-(Undecyloxy)phenyl]pyridine (Example compound 136-1)

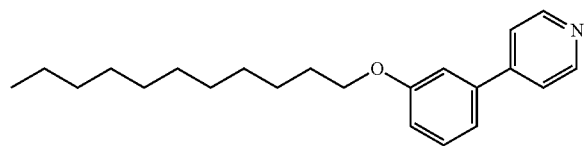 [SMILES: CCCCCCCCCCCOc1cccc(-c2ccncc2)c1]

A mixture of 3-(4-pyridyl)phenol (2.50 g), 1-bromodecane (3.58 mL), cesium carbonate (9.51 g) and N,N-dimethylformamide (36 mL) was stirred at 70° C. for 3 hr. Water was added to the reaction mixture, and the mixture was extracted with diethyl ether. The organic layer was washed with water and saturated brine, and dried over sodium sulfate. The desiccant was filtered off, and the filtrate was concentrated under reduced pressure. The obtained residue was purified by silica gel column chromatography (hexane:ethyl acetate=90:10-65:35) to give the title compound (4.42 g) as a white solid.
MS(ESI) m/z: 326.3[M+H]$^+$ (136-2) 1-Oxide-4-(3-undecoxyphenyl)pyridin-1-ium (Example compound 136-2)

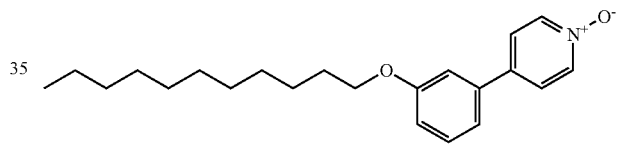

To a solution of Example compound 136-1 (4.40 g) in dichloromethane (45 mL) was added under ice-cooling metachloroperbenzoic acid (5.83 g), and the mixture was stirred at the same temperature for 3 hr. To the reaction mixture were added 1N aqueous sodium hydroxide solution and chloroform, and the mixture was stirred. The organic layer was separated by a Phase-separator (registered trade mark), and concentrated under reduced pressure. The obtained residue was purified by silica gel column chromatography (chloroformmethanol=100:0-90:10), and NH silica gel column chromatography (ethyl acetate:methanol=100:0-95:5) to give the title compound (3.88 g) as a white solid. MS(ESI) m/z: 342.4[M+H]$^+$ (136-3) Di-tert-butyl 2-({4-[3-(undecyloxy)phenyl]pyridin-2-yl}amino)ethyl phosphate (Example compound 136-3)

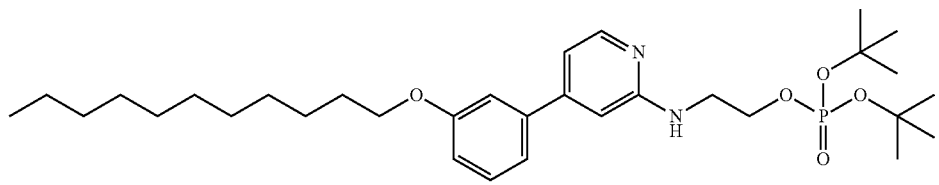 [SMILES: CCCCCCCCCCCOc1cccc(-c2ccnc(NCCOP(=O)(OC(C)(C)C)OC(C)(C)C)c2)c1]

To a solution of Example compound 136-2 (200 mg) in dichloromethane (5.86 mL) were added Reference Example compound 7-2 (178 mg), N,N-diisopropylethylamine (0.355 mL) and bromo(tripyrrolidino)phosphonium hexafluorophosphate (328 mg), and the mixture was stirred at room temperature overnight. To the reaction mixture were added saturated aqueous sodium hydrogen carbonate solution and chloroform, and the mixture was stirred. The organic layer was separated by a Phase-separator (registered trade mark), and concentrated under reduced pressure. The obtained residue was purified by silica gel column chromatography (hexane:ethyl acetate=40:60-15:85) to give the title compound (186 mg) as a yellow oil.

MS(ESI) m/z: 577.6[M+H]$^+$ (136-4) 2-({4-[3-(Undecyloxy)phenyl]pyridin-2-yl}amino)ethyl dihydrogen phosphate ammonium salt (Example compound 136)

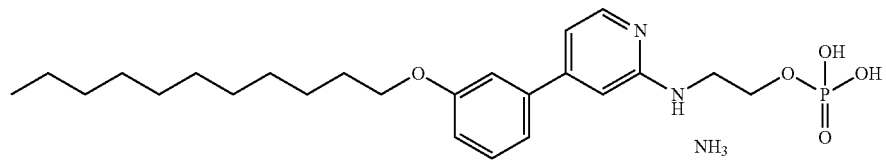

To a solution of Example compound 136-3 (180 mg) in dichloromethane (3.2 mL) was added trifluoroacetic acid (0.624 mL), and the mixture was stirred at room temperature for 3 hr. The reaction mixture was concentrated under reduced pressure. The obtained residue was purified by preparative HPLC (10 mM aqueous ammonium carbonate solution-acetonitrile) to give the title compound (88 mg) as a white solid.

MS(ESI) m/z: 465.4[M+H]$^+$

Example 137

(137-1) (2S)-1-({4-[3-(Undecyloxy)phenyl]pyridin-2-yl}amino)propan-2-yl dihydrogen phosphate (Example compound 137)

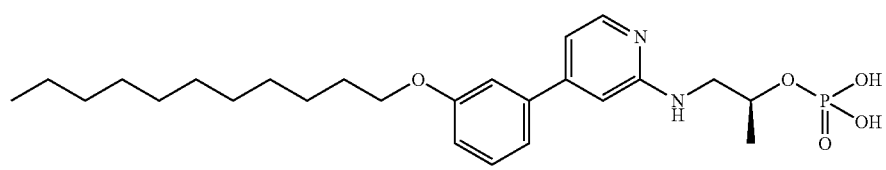 [SMILES: CCCCCCCCCCCOc1cccc(-c2ccnc(NC[C@H](C)OP(=O)(O)O)c2)c1]

In Example 133, the reaction and treatment similar to those in (133-3)-(133-5) were performed using (2S)-1-aminopropan-2-ol instead of (2R)-1-aminopropan-2-ol to give the title compound (122 mg) as a white solid. MS(ESI) m/z: 477.5[M−H]⁻

Example 138

(138-1) O,O-Di-tert-butyl O-[(2R)-1-({4-[3-(undecyloxy)phenyl]pyridin-2-yl}amino)propan-2-yl] phosphorothioate (Example compound 138-1)

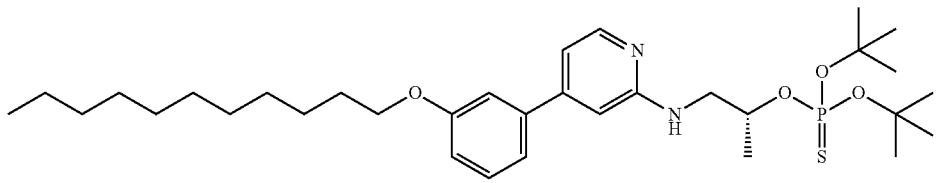 [SMILES: CCCCCCCCCCCOc1cccc(-c2ccnc(NC[C@@H](C)OP(=S)(OC(C)(C)C)OC(C)(C)C)c2)c1]

To a solution of Example compound 133-3 (140 mg) in dichloromethane (3.5 mL) and acetonitrile (3.5 mL) were added 1H-tetrazole (49 mg) and di-tert-butyl N,N-diisopropyl phosphoramidite (0.222 mL), and the mixture was stirred at room temperature for 2 hr. To the reaction mixture was added bis(phenylacetyl)disulfide (531 mg), and the mixture was stirred at room temperature for 1 hr. To the reaction mixture were added saturated brine and ethyl acetate, and the mixture was stirred. The organic layer was separated by a Phase-separator (registered trade mark), and concentrated under reduced pressure. The obtained residue was purified by silica gel column chromatography (hexane:ethyl acetate=90:10-75:25) to give the title compound (213 mg) as a pale-yellow oil.

(138-2) O-[(2R)-1-({4-[3-(Undecyloxy)phenyl]pyridin-2-yl}amino)propan-2-yl] dihydrogen phosphorothioate-ammonium salt (Example compound 138)

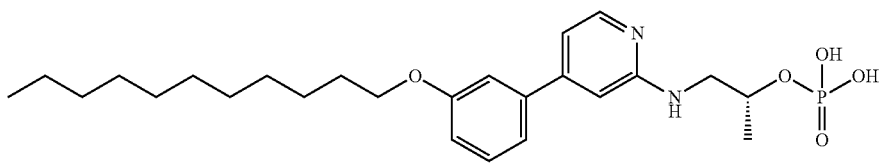

To a solution of Example compound 138-1 (205 mg), p-toluenethiol (420 mg) in dichloromethane (3.4 mL) were added trifluoroacetic acid (0.676 mL) and bromotrimethylsilane (0.446 mL), and the mixture was stirred at room temperature for 3 hr. The reaction mixture Was concentrated under reduced pressure. The obtained residue was purified by preparative HPLC (10 mM aqueous ammonium carbonate solution-acetonitrile) to give the title compound (57 mg) as a white solid.

MS(ESI) m/z: 495.4[M+H]$^+$

Example 139

(139-1) [3-({4-[3-(Undecyloxy)phenyl]pyridin-2-yl}amino)propyl]phosphonic acid (Example compound 139)

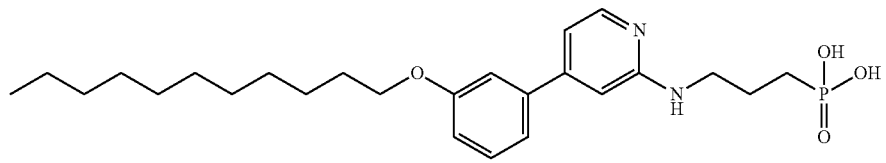 [SMILES: CCCCCCCCCCCOc1cccc(-c2ccnc(NCCCP(=O)(O)O)c2)c1]

To a mixture of Example compound 136-2 (200 mg), diethyl(3-aminopropyl)phosphonate (137 mg), N,N-diisopropylethylamine (0.355 mL), and dichloromethane (5.86 mL) was added bromo(tripyrrolidino)phosphonium hexafluorophosphate (328 mg), and the mixture was stirred at room temperature overnight. To the reaction mixture were added saturated aqueous sodium hydrogen carbonate solution and chloroform, and the mixture was stirred. The organic layer was separated by a Phase-separator (registered trade mark), and concentrated under reduced pressure. The obtained residue was purified by silica gel column chromatography (chloroform:methanol=100:0-95:5) to give a yellow oil (536 mg). To a solution of the obtained oil in dichloromethane (1.9 mL) was added bromotrimethylsilane (0.773 mL), and the mixture was stirred at room temperature for 5 hr. The reaction mixture was concentrated under reduced pressure. The obtained residue was purified by preparative HPLC (10 mM aqueous ammonium carbonate solution-acetonitrile) to give the title compound (44 mg) as a white solid.

MS(ESI) m/z: 463.5[M+H]$^+$

Example 140

(140-1) (2S)-1-({4-[3-(Undecyloxy)phenyl]pyrimidin-2-yl}oxy)propan-2-yl dihydrogen phosphate ammonium salt (Example compound 140)

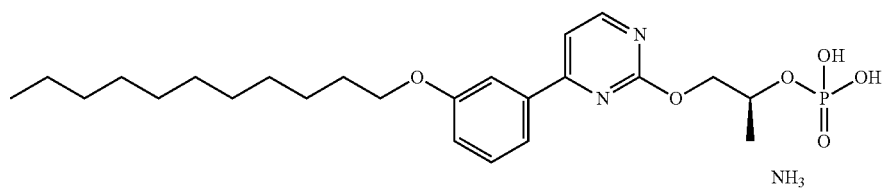

In Example 135, the reaction and treatment similar to those in (135-1)-(135-3) were performed using (S)-(+)-1,2-propanediol instead of (R)-(−)-1,2-propanediol to give the title compound (66 mg) as a white solid.

MS(ESI) m/z: 481.4[M+H]⁺

Example 141

(141-1) 2-Methyl-1-({4-[3-(undecyloxy)phenyl]pyrimidin-2-yl}oxy)propan-2-yl dihydrogen phosphate ammonium salt (Example compound 141)

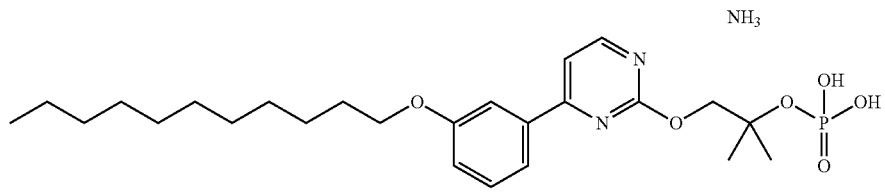

In Example 135, the reaction and treatment similar to those in (135-1)-(149-2) were performed using 2-methylpropane-1,2-diol instead of (R)-(−)-1,2-propanediol to give the title compound (69 mg) as a white solid. MS(ESI) m/z: 495.2[M+H]⁺

Example 142

(142-1) (1S,2R)-2-({4-[3-(Undecyloxy)phenyl]pyridin-2-yl}amino)cyclopentan-1-ol (Example compound 142-1)

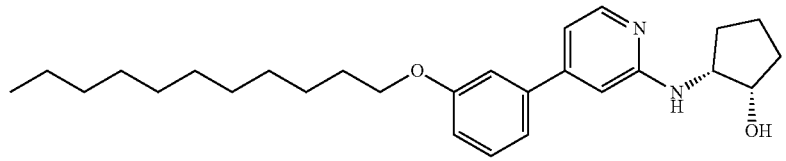 [SMILES: CCCCCCCCCCCOc1cccc(-c2ccnc(N[C@@H]3CCC[C@@H]3O)c2)c1]

To a solution of Example compound 136-2 (200 mg) in dichloromethane (5.86 mL) were added a mixture of cis-(1S,2R)-2-aminocyclopentanol hydrochloride (97 mg), N,N-diisopropylethylamine (0.507 mL) and bromo(tripyrrolidino)phosphonium hexafluorophosphate (328 mg), and the mixture was stirred at room temperature overnight. To the reaction mixture were added saturated aqueous sodium hydrogen carbonate solution and chloroform, and the mixture was stirred. The organic layer was separated by a Phase-separator (registered trade mark), and concentrated under reduced pressure. The obtained residue was purified by silica gel column chromatography (hexane:ethyl acetate=70:30-40:60) to give the title compound (3.88 g) as a yellow viscous oil.

MS(ESI) m/z: 425.4[M+H]⁺

(142-2) Di-tert-butyl (1S,2R)-2-({4-[3-(undecyloxy)phenyl]pyridin-2-yl}amino)cyclopentyl phosphate (Example compound 142-2)

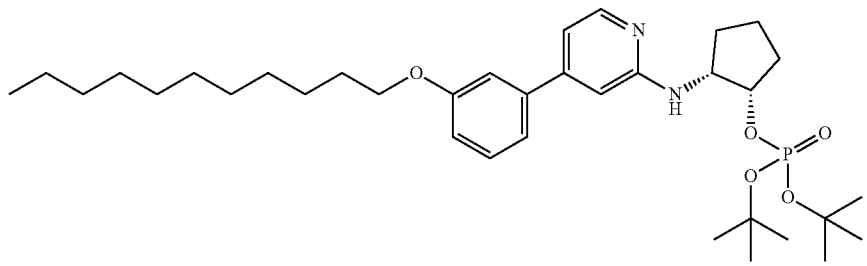 [SMILES: CCCCCCCCCCCOc1cccc(-c2ccnc(N[C@@H]3CCC[C@@H]3OP(=O)(OC(C)(C)C)OC(C)(C)C)c2)c1]

To a mixed solution of Example compound 142-1 (180 mg) in dichloromethane (4.2 mL) and acetonitrile (2.1 mL) were added under ice-cooling 1H-tetrazole (59 mg) and di-tert-butyl N,N-diisopropyl phosphoramidite (0.268 mL), and the mixture was stirred at room temperature for 1 hr. tert-Butyl hydroperoxide (70% aqueous solution, 0.20 mL) was added thereto, and the mixture was stirred at room temperature for 1 hr. To the reaction mixture was added under ice-cooling saturated aqueous sodium thiosulfate solution, and the mixture was stirred. Water was added to the mixture, and the mixture was extracted with ethyl acetate, dried over anhydrous sodium sulfate, and filtered. The solvent was evaporated. The obtained residue was purified by silica gel column chromatography (hexane:ethyl acetate=60:40-30:70) to give the title compound (245 mg) as a white solid.

(142-3) (1S,2R)-2-({4-[3-(Undecyloxy)phenyl]pyridin-2-yl}amino)cyclopentyl dihydrogen phosphate ammonium salt (Example compound 142)

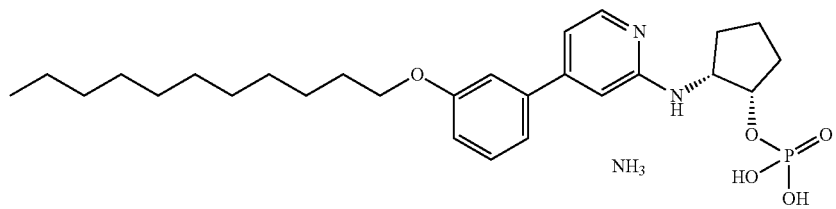

To a solution of Example compound 142-2 (240 mg) in dichloromethane (3.9 mL) was added under ice-cooling trifluoroacetic acid (0.78 mL), and the mixture was stirred at room temperature for 4 hr. The reaction mixture was concentrated under reduced pressure. The obtained residue was purified by preparative HPLC (10 mM aqueous ammonium carbonate solution-acetonitrile) to give the title compound (143 mg) as a yellow solid. MS(ESI) m/z: 505.2[M+H]$^+$ Example 143

(143-1) (1R,2S)-2-({4-[3-(Undecyloxy)phenyl]pyridin-2-yl}amino)cyclopentyl dihydrogen phosphate ammonium salt (Example compound 143)

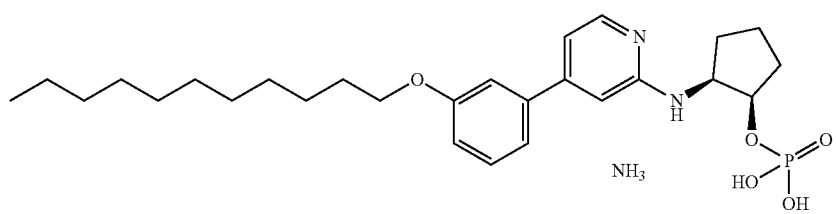

In Example 142, the reaction and treatment similar to those in (142-1)-(142-3) were performed using cis-(1R,2S)-2-aminocyclopentanol hydrochloride instead of cis-(1S,2R)-2-aminocyclopentanol hydrochloride to give the title compound (137 mg) as a yellow solid. MS(ESI) m/z: 505.2[M+H]$^+$ Experimental Example 1

<Experiment Method>
A stably expressing cell line that constantly expresses the human LPA4 receptor and SRE-Luc2 was established by the gene targeting introduction method of the rat hepatocellular carcinoma cell line RH7777 into rRosa26 site. Similarly, stably expressing cell lines for human LPA1 receptor and SRE-Luc2 were also established. Each cell line was seeded on a collagen-coated dish and maintained in culture, and cells were collected with trypsin EDTA and the required number ($5 \times 10^3$ cells/well) was seeded on a 96-well plate. After culturing overnight at 37° C., LPA (Avanti Polar Lipids, Inc.) or each Example compound diluted with an assay medium added or not added with BSA was added, and the cells were cultured at 37° C. for 6 hr. Thereafter, a luciferase detection reagent (Bright-Glo, Promega) was added, and the chemiluminescence amount was quantified with an Envision (registered trade mark) multi-label counter (PerkinElmer) and used as an index of agonist activity.
<Experimental Results>
The results are shown in Table 1. The $EC_{50}$ value of LPA or each Example compound was calculated using the maximum response ($E_x$) Graph pad Prism for Windows ver.5.02 and ver.7.04. % $E_{max}$ was expressed as the ratio of the maximum response (Emax) of LPA or each Example compound to the maximum response (Emax) of the positive control compound VPC 31144S (N-{(1S)-2-hydroxy-1-[(phosphonooxy)methyl]ethyl}(9Z) cctadec-9-enamide), with the $E_{max}$ of the positive control compound VPC 31144S as 100%.

TABLE 1

| Example compound No. | LPA4/SRE-luc | | LPA1/SRE-luc | BSA |
|---|---|---|---|---|
| | $EC_{50}$ (nM) | % Emax (%) | $EC_{50}$ (μM) | |
| LPA | 479 | 112 | 0.02 | added |
| 1 | 28 | 119 | >10 | not added |
| 7 | 37 | 125 | >10 | not added |
| 10 | 30 | 101 | >10 | not added |
| 15 | 42 | 75 | >10 | not added |
| 16 | 12 | 162 | >10 | not added |
| 18 | 1.9 | 122 | >10 | not added |
| 20 | 20 | 153 | >10 | not added |
| 24 | 5.6 | 138 | >10 | not added |
| 26 | 10 | 125 | >10 | not added |
| 29 | 45 | 145 | >10 | not added |
| 33 | 33 | 121 | >10 | not added |
| 43 | 27 | 86 | >10 | not added |
| 47 | 46 | 94 | >10 | not added |
| 50 | 23 | 79 | >1 | not added |
| 54 | <41 | 106 | >10 | not added |
| 58 | <41 | 148 | >3 | not added |
| 59 | <41 | 86 | >10 | not added |
| 66 | <41 | 280 | >10 | not added |
| 70 | <41 | 239 | >10 | not added |
| 82 | 1.9 | 129 | >10 | added |
| 84 | 4.1 | 94 | >3 | added |
| 87 | 50 | 97 | >10 | added |
| 88 | 20 | 152 | >10 | added |
| 93 | <41 | 113 | >10 | added |

TABLE 1-continued

| Example compound No. | LPA4/SRE-luc | | LPA1/SRE-luc | BSA |
|---|---|---|---|---|
| | $EC_{50}$ (nM) | % Emax (%) | $EC_{50}$ (μM) | |
| 95 | <41 | 136 | >10 | added |
| 100 | 40 | 108 | >10 | added |
| 102 | 47 | 121 | >10 | added |
| 104 | <41 | 127 | >10 | added |
| 115 | <41 | 114 | >10 | added |
| 118 | <41 | 114 | >10 | added |
| 129 | <41 | 120 | >10 | added |
| 133 | <41 | 101 | >10 | added |
| 134 | <41 | 87 | >10 | added |
| 138 | <41 | 73 | >10 | added |
| 142 | 43 | 103 | >10 | added |

It was confirmed that each of the Example compounds had higher agonistic activity against the LPA4 receptor compared to LPA. It was also confirmed that each of the Example compounds had more selective agonistic activity against the LPA4 receptor than the LPA1 receptor, compared to LPA.

Experimental Example 2

<Experiment method>
A 5-week-old male Balb/c nu/nu mouse (CLEA Japan, Inc.) was subcutaneously transplanted with 500 μL of Matrigel (Corning) admixed with recombinant mouse basicFGF (Biobyt Ltd.) to a final concentration of 200 ng/mL. The test compound was dissolved in a 50% aqueous ethanol solution at a concentration of 10 mg/mL to give a stock solution, diluted with phosphate-buffered saline (PBS) immediately before administration, and used for consecutive administration into the tail vein of mouse at a dose of 3 mg/kg once per day from the 5th day to the 7th day of the transplantation. On the 7th day of transplantation, after 4 hours from the administration of the test compound, Genhance750 (PerkinElmer) was administered to the tail vein, and 20 min later under isoflurane anesthesia, whole body fluorescence at 800 nm was imaged using an in vivo analyzer (IVIS Spectrum, PerkinElmer) at an excitation wavelength of 745 nm. The gel blood flow ratio was calculated by dividing the radiance of Matrigel by the radiance of the auricle.
<Experimental Results>
The results are shown in FIG. 1. The gel blood flow ratio of Example compounds 16, 70, 82, and 84 significantly increased compared to the solvent administration group (t-test. p<0.01).

Experimental Example 3

<Experiment Method>
An 8-week-old female C5713L/6NCrSlc mouse (Nippon SLC) was subcutaneously transplanted with $1 \times 10^6$ cells/100 μL of mouse lung cancer cell line LLC-1 suspended in D-MEM medium containing 50% Matrigel (Corning). On the 9th day after transplantation of the cell line, 8 mice were grouped such that the tumor volume and body weight were uniform (Day 0). The tumor volume was calculated by measuring the minor axis and the major axis of the tumor with a vernier caliper (minor axis x minor axis x major axis/2). Example compound 16 was intraperitoneally administered every day from Day 0 at a dose of 30 mg/kg. As an existing anticancer drug, paclitaxel (paclitaxel injection, Pfizer) was intraperitoneally administered to mice at a dose of 20 mg/kg twice in total on Day 3 and Day 10. The tumor volume of each group was calculated every other day from Day 0 to Day 15. Phosphate-buffered saline in the same amount as the drug solution was administered to the solvent administration group.

<Experimental Results>

Figure 2:
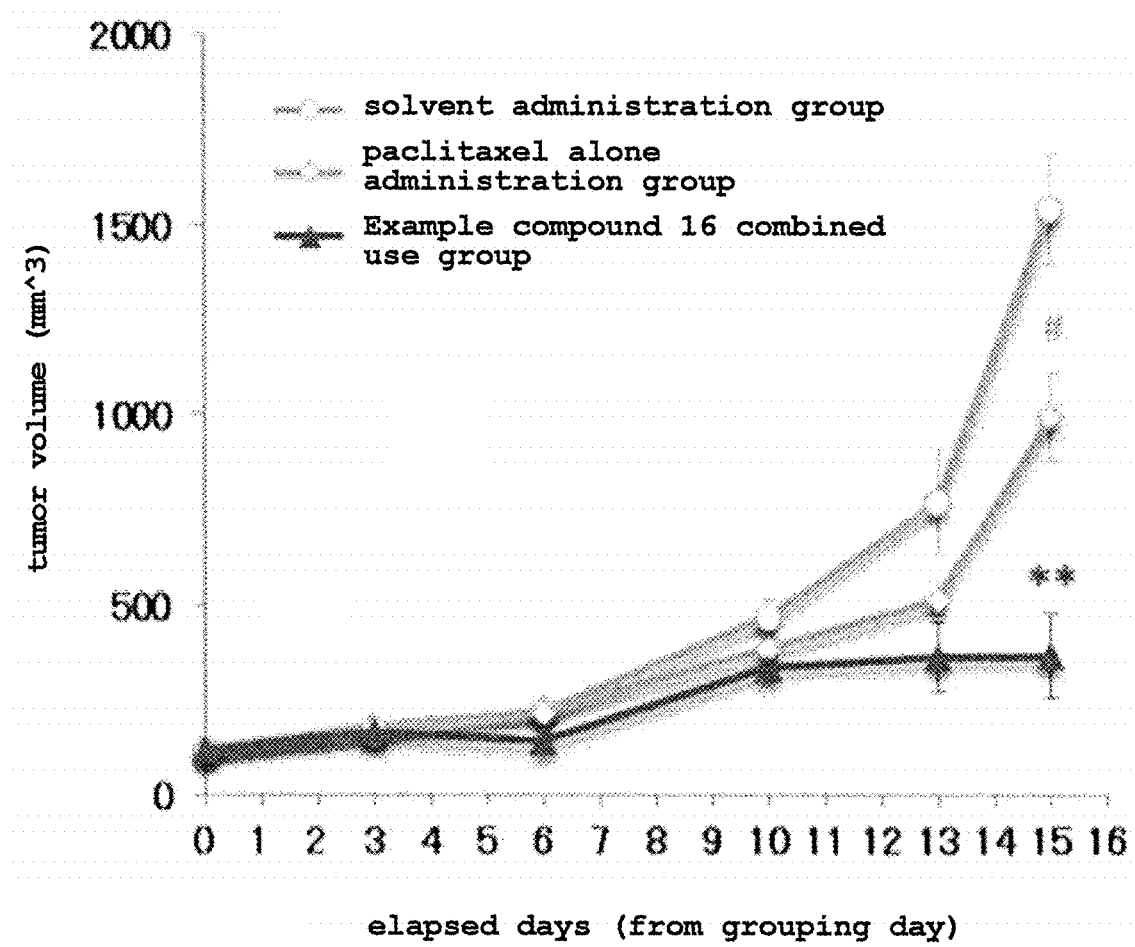
FIG. 2 shows changes in tumor volume over time in a paclitaxel alone administration group (positive control), Example compound 16 and paclitaxel combination use group, and a phosphate buffered saline administration group (control) from day 9 after transplantation of mouse lung cancer cell line LLC-1.

The results are shown in FIG. 2. In the paclitaxel alone administration group, the tumor volume on Day 15 was significantly smaller than that of the solvent administration group (t-test, p<0.05). In the Example compound 16 combined use group, the tumor volume on Day 15 was further reduced significantly as compared with the paclitaxel alone administration group (t-test, p<0.01).

Experimental Example 4

Evaluation of Chemical Stability

<Experiment Method>

About 0.5 mg of each of test sample (lysophosphatidic acid (LPA) and Example compound 16) preserved at 60° C. (sealed) for a week and non-preserved sample (at the start of testing) was weighed, and dissolved in a mixed solution (1 mL) of acetonitrile/water (1:1) to prepare test solutions. Test was performed by the liquid chromatographic method under the following conditions, and individual peak area % was determined. It was measured by Waters ACQUITY UPLC under the following conditions.

Detector: photodiode array (measurement wavelength 220 nm)

Column: Waters ACQUITY BEH C18 (2.1 mm×100 mm, 1.7 μm)

Column temperature: constant temperature around 40° C.

Mobile phase: Solution A; 20M ammonium acetate in water (pH 8.5),

Solution B; 20M ammonium acetate in acetonitrile/water (17:3) (pH8.5)

Concentration gradient control: B % 2→100% (15 min)

Flow rate: 0.5 mL/min

Injection volume: 3.5

<Experimental Results>

The results are shown in Table 2.

TABLE 2

Comparison of test results of chemical stability of LPA and Example compound 16

| compound | preservation conditions | | | total ratio (%) of increment of related substances |
|---|---|---|---|---|
| | temperature | humidity | period | |
| LPA | 60° C. | without artificial control | 1 week | 10.99% |
| Example compound 16 | 60° C. | without artificial control | 1 week | 1.29% |

According to the results shown in Table 2, it was confirmed that use of the compound (I) of the present invention (Example compound 16) caused less increment of related compounds after preserved at 60° C. (sealed) for a week in comparison with the use of LPA, an in vivo ligand, and shows high chemical stability.

Experimental Example 5

<Experiment Method>

Figure 3:
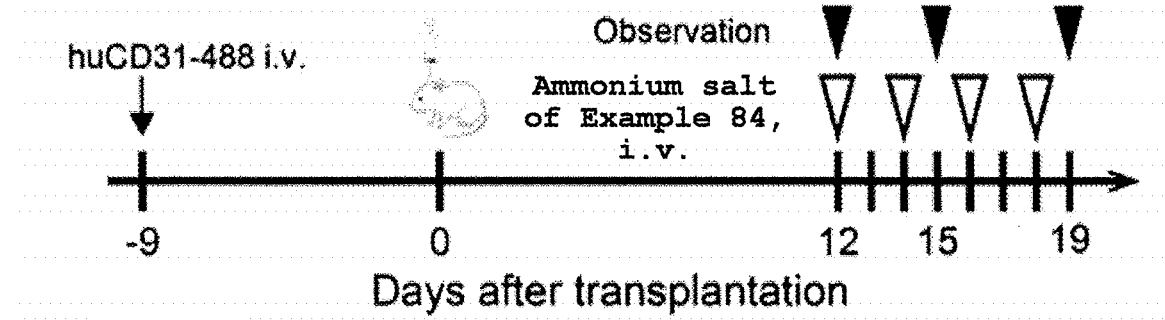
FIG. 3 shows the administration schedule of the compound (I) of the present invention (ammonium salt of Example Compound 84) and the schedule of fluorescence observation of human tumor blood vessels for 19 days after transplantation of human tumor colon tissue into mouse.

Colorectal tissue purchased from the Laboratory of Cell Cultures of the National Institutes of Biomedical Innovation, Health and Nutrition (purchase date: Feb. 5, 2019, resource code: HT8295, Japanese, male, descending and ascending colon cancer, histological type Tub2, no treatment), was transplanted into NOD-Scid mice (CLEA). Alexa Fluor 488 conjugated anti-human CD31 antibody (huCD31-AF488) (Biolegend) for human tumor vascular imaging was administered at a dose of 5 μg/mouse (i.v.) according to the schedule in FIG. 3. Fluorescence observation of human tumor blood vessels was performed, and 1 mg/kg or 3 mg/kg (i.v.) of the test compound (ammonium salt of example compound 84) was administered. In addition, PBS (phosphate buffered saline) (1x, pH 7.4) was administered to the control group. To confirm the perfusion of blood vessels on day 19 after transplantation, 100 μg/mouse (i.v.) of Rhodamine labeled Ulex Europaeus Agglutinin I (UEAI) (Vector Laboratories), which specifically recognizes glycans of human endothelial cells, was administered. After 20 min of perfusion, followed by perfusion fixation (PBS: 10 mL, 4% PFA: 10 mL), 4% PFA fixation (2 hr, 4° C.), 15% sucrose, and 30% sucrose replacement, and tissue embedding using FSC22 freeze embedding compound (Tissue UI). 14-μm thin sections were prepared using the Kawamoto method (Tadafumi Kawamoto, Non-demineralized hard tissue frozen section preparation technique (Kawamoto method 2008) and its application, Pathological Technology, vol. 72, no. 2, p. 76-83, 2009), and fluorescence observation was performed using Leica TCS SP8. Quantification of immunostained images was performed with Image J, Angiotool.

The presence of blood flow in blood vessels constructed with human vascular endothelial cells is an indicator of vascular normalization or maturation, and the presence of blood flow was examined by examining whether or not UEA I, which specifically recognizes glycans of human vascular endothelial cells, was taken up by vascular endothelial cells. The perfusion rate was calculated by dividing the area of human CD31-positive blood vessels with UEA I-positive perfusion by the total area of human CD31-positive blood vessels (%). The percentage of perfused vessels was calculated in 6-10 random regions where human CD31 positive vessels were observed.

<Synthetic Method of Ammonium Salt of Example Compound 84>

Example compound 84 (599 mg) was purified by preparative HPLC (10 mM aqueous ammonium carbonate solution-acetonitrile), and the fractions collected by Milli Q water and tert-butanol, and then lyophilized. Then, the title compound (208 mg) was obtained as a white solid by drying under reduced pressure at room temperature for 15 h. MS(ESI) m/z: 424.3[M−H]−.

<Experimental Results>

Figure 4:
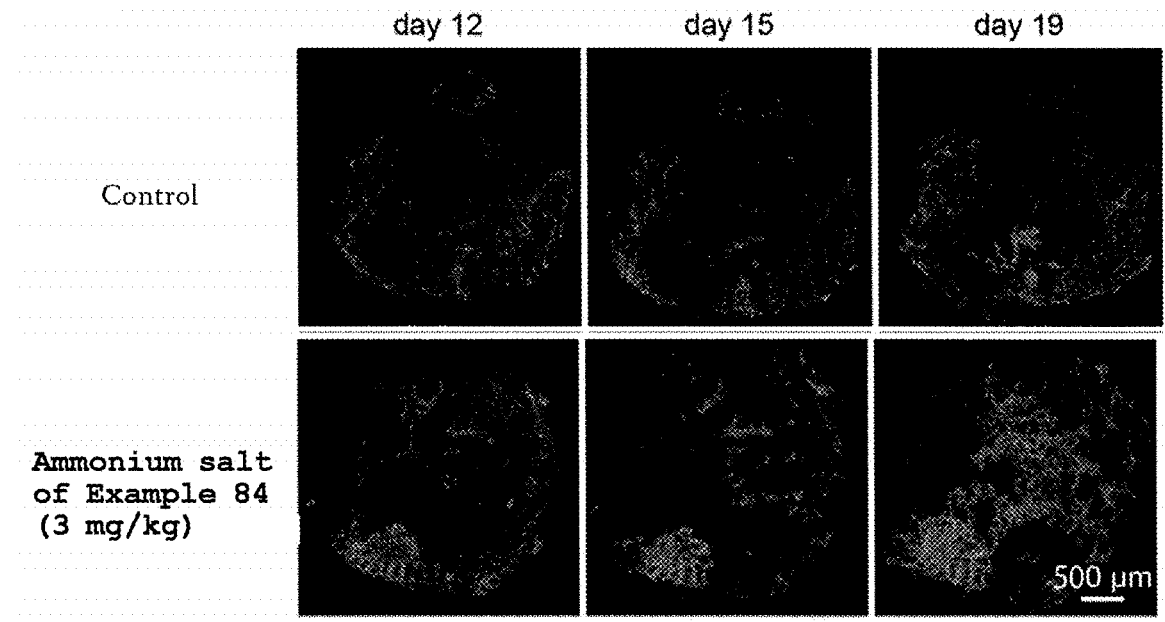
FIG. 4 shows immunostained images of human tumor blood vessels in the control group (solvent group) and the compound (I) of the present invention (ammonium salt of Example Compound 84)-treated group on days 12, 15, and 19 after transplantation of human tumor colon tissue into mouse.

The results of fluorescence observation (immunostained images of human tumor blood vessels) of the test compound-treated group and solvent-treated group (control group) on days 12, 15, and 19 after transplantation are shown in FIG. 4. According to FIG. 4, the ammonium salt of Example 84-treated group (3 mg/kg dose) showed a significant improvement in the construction of the vascular network compared to the control group.

Also, according to FIG. 5, a significant increase in the perfusion status (percentage of perfused vessels) of human tumor vessels was confirmed by the ammonium salt of Example 84-treated group (1 mg/kg or 3 mg/kg administration).

Formulation Example 1

Production of Capsule

| | | |
|---|---|---|
| 1) | compound (I) | 50 mg |
| 2) | microcrystalline cellulose | 10 mg |
| 3) | lactose | 19 mg |
| 4) | magnesium stearate | 1 mg |

1), 2), 3) and 4) are mixed and filled in a gelatin capsule.

Formulation Example 2

Production of Tablet

| | | |
|---|---|---|
| 1) | compound (I) | 50 g |
| 2) | lactose | 50 g |
| 3) | cornstarch | 15 g |
| 4) | carmellose calcium | 44 g |
| 5) | magnesium stearate | 1 g |

The total amount of 1), 2) and 3) and 30 g of 4) are kneaded with water, vacuum dried, and granulated. The granulated powder is mixed with 14 g of 4) and 1 g of 5) and punched by a tableting machine. In this way, 1000 tablets containing 50 mg of compound A monohydrate per tablet are obtained.

INDUSTRIAL APPLICABILITY

The compound (I) of the present invention or a pharmacologically acceptable salt thereof has a selective and superior agonistic activity for LPA4 receptor. Therefore, it is useful for the treatment or prophylaxis of a disease associated with angiogenesis abnormality or a disease associated with a vascular disorder. Examples of the disease associated with angiogenesis abnormality or the disease associated with a vascular disorder include solid cancer, pressure ulcer, diabetic necrosis, diabetic nephropathy, diabetic retinopathy, acute renopathy, cerebral infarction, age-related macular degeneration, rheumatoid arthritis, scleroderma, psoriasis, systemic lupus erythematosus, lung fibrosis, arteriosclerosis obliterans, arteriosclerosis, angina pectoris, myocardial infarction, Buerger disease, brain edema due to infectious disease, hemorrhage due to hemorrhagic virus (Ebola, dengue), acute respiratory distress syndrome and the like. The compound (I) of the present invention or a pharmacologically acceptable salt thereof is particularly useful for the prophylaxis and/or treatment of these diseases. In addition, the compound (I) of the present invention, or a pharmacologically acceptable salt thereof can remarkably improve the usefulness in the prophylaxis and/or treatment of the abovementioned diseases when used in combination with at least one kind of drug selected from the group consisting of a chemotherapeutic agent, an immunotherapeutic agent, and a hormonal therapeutic agent.

In addition, the compound (I) of the present invention or a pharmacologically acceptable salt thereof can normalize abnormal blood vessels and normalize vascular permeability when administered to a patient with a disease associated with angiogenesis abnormality or a disease associated with a vascular disorder together with other drug(s) useful for the treatment of such diseases (by a combination use with other drug(s)), thereby remarkably increasing the delivery efficiency of other drug(s) to the disease site, and enhancing the action of other drug(s).

The invention claimed is:

1. A compound represented by the following formula (I)

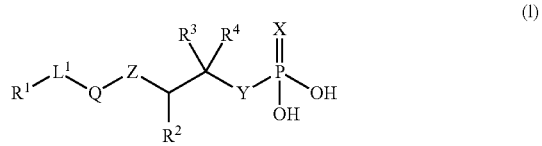

wherein
X is oxygen,
Y is oxygen, —O—CH$_2$—, or —CH$_2$—O—,
Q is —C(=O)—,
R$^1$ is a group represented by the following formula (A-2)

wherein ring B is cycloalkane or benzene, R$^7$ in the number of n are each independently
halogen,
cyano,
optionally substituted alkyl,
optionally substituted cycloalkyl,
optionally substituted alkoxy, or
an optionally substituted aromatic hydrocarbon group, and
n is an integer of 0-5,
L$^1$ is R$^6$—, —R$^6$O—, —OR$^6$—, —R$^6$NH—, or —NHR$^6$—,
R$^6$ is an optionally substituted alkylene,
R$^2$ is hydrogen or alkyl, and
one of R$^3$ and R$^4$ is hydrogen or optionally substituted alkyl, and the other is bonded to R$^5$ to form, together with a carbon atom bonded to R$^3$ and R$^4$, a carbon bonded to R$^2$, and a nitrogen atom bonded to R$^5$, an optionally substituted cyclic amine,
or a pharmacologically acceptable salt thereof.

2. The compound according to claim 1, wherein
R$^6$ is alkylene optionally substituted by alkyl,
R$^7$ in the number of n are each independently
halogen;
cyano;
alkyl optionally substituted by
  halogen,
  cycloalkyl, or
  phenyl optionally substituted by alkyl;
cycloalkyl optionally substituted by alkyl;
an aromatic hydrocarbon group optionally substituted by
  alkoxy optionally substituted by phenyl or alkyl; or
alkoxy optionally substituted by
  phenyl optionally substituted by
    halogen,
    alkyl,
    haloalkoxy or
    phenyl, or cycloalkyl optionally substituted by alkyl,
n is 1 or 2, and
one of $R^3$ and $R^4$ is hydrogen, or alkyl optionally substituted by hydroxy or alkoxy, and the other is bonded to $R^5$ to form, together with a carbon atom bonded to $R^3$ and $R^4$, a carbon bonded to $R^2$, and a nitrogen atom bonded to $R^5$, a cyclic amine optionally substituted by
hydroxy,
alkoxy, or
alkyl optionally substituted by hydroxy or alkoxy,
or a pharmacologically acceptable salt thereof.

3. The compound according to claim 1, wherein
Y is oxygen or —O—CH$_2$—* (wherein * denotes a binding position with a phosphorus atom),
$L^1$ is $R^6$—, —$R^6$O—, —O$R^6$—, or —$R^6$NH— (wherein  denotes a binding position with Q),
$R^6$ is alkylene optionally substituted by alkyl,
$R^7$ in the number of n are each independently
halogen;
cyano;
alkyl optionally substituted by
halogen,
cycloalkyl, or
phenyl optionally substituted by alkyl;
cycloalkyl optionally substituted by alkyl;
an aromatic hydrocarbon group optionally substituted by
alkoxy optionally substituted by phenyl, or
alkyl; or
alkoxy optionally substituted by
phenyl optionally substituted by
halogen,
alkyl,
haloalkoxy or
phenyl, or
cycloalkyl optionally substituted by alkyl,
n is 1 or 2, and
one of $R^3$ and $R^4$ is hydrogen, or alkyl optionally substituted by hydroxy or alkoxy, and the other is bonded to $R^5$ to form, together with a carbon atom bonded to $R^3$ and $R^4$, a carbon bonded to $R^2$, and a nitrogen atom bonded to $R^5$, a cyclic amine optionally substituted by
hydroxy,
alkoxy, or
alkyl optionally substituted by hydroxy or alkoxy,
or a pharmacologically acceptable salt thereof.

4. The compound according to claim 1, wherein
Y is oxygen,
$L^1$ is a single bond, —$R^6$—, or —$R^6$O—* (wherein * denotes a binding position with Q),
$R^6$ is alkylene,
$R^7$ in the number of n are each independently
halogen;
alkyl optionally substituted by
halogen,
cycloalkyl, or
phenyl optionally substituted by alkyl;
cycloalkyl;
phenyl optionally substituted by alkyl; or
alkoxy optionally substituted by
phenyl optionally substituted by
halogen,
alkyl,
haloalkoxy or
phenyl, or
cycloalkyl,
n is 1 or 2, and
one of $R^3$ and $R^4$ is hydrogen, and the other is bonded to $R^5$ to form, together with a carbon atom bonded to $R^3$ and $R^4$, a carbon bonded to $R^2$, and a nitrogen atom bonded to $R^5$, azetidine, pyrrolidine or piperidine each optionally substituted by
hydroxy,
alkoxy, or
alkyl optionally substituted by hydroxy or alkoxy,
or a pharmacologically acceptable salt thereof.

5. The compound of claim 1, wherein
Y is oxygen,
$L^1$ is a single bond, —$R^6$—, or —$R^6$O—* (wherein * denotes a binding position with Q),
$R^6$ is alkylene,
$R^2$ is hydrogen, and
one of $R^3$ and $R^4$ is hydrogen, and the other is bonded to $R^5$ to form, together with a carbon atom bonded to $R^3$ and $R^4$, a carbon bonded to $R^2$, and a nitrogen atom bonded to $R^5$, azetidine optionally substituted by
hydroxy,
alkoxy, or
alkyl optionally substituted by hydroxy or alkoxy,
or a pharmacologically acceptable salt thereof.

6. The compound of claim 1, wherein ring B is benzene, or a pharmacologically acceptable salt thereof.

7. The compound according to claim 1, wherein the compound of the formula (I) is any of the following a to i, or a pharmacologically acceptable salt thereof:
a. 1-[9-(4-ethylphenyl)nonanoyl]azetidin-3-yl dihydrogen phosphate,
b. 1-{4-[4-(octyloxy)phenyl]butanoyl}azetidin-3-yl dihydrogen phosphate,
c. 1-[8-(3-octylphenyl)octanoyl]azetidin-3-yl dihydrogen phosphate,
d. 1-[9-(4-butylphenyl)nonanoyl]azetidin-3-yl dihydrogen phosphate,
e. 1[9-(biphenyl-4-yl)nonanoyl]azetidin-3-yl dihydrogen phosphate,
f. 1-[9-(4-tert-butylphenyl)nonanoyl]azetidin-3-yl dihydrogen phosphate,
g. 1-[9-(4-cyclopropylphenyl)nonanoyl]azetidin-3-yl dihydrogen phosphate,
h. 1-[9-(4-cyclohexylphenyl)nonanoyl]azetidin-3-yl dihydrogen phosphate, and
i. 1-[9-(4-hexylphenyl)nonanoyl]azetidin-3-yl dihydrogen phosphate.

8. A pharmaceutical composition comprising the compound according to claim 1 or a pharmacologically acceptable salt thereof, and a pharmacologically acceptable carrier.

9. A pharmaceutical composition according to claim 8 for use in the treatment of a disease associated with angiogenesis abnormality, or a disease associated with a vascular disorder.

10. The pharmaceutical composition according to claim 8 for use in combination with an anticancer drug.

11. The pharmaceutical composition according to claim 10, wherein the anticancer drug is a drug for treating a disease associated with angiogenesis abnormality, or a disease associated with a vascular disorder.

12. The pharmaceutical composition according to claim 10, wherein the anticancer drug is at least one kind of drug selected from the group consisting of a chemotherapeutic agent, an immunotherapeutic agent, and a hormonal therapeutic agent.

13. The pharmaceutical composition according to claim 10, wherein the compound or a pharmacologically acceptable salt thereof, and the anticancer drug are separately administered.

14. The pharmaceutical composition according to claim 10, wherein the compound or a pharmacologically acceptable salt thereof, and the anticancer drug are simultaneously or sequentially administered.

15. The pharmaceutical composition according to claim 9, wherein the disease associated with angiogenesis abnormality, or the disease associated with a vascular disorder is solid cancer, pressure ulcer, diabetic necrosis, diabetic nephropathy, diabetic retinopathy, acute nephropathy, cerebral infarction, age-related macular degeneration, rheumatoid arthritis, scleroderma, psoriasis, systemic lupus erythematosus, lung fibrosis, arteriosclerosis obliterans, arteriosclerosis, angina pectoris, myocardial infarction, Buerger disease, brain edema due to infectious disease, hemorrhage due to hemorrhagic virus (Ebola, dengue), or acute respiratory distress syndrome.

16. A method of inducing an agonistic action on an LPA4 receptor in a subject comprising administering the compound according to claim 1 or a pharmacologically acceptable salt thereof.

* * * * *